US012668811B2

(12) United States Patent
Chuah et al.

(10) Patent No.: US 12,668,811 B2
(45) Date of Patent: Jun. 30, 2026

(54) LIVER-SPECIFIC NUCLEIC ACID REGULATORY ELEMENTS AND METHODS AND USE THEREOF

(71) Applicant: Vrije Universiteit Brussel, Brussels (BE)

(72) Inventors: Lay Khim Chuah, Bierbeek (BE); Thierry Vandendriessche, Bierbeek (BE)

(73) Assignee: Vrije Universiteit Brussel, Brussels (BE)

( * ) Notice: Subject to any disclaimer, the term of this patent is extended or adjusted under 35 U.S.C. 154(b) by 1184 days.

(21) Appl. No.: 17/288,425

(22) PCT Filed: Oct. 28, 2019

(86) PCT No.: PCT/EP2019/079358
§ 371 (c)(1),
(2) Date: Apr. 23, 2021

(87) PCT Pub. No.: WO2020/084162
PCT Pub. Date: Apr. 30, 2020

(65) Prior Publication Data
US 2021/0403948 A1 Dec. 30, 2021

(30) Foreign Application Priority Data

Oct. 26, 2018 (EP) .................................... 18202986

(51) Int. Cl.
*C12N 15/86* (2006.01)
*A61K 48/00* (2006.01)
(52) U.S. Cl.
CPC .......... *C12N 15/86* (2013.01); *A61K 48/0058* (2013.01); *C12N 2750/14143* (2013.01); *C12N 2830/008* (2013.01); *C12N 2830/42* (2013.01)
(58) Field of Classification Search
CPC .......... C12N 15/86; C12N 2750/14143; C12N 2830/008; A61K 48/0058
See application file for complete search history.

(56) References Cited

U.S. PATENT DOCUMENTS

| | | | | |
|---|---|---|---|---|
| 10,077,430 B2 * | 9/2018 | Lee | ...................... | A61K 31/713 |
| 2007/0161031 A1 * | 7/2007 | Trinklein | ........... | C12N 15/1086 435/325 |
| 2010/0323376 A1 * | 12/2010 | Contois | .................. | G01N 33/92 435/7.1 |
| 2015/0141320 A1 * | 5/2015 | Krieg | ..................... | A61K 48/00 435/375 |

FOREIGN PATENT DOCUMENTS

| | | | |
|---|---|---|---|
| JP | 2011-517955 A | 6/2011 | |
| WO | WO2008/073303 | 6/2008 | |
| WO | WO2011/034935 | 3/2011 | |
| WO | WO2013/186398 | 12/2013 | |
| WO | WO-2013186398 A1 * | 12/2013 | ......... A61K 48/0058 |
| WO | WO2016/146757 | 9/2016 | |

OTHER PUBLICATIONS

Inukai et al. Curr Opin Genet Dev. Apr. 2017; 43: 110-119. Published online Mar. 27, 2017. doi: 10.1016/j.gde.2017.02.007 (Year: 2017).*
Kennell, Progr. Nucleic Acid Res. Mol. Biol. 11: 259-301, 1971 (Year: 1971).*
Yale J Biol Med. Dec. 2016; 89(4): 513-525. Published online Dec. 23, 2016 (Year: 2016).*
International Search Report mailed Apr. 3, 2020 for International Application No. PCT/EP2019/079358 filed Oct. 28, 2019, 8 pages.

* cited by examiner

*Primary Examiner* — Christopher M Babic
*Assistant Examiner* — Joel D Levin
(74) *Attorney, Agent, or Firm* — McDonnell Boehnen Hulbert & Berghoff LLP

(57) ABSTRACT

The disclosure presents nucleic acid regulatory elements that are able to enhance liver-specific expression of genes, methods employing these regulatory elements and uses of these elements. Expression cassettes and vectors containing these nucleic acid regulatory elements are also disclosed. The nucleic acid regulatory elements, methods employing these regulatory elements and uses of these elements are particularly useful for applications using gene therapy, more particularly liver-directed gene therapy, and for vaccination purposes.

17 Claims, 3 Drawing Sheets

Specification includes a Sequence Listing.

SEQUENCE LISTING

<160> NUMBER OF SEQ ID NOS: 58

<210> SEQ ID NO 1
<211> LENGTH: 336
<212> TYPE: DNA
<213> ORGANISM: Homo sapiens

<400> SEQUENCE: 1
tgggaaatta cagttaaata ccatggtaat gaataaaagg tacaaatcgt ttaaactctt      60
atgtaaaatt tgataagatg ttttacacaa ctttaataca ttgacaaggt cttgtggaga     120
aaacagttcc agatggtaaa tatacacaag ggatttagtc aaacaatttt ttggcaagaa     180
tattatgaat tttgtaatcg gttggcagcc aatgaaatac aaagatgagt ctagttaata     240
atctacaatt attggttaaa gaagtatatt agtgctaatt ccctccgtt tgtcctagct     300 tttctcttct gtcaacccca cacgcctttg gcacaa                              336

<210> SEQ ID NO 2
<211> LENGTH: 347
<212> TYPE: DNA
<213> ORGANISM: Homo sapiens

<400> SEQUENCE: 2
tttttctttt tctaaatgat cagtacactt attctttcta aagaaaatac ttttcttaac      60
tactctctat ttttaaactt ctcccacaaa gatgagaaaa catttaaaaa tcattggggc     120
tatttttctg tttaccgagt aaagagaatc tctaaaccat atttataact cttactctaa     180
atatttgcat ttaccctcat gccagagccc gttgatgact gactaaacag agtttcaaag     240
tttgaagaac aggaaattta gaaatgacta acaattatgt aggtttattt ctctcagtat     300
agaatgttca tatagaatta atgccagagg ttttcagaga aaaatgc                  347

<210> SEQ ID NO 3
<211> LENGTH: 386
<212> TYPE: DNA
<213> ORGANISM: Homo sapiens

<400> SEQUENCE: 3
gggacactga agccaaatgg gcttcagctc ctccccaggg atctccctac ctgctgccca      60
ttccaacctg gctctctccc tctccacaac tgaagcccag gcctctttgg atgctgctca     120
cacatcttgc ctccttatct tacctagcca gcgtctctgt ccttggtgtc tgtgcctgcc     180
ctggctggag aggaaggggc tatatacctg tctgtttacc caccccctgt caggtgacag     240
ggactatgga tgggcccagt ggggcaggga ttatgtgagg ataaacaagt tggagaaatg     300
ggggaggaga ggacaagcac atggaagact catggtgatg gggtgagagg caggggggtac     360 agctcttagt ggaggctaag ggggta                                         386

<210> SEQ ID NO 4
<211> LENGTH: 426
<212> TYPE: DNA
<213> ORGANISM: Homo sapiens

<400> SEQUENCE: 4
gagttaatgt gtaatgagac ggggagaaaa caggagagcc cagaatgacc tggatgctga      60
tcactgaaca taccctaccc ccagtaaaac aaattcagaa aacagcttcc gcccgtcccc     120
tcccaatgga gggctctggc aggaaaagag gtgaataaga ggcttctacc agggtaaagg     180
ttgaaggcac ctggtcattt gatcacctta tcagttctag gcagtgatta gccaatattg     240

-continued

```
agtcagcagg ggcaatagcc ctggcccttg tctcactcct gttggggggtg ggggaggggg      300 agaggtacat tcccaggttc aaagcatttg ggtgaaatca gttaaataga tatcagaagc      360
ttttgtatct ttcacccttt tgcccccaa gcatactcgc tgagtatgtg gaacattcct       420
gagggt                                                                  426
```

```
<210> SEQ ID NO 5
<211> LENGTH: 260
<212> TYPE: DNA
<213> ORGANISM: Homo sapiens

<400> SEQUENCE: 5
tgttttgttt tggtgaccta actggtcaaa tgacctatta agaatatttc atagaacgaa        60
tgttccgatg ctctaatctc tctagacaag gttcatattt gtatgggtta cttattctct       120
ctttgttgac taagtcaata atcagaatca gcaggtttgc agtcagattg gcagggataa       180
gcagcctagc tcaggagaag tgagtataaa agccccaggc tgggagcagc catcacagaa       240
gtccactcat tcttggcagg                                                   260
```

```
<210> SEQ ID NO 6
<211> LENGTH: 267
<212> TYPE: DNA
<213> ORGANISM: Homo sapiens

<400> SEQUENCE: 6 agggggggccc ctggggctga cagggactgg aagctctgag ctggccagag ggatgttgca       60
atcctgccag ggtcttgtct atgctgtcct tttcacaacc atccccctac tgccaggctg       120
acacgtggtt gcgggggcac aaggccagcc aacctagagt ctgaggctag gcggaggaca       180 ccctcccccac cagctgccag ggtcactggc ggtcaaaggc agctggtggg gaaggcattg       240
gactccagcc ttgggggacg gatgtag                                          267
```

```
<210> SEQ ID NO 7
<211> LENGTH: 313
<212> TYPE: DNA
<213> ORGANISM: Homo sapiens

<400> SEQUENCE: 7
tacaggcctg gggtcccggc ttagaggacc tctgagagct ccggggcccc ttctgggtcg        60
tggttgcctc atcgtggtcg ggtgggtctc caggttctcc caggctcagt cccgcaggcg       120
ccaaatctgc gcaggagagc actagcaacc gatgacgtat tgaggcccac acctctggga       180
ttggctgtcc tgcttcgaca gccttgaaag tgggtaagct gggtgggggg ctctgggaga       240
ggtcagtgct gagtaaggca attcccagca gcttgagccc caccaggtca ctccagtatt       300 cctcccatt ctt                                                          313
```

```
<210> SEQ ID NO 8
<211> LENGTH: 513
<212> TYPE: DNA
<213> ORGANISM: Homo sapiens

<400> SEQUENCE: 8
cccgaacgaa taaaccccctt ccttaactca gcgtctgagg aattttgtct gcggctcctc       60
ctgctacatt ctgagtgggg aaagggacta aggtggtctg aggaccccac agagtcagga       120
agattgagag gtgagagtgc tgaacgggga ggggctttgg ggctaaggga agtgcccggg       180
```

```
accccacctg accccaacgc tcacgggaca ggggcagagg agaaaaacgt gggtggacag     240
agggaggcag gcggtcaggg gaaggctcag gaggagggag atcaacatca acctgccccg     300 cccctcccc agcctgataa aggtcctgcg ggcaggacag gacctcccaa ccaagccctc      360
cagcaaggat tcaggttggt gctgagtgcc tgggagggac acccgcctac actctgcaag     420
aaactcaaaa agggagatga ggggatcgtg ggagggaggt agggaggggag gagggtgcca    480 ctgatcccct gaacccctgc ctctgcctcc aga                                 513

<210> SEQ ID NO 9
<211> LENGTH: 306
<212> TYPE: DNA
<213> ORGANISM: Homo sapiens

<400> SEQUENCE: 9
gatgagtgca gggaaccccg accccacccg ggagacctgc aagcctgcag acactcccct      60
cccgccccca ctgaacccttt gacccctgcc ctgcagcccc cgcagcttgc tgtttgccca     120
ctctatttgc ccagccccag ggacagagct gatccttgaa ctcttaagtt ccacattgcc     180
aggaccagtg agcagcaaca gggccggggc tgggcttatc agcctcccag cccagaccct     240
ggctgcagac ataaataggc cctgcaagag ctggctgctt agagactgcg agaaggaggt     300
gcgtcc                                                               306

<210> SEQ ID NO 10
<211> LENGTH: 406
<212> TYPE: DNA
<213> ORGANISM: Homo sapiens

<400> SEQUENCE: 10
ttctatcatt atcttcaatc agaaactgat gtgtggggag gtgatgtatc ataactcatc      60
cagggtcagg cagctggatt tgaacctgcc tgacccttag atttgaggtt ttctggctcc     120
agaatcttct ctgaagtgaa aggcatgagg ccgaccactc cctgatctgg taaacagaga     180
tgtcagcctg gtttctagtg ttagggagtt tcctggagtg atggtacagg gtacatttct     240
gccctgcatc ccaagtccag agactgggtt ctaggtccag cctttcttct aactccctga     300
gagatgacag cctctgggca aagtccctct gtgctcttca gtctcttcat ctgtgagatg     360
gtggcatggg gagaggctgg agtgatgtca cagttcctct cagcct                    406

<210> SEQ ID NO 11
<211> LENGTH: 504
<212> TYPE: DNA
<213> ORGANISM: Homo sapiens

<400> SEQUENCE: 11
acaaaagctg cagcaaaatt gccaaaagta ggaactactg ggggtggggg tcctgtctcc      60
cctgctcagt caccacctcc cctccctaac tctcattctg gctcatacca cgtgctccca     120
gaagaaacgt tctgagcagg ggctggtatg agactgcctc ccctcccagg acccactcct     180
ccctatgacc aggctggtga ccctccctct agggtgccag tgccattcac tgagcagatg     240
tttggcaggt gtctgttatg tgccagacct agcaggggac agagtcctcc cgatacagat     300
ggaccagtat gtttggacat aaattgtgaa aggagttgct aatctttctg tgcaaaatcc     360
actcttgcgg tcaccgccaa cactcctaca catgtcaggg catccagggc caggacttgg     420
taaccctgtt caggagcagt cgctctggag actcccaaga cgagggaaag aaatgggtgg     480
aaacaggggc ctacactgtg ggcc                                           504
```

<210> SEQ ID NO 12
<211> LENGTH: 431
<212> TYPE: DNA
<213> ORGANISM: Homo sapiens

<400> SEQUENCE: 12
gtgaggccac ggtcttcccg ccaggttgac tcgagcctcc tgccagagcc actggccccg        60
gaggccaccc tagaccgcag ctggcggccg ctggcacgag tgcagggtaa ctgagccagg       120
gccgctggcg catttggcct ggccgaggcc accccgcgcg gccgctccac tgtgcccgag       180
gctgtcctgg aggtgaggcc ggcccacagg gaccctgccc gtgcccgggc tccggtgagt       240
cagggcgcgt tatgcaagtg cccccggcgc ctcccctctcg gtctttcacc ccgcgcggtt       300
acgaaagcgc gacccactcc cccggcgct ataaagcagc gggcggccg cggcgcgctc         360 gcctccctcg ctccacgcgc gcccggactc ggcggccagg cttgcgcgcg gttcccctcc       420
cggtggtgag t                                                           431

<210> SEQ ID NO 13
<211> LENGTH: 448
<212> TYPE: DNA
<213> ORGANISM: Homo sapiens

<400> SEQUENCE: 13
aaatacctaa actagtcaca ctgttttgat tcaattggct actgaagtta tagaatgttg        60
tttactcttc tctcctttgt ctactcccca gccaacaaaa caaccgacct tagctgtttt       120
gaaaataaat gaaaattcca acatgggttt gaaataaaat tgcatcataa acaatcggta       180
ggtgtttttc aaagtggttt cagggaagtg ccacggagta agcaggcgac caccgaggct       240
gctaaaatat ttcctgtcct gaccagggtt gcgtttctgg agaatattta acagggaggg       300
ttttaacgct tttaaagatg ttgaaactaa agaacaaata ttgaccagag ggcaccacaa       360
cgctcctgaa agagagtaaa atacatcctt tataaaatga aaaactactt ggatgaatta       420
ttccaaaatt cctgcacaag tggacctc                                        448

<210> SEQ ID NO 14
<211> LENGTH: 335
<212> TYPE: DNA
<213> ORGANISM: Homo sapiens

<400> SEQUENCE: 14
ctgagctcat ctgggctgca gggctggcgg gacagcagcg tggactcagt ctcctaggga        60
tttcccaact ctcccgcccg cttgctgcat ctggacaccc tgcctcaggc cctcatctcc       120
actggtcagc aggtgacctt tgcccagcgc cctgggtcct cagtgcctgc tgccctggag       180
atgatataaa acaggtcaga accctcctgc ctgtctgctc agttcatccc tagaggcagc       240
tgctccaggt aatgccctct ggggagggga aagaggaggg gaggaggatg aagagggggca      300 agaggagctc cctgcccagc ccagccagca agcct                                 335

<210> SEQ ID NO 15
<211> LENGTH: 431
<212> TYPE: DNA
<213> ORGANISM: Homo sapiens

<400> SEQUENCE: 15
agaagggtca gcggcccctc ctggaccacc gactccccgc agaactcctc tgtgccctct        60

```
cctcaccaga ccttgttcct cccagttgct cccacagcca gggggcagtg agggctgctc       120
ttcccccagc cccactgagg aacccaggaa ggtgaacgag agaatcagtc ctggtggggg       180
ctggggaggg ccccagacat gagaccagct cctcccccag gggatgttat cagtgggtcc       240
agagggcaaa ataggggagcc tggtggaggg agggggcaaag gcctcgggct ctgagcggcc      300
ttggcccttc tccaccaacc cctgccctac actaaggggg aggcagcggg gggcacacag       360
ggtgggggcg ggtgggggggc tgctgggtga gcagcactcg cctgcctgga ttgaaaccca      420
gagatggagg t                                                            431
```

```
<210> SEQ ID NO 16
<211> LENGTH: 559
<212> TYPE: DNA
<213> ORGANISM: Homo sapiens

<400> SEQUENCE: 16
gtagctgatg ggaagagcag actgccttcc agccaggcct ggtcctgtga gtcagggacg        60
tccatcttag tgggcatgaa aggcctgtgt gatctcgagg gagacatcgc ctctccaagc       120
ctctccttat ctgtgcaaca ggcagactta atgattggtg aggcaatgag gctgatagct       180
cagcattagc tacagccacc cctcctggcc aaccacacag ggatcaaacc aggggtcagt       240
ccagaggtca gagtcaggag cagacaactc agatccagcc agggacaggc aggtcacacg       300
gacatgtgcc tcacgtatgc ttcaaggggc cctcccccgg gcagaactga aggacagctc       360
ctgttgccat aggagggagc tgggtgagat actaggagga acttccggca tgatgatgtg       420
tgatgaacaa gggcctctgg ccaacaggtc tgaatcaggg ctgcccagcc cagcctggtg       480
ggaagggcat ggagcatggg ggctcatgta ctaaacctca cctggacaca aggtgaaaca       540
gcccaacccc agaggacca                                                    559
```

```
<210> SEQ ID NO 17
<211> LENGTH: 370
<212> TYPE: DNA
<213> ORGANISM: Homo sapiens

<400> SEQUENCE: 17
gcttgcaaca atgtctggca cataggaaaa gtgatcacta aatgttagcc acgtcttact        60
cctgcaaggc tcacctccct ggaacccatc ggtcccaacc ctgctcctga atcaggcaca       120
gtccagcttg cagcgggagc aaaggtcagt actcagtgcc cctgtccctt ccccaggcca       180
gaggggagga ggagactgag tcacgaatga cacctcagcc gcagtttgac ctccaggact       240
tacagtccta gcagccggtg ccactagcat gtgagaggtc cagaggcgct tctgtctcac       300
ccgcccgcct gggtgcaccc atgctgggag cgcctgcacc atttgagcat gtccgagagc       360
atccaccaga                                                              370
```

```
<210> SEQ ID NO 18
<211> LENGTH: 431
<212> TYPE: DNA
<213> ORGANISM: Homo sapiens

<400> SEQUENCE: 18
ctgggcagga gcagctggct tgagcagaat cttgggacct gaggctctca ggggacctcc        60
cattggggga tggagggcaa tggtggtggt gcccaggagg tcttctactt agatgtctat       120
tggatctcta aatgaggctg catgcataat cacacacaaa catccactga gaaggtgaca       180
caccacgtca gcatgggtcc ctctgccgga ccacaccact cctagtgact atgaggtgac       240
```
atccaggcac gttgcactat tggctcctgt cggtgagtgc agtgcctgac aacagtgagc        300
tacatttatt tgtaaaaatg aacgccatca gagtagacca caattgtact aactctaatt        360
tgctttgtgt tcattttttc agtttccaga agtggcttaa tgtttcctag ggtcaaaggc        420
agtcaaatga c        431

<210> SEQ ID NO 19
<211> LENGTH: 481
<212> TYPE: DNA
<213> ORGANISM: Homo sapiens

<400> SEQUENCE: 19 gaaggggggaa gagacccact gaaatcctat ctcccagcct cacctctgct gtctcctcca        60
cgcttcctgt ctccagagcc ccgagttcag cataagcaga aagcggcctg ttccctctct        120
agggagagga gggttgcggt ctggaggtct ggctcgtctt tatctgcgca ttctcccagc        180
ctcctggctt cagacctcag cgaggcggcg gctgccggcc ggctctcctc ttcctgcctg        240
cagacctggc ctgctgcttc tttctccttc ctccctccct gcctgccctg cggtttcaaa        300
gtagattaga aataacagtg tcccacatgg aagcctctac ttcttcctgg gtcaactttg        360
atgacgaggc tccagaaaac ctttgcaatg ctgtgtggaa tttttaaatc ggtgagctcg        420
tgctcttgcc ctatttattt gtccagcgta catttctgaa cattgtgaac gtcgaatggg        480
c        481

<210> SEQ ID NO 20
<211> LENGTH: 345
<212> TYPE: DNA
<213> ORGANISM: Homo sapiens

<400> SEQUENCE: 20
ggaaaacagg gagacagttt cctgtttgag atgttgggag atgcttcgag tagtatattt        60
actggaaata gacattcaac ttggatgtcc cttttttggaa atgtgcctgc gtccagggct        120
gggttggggc cccaatgaac tttggctctg acacagctgt tgccacactc agtggaactg        180
aatctatgtt tgtcttcccc ggcatccttc accccaactc tccccgccac aacatacatc        240
ccatgccagc ctggggaccc tcaaaggtgg cttcatcatt aggtttgtgg ctgggtccca        300
ctgaagtaag tcttggcact cagagggata ggaattgaat gaaga        345

<210> SEQ ID NO 21
<211> LENGTH: 386
<212> TYPE: DNA
<213> ORGANISM: Homo sapiens

<400> SEQUENCE: 21
ggaggttgca gtaagccaag attgtgccac tgcactccaa cctgggtgac agagccagac        60
tctgtctcaa gaaataaag agaaaaagaa ctagattcag gctgtatgtg ggcaccatct        120
acagacatca gacacacaca tttaggagta ataatgatgc aatattgcca aatgtttctc        180
agcaaccatg tgcaactgtt gcatgtactg tttatttcta actcaggagg atctctctaa        240
ccacacattg caagaaaata gactttcagt gtttctggca aaacaaagag ttttttttgtt        300 ggcatttatg ctgaaaggga agagttaaaa tgttaatttg tcttttttct tacctccaag        360
ttcactcaaa tcctctcttg aagcag        386

<210> SEQ ID NO 22

-continued

```
<211> LENGTH: 72
<212> TYPE: DNA
<213> ORGANISM: Artificial Sequence
<220> FEATURE:
<223> OTHER INFORMATION: SerpEnh

<400> SEQUENCE: 22
gggggaggct gctggtgaat attaaccaag gtcaccccag ttatcggagg agcaaacagg      60
ggctaagtcc ac                                                         72

<210> SEQ ID NO 23
<211> LENGTH: 218
<212> TYPE: DNA
<213> ORGANISM: Artificial Sequence
<220> FEATURE:
<223> OTHER INFORMATION: 3xSerpEnh

<400> SEQUENCE: 23
gggggaggct gctggtgaat attaaccaag gtcaccccag ttatcggagg agcaaacagg      60
ggctaagtcc accggggggag gctgctggtg aatattaacc aaggtcaccc cagttatcgg    120
aggagcaaac aggggctaag tccaccgggg gaggctgctg gtgaatatta accaaggtca    180
ccccagttat cggaggagca acagggggct aagtccac                            218

<210> SEQ ID NO 24
<211> LENGTH: 100
<212> TYPE: DNA
<213> ORGANISM: Artificial Sequence
<220> FEATURE:
<223> OTHER INFORMATION: TTRe

<400> SEQUENCE: 24
cactgggagg atgttgagta agatggaaaa ctactgatga cccttgcaga gacagagtat      60
taggacatgt ttgaacaggg gccgggcgat cagcaggtag                           100

<210> SEQ ID NO 25
<211> LENGTH: 1389
<212> TYPE: DNA
<213> ORGANISM: Artificial Sequence
<220> FEATURE:
<223> OTHER INFORMATION: co-FIX-R338L

<400> SEQUENCE: 25
atgcagcgcg tgaacatgat catggccgag agccccggcc tgatcaccat ctgcctgctg      60
ggctacctgc tgagcgccga gtgcaccgtg ttcctggacc acgagaacgc caacaagatc    120
ctgaaccgcc ccaagcgcta caacagcggc aagctggagg agttcgtgca gggcaacctg    180
gagcgcgagt gcatggagga gaagtgcagc ttcgaggagg cccgcgaggt gttcgagaac    240
accgagcgca ccaccgagtt ctggaagcag tacgtggacg gcgaccagtg cgagagcaac    300
ccctgcctga acggcggcag ctgcaaggac gacatcaaca gctacgagtg ctggtgcccc    360
ttcggcttcg agggcaagaa ctgcgagctg gacgtgacct gcaacatcaa gaacggccgc    420
tgcgagcagt tctgcaagaa cagcgccgac aacaaggtgg tgtgcagctg caccgagggc    480
taccgcctgg ccgagaacca gaagagctgc gagcccgccg tgcccttccc ctgcggccgc    540
gtgagcgtga gccagaccag caagctgacc cgcgccgagg ccgtgttccc cgacgtggac    600
tacgtgaaca gcaccgaggc cgagaccatc ctggacaaca tcacccagag cacccagagc    660
ttcaacgact tcacccgcgt ggtgggcggc gaggacgcca gcccggcca gttcccctgg    720 caggtggtgc tgaacggcaa ggtggacgcc ttctgcggcg gcagcatcgt gaacgagaag    780
```

```
tggatcgtga ccgccgccca ctgcgtggag accggcgtga agatcaccgt ggtggccggc      840
gagcacaaca tcgaggagac cgagcacacc gagcagaagc gcaacgtgat ccgcatcatc      900
ccccaccaca actacaacgc cgccatcaac aagtacaacc acgacatcgc cctgctggag      960
ctggacgagc ccctggtgct gaacagctac gtgaccccca tctgcatcgc cgacaaggag      1020
tacaccaaca tcttcctgaa gttcggcagc ggctacgtga gcggctgggg ccgcgtgttc      1080
cacaagggcc gcagcgccct ggtgctgcag tacctgcgcg tgcccctggt ggaccgcgcc      1140
acctgcctgc tgagcaccaa gttcaccatc tacaacaaca tgttctgcgc cggcttccac      1200
gagggcggcc gcgacagctg ccagggcgac agcggcggcc cccacgtgac cgaggtggag      1260
ggcaccagct tcctgaccgg catcatcagc tggggcgagg agtgcgccat gaagggcaag      1320
tacggcatct acaccaaggt gagccgctac gtgaactgga tcaaggagaa gaccaagctg      1380
acctaatga                                                              1389

<210> SEQ ID NO 26
<211> LENGTH: 4377
<212> TYPE: DNA
<213> ORGANISM: Artificial Sequence
<220> FEATURE:
<223> OTHER INFORMATION: co-FVIIIdeltaB

<400> SEQUENCE: 26
atgcagatcg agctgtccac ctgctttttt ctgtgcctgc tgcggttctg cttcagcgcc      60
acccggcggt actacctggg cgccgtggag ctgtcctggg actacatgca gagcgacctg      120
ggcgagctgc ccgtggacgc ccggttcccc cccagagtgc ccaagagctt cccccttcaac      180 accagcgtgg tgtacaagaa aaccctgttc gtggagttca ccgaccacct gttcaatatc      240
gccaagccca ggcccccctg gatgggcctg ctgggcccca ccatccaggc cgaggtgtac      300
gacaccgtgg tgatcaccct gaagaacatg gccagccacc ccgtgagcct gcacgccgtg      360
ggcgtgagct actggaaggc cagcgagggc gccgagtacg acgaccagac cagccagcgg      420 gagaagaag atgacaaggt gttccctggc ggcagccaca cctacgtgtg gcaggtgctg      480
aaagaaaacg gccccatggc ctccgacccc ctgtgcctga cctacagcta cctgagccac      540
gtggacctgg tgaaggacct gaacagcggc ctgatcggcg ctctgctcgt ctgccgggag      600
ggcagcctgg ccaaagagaa aacccagacc ctgcacaagt tcatcctgct gttcgccgtg      660
ttcgacgagg gcaagagctg gcacagcgag acaaagaaca gcctgatgca ggaccgggac      720
gccgcctctg ccagagcctg gcccaagatg cacaccgtga cggctacgt gaacagaagc      780 ctgcccggcc tgattggctg ccaccggaag agcgtgtact ggcacgtgat cggcatgggc      840
accacacccg aggtgcacag catctttctg aagggcaca cctttctggt ccggaaccac      900
cggcaggcca gctggaaat cagccctatc accttcctga ccgcccagac actgctgatg      960
gacctgggcc agtcctgct gttttgccac atcagctctc accagcacga cggcatggaa      1020
gcctacgtga aggtggactc ttgccccgag gaaccccagc tgcggatgaa gaacaacgag      1080
gaagccgagg actacgacga cgacctgacc gacagcgaga tggacgtggt gcggttcgac      1140
gacgacaaca gccccagctt catccagatc agaagcgtgg ccaagaagca ccccaagacc      1200
tgggtgcact atatcgccgc cgaggaagag gactgggact acgccccct ggtgctggcc      1260 cccgacgaca agagctacaa gagccagtac ctgaacaatg cccccagcg gatcggccgg      1320 aagtacaaga aagtgcggtt catggcctac accgacgaga cattcaagac ccgggaggcc      1380
```

-continued

```
atccagcacg agagcggcat cctgggcccc ctgctgtacg gcgaagtggg cgacacactg    1440
ctgatcatct tcaagaacca ggctagccgg ccctacaaca tctacccca cggcatcacc    1500 gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccagatg cctgacccgg tactacagca gcttcgtgaa catggaacgg    1680
gacctggcct ccgggctgat cggacctctg ctgatctgct acaaagaaag cgtgaccag    1740 cggggcaacc agatcatgag cgacaagcgg aacgtgatcc tgttcagcgt gttcgatgag    1800
aaccggtcct ggtatctgac cgagaacatc cagcggtttc tgcccaaccc tgccggcgtg    1860
cagctggaag atcccgagtt ccaggccagc aacatcatgc actccatcaa tggctacgtg    1920
ttcgactctc tgcagctctc cgtgtgtctg cacgaggtgg cctactggta catcctgagc    1980
atcggcgccc agaccgactt cctgagcgtg ttcttcagcg gctacacctt caagcacaag    2040
atggtgtacg aggacaccct gacctgttc cctttcagcg gcgagacagt gttcatgagc    2100
atggaaaacc ccggcctgtg gattctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca acgccatcga accccggagc    2280
ttcagccaga acccccccgt gctgacgcgt caccagcggg agatcacccg gacaaccctg    2340
cagtccgacc aggaagagat cgattacgac gacaccatca gcgtggagat gaagaaaag    2400 gatttcgata tctacgacga ggacgagaac cagagcccca gaagcttcca gaagaaaacc    2460
cggcactact tcattgccgc cgtggagagg ctgtgggact acggcatgag ttctagcccc    2520
cacgtgctgc ggaaccgggc ccagagcggc agcgtgcccc agttcaagaa agtggtgttc    2580
caggaattca cagacggcag cttcacccag cctctgtata gaggcgagct gaacgagcac    2640
ctggggctgc tggggcccta catcagggcc gaagtggagg acaacatcat ggtgaccttc    2700
cggaatcagg ccagcagacc ctactccttc tacagcagcc tgatcagcta cgaagaggac    2760
cagcggcagg gcgccgaacc ccggaagaac ttcgtgaagc ccaacgaaac caagacctac    2820
ttctggaaag tgcagcacca catggccccc accaaggacg agttcgactg caaggcctgg    2880
gcctacttca gcgacgtgga tctggaaaag gacgtgcact ctggactgat tggcccactc    2940
ctggtctgcc acactaacac cctcaacccc gcccacggcc gccaggtgac cgtgcaggaa    3000
ttcgccctgt tcttcaccat cttcgacgag acaaagtcct ggtacttcac cgagaatatg    3060
gaacggaact gcagagcccc ctgcaacatc cagatggaag atcctacctt caaagagaac    3120
taccggttcc acgccatcaa cggctacatc atggacaccc tgcctggcct ggtgatggcc    3180
caggaccaga gaatccggtg gtatctgctg tccatgggca gcaacgagaa tatccacagc    3240
atccacttca gcggccacgt gttcaccgtg cggaagaaag aagagtacaa gatggccctg    3300
tacaacctgt accccggcgt gttcgagaca gtggagatgc tgcccagcaa ggccggcatc    3360
tggcgggtgg agtgtctgat cggcgagcac ctgcacgctg gcatgagcac cctgtttctg    3420
gtgtacagca acaagtgcca gacccccactg ggcatggcct ctggccacat ccgggacttc    3480
cagatcaccg cctccggcca gtacggccag tgggccccca agctggccag actgcactac    3540
agcggcagca tcaacgcctg gtccaccaaa gagcccttca gctggatcaa ggtggacctg    3600 ctggcccccta tgatcatcca cggcattaag acccagggcg ccaggcagaa gttcagcagc    3660
ctgtacatca gccagttcat catcatgtac agcctggacg caagaagtg gcagacctac    3720 cggggcaaca gcaccggcac cctgatggtg ttcttcggca atgtggacag cagcggcatc    3780
```

-continued

```
aagcacaaca tcttcaaccc ccccatcatt gcccggtaca tccggctgca ccccacccac     3840
tacagcatta gatccacact gagaatggaa ctgatgggct gcgacctgaa ctcctgcagc     3900
atgcctctgg gcatggaaag caaggccatc agcgacgccc agatcacagc cagcagctac     3960
ttcaccaaca tgttcgccac ctggtccccc tccaaggcca ggctgcacct gcagggccgg     4020
tccaacgcct ggcggcctca ggtcaacaac cccaaagaat ggctgcaggt ggactttcag     4080
aaaaccatga aggtgaccgg cgtgaccacc cagggcgtga aaagcctgct gaccagcatg     4140
tacgtgaaag agtttctgat cagcagctct caggatggcc accagtggac cctgttcttt     4200
cagaacggca aggtgaaagt gttccagggc aaccaggact ccttcacccc cgtggtgaac     4260
tccctggacc cccccctgct gacccgctac ctgagaatcc accccagtc ttgggtgcac     4320 cagatcgccc tcaggatgga agtcctggga tgtgaggccc aggatctgta ctgatga     4377

<210> SEQ ID NO 27
<211> LENGTH: 202
<212> TYPE: DNA
<213> ORGANISM: Artificial Sequence
<220> FEATURE:
<223> OTHER INFORMATION: TTRm

<400> SEQUENCE: 27
gtctgtctgc acatttcgta gagcgagtgt tccgatactc taatctccct aggcaaggtt       60
catatttgtg taggttactt attctccttt tgttgactaa gtcaataatc agaatcagca      120
ggtttggagt cagcttggca gggatcagca gcctgggttg aaggagggg gtataaaagc      180 cccttcacca ggagaagccg tc                                              202

<210> SEQ ID NO 28
<211> LENGTH: 317
<212> TYPE: DNA
<213> ORGANISM: Artificial Sequence
<220> FEATURE:
<223> OTHER INFORMATION: TTRe-TTRm

<400> SEQUENCE: 28
cactgggagg atgttgagta agatggaaaa ctactgatga cccttgcaga gacagagtat       60
taggacatgt ttgaacaggg gccgggcgat cagcaggtag ctctagagga tccccgtctg      120
tctgcacatt tcgtagagcg agtgttccga tactctaatc tccctaggca aggttcatat      180
ttgtgtaggt tacttattct cctttttgttg actaagtcaa taatcagaat cagcaggttt      240
ggagtcagct tggcagggat cagcagcctg ggttggaagg aggggtata aaagcccctt      300 caccaggaga agccgtc                                                    317

<210> SEQ ID NO 29
<211> LENGTH: 92
<212> TYPE: DNA
<213> ORGANISM: Artificial Sequence
<220> FEATURE:
<223> OTHER INFORMATION: MVM intron

<400> SEQUENCE: 29
aagaggtaag ggtttaaggg atggttggtt ggtgggggtat taatgtttaa ttacctggag       60
cacctgcctg aaatcacttt ttttcaggtt gg                                    92

<210> SEQ ID NO 30
<211> LENGTH: 295
<212> TYPE: DNA
```

-continued

<213> ORGANISM: Artificial Sequence
<220> FEATURE:
<223> OTHER INFORMATION: BGHpolyA

<400> SEQUENCE: 30

```
gatctgagcc gaattcctgc agcccggggg atcagcctcg actgtgcctt ctagttgcca      60
gccatctgtt gtttgcccct cccccgtgcc ttccttgacc ctggaaggtg ccactcccac     120
tgtcctttcc taataaaatg aggaaattgc atcgcattgt ctgagtaggt gtcattctat     180
tctggggggt ggggtggggc aggacagcaa gggggaggat tgggaagaca atagcaggca     240
tgctggggat gcggtgggct ctatggcttc tgaggcggaa agaaccagct gggga          295
```

<210> SEQ ID NO 31
<211> LENGTH: 6228
<212> TYPE: DNA
<213> ORGANISM: Artificial Sequence
<220> FEATURE:
<223> OTHER INFORMATION: pAAVsc-TTRe-TTRm-MVM-co-FIX-R338L-BGHpA

<400> SEQUENCE: 31

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca cggttaatt tgcgtgatgg acagactctt ttactcggtg cctcactga     240 ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctcccttag     540 ggttccgatt tagtgcttta cggcacctcg accccaaaaa acttgattag ggtgatggtt     600
cacgtagtgg gccatcgccc tgatagacgg tttttcgccc tttgacgttg gagtccacgt     660
tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt acaatttaa atatttgctt     840 atacaatctt cctgtttttg gggcttttct gattatcaac cggggtacat atgattgaca     900
tgctagtttt acgattaccg ttcatcgccc tgcgcgctcg ctcgctcact gaggccgccc     960
gggcaaagcc cggcgtcgg gcgacctttg gtcgcccggc ctcagtgagc gagcgagcgc    1020
gcagagaggg agtggaattc acgcgtggat ctgaattcaa ttcacgcgtg gtacggccgc    1080
ggtacccact gggaggatgt tgagtaagat ggaaaactac tgatgaccct gcagagaca    1140 gagtattagg acatgtttga acaggggccg ggcgatcagc aggtagctct agaggatccc    1200
cgtctgtctg cacatttcgt agagcgagtg ttccgatact ctaatctccc taggcaaggt    1260
tcatatttgt gtaggttact tattctcctt ttgttgacta agtcaataat cagaatcagc    1320
aggtttggag tcagcttggc agggatcagc agcctgggtt ggaaggaggg ggtataaaag    1380
ccccttcacc aggagaagcc gtcacacaga tccacaagct cctggctaga aagaggtaag    1440
ggtttaaggg atggttggtt ggtggggtat taatgtttaa ttacctggag cacctgcctg    1500
aaatcacttt ttttcaggtt gggctagccc accatgcagc gcgtgaacat gatcatggcc    1560
gagagccccg gcctgatcac catctgcctg ctgggctacc tgctgagcgc cgagtgcacc    1620
```

-continued

```
gtgttcctgg accacgagaa cgccaacaag atcctgaacc gccccaagcg ctacaacagc   1680
ggcaagctgg aggagttcgt gcagggcaac ctggagcgcg agtgcatgga ggagaagtgc   1740
agcttcgagg aggcccgcga ggtgttcgag aacaccgagc gcaccaccga gttctggaag   1800
cagtacgtga cggcgacca gtgcgagagc aaccccctgcc tgaacggcgg cagctgcaag   1860
gacgacatca acagctacga gtgctggtgc cccttcggct tcgagggcaa gaactgcgag   1920
ctggacgtga cctgcaacat caagaacggc cgctgcgagc agttctgcaa gaacagcgcc   1980
gacaacaagg tggtgtgcag ctgcaccgag ggctaccgcc tggccgagaa ccagaagagc   2040
tgcgagcccg ccgtgccctt ccctgcggc cgcgtgagcg tgagccagac cagcaagctg   2100
acccgcgccg aggccgtgtt ccccgacgtg gactacgtga acagcaccga ggccgagacc   2160
atcctggaca acatcacca gagcacccag agcttcaacg acttcacccg cgtggtgggc   2220
ggcgaggacg ccaagcccgg ccagttcccc tggcaggtgg tgctgaacgg caaggtggac   2280
gccttctgcg gcggcagcat cgtgaacgag aagtggatcg tgaccgccgc ccactgcgtg   2340
gagaccggcg tgaagatcac cgtggtggcc ggcgagcaca acatcgagga gaccgagcac   2400
accgagcaga agcgcaacgt gatccgcatc atcccccacc acaactacaa cgccgccatc   2460
aacaagtaca accacgacat cgccctgctg gagctggacg agcccctggt gctgaacagc   2520
tacgtgaccc ccatctgcat cgccgacaag gagtacacca acatcttcct gaagttcggc   2580
agcggctacg tgagcggctg gggccgcgtg ttccacaagg gccgcagcgc cctggtgctg   2640
cagtacctgc gcgtgcccct ggtggaccgc gccacctgcc tgctgagcac caagttcacc   2700
atctacaaca acatgttctg cgccggcttc cacgagggcg gccgcgacag ctgccagggc   2760
gacagcggcg gcccccacgt gaccgaggtg gagggcacca gcttcctgac cggcatcatc   2820
agctggggcg aggagtgcgc catgaagggc aagtacggca tctacaccaa ggtgagccgc   2880
tacgtgaact ggatcaagga gaagaccaag ctgacctaat gaaagatgga tttccaaggt   2940
taattcattg gaattgaaaa ttaacagccc cccccccccc cccctgcag atctgagccg   3000 aattcctgca gcccggggga tcagcctcga ctgtgccttc tagttgccag ccatctgttg   3060
tttgcccctc ccccgtgcct tccttgaccc tggaaggtgc cactcccact gtcctttcct   3120
aataaaatga ggaaattgca tcgcattgtc tgagtaggtg tcattctatt ctggggggtg   3180
gggtggggca ggacagcaag ggggaggatt gggaagacaa tagcaggcat gctgggggatg   3240 cggtgggctc tatggcttct gaggcggaaa gaaccagctg gggaccggtg gatctcgata   3300
gcaggcatgc tggggagaga tcgatctgag gaacccctag tgatggagtt ggccactccc   3360
tctctgcgcg ctcgctcgct cactgaggcc gcccgggcaa agcccgggcg tcgggcgacc   3420
tttggtcgcc cggcctcagt gagcgagcga gcgcgcagag agggagtggc caaccccccc   3480
cccccccccc cccggcgatt ctcttgtttg ctccagactc tcaggcaatg acctgatagc   3540
ctttgtagag acctctcaaa aatagctacc ctctccggca tgaatttatc agctagaacg   3600
gttgaatatc atattgatgg tgatttgact gtctccggcc tttctcaccc gtttgaatct   3660
ttacctacac attactcagg cattgcattt aaaatatatg agggttctaa aaatttttat   3720
ccttgcgttg aaataaaggc ttctccccgca aaagtattac agggtcataa tgttttttggt   3780 acaaccgatt tagctttatg ctctgaggct ttattgctta attttgctaa ttctttgcct   3840
tgcctgtatg atttattgga tgttggaatc gcctgatgcg gtattttctc cttacgcatc   3900
tgtgcggtat ttcacaccgc atatggtgca ctctcagtac aatctgctct gatgccgcat   3960
```

-continued

```
agttatatgg tgcactctca gtacaatctg ctctgatgcc gcatagttaa gccagccccg    4020
acacccgcca acacagccag ccccgacacc cgccaacacc cgctgacgcg ccctgacggg    4080
cttgtctgct cccggcatcc gcttacagac aagctgtgac cgtctccggg agctgcatgt    4140
gtcagaggtt ttcaccgtca tcaccgaaac gcgcgagacg aaaggcctc gtgatacgcc      4200 tattttttata ggttaatgtc atgataataa tggtttctta gacgtcaggt ggcactttc     4260 ggggaaatgt gcgcggaacc cctatttgtt tattttttcta aatacattca aatatgtatc    4320
cgctcatgag acaataaccc tgataaatgc tcaataatat tgaaaaagga agagtatgag      4380
tattcaacat ttccgtgtcg cccttattcc ctttttttgcg gcattttgcc ttcctgtttt    4440
tgctcaccca gaaacgctgg tgaaagtaaa agatgctgaa gatcagttgg gtgcacgagt      4500
gggttacatc gaactggatc tcaacagcgg taagatcctt gagagttttc gccccgaaga      4560
acgttttcca atgatgagca cttttaaagt tctgctatgt ggcgcggtat tatcccgtat      4620
tgacgccggg caagagcaac tcggtcgccg catacactat tctcagaatg acttggttga      4680
gtactcacca gtcacagaaa agcatcttac ggatggcatg acagtaagag aattatgcag      4740
tgctgccata accatgagtg ataacactgc ggccaactta cttctgacaa cgatcggagg      4800
accgaaggag ctaaccgctt ttttgcacaa catgggggat catgtaactc gccttgatcg      4860
ttgggaaccg gagctgaatg aagccatacc aaacgacgag cgtgacacca cgatgcctgt      4920
agcaatggca acaacgttgc gcaaactatt aactggcgaa ctacttactc tagcttcccg      4980
gcaacaatta atagactgga tggaggcgga taaagttgca ggaccacttc tgcgctcggc      5040
ccttccggct ggctggttta ttgctgataa atctggagcc ggtgagcgtg ggtctcgcgg      5100
tatcattgca gcactggggc cagatggtaa gccctcccgt atcgtagtta tctacacgac      5160
ggggagtcag gcaactatgg atgaacgaaa tagacagatc gctgagatag gtgcctcact      5220
gattaagcat tggtaactgt cagaccaagt ttactcatat atactttaga ttgatttaaa      5280
acttcatttt taatttaaaa ggatctaggt gaagatcctt tttgataatc tcatgaccaa      5340
aatcccttaa cgtgagtttt cgttccactg agcgtcagac cccgtagaaa agatcaaagg      5400
atcttcttga gatccttttt ttctgcgcgt aatctgctgc ttgcaaacaa aaaaaccacc      5460
gctaccagcg gtggtttgtt tgccggatca agagctacca actctttttc cgaaggtaac      5520
tggcttcagc agagcgcaga taccaaatac tgtccttcta gtgtagccgt agttaggcca      5580
ccacttcaag aactctgtag caccgcctac atacctcgct ctgctaatcc tgttaccagt      5640
ggctgctgcc agtggcgata agtcgtgtct taccgggttg gactcaagac gatagttacc      5700
ggataaggcg cagcggtcgg gctgaacggg gggttcgtgc acacagccca gcttggagcg      5760
aacgacctac accgaactga gatacctaca gcgtgagcta tgagaaagcg ccacgcttcc      5820
cgaagggaga aaggcggaca ggtatccggt aagcggcagg tcggaacag gagagcgcac       5880 gagggagctt ccaggggggaa acgcctggta tctttatagt cctgtcgggt ttcgccacct     5940
ctgacttgag cgtcgatttt tgtgatgctc gtcaggggggg cggagcctat ggaaaaacgc     6000
cagcaacgcg gcctttttac ggttcctggc cttttgctgg ccttttgctc acatgttctt      6060
tcctgcgtta tcccctgatt ctgtggataa ccgtattacc gcctttgagt gagctgatac      6120
cgctcgccgc agccgaacga ccgagcgcag cgagtcagtg agcgaggaag cggaagagcg      6180
cccaatacgc aaaccgcctc tccccgcgcg ttggccgatt cattaatg                   6228
```

```
<210> SEQ ID NO 32
<211> LENGTH: 6448
```

-continued

<212> TYPE: DNA
<213> ORGANISM: Artificial Sequence
<220> FEATURE:
<223> OTHER INFORMATION: pAAVsc-3xSerpEnh-TTRe-TTRm-MVM-co-FIX-R338L-
     BGHpA

<400> SEQUENCE: 32

```
agctggcgta atagcgaaga ggcccgcacc gatcgccctt cccaacagtt gcgcagcctg        60
aatggcgaat ggcgattccg ttgcaatggc tggcggtaat attgttctgg atattaccag       120
caaggccgat agtttgagtt cttctactca ggcaagtgat gttattacta atcaaagaag       180
tattgcgaca acggttaatt tgcgtgatgg acagactctt ttactcggtg gcctcactga       240
ttataaaaac acttctcagg attctggcgt accgttcctg tctaaaatcc ctttaatcgg       300
cctcctgttt agctcccgct ctgattctaa cgaggaaagc acgttatacg tgctcgtcaa       360
agcaaccata gtacgcgccc tgtagcggcg cattaagcgc ggcgggtgtg gtggttacgc       420
gcagcgtgac cgctacactt gccagcgccc tagcgcccgc tcctttcgct ttcttccctt       480
cctttctcgc cacgttcgcc ggctttcccc gtcaagctct aaatcggggg ctccctttag       540
ggttccgatt tagtgcttta cggcacctcg accccaaaaa acttgattag ggtgatggtt       600
cacgtagtgg gccatcgccc tgatagacgg ttttttcgcc tttgacgttg gagtccacgt       660
tctttaatag tggactcttg ttccaaactg gaacaacact caaccctatc tcggtctatt       720
cttttgattt ataagggatt ttgccgattt cggcctattg gttaaaaaat gagctgattt       780
aacaaaaatt taacgcgaac tttaacaaaa tattaacgtt tacaatttaa atatttgctt       840
atacaatctt cctgttttg gggcttttct gattatcaac cggggtacat atgattgaca       900
tgctagtttt acgattaccg ttcatcgccc tgcgcgctcg ctcgctcact gaggccgccc       960
gggcaaagcc cggcgtcgg gcgacctttg gtcgcccggc ctcagtgagc gagcgagcgc      1020
gcagagaggg agtggaattc acgcgtggat ctgaattcaa ttcacgcgtg gtacggccgc      1080
gggggggagg ctgctggtga atattaacca aggtcacccc agttatcgga ggagcaaaca      1140
ggggctaagt ccaccggggg aggctgctgg tgaatattaa ccaaggtcac cccagttatc      1200
ggaggagcaa acaggggcta agtccaccgg gggaggctgc tggtgaatat taaccaaggt      1260 cacccagtt atcggaggag caaacagggg ctaagtccac ggtacccact gggaggatgt      1320
tgagtaagat ggaaaactac tgatgaccct tgcagagaca gagtattagg acatgtttga      1380 acagggccg ggcgatcagc aggtagctct agaggatccc cgtctgtctg cacatttcgt      1440
agagcgagtg ttccgatact ctaatctccc taggcaaggt tcatatttgt gtaggttact      1500
tattctcctt ttgttgacta agtcaataat cagaatcagc aggtttggag tcagcttggc      1560
agggatcagc agcctgggtt ggaaggaggg ggtataaaag cccctcacc aggagaagcc      1620 gtcacacaga tccacaagct cctggctaga aagaggtaag ggtttaaggg atggttggtt      1680
ggtggggtat taatgtttaa ttacctggag cacctgcctg aaatcacttt ttttcaggtt      1740
gggctagccc accatgcagc gcgtgaacat gatcatggcc gagagccccg cctgatcac      1800 catctgcctg ctgggctacc tgctgagcgc cgagtgcacc gtgttcctgg accacgagaa      1860
cgccaacaag atcctgaacc gccccaagcg ctacaacagc ggcaagctgg aggagttcgt      1920
gcagggcaac ctggagcgcg agtgcatgga ggagaagtgc agcttcgagg aggcccgcga      1980
ggtgttcgag aacaccgagc gcaccaccga gttctggaag cagtacgtgg acggcgacca      2040
gtgcgagagc aaccccctgcc tgaacggcgg cagctgcaag gacgacatca acagctacga      2100
gtgctggtgc cccttcggct cgagggcaa gaactgcgag ctggacgtga cctgcaacat      2160
```

-continued

```
caagaacggc cgctgcgagc agttctgcaa gaacagcgcc gacaacaagg tggtgtgcag    2220
ctgcaccgag ggctaccgcc tggccgagaa ccagaagagc tgcgagcccg ccgtgccctt    2280
cccctgcggc cgcgtgagcg tgagccagac cagcaagctg acccgcgccg aggccgtgtt    2340
ccccgacgtg gactacgtga acagcaccga ggccgagacc atcctggaca acatcaccca    2400
gagcacccag agcttcaacg acttcacccg cgtggtgggc ggcgaggacg ccaagcccgg    2460
ccagttcccc tggcaggtgg tgctgaacgg caaggtggac gccttctgcg gcggcagcat    2520
cgtgaacgag aagtggatcg tgaccgccgc ccactgcgtg gagaccggcg tgaagatcac    2580
cgtggtggcc ggcgagcaca acatcgagga gaccgagcac accgagcaga agcgcaacgt    2640
gatccgcatc atcccccacc acaactacaa cgccgccatc aacaagtaca accacgacat    2700
cgccctgctg gagctggacg agccctggt gctgaacagc tacgtgaccc ccatctgcat    2760
cgccgacaag gagtacacca acatcttcct gaagttcggc agcggctacg tgagcggctg    2820
gggccgcgtg ttccacaagg gccgcagcgc cctggtgctg cagtacctgc gcgtgcccct    2880
ggtggaccgc gccacctgcc tgctgagcac caagttcacc atctacaaca acatgttctg    2940
cgccggcttc cacgagggcg gccgcgacag ctgccagggc gacagcggcg gcccccacgt    3000
gaccgaggtg gagggcacca gcttcctgac cggcatcatc agctggggcg aggagtgcgc    3060
catgaagggc aagtacggca tctacaccaa ggtgagccgc tacgtgaact ggatcaagga    3120
gaagaccaag ctgacctaat gaaagatgga tttccaaggt taattcattg gaattgaaaa    3180
ttaacagccc ccccccccc ccccctgcag atctgagccg aattcctgca gcccggggga    3240
tcagcctcga ctgtgccttc tagttgccag ccatctgttg tttgcccctc ccccgtgcct    3300
tccttgaccc tggaaggtgc cactcccact gtcctttcct aataaaatga ggaaattgca    3360
tcgcattgtc tgagtaggtg tcattctatt ctggggggtg gggtggggca ggacagcaag    3420
ggggaggatt gggaagacaa tagcaggcat gctggggatg cggtgggctc tatggcttct    3480
gaggcggaaa gaaccagctg gggaccggtg gatctcgata gcaggcatgc tggggagaga    3540
tcgatctgag gaacccctag tgatggagtt ggccactccc tctctgcgcg ctcgctcgct    3600
cactgaggcc gcccgggcaa gcccgggcg tcgggcgacc tttggtcgcc cggcctcagt    3660
gagcgagcga gcgcgcagag agggagtggc caacccccc cccccccccc cccggcgatt    3720
ctcttgtttg ctccagactc tcaggcaatg acctgatagc ctttgtagag acctctcaaa    3780
aatagctacc ctctccggca tgaatttatc agctagaacg gttgaatatc atattgatgg    3840
tgatttgact gtctccggcc tttctcaccc gtttgaatct ttacctacac attactcagg    3900
cattgcattt aaaatatatg agggttctaa aaatttttat ccttgcgttg aaataaaggc    3960
ttctcccgca aaagtattac agggtcataa tgttttggt acaaccgatt tagctttatg    4020
ctctgaggct ttattgctta attttgctaa ttctttgcct tgcctgtatg atttattgga    4080
tgttggaatc gcctgatgcg gtattttctc cttacgcatc tgtgcggtat ttcacaccgc    4140
atatggtgca ctctcagtac aatctgctct gatgccgcat agttatatgg tgcactctca    4200
gtacaatctg ctctgatgcc gcatagttaa gccagccccg acaccgccaa cacagccag    4260 ccccgacacc cgccaacacc cgctgacgcg ccctgacggg cttgtctgct cccggcatcc    4320
gcttacagac aagctgtgac cgtctccggg agctgcatgt gtcagaggtt ttcaccgtca    4380
tcaccgaaac gcgcgagacg aaagggcctc gtgatacgcc tatttttata ggttaatgtc    4440
atgataataa tggtttctta cgtcaggt ggcactttc ggggaaatgt gcgcggaacc    4500
```

-continued

```
cctatttgtt tattttttcta aatacattca aatatgtatc cgctcatgag acaataacccc      4560 tgataaatgc tcaataatat tgaaaaagga agagtatgag tattcaacat ttccgtgtcg      4620
cccttattcc ctttttttgcg gcattttgcc ttcctgtttt tgctcaccca gaaacgctgg      4680
tgaaagtaaa agatgctgaa gatcagttgg gtgcacgagt gggttacatc gaactggatc      4740
tcaacagcgg taagatcctt gagagttttc gccccgaaga acgttttcca atgatgagca      4800
cttttaaagt tctgctatgt ggcgcggtat tatcccgtat tgacgccggg caagagcaac      4860
tcggtcgccg catacactat tctcagaatg acttggttga gtactcacca gtcacagaaa      4920
agcatcttac ggatggcatg acagtaagag aattatgcag tgctgccata accatgagtg      4980
ataacactgc ggccaactta cttctgacaa cgatcggagg accgaaggag ctaaccgctt      5040
ttttgcacaa catgggggat catgtaactc gccttgatcg ttgggaaccg gagctgaatg      5100
aagccatacc aaacgacgag cgtgacacca cgatgcctgt agcaatggca acaacgttgc      5160
gcaaactatt aactggcgaa ctacttactc tagcttcccg gcaacaatta atagactgga      5220
tggaggcgga taaagttgca ggaccacttc tgcgctcggc ccttccggct ggctggttta      5280
ttgctgataa atctggagcc ggtgagcgtg ggtctcgcgg tatcattgca gcactggggc      5340
cagatggtaa gccctcccgt atcgtagtta tctacacgac ggggagtcag gcaactatgg      5400
atgaacgaaa tagacagatc gctgagatag gtgcctcact gattaagcat tggtaactgt      5460
cagaccaagt ttactcatat atactttaga ttgatttaaa acttcatttt taatttaaaa      5520
ggatctaggt gaagatcctt tttgataatc tcatgaccaa aatcccttaa cgtgagtttt      5580
cgttccactg agcgtcagac cccgtagaaa agatcaaagg atcttcttga tccttttttt      5640
ttctgcgcgt aatctgctgc ttgcaaacaa aaaaaccacc gctaccagcg gtggtttgtt      5700
tgccggatca gagctacca actctttttc gaaggtaac tggcttcagc agagcgcaga      5760
taccaaatac tgtccttcta gtgtagccgt agttaggcca ccacttcaag aactctgtag      5820
caccgcctac atacctcgct ctgctaatcc tgttaccagt ggctgctgcc agtggcgata      5880
agtcgtgtct taccgggttg gactcaagac gatagttacc ggataaggcg cagcggtcgg      5940
gctgaacggg gggttcgtgc acacagccca gcttggagcg aacgacctac accgaactga      6000
gatacctaca gcgtgagcta tgagaaagcg ccacgcttcc cgaagggaga aaggcggaca      6060
ggtatccggt aagcggcagg gtcggaacag gagagcgcac gagggagctt ccagggggaa      6120
acgcctggta tctttatagt cctgtcgggt ttcgccacct ctgacttgag cgtcgatttt      6180
tgtgatgctc gtcagggggg cggagcctat ggaaaaacgc cagcaacgcg gcctttttac      6240
ggttcctggc cttttgctgg ccttttgctc acatgttctt tcctgcgtta tcccctgatt      6300
ctgtggataa ccgtattacc gcctttgagt gagctgatac cgctcgccgc agccgaacga      6360
ccgagcgcag cgagtcagtg agcgaggaag cggaagagcg cccaatacgc aaaccgcctc      6420
tccccgcgcg ttggccgatt cattaatg                                        6448
```

<210> SEQ ID NO 33
<211> LENGTH: 6566
<212> TYPE: DNA
<213> ORGANISM: Artificial Sequence
<220> FEATURE:
<223> OTHER INFORMATION: AAVsc-HS-CRE1-TTRenh-TTRm-MVM-hFIXcoPadua-
      bghpolyA

<400> SEQUENCE: 33

```
agctggcgta atagcgaaga ggcccgcacc gatcgccctt cccaacagtt gcgcagcctg        60
```

-continued

```
aatggcgaat ggcgattccg ttgcaatggc tggcggtaat attgttctgg atattaccag      120
caaggccgat agtttgagtt cttctactca ggcaagtgat gttattacta atcaaagaag      180
tattgcgaca acggttaatt tgcgtgatgg acagactctt ttactcggtg gcctcactga      240
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg tttttcgccc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt acaatttaa atatttgctt      840 atacaatctt cctgtttttg gggcttttct gattatcaac cggggtacat atgattgaca      900
tgctagtttt acgattaccg ttcatcgccc tgcgcgctcg ctcgctcact gaggccgccc      960
gggcaaagcc cggacgtcgg cgacctttg gtcgcccggc ctcagtgagc gagcgagcgc     1020
gcagagaggg agtggaattc acgcgtggat ctgaattctg tacaggcgtg gtacggccgc     1080
ggtgggaaat tacagttaaa taccatggta atgaataaaa ggtacaaatc gtttaaactc     1140
ttatgtaaaa tttgataaga tgttttacac aactttaata cattgacaag gtcttgtgga     1200
gaaaacagtt ccagatggta aatatacaca agggatttag tcaaacaatt ttttggcaag     1260
aatattatga attttgtaat cggttggcag ccaatgaaat acaaagatga gtctagttaa     1320
taatctacaa ttattggtta aagaagtata ttagtgctaa tttccctccg tttgtcctag     1380
cttttctctt ctgtcaaccc cacacgcctt tggcacaagg tacccactgg gaggatgttg     1440
agtaagatgg aaaactactg atgacccttg cagagacaga gtattaggac atgtttgaac     1500
aggggccggg cgatcagcag gtagctctag aggatccccg tctgtctgca catttcgtag     1560
agcgagtgtt ccgatactct aatctcccta ggcaaggttc atatttgtgt aggttactta     1620
ttctcctttt gttgactaag tcaataatca gaatcagcag gtttggagtc agcttggcag     1680
ggatcagcag cctgggttgg aaggaggggg tataaaagcc ccttcaccag gagaagccgt     1740
cacacagatc cacaagctcc tggctagaaa gaggtaaggg tttaagggat ggttggttgg     1800
tggggtatta atgtttaatt acctggagca cctgcctgaa atcactttt ttcaggttgg     1860 gctagcccac catgcagcgc gtgaacatga tcatggccga gagccccggc ctgatcacca     1920
tctgcctgct gggctacctg ctgagcgccg agtgcaccgt gttcctggac cacgagaacg     1980
ccaacaagat cctgaaccgc cccaagcgct acaacagcgg caagctggag gagttcgtgc     2040
agggcaacct ggagcgcgag tgcatggagg agaagtgcag cttcgaggag gcccgcgagg     2100
tgttcgagaa caccgagcgc accaccgagt ctggaagca gtacgtggac ggcgaccagt     2160
gcgagagcaa cccctgcctg aacggcggca gctgcaagga cgacatcaac agctacgagt     2220
gctggtgccc cttcggcttc gagggcaaga actgcgagct ggacgtgacc tgcaacatca     2280
agaacggccg ctgcgagcag ttctgcaaga cacagcgccga caacaaggtg gtgtgcagct     2340
gcaccgaggg ctaccgcctg gccgagaacc agaagagctg cgagcccgcc gtgcccttcc     2400
cctgcggccg cgtgagcgtg agccagacca gcaagctgac ccgcgccgag gccgtgttcc     2460
```

```
ccgacgtgga ctacgtgaac agcaccgagg ccgagaccat cctggacaac atcacccaga   2520
gcacccagag cttcaacgac ttcacccgcg tggtgggcgg cgaggacgcc aagcccggcc   2580
agttcccctg gcaggtggtg ctgaacggca aggtggacgc cttctgcggc ggcagcatcg   2640
tgaacgagaa gtggatcgtg accgccgccc actgcgtgga gaccggcgtg aagatcaccg   2700
tggtggccgg cgagcacaac atcgaggaga ccgagcacac cgagcagaag cgcaacgtga   2760
tccgcatcat ccccccaccac aactacaacg ccgccatcaa caagtacaac cacgacatcg   2820
ccctgctgga gctggacgag cccctggtgc tgaacagcta cgtgacccc atctgcatcg    2880 ccgacaagga gtacaccaac atcttcctga agttcggcag cggctacgtg agcggctggg   2940
gccgcgtgtt ccacaagggc cgcagcgccc tggtgctgca gtacctgcgc gtgcccctgg   3000
tggaccgcgc cacctgcctg ctgagcacca agttcaccat ctacaacaac atgttctgcg   3060
ccggcttcca cgagggcggc cgcgacagct gccagggcga cagcggcggc ccccacgtga   3120
ccgaggtgga gggcaccagc ttcctgaccg gcatcatcag ctggggcgag gagtgcgcca   3180
tgaagggcaa gtacggcatc tacaccaagg tgagccgcta cgtgaactgg atcaaggaga   3240
agaccaagct gacctaatga aagatggatt tccaaggtta attcattgga attgaaaatt   3300
aacagccccc cccccccccc ccctgcagat ctgagccgaa ttcctgcagc ccgggggatc   3360
agcctcgact gtgccttcta gttgccagcc atctgttgtt tgcccctccc ccgtgccttc   3420
cttgaccctg gaaggtgcca ctcccactgt cctttcctaa taaaatgagg aaattgcatc   3480
gcattgtctg agtaggtgtc attctattct gggggtggg gtgggcagg acagcaaggg     3540 ggaggattgg gaagacaata gcaggcatgc tggggatgcg gtgggctcta tggcttctga   3600
ggcggaaaga accagctggg gaccggtgga tctcgatagc aggcatgctg gggagagatc   3660
gatctgagga accccctagtg atggagttgg ccactccctc tctgcgcgct cgctcgctca   3720
ctgaggccgc ccgggcaaag cccggcgtc gggcgacctt tggtcgcccg gcctcagtga    3780
gcgagcgagc gcgcagagag ggagtggcca acccccccccc cccccccccc cggcgattct   3840
cttgtttgct ccagactctc aggcaatgac ctgatagcct ttgtagagac ctctcaaaaa   3900
tagctaccct ctccggcatg aatttatcag ctagaacggt tgaatatcat attgatggtg   3960
atttgactgt ctccggcctt tctcacccgt ttgaatcttt acctacacat tactcaggca   4020
ttgcatttaa aatatatgag ggttctaaaa attttttatcc ttgcgttgaa ataaaggctt   4080
ctcccgcaaa agtattacag ggtcataatg ttttttggtac aaccgattta gctttatgct   4140
ctgaggcttt attgcttaat tttgctaatt cttttgccttg cctgtatgat ttattggatg   4200
ttggaatcgc ctgatgcggt attttctcct tacgcatctg tgcggtattt cacaccgcat   4260
atggtgcact ctcagtacaa tctgctctga tgccgcatag ttatatggtg cactctcagt    4320
acaatctgct ctgatgccgc atagttaagc cagccccgac acccgccaac acagccagcc   4380
ccgacacccg ccaacacccg ctgacgcgcc ctgacgggct tgtctgctcc cggcatccgc   4440
ttacagacaa gctgtgaccg tctccgggag ctgcatgtgt cagaggtttt caccgtcatc   4500
accgaaacgc gcgagacgaa agggcctcgt gatacgccta ttttttatagg ttaatgtcat   4560 gataataatg gtttcttaga cgtcaggtgg cactttcggg gaaatgtgc gcggaacccc     4620 tatttgtttta ttttttctaaa tacattcaaa tatgtatccg ctcatgagac aataaccctg   4680
ataaatgctc aataatattg aaaaaggaag agtatgagta ttcaacattt ccgtgtcgcc   4740
cttattccct tttttgcggc attttgcctt cctgttttttg ctcacccaga aacgctggtg   4800
```

-continued

```
aaagtaaaag atgctgaaga tcagttgggt gcacgagtgg gttacatcga actggatctc    4860
aacagcggta agatccttga gagttttcgc cccgaagaac gttttccaat gatgagcact    4920
tttaaagttc tgctatgtgg cgcggtatta tcccgtattg acgccgggca agagcaactc    4980
ggtcgccgca tacactattc tcagaatgac ttggttgagt actcaccagt cacagaaaag    5040
catcttacgg atggcatgac agtaagagaa ttatgcagtg ctgccataac catgagtgat    5100
aacactgcgg ccaacttact tctgacaacg atcggaggac cgaaggagct aaccgctttt    5160
ttgcacaaca tgggggatca tgtaactcgc cttgatcgtt gggaaccgga gctgaatgaa    5220
gccataccaa acgacgagcg tgacaccacg atgcctgtag caatggcaac aacgttgcgc    5280
aaactattaa ctggcgaact acttactcta gcttcccggc aacaattaat agactggatg    5340
gaggcggata aagttgcagg accacttctg cgctcggccc ttccggctgg ctggtttatt    5400
gctgataaat ctggagccgg tgagcgtggg tctcgcggta tcattgcagc actggggcca    5460
gatggtaagc cctcccgtat cgtagttatc tacacgacgg ggagtcaggc aactatggat    5520
gaacgaaata gacagatcgc tgagataggt gcctcactga ttaagcattg gtaactgtca    5580
gaccaagttt actcatatat actttagatt gatttaaaac ttcatttttta atttaaaagg    5640 atctaggtga agatcctttt tgataatctc atgaccaaaa tcccttaacg tgagttttcg    5700
ttccactgag cgtcagaccc cgtagaaaag atcaaaggat cttcttgaga tccttttttt    5760
ctgcgcgtaa tctgctgctt gcaaacaaaa aaaccaccgc taccagcggt ggtttgtttg    5820
ccggatcaag agctaccaac tctttttccg aaggtaactg gcttcagcag agcgcagata    5880
ccaaatactg tccttctagt gtagccgtag ttaggccacc acttcaagaa ctctgtagca    5940
ccgcctacat acctcgctct gctaatcctg ttaccagtgg ctgctgccag tggcgataag    6000
tcgtgtctta ccgggttgga ctcaagacga tagttaccgg ataaggcgca gcggtcgggc    6060
tgaacggggg gttcgtgcac acagcccagc ttggagcgaa cgacctacac gaactgaga    6120 tacctacagc gtgagctatg agaaagcgcc acgcttcccg aagggagaaa ggcggacagg    6180
tatccggtaa gcggcagggt cggaacagga gagcgcacga gggagcttcc aggggggaaac    6240 gcctggtatc tttatagtcc tgtcgggttt cgccacctct gacttgagcg tcgatttttg    6300
tgatgctcgt caggggggcg gagcctatgg aaaaacgcca gcaacgcggc cttttttacgg    6360 ttcctggcct tttgctggcc ttttgctcac atgttctttc ctgcgttatc ccctgattct    6420
gtggataacc gtattaccgc ctttgagtga gctgataccg ctcgccgcag ccgaacgacc    6480
gagcgcagcg agtcagtgag cgaggaagcg gaagagcgcc caatacgcaa accgcctctc    6540
cccgcgcgtt ggccgattca ttaatg                                         6566
```

<210> SEQ ID NO 34
<211> LENGTH: 6577
<212> TYPE: DNA
<213> ORGANISM: Artificial Sequence
<220> FEATURE:
<223> OTHER INFORMATION: AAVsc-HS-CRE2-TTRenh-TTRm-MVM-hFIXcoPadua-
    bghpolyA

<400> SEQUENCE: 34

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
```

```
ttataaaaac acttctcagg attctggcgt accgttcctg tctaaaatcc cttttaatcgg      300 cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg tttttcgccc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt tacaatttaa atatttgctt      840
atacaatctt cctgtttttg gggctttttct gattatcaac cggggtacat atgattgaca      900
tgctagtttt acgattaccg ttcatcgccc tgcgcgctcg ctcgctcact gaggccgccc      960
gggcaaagcc cggcgtcgg gcgacctttg gtcgcccggc ctcagtgagc gagcgagcgc     1020
gcagagaggg agtggaattc acgcgtggat ctgaattctg tacaggcgtg gtacggccgc     1080
ggttttttct tttctaaatg atcagtacac ttattctttc taaagaaaat acttttctta     1140
actactctct attttttaaac ttctcccaca aagatgagaa aacatttaaa aatcattggg     1200
gctatttttc tgtttaccga gtaaagagaa tctctaaacc atatttataa ctcttactct     1260
aaatatttgc atttaccctc atgccagagc ccgttgatga ctgactaaac agagtttcaa     1320
agtttgaaga acaggaaatt tagaaatgac taacaattat gtaggtttat ttctctcagt     1380
atagaatgtt catatagaat taatgccaga ggttttcaga gaaaaatgcg gtacccactg     1440
ggaggatgtt gagtaagatg gaaaactact gatgacccctt gcagagacag agtattagga     1500
catgtttgaa caggggccgg gcgatcagca ggtagctcta gaggatcccc gtctgtctgc     1560
acatttcgta gagcgagtgt tccgatactc taatctccct aggcaaggtt catatttgtg     1620
taggttactt attctccttt tgttgactaa gtcaataatc agaatcagca ggtttggagt     1680
cagcttggca gggatcagca gcctgggttg gaaggagggg gtataaaagc cccttcacca     1740
ggagaagccg tcacacagat ccacaagctc ctggctagaa agaggtaagg gtttaaggga     1800
tggttggttg gtggggtatt aatgtttaat tacctggagc acctgcctga aatcacttttt     1860 tttcaggttg ggctagccca ccatgcagcg cgtgaacatg atcatggccg agagccccgg     1920
cctgatcacc atctgcctgc tgggctacct gctgagcgcc gagtgcaccg tgttcctgga     1980
ccacgagaac gccaacaaga tcctgaaccg ccccaagcgc tacaacagcg gcaagctgga     2040
ggagttcgtg cagggcaacc tggagcgcga gtgcatggag gagaagtgca gcttcgagga     2100
ggcccgcgag gtgttcgaga acaccgagcg caccaccgag ttctggaagc agtacgtgga     2160
cggcgaccag tgcgagagca accccctgcct gaacggcggc agctgcaagg acgacatcaa     2220
cagctacgag tgctggtgcc ccttcggctt cgagggcaag aactgcgagc tggacgtgac     2280
ctgcaacatc aagaacggcc gctgcgagca gttctgcaag aacagcgccg acaacaaggt     2340
ggtgtgcagc tgcaccgagg ctaccgcct ggccgagaac cagaagagct gcgagcccgc     2400
cgtgcccttc ccctgcggcc gcgtgagcgt gagccagacc agcaagctga cccgcgccga     2460
ggccgtgttc cccgacgtgg actacgtgaa cagcaccgag gccgagacca tcctggacaa     2520
catcacccag agcacccaga gcttcaacga cttcacccgc gtggtgggcg gcgaggacgc     2580
caagcccggc cagttcccct ggcaggtggt gctgaacggc aaggtggacg ccttctgcgg     2640
```

-continued

```
cggcagcatc gtgaacgaga agtggatcgt gaccgccgcc cactgcgtgg agaccggcgt    2700
gaagatcacc gtggtggccg gcgagcacaa catcgaggag accgagcaca ccgagcagaa    2760
gcgcaacgtg atccgcatca tcccccacca caactacaac gccgccatca acaagtacaa    2820
ccacgacatc gccctgctgg agctggacga gccctggtg ctgaacagct acgtgacccc     2880
catctgcatc gccgacaagg agtacaccaa catcttcctg aagttcggca gcggctacgt    2940
gagcggctgg ggccgcgtgt ccacaaggg ccgcagcgcc ctggtgctgc agtacctgcg     3000
cgtgcccctg gtggaccgcg ccacctgcct gctgagcacc aagttcacca tctacaacaa    3060
catgttctgc gccggcttcc acgagggcgg ccgcgacagc tgccagggcg acagcggcgg    3120
cccccacgtg accgaggtgg agggcaccag cttcctgacc ggcatcatca gctggggcga    3180
ggagtgcgcc atgaagggca agtacggcat ctacaccaag gtgagccgct acgtgaactg    3240
gatcaaggag aagaccaagc tgacctaatg aaagatggat ttccaaggtt aattcattgg    3300
aattgaaaat taacagcccc cccccccccc cccctgcaga tctgagccga attcctgcag    3360
cccgggggat cagcctcgac tgtgccttct agttgccagc catctgttgt ttgcccctcc    3420
cccgtgcctt ccttgaccct ggaaggtgcc actcccactg tcctttccta ataaaatgag    3480
gaaattgcat cgcattgtct gagtaggtgt cattctattc tggggggtgg ggtggggcag    3540
gacagcaagg gggaggattg ggaagacaat agcaggcatg ctggggatgc ggtgggctct    3600
atggcttctg aggcggaaag aaccagctgg ggaccggtgg atctcgatag caggcatgct    3660
ggggagagat cgatctgagg aacccctagt gatggagttg gccactccct ctctgcgcgc    3720
tcgctcgctc actgaggccg cccgggcaaa gcccgggcgt cgggcgacct ttggtcgccc     3780
ggcctcagtg agcgagcgag cgcgcagaga gggagtggcc aacccccccc ccccccccc     3840 ccggcgattc tcttgtttgc tccagactct caggcaatga cctgatagcc tttgtagaga    3900
cctctcaaaa atagctaccc tctccggcat gaatttatca gctagaacgg ttgaatatca    3960
tattgatggt gatttgactg tctccggcct ttctcacccg tttgaatctt tacctacaca    4020
ttactcaggc attgcattta aaatatatga gggttctaaa aatttttatc cttgcgttga    4080
aataaaggct tctcccgcaa aagtattaca gggtcataat gtttttggta caaccgattt    4140
agctttatgc tctgaggctt tattgcttaa ttttgctaat tctttgcctt gcctgtatga    4200
tttattggat gttggaatcg cctgatgcgg tattttctcc ttacgcatct gtgcggtatt    4260
tcacaccgca tatggtgcac tctcagtaca atctgctctg atgccgcata gttatatggt    4320
gcactctcag tacaatctgc tctgatgccg catagttaag ccagccccga cacccgccaa    4380
cacagccagc cccgacaccc gccaacaccc gctgacgcgc cctgacgggc ttgtctgctc    4440
ccggcatccg cttacagaca agctgtgacc gtctccggga gctgcatgtg tcagaggttt    4500
tcaccgtcat caccgaaacg cgcgagacga aagggcctcg tgatacgcct attttttatag   4560 gttaatgtca tgataataat ggtttcttag acgtcaggtg gcacttttcg gggaaatgtg    4620
cgcggaaccc ctatttgttt attttttctaa atacattcaa atatgtatcc gctcatgaga   4680
caataaccct gataaatgct caataatatt gaaaaaggaa gagtatgagt attcaacatt    4740
tccgtgtcgc ccttattccc ttttttgcgg cattttgcct tcctgttttt gctcacccag    4800
aaacgctggt gaaagtaaaa gatgctgaag atcagttggg tgcacgagtg ggttacatcg    4860
aactggatct caacagcggt aagatccttg agagttttcg ccccgaagaa cgttttccaa    4920
tgatgagcac ttttaaagtt ctgctatgtg gcgcggtatt atcccgtatt gacgccgggc    4980
```

-continued

```
aagagcaact cggtcgccgc atacactatt ctcagaatga cttggttgag tactcaccag    5040
tcacagaaaa gcatcttacg gatggcatga cagtaagaga attatgcagt gctgccataa    5100
ccatgagtga taacactgcg gccaacttac ttctgacaac gatcggagga ccgaaggagc    5160
taaccgcttt tttgcacaac atgggggatc atgtaactcg ccttgatcgt tgggaaccgg    5220
agctgaatga agccatacca aacgacgagc gtgacaccac gatgcctgta gcaatggcaa    5280
caacgttgcg caaactatta actggcgaac tacttactct agcttcccgg caacaattaa    5340
tagactggat ggaggcggat aaagttgcag gaccacttct gcgctcggcc cttccggctg    5400
gctggtttat tgctgataaa tctggagccg gtgagcgtgg gtctcgcggt atcattgcag    5460
cactggggcc agatggtaag ccctcccgta tcgtagttat ctacacgacg gggagtcagg    5520
caactatgga tgaacgaaat agacagatcg ctgagatagg tgcctcactg attaagcatt    5580
ggtaactgtc agaccaagtt tactcatata cactttagat tgatttaaaa cttcattttt    5640
aatttaaaag gatctaggtg aagatccttt ttgataatct catgaccaaa atcccttaac    5700
gtgagttttc gttccactga gcgtcagacc ccgtagaaaa gatcaaagga tcttcttgag    5760
atcctttttt tctgcgcgta atctgctgct tgcaaacaaa aaaaccaccg ctaccagcgg    5820
tggtttgttt gccggatcaa gagctaccaa ctctttttcc gaaggtaact ggcttcagca    5880
gagcgcagat accaaatact gtccttctag tgtagccgta gttaggccac cacttcaaga    5940
actctgtagc accgcctaca tacctcgctc tgctaatcct gttaccagtg ctgctgcca    6000 gtggcgataa gtcgtgtctt accgggttgg actcaagacg atagttaccg gataaggcgc    6060
agcggtcggg ctgaacgggg ggttcgtgca cacagcccag cttggagcga acgacctaca    6120
ccgaactgag atacctacag cgtgagctat gagaaagcgc cacgcttccc gaagggagaa    6180
aggcggacag gtatccggta agcggcaggg tcggaacagg agagcgcacg agggagcttc    6240 caggggg aaa cgcctggtat ctttatagtc ctgtcgggtt tcgccacctc tgacttgagc    6300 gtcgatttt t gtgatgctcg tcaggggggc ggagcctatg gaaaaacgcc agcaacgcgg    6360
cctttttacg gttcctggcc ttttgctggc cttttgctca catgttcttt cctgcgttat    6420
cccctgattc tgtggataac cgtattaccg cctttgagtg agctgatacc gctcgccgca    6480
gccgaacgac cgagcgcagc gagtcagtga gcgaggaagc ggaagagcgc ccaatacgca    6540
aaccgcctct ccccgcgcgt tggccgattc attaatg                            6577
```

<210> SEQ ID NO 35
<211> LENGTH: 6616
<212> TYPE: DNA
<213> ORGANISM: Artificial Sequence
<220> FEATURE:
<223> OTHER INFORMATION: AAVsc-HS-CRE3-TTRenh-TTRm-MVM-hFIXcoPadua-
      bghpolyA

<400> SEQUENCE: 35

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
```

-continued

```
gcagcgtgac cgctacactt gccagcgccc tagcgcccgc tcctttcgct ttcttccctt    480
cctttctcgc cacgttcgcc ggctttcccc gtcaagctct aaatcggggg ctcccttttag   540 ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt tacaatttaa atatttgctt    840
atacaatctt cctgtttttg gggctttttct gattatcaac cggggtacat atgattgaca   900
tgctagtttt acgattaccg ttcatcgccc tgcgcgctcg ctcgctcact gaggccgccc    960
gggcaaagcc cggcgtcgg gcgaccttg gtcgcccggc ctcagtgagc gagcgagcgc     1020
gcagagaggg agtggaattc acgcgtggat ctgaattctg tacaggcgtg gtacggccgc    1080
gggggacact gaagccaaat gggcttcagc tcctccccag ggatctccct acctgctgcc    1140
cattccaacc tggctctctc cctctccaca actgaagccc aggcctcttt ggatgctgct    1200
cacacatctt gcctccttat cttacctagc cagcgtctct gtccttggtg tctgtgcctg    1260
ccctggctgg agaggaaggg gctatatacc tgtctgttta cccacccccct gtcaggtgac   1320 agggactatg gatgggccca gtggggcagg gattatgtga ggataaacaa gttggagaaa    1380
tgggggagga gaggacaagc acatggaaga ctcatggtga tggggtgaga ggcagggggt    1440
acagctctta gtggaggcta aggggggtagg tacccactgg gaggatgttg agtaagatgg    1500
aaaactactg atgaccttg cagagacaga gtattaggac atgtttgaac aggggccggg    1560
cgatcagcag gtagctctag aggatccccg tctgtctgca catttcgtag agcgagtgtt    1620
ccgatactct aatctcccta ggcaaggttc atatttgtgt aggttactta ttctcctttt    1680
gttgactaag tcaataatca gaatcagcag gtttggagtc agcttggcag ggatcagcag    1740
cctgggttgg aaggaggggg tataaaagcc ccttcaccag gagaagccgt cacacagatc    1800
cacaagctcc tggctagaaa gaggtaaggg tttaagggat ggttggttgg tggggtatta    1860
atgtttaatt acctggagca cctgcctgaa atcactttt ttcaggttgg gctagcccac      1920
catgcagcgc gtgaacatga tcatggccga gagccccggc ctgatcacca tctgcctgct    1980
gggctacctg ctgagcgccg agtgcaccgt gttcctggac cacgagaacg ccaacaagat    2040
cctgaaccgc cccaagcgct acaacagcgg caagctggag gagttcgtgc agggcaacct    2100
ggagcgcgag tgcatggagg agaagtgcag cttcgaggag gcccgcgagg tgttcgagaa    2160
caccgagcgc accaccgagt tctggaagca gtacgtggac ggcgaccagt gcgagagcaa    2220 ccccctgcctg aacggcggca gctgcaagga cgacatcaac agctacgagt gctggtgccc    2280
cttcggcttc gagggcaaga actgcgagct ggacgtgacc tgcaacatca gaacggccg    2340 ctgcgagcag ttctgcaaga acagcgccga caacaaggtg gtgtgcagct gcaccgaggg    2400
ctaccgcctg gccgagaacc agaagagctg cgagcccgcc gtgcccttcc cctgcggccg    2460
cgtgagcgtg agccagacca gcaagctgac ccgcgccgag gccgtgttcc cgacgtgga    2520 ctacgtgaac agcaccgagg ccgagaccat cctggacaac atcacccaga gcacccagag    2580
cttcaacgac ttcacccgcg tggtgggcgg cgaggacgcc aagccggcc agttcccctg    2640 gcaggtggtg ctgaacggca aggtggacgc cttctgcggc ggcagcatcg tgaacgagaa    2700
gtggatcgtg accgccgccc actgcgtgga gaccggcgtg aagatcaccg tggtggccgg    2760
cgagcacaac atcgaggaga ccgagcacac cgagcagaag cgcaacgtga tccgcatcat    2820
```

```
cccccaccac aactacaacg ccgccatcaa caagtacaac cacgacatcg ccctgctgga    2880
gctggacgag cccctggtgc tgaacagcta cgtgacccccc atctgcatcg ccgacaagga    2940
gtacaccaac atcttcctga agttcggcag cggctacgtg agcggctggg gccgcgtgtt    3000
ccacaagggc cgcagcgccc tggtgctgca gtacctgcgc gtgcccctgg tggaccgcgc    3060
cacctgcctg ctgagcacca agttcaccat ctacaacaac atgttctgcg ccggcttcca    3120
cgagggcggc cgcgacagct gccagggcga cagcggcggc ccccacgtga ccgaggtgga    3180
gggcaccagc ttcctgaccg gcatcatcag ctggggcgag gagtgcgcca tgaagggcaa    3240
gtacggcatc tacaccaagg tgagccgcta cgtgaactgg atcaaggaga agaccaagct    3300
gacctaatga aagatggatt tccaaggtta attcattgga attgaaaatt aacagccccc    3360
cccccccccc ccctgcagat ctgagccgaa ttcctgcagc ccgggggatc agcctcgact    3420
gtgccttcta gttgccagcc atctgttgtt tgcccctccc ccgtgccttc cttgaccctg    3480
gaaggtgcca ctcccactgt cctttcctaa taaaatgagg aaattgcatc gcattgtctg    3540
agtaggtgtc attctattct ggggggtggg gtggggcagg acagcaaggg ggaggattgg    3600
gaagacaata gcaggcatgc tggggatgcg gtgggctcta tggcttctga ggcggaaaga    3660
accagctggg gaccggtgga tctcgatagc aggcatgctg gggagagatc gatctgagga    3720
acccctagtg atggagttgg ccactccctc tctgcgcgct cgctcgctca ctgaggccgc    3780
ccgggcaaag cccgggcgtc gggcgacctt tggtcgcccg gcctcagtga gcgagcgagc    3840
gcgcagagag ggagtggcca acccccccccc ccccccccccc cggcgattct cttgtttgct    3900
ccagactctc aggcaatgac ctgatagcct ttgtagagac ctctcaaaaa tagctaccct    3960
ctccggcatg aatttatcag ctagaacggt tgaatatcat attgatggtg atttgactgt    4020
ctccggcctt tctcacccgt ttgaatcttt acctacacat tactcaggca ttgcatttaa    4080
aatatatgag ggttctaaaa atttttatcc ttgcgttgaa ataaaggctt ctcccgcaaa    4140
agtattacag ggtcataatg tttttggtac aaccgattta gctttatgct ctgaggcttt    4200
attgcttaat tttgctaatt ctttgccttg cctgtatgat ttattggatg ttggaatcgc    4260
ctgatgcggt attttctcct tacgcatctg tgcggtattt cacaccgcat atggtgcact    4320
ctcagtacaa tctgctctga tgccgcatag ttatatggtg cactctcagt acaatctgct    4380
ctgatgccgc atagttaagc cagccccgac acccgccaac acagccagcc ccgacacccg    4440
ccaacacccg ctgacgcgcc ctgacgggct tgtctgctcc cggcatccgc ttacagacaa    4500
gctgtgaccg tctccgggag ctgcatgtgt cagaggtttt caccgtcatc accgaaacgc    4560
gcgagacgaa agggcctcgt gatacgccta tttttatagg ttaatgtcat gataataatg    4620
gtttcttaga cgtcaggtgg cacttttcgg ggaaatgtgc gcggaacccc tatttgttta    4680
tttttctaaa tacattcaaa tatgtatccg ctcatgagac aataaccctg ataaatgctc    4740
aataatattg aaaaggaag agtatgagta ttcaacattt ccgtgtcgcc cttattccct    4800
tttttgcggc attttgcctt cctgtttttg ctcacccaga aacgctggtg aaagtaaaag    4860
atgctgaaga tcagttgggt gcacgagtgg gttacatcga actggatctc aacagcggta    4920
agatccttga gagtttttcgc cccgaagaac gttttccaat gatgagcact tttaaagttc    4980
tgctatgtgg cgcggtatta tcccgtattg acgccgggca agagcaactc ggtcgccgca    5040
tacactattc tcagaatgac ttggttgagt actcaccagt cacagaaaag catcttacgg    5100
atggcatgac agtaagagaa ttatgcagtg ctgccataac catgagtgat aacactgcgg    5160
```

-continued

```
ccaacttact tctgacaacg atcggaggac cgaaggagct aaccgctttt ttgcacaaca    5220
tgggggatca tgtaactcgc cttgatcgtt gggaaccgga gctgaatgaa gccataccaa    5280
acgacgagcg tgacaccacg atgcctgtag caatggcaac aacgttgcgc aaactattaa    5340
ctggcgaact acttactcta gcttcccggc aacaattaat agactggatg gaggcggata    5400
aagttgcagg accacttctg cgctcggccc ttccggctgg ctggtttatt gctgataaat    5460
ctggagccgg tgagcgtggg tctcgcggta tcattgcagc actggggcca gatggtaagc    5520
cctcccgtat cgtagttatc tacacgacgg ggagtcaggc aactatggat gaacgaaata    5580
gacagatcgc tgagataggt gcctcactga ttaagcattg gtaactgtca gaccaagttt    5640
actcatatat actttagatt gatttaaaac ttcattttta atttaaaagg atctaggtga    5700
agatcctttt tgataatctc atgaccaaaa tcccttaacg tgagttttcg ttccactgag    5760
cgtcagaccc cgtagaaaag atcaaaggat cttcttgaga tccttttttt ctgcgcgtaa    5820
tctgctgctt gcaaacaaaa aaaccaccgc taccagcggt ggtttgtttg ccggatcaag    5880
agctaccaac tctttttccg aaggtaactg gcttcagcag agcgcagata ccaaatactg    5940
tccttctagt gtagccgtag ttaggccacc acttcaagaa ctctgtagca ccgcctacat    6000
acctcgctct gctaatcctg ttaccagtgg ctgctgccag tggcgataag tcgtgtctta    6060
ccgggttgga ctcaagacga tagttaccgg ataaggcgca gcggtcgggc tgaacggggg    6120
gttcgtgcac acagcccagc ttggagcgaa cgacctacac cgaactgaga tacctacagc    6180
gtgagctatg agaaagcgcc acgcttcccg aagggagaaa ggcggacagg tatccggtaa    6240
gcggcagggt cggaacagga gagcgcacga gggagcttcc aggggaaac gcctggtatc     6300 tttatagtcc tgtcgggttt cgccacctct gacttgagcg tcgatttttg tgatgctcgt    6360
caggggggcg gagcctatgg aaaaacgcca gcaacgcggc ctttttacgg ttcctggcct    6420
tttgctggcc ttttgctcac atgttctttc ctgcgttatc ccctgattct gtggataacc    6480
gtattaccgc ctttgagtga gctgataccg ctcgccgcag ccgaacgacc gagcgcagcg    6540
agtcagtgag cgaggaagcg gaagagcgcc caatacgcaa accgcctctc cccgcgcgtt    6600
ggccgattca ttaatg                                                   6616
```

```
<210> SEQ ID NO 36
<211> LENGTH: 6656
<212> TYPE: DNA
<213> ORGANISM: Artificial Sequence
<220> FEATURE:
<223> OTHER INFORMATION: AAVsc-HS-CRE4-TTRenh-TTRm-MVM-hFIXcoPadua-
      bghpolyA

<400> SEQUENCE: 36
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt gcgtgatgg acagactctt ttactcggtg gcctcactga      240
ttataaaaac acttctcagg attctggcgt accgttcctg tctaaatcc ctttaatcgg       300 cctcctgttt agctcccgct ctgattctaa cgaggaaagc acgttatacg tgctcgtcaa     360
agcaaccata gtacgcgccc tgtagcggcg cattaagcgc ggcgggtgtg tggttacgc      420 gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
```

-continued

```
ggttccgatt tagtgcttta cggcacctcg accccaaaaa acttgattag ggtgatggtt     600
cacgtagtgg gccatcgccc tgatagacgg tttttcgccc tttgacgttg gagtccacgt     660
tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt tacaatttaa atatttgctt     840
atacaatctt cctgtttttg gggctttttct gattatcaac cggggtacat atgattgaca     900
tgctagtttt acgattaccg ttcatcgccc tgcgcgctcg ctcgctcact gaggccgccc     960
gggcaaagcc cgggcgtcgg gcgacctttg gtcgcccggc ctcagtgagc gagcgagcgc     1020
gcagagaggg agtggaattc acgcgtggat ctgaattctg tacaggcgtg gtacggccgc     1080
gggagttaat gtgtaatgag acggggagaa aacaggagag cccagaatga cctggatgct     1140
gatcactgaa cataccctac ccccagtaaa acaaattcag aaaacagctt ccgcccgtcc     1200
cctcccaatg gagggctctg gcaggaaaag aggtgaataa gaggcttcta ccagggtaaa     1260
ggttgaaggc acctggtcat ttgatcacct tatcagttct aggcagtgat tagccaatat     1320
tgagtcagca ggggcaatag ccctggccct tgtctcactc ctgttggggg tgggggaggg     1380
ggagaggtac attcccaggt tcaaagcatt tgggtgaaat cagttaaata gatatcagaa     1440
gcttttgtat ctttcaccct tttgcccccc aagcatactc gctgagtatg tggaacattc     1500
ctgagggtgg tacccactgg gaggatgttg agtaagatgg aaaactactg atgacccttg     1560
cagagacaga gtattaggac atgtttgaac aggggccggg cgatcagcag gtagctctag     1620
aggatccccg tctgtctgca catttcgtag agcgagtgtt ccgatactct aatctcccta     1680
ggcaaggttc atatttgtgt aggttactta ttctcctttt gttgactaag tcaataatca     1740
gaatcagcag gtttggagtc agcttggcag ggatcagcag cctgggttgg aaggaggggg     1800
tataaaagcc ccttcaccag gagaagccgt cacacagatc cacaagctcc tggctagaaa     1860
gaggtaaggg tttaagggat ggttggttgg tggggtatta atgtttaatt acctggagca     1920
cctgcctgaa atcactttt ttcaggttgg gctagcccac catgcagcgc gtgaacatga     1980
tcatggccga gagcccggc ctgatcacca tctgcctgct gggctacctg ctgagcgccg     2040
agtgcaccgt gttcctggac cacgagaacg ccaacaagat cctgaaccgc cccaagcgct     2100
acaacagcgg caagctggag gagttcgtgc agggcaacct ggagcgcgag tgcatggagg     2160
agaagtgcag cttcgaggag gcccgcgagg tgttcgagaa caccgagcgc accaccgagt     2220
tctggaagca gtacgtggac ggcgaccagt gcgagagcaa cccctgcctg aacggcggca     2280
gctgcaagga cgacatcaac agctacgagt gctggtgccc cttcggcttc gagggcaaga     2340
actgcgagct ggacgtgacc tgcaacatca gaacggccg ctgcgagcag ttctgcaaga     2400
acagcgccga caacaaggtg gtgtgcagct gcaccgaggg ctaccgcctg gccgagaacc     2460
agaagagctg cgagcccgcc gtgccttcc cctgcggccg cgtgagcgtg agccagacca     2520
gcaagctgac ccgcgccgag gccgtgttcc cgacgtgga ctacgtgaac agcaccgagg     2580
ccgagaccat cctggacaac atcacccaga gcacccagag cttcaacgac ttcacccgcg     2640
tggtgggcgg cgaggacgcc aagcccggcc agttcccctg gcaggtggtg ctgaacggca     2700
aggtggacgc cttctgcggc ggcagcatcg tgaacgagaa gtggatcgtg accgccgccc     2760
actgcgtgga gaccggcgtg aagatcaccg tggtggccgg cgagcacaac atcgaggaga     2820
ccgagcacac cgagcagaag cgcaacgtga tccgcatcat cccccaccac aactacaacg     2880
ccgccatcaa caagtacaac cacgacatcg ccctgctgga gctggacgag ccctggtgc     2940
```

```
tgaacagcta cgtgaccccc atctgcatcg ccgacaagga gtacaccaac atcttcctga    3000
agttcggcag cggctacgtg agcggctggg gccgcgtgtt ccacaagggc cgcagcgccc    3060
tggtgctgca gtacctgcgc gtgcccctgg tggaccgcgc cacctgcctg ctgagcacca    3120
agttcaccat ctacaacaac atgttctgcg ccggcttcca cgagggcggc cgcgacagct    3180
gccagggcga cagcggcggc ccccacgtga ccgaggtgga gggcaccagc ttcctgaccg    3240
gcatcatcag ctggggcgag gagtgcgcca tgaagggcaa gtacggcatc tacaccaagg    3300
tgagccgcta cgtgaactgg atcaaggaga agaccaagct gacctaatga aagatggatt    3360
tccaaggtta attcattgga attgaaaatt aacagccccc cccccccccc ccctgcagat    3420
ctgagccgaa ttcctgcagc ccggggggatc agcctcgact gtgccttcta gttgccagcc    3480
atctgttgtt tgcccctccc ccgtgccttc cttgaccctg gaaggtgcca ctcccactgt    3540
cctttcctaa taaaatgagg aaattgcatc gcattgtctg agtaggtgtc attctattct    3600
gggggtgggg gtggggcagg acagcaaggg ggaggattgg gaagacaata gcaggcatgc    3660
tggggatgcg gtgggctcta tggcttctga ggcggaaaga accagctggg gaccggtgga    3720
tctcgatagc aggcatgctg gggagagatc gatctgagga acccctagtg atggagttgg    3780
ccactccctc tctgcgcgct cgctcgctca ctgaggccgc ccgggcaaag cccgggcgtc    3840
gggcgacctt tggtcgcccg gcctcagtga gcgagcgagc gcgcagagag ggagtggcca    3900
accccccccc ccccccccc cggcgattct cttgtttgct ccagactctc aggcaatgac    3960
ctgatagcct ttgtagagac ctctcaaaaa tagctaccct ctccggcatg aatttatcag    4020
ctagaacggt tgaatatcat attgatggtg atttgactgt ctccggcctt tctcacccgt    4080
ttgaatcttt acctacacat tactcaggca ttgcatttaa aatatatgag ggttctaaaa    4140
atttttatcc ttgcgttgaa ataaaggctt ctcccgcaaa agtattacag ggtcataatg    4200
tttttggtac aaccgattta gctttatgct ctgaggcttt attgcttaat tttgctaatt    4260
ctttgccttg cctgtatgat ttattggatg ttggaatcgc ctgatgcggt attttctcct    4320
tacgcatctg tgcggtattt cacaccgcat atggtgcact ctcagtacaa tctgctctga    4380
tgccgcatag ttatatggtg cactctcagt acaatctgct ctgatgccgc atagttaagc    4440
cagccccgac acccgccaac acagccagcc ccgacacccg ccaacacccg ctgacgcgcc    4500
ctgacgggct tgtctgctcc cggcatccgc ttacagacaa gctgtgaccg tctccgggag    4560
ctgcatgtgt cagaggtttt caccgtcatc accgaaacgc gcgagacgaa agggcctcgt    4620
gatacgccta ttttttatagg ttaatgtcat gataataatg gtttcttaga cgtcaggtgg    4680
cacttttcgg ggaaatgtgc gcggaacccc tatttgttta ttttttctaaa tacattcaaa    4740 tatgtatccg ctcatgagac aataaccctg ataaatgctc aataatattg aaaaaggaag    4800
agtatgagta ttcaacattt ccgtgtcgcc cttattccct ttttttgcggc attttgcctt    4860 cctgtttttg ctcacccaga aacgctggtg aaagtaaaag atgctgaaga tcagttgggt    4920
gcacgagtgg gttacatcga actggatctc aacagcggta agatccttga gagttttcgc    4980
cccgaagaac gttttccaat gatgagcact tttaaagttc tgctatgtgg cgcggtatta    5040
tcccgtattg acgccgggca agagcaactc ggtcgccgca tacactattc tcagaatgac    5100
ttggttgagt actcaccagt cacagaaaag catcttacgg atggcatgac agtaagagaa    5160
ttatgcagtg ctgccataac catgagtgat aacactgcgg ccaacttact ctgacaacg    5220 atcggaggac cgaaggagct aaccgctttt ttgcacaaca tgggggatca tgtaactcgc    5280
```

-continued

```
cttgatcgtt gggaaccgga gctgaatgaa gccataccaa acgacgagcg tgacaccacg    5340
atgcctgtag caatggcaac aacgttgcgc aaactattaa ctggcgaact acttactcta    5400
gcttcccggc aacaattaat agactggatg gaggcggata aagttgcagg accacttctg    5460
cgctcggccc ttccggctgg ctggtttatt gctgataaat ctggagccgg tgagcgtggg    5520
tctcgcggta tcattgcagc actggggcca gatggtaagc cctcccgtat cgtagttatc    5580
tacacgacgg ggagtcaggc aactatggat gaacgaaata gacagatcgc tgagataggt    5640
gcctcactga ttaagcattg gtaactgtca gaccaagttt actcatatat actttagatt    5700
gatttaaaac ttcattttta atttaaaagg atctaggtga agatcctttt tgataatctc    5760
atgaccaaaa tcccttaacg tgagttttcg ttccactgag cgtcagaccc cgtagaaaag    5820
atcaaaggat cttcttgaga tccttttttt ctgcgcgtaa tctgctgctt gcaaacaaaa    5880
aaaccaccgc taccagcggt ggtttgtttg ccggatcaag agctaccaac tcttttttccg    5940 aaggtaactg gcttcagcag agcgcagata ccaaatactg tccttctagt gtagccgtag    6000
ttaggccacc acttcaagaa ctctgtagca ccgcctacat acctcgctct gctaatcctg    6060
ttaccagtgg ctgctgccag tggcgataag tcgtgtctta ccgggttgga ctcaagacga    6120
tagttaccgg ataaggcgca gcggtcgggc tgaacggggg gttcgtgcac acagcccagc    6180
ttggagcgaa cgacctacac cgaactgaga tacctacagc gtgagctatg agaaagcgcc    6240
acgcttcccg aagggagaaa ggcggacagg tatccggtaa gcggcagggt cggaacagga    6300
gagcgcacga gggagcttcc aggggggaaac gcctggtatc tttatagtcc tgtcgggttt    6360
cgccacctct gacttgagcg tcgatttttg tgatgctcgt caggggggcg gagcctatgg    6420
aaaaacgcca gcaacgcggc ctttttacgg ttcctggcct tttgctggcc ttttgctcac    6480
atgttctttc ctgcgttatc ccctgattct gtggataacc gtattaccgc ctttgagtga    6540
gctgataccg ctcgccgcag ccgaacgacc gagcgcagcg agtcagtgag cgaggaagcg    6600
gaagagcgcc caatacgcaa accgcctctc cccgcgcgtt ggccgattca ttaatg       6656
```

<210> SEQ ID NO 37
<211> LENGTH: 6490
<212> TYPE: DNA
<213> ORGANISM: Artificial Sequence
<220> FEATURE:
<223> OTHER INFORMATION: AAVsc-HS-CRE5-TTRenh-TTRm-MVM-hFIXcoPadua-
     bghpolyA

<400> SEQUENCE: 37

```
agctggcgta atagcgaaga ggcccgcacc gatcgccctt cccaacagtt gcgcagcctg       60
aatggcgaat ggcgattccg ttgcaatggc tggcggtaat attgttctgg atattaccag      120
caaggccgat agtttgagtt cttctactca ggcaagtgat gttattacta atcaaagaag      180
tattgcgaca acggttaatt tgcgtgatgg acagactctt ttactcggtg gcctcactga      240
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg tggttacgc       420 gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg tttttcgccc tttgacgttg gagtccacgt      660
```

-continued

```
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt tacaatttaa atatttgctt    840
atacaatctt cctgtttttg gggctttttct gattatcaac cggggtacat atgattgaca    900
tgctagtttt acgattaccg ttcatcgccc tgcgcgctcg ctcgctcact gaggccgccc    960
gggcaaagcc cggcgtcgg gcgacctttg gtcgcccggc ctcagtgagc gagcgagcgc    1020
gcagagaggg agtggaattc acgcgtggat ctgaattctg tacaggcgtg gtacggccgc    1080
ggtgttttgt tttggtgacc taactggtca aatgacctat taagaatatt tcatagaacg    1140
aatgttccga tgctctaatc tctctagaca aggttcatat ttgtatgggt tacttattct    1200
ctctttgttg actaagtcaa taatcagaat cagcaggttt gcagtcagat tggcagggat    1260
aagcagccta gctcaggaga agtgagtata aaagccccag gctgggagca gccatcacag    1320
aagtccactc attcttggca ggggtacccca ctgggaggat gttgagtaag atggaaaact    1380
actgatgacc cttgcagaga cagagtatta ggacatgttt gaacaggggc cgggcgatca    1440
gcaggtagct ctagaggatc cccgtctgtc tgcacatttc gtagagcgag tgttccgata    1500
ctctaatctc cctaggcaag gttcatattt gtgtaggtta cttattctcc ttttgttgac    1560
taagtcaata atcagaatca gcaggtttgg agtcagcttg gcaggatca gcagcctggg    1620 ttggaaggag ggggtataaa agccccttca ccaggagaag ccgtcacaca gatccacaag    1680
ctcctggcta gaaagaggta agggtttaag ggatggttgg ttggtggggt attaatgttt    1740
aattacctgg agcacctgcc tgaaatcact tttttttcagg ttgggctagc ccaccatgca    1800
gcgcgtgaac atgatcatgg ccgagagccc cggcctgatc accatctgcc tgctgggcta    1860
cctgctgagc gccgagtgca ccgtgttcct ggaccacgag aacgccaaca agatcctgaa    1920
ccgccccaag cgctacaaca gcggcaagct ggaggagttc gtgcagggca acctggagcg    1980
cgagtgcatg gaggagaagt gcagcttcga ggaggcccgc gaggtgttcg agaacaccga    2040
gcgcaccacc gagttctgga agcagtacgt ggacggcgac cagtgcgaga gcaacccctg    2100
cctgaacggc ggcagctgca aggacgacat caacagctac gagtgctggt gcccccttcgg    2160 cttcgagggc aagaactgcg agctggacgt gacctgcaac atcaagaacg gccgctgcga    2220
gcagttctgc aagaacagcg ccgacaacaa ggtggtgtgc agctgcaccg agggctaccg    2280
cctggccgag aaccagaaga gctgcgagcc cgccgtgccc ttcccctgcg gccgcgtgag    2340
cgtgagccag accagcaagc tgacccgcgc cgaggccgtg ttccccgacg tggactacgt    2400
gaacagcacc gaggccgaga ccatcctgga caacatcacc cagagcaccc agagcttcaa    2460
cgacttcacc cgcgtggtgg gcggcgagga cgccaagccc ggccagttcc cctggcaggt    2520
ggtgctgaac ggcaaggtgg acgccttctg cggcggcagc atcgtgaacg agaagtggat    2580
cgtgaccgcc gcccactgcg tggagaccgg cgtgaagatc accgtggtgg ccggcgagca    2640
caacatcgag gagaccgagc acaccgagca gaagcgcaac gtgatccgca tcatcccccca    2700 ccacaactac aacgccgcca tcaacaagta caaccacgac atcgccctgc tggagctgga    2760
cgagcccctg gtgctgaaca gctacgtgac ccccatctgc atcgccgaca aggagtacac    2820
caacatcttc ctgaagttcg gcagcggcta cgtgagcggc tggggccgcg tgttccacaa    2880
gggccgcagc gccctggtgc tgcagtacct gcgcgtgccc ctggtggacc gcgccacctg    2940
cctgctgagc accaagttca ccatctacaa caacatgttc tgcgccggct ccacgagggg    3000
cggccgcgac agctgccagg gcgacagcgg cggccccccac gtgaccgagg tggagggcac    3060
```

```
cagcttcctg accggcatca tcagctgggg cgaggagtgc gccatgaagg gcaagtacgg      3120
catctacacc aaggtgagcc gctacgtgaa ctggatcaag gagaagacca agctgaccta      3180
atgaaagatg gatttccaag gttaattcat tggaattgaa aattaacagc cccccccccc      3240 cccccctgc agatctgagc cgaattcctg cagcccgggg gatcagcctc gactgtgcct      3300
tctagttgcc agccatctgt tgtttgcccc tccccgtgc cttccttgac cctggaaggt      3360
gccactccca ctgtcctttc ctaataaaat gaggaaattg catcgcattg tctgagtagg      3420
tgtcattcta ttctgggggg tggggtgggg caggacagca aggggagga ttgggaagac      3480 aatagcaggc atgctgggga tgcggtgggc tctatggctt ctgaggcgga aagaaccagc      3540
tggggaccgg tggatctcga tagcaggcat gctggggaga gatcgatctg aggaacccct      3600
agtgatggag ttggccactc cctctctgcg cgctcgctcg ctcactgagg ccgcccgggc      3660
aaagcccggg cgtcgggcga cctttggtcg cccggcctca gtgagcgagc gagcgcgcag      3720
agagggagtg gccaaccccc cccccccccc ccccggcga ttctcttgtt tgctccagac      3780
tctcaggcaa tgacctgata gcctttgtag agacctctca aaaatagcta ccctctccgg      3840
catgaattta tcagctagaa cggttgaata tcatattgat ggtgatttga ctgtctccgg      3900
cctttctcac ccgtttgaat ctttacctac acattactca ggcattgcat ttaaaatata      3960
tgagggttct aaaaattttt atccttgcgt tgaaataaag gcttctcccg caaaagtatt      4020
acagggtcat aatgtttttg gtacaaccga tttagcttta tgctctgagg ctttattgct      4080
taattttgct aattctttgc cttgcctgta tgatttattg gatgttggaa tcgcctgatg      4140
cggtattttc tccttacgca tctgtgcggt atttcacacc gcatatggtg cactctcagt      4200
acaatctgct ctgatgccgc atagttatat ggtgcactct cagtacaatc tgctctgatg      4260
ccgcatagtt aagccagccc cgacacccgc caacacagcc agccccgaca cccgccaaca      4320
cccgctgacg cgccctgacg ggcttgtctg ctcccggcat ccgcttacag acaagctgtg      4380
accgtctccg ggagctgcat gtgtcagagg ttttcaccgt catcaccgaa acgcgcgaga      4440
cgaaagggcc tcgtgatacg cctattttta taggttaatg tcatgataat aatggtttct      4500
tagacgtcag gtggcacttt tcggggaaat gtgcgcggaa cccctatttg tttattttc      4560 taaatacatt caaatatgta tccgctcatg agacaataac cctgataaat gctcaataat      4620
attgaaaaag gaagagtatg agtattcaac atttccgtgt cgcccttatt ccctttttg      4680 cggcattttg ccttcctgtt tttgctcacc cagaaacgct ggtgaaagta aaagatgctg      4740
aagatcagtt gggtgcacga gtgggttaca tcgaactgga tctcaacagc ggtaagatcc      4800
ttgagagttt cgccccgaa gaacgttttc caatgatgag cacttttaaa gttctgctat      4860
gtggcgcggt attatcccgt attgacgccg ggcaagagca actcggtcgc cgcatacact      4920
attctcagaa tgacttggtt gagtactcac cagtcacaga aaagcatctt acggatggca      4980
tgacagtaag agaattatgc agtgctgcca taaccatgt tgataacact gcggccaact      5040
tacttctgac aacgatcgga ggaccgaagg agctaaccgc tttttttgcac aacatggggg      5100 atcatgtaac tcgccttgat cgttgggaac cggagctgaa tgaagccata ccaaacgacg      5160
agcgtgacac cacgatgcct gtagcaatgg caacaacgtt gcgcaaacta ttaactggcg      5220
aactacttac tctagcttcc cggcaacaat aatagactg gatggaggcg gataaagttg      5280
caggaccact tctcgctcg gcccttccgg ctggctggtt tattgctgat aaatctggag      5340
ccggtgagcg tgggtctcgc ggtatcattg cagcactggg gccagatggt aagccctccc      5400
```

```
gtatcgtagt tatctacacg acggggagtc aggcaactat ggatgaacga aatagacaga       5460
tcgctgagat aggtgcctca ctgattaagc attggtaact gtcagaccaa gtttactcat       5520
atatacttta gattgattta aaacttcatt tttaatttaa aaggatctag gtgaagatcc       5580
tttttgataa tctcatgacc aaaatcccTt aacgtgagtt ttcgttccac tgagcgtcag       5640
accccgtaga aaagatcaaa ggatcttctt gagatccttt ttttctgcgc gtaatctgct       5700
gcttgcaaac aaaaaaacca ccgctaccag cggtggtttg tttgccggat caagagctac       5760
caactctttt tccgaaggta actggcttca gcagagcgca gataccaaat actgtccttc       5820
tagtgtagcc gtagttaggc caccacttca agaactctgt agcaccgcct acatacctcg       5880
ctctgctaat cctgttacca gtggctgctg ccagtggcga taagtcgtgt cttaccgggt       5940
tggactcaag acgatagtta ccggataagg cgcagcggtc gggctgaacg gggggttcgt       6000
gcacacagcc cagcttggag cgaacgacct acaccgaact gagataccta cagcgtgagc       6060
tatgagaaag cgccacgctt cccgaaggga gaaaggcgga caggtatccg gtaagcggca       6120
gggtcggaac aggagagcgc acgagggagc ttccaggggg aaacgcctgg tatctttata       6180
gtcctgtcgg gtttcgccac ctctgacttg agcgtcgatt tttgtgatgc tcgtcagggg       6240
ggcggagcct atggaaaaac gccagcaacg cggccttttt acggttcctg gccttttgct       6300
ggcctTttgc tcacatgttc tttcctgcgt tatcccctga ttctgtggat aaccgtatta       6360
ccgcctttga gtgagctgat accgctcgcc gcagccgaac gaccgagcgc agcgagtcag       6420
tgagcgagga agcggaagag cgcccaatac gcaaaccgcc tctccccgcg cgttggccga       6480
ttcattaatg                                                             6490
```

<210> SEQ ID NO 38
<211> LENGTH: 6497
<212> TYPE: DNA
<213> ORGANISM: Artificial Sequence
<220> FEATURE:
<223> OTHER INFORMATION: AAVsc-HS-CRE6-TTRenh-TTRm-MVM-hFIXcoPadua-
      bghpolyA

<400> SEQUENCE: 38

```
agctggcgta atagcgaaga ggcccgcacc gatcgccctt cccaacagtt gcgcagcctg         60
aatggcgaat ggcgattccg ttgcaatggc tggcggtaat attgttctgg atattaccag        120
caaggccgat agtttgagtt cttctactca ggcaagtgat gttattacta atcaaagaag        180
tattgcgaca cggttaatt tgcgtgatgg acagactctt ttactcggtg gcctcactga        240
ttataaaaac acttctcagg attctggcgt accgttcctg tctaaaatcc ctttaatcgg        300
cctcctgttt agctcccgct ctgattctaa cgaggaaagc acgttatacg tgctcgtcaa        360
agcaaccata gtacgcgccc tgtagcggcg cattaagcgc ggcgggtgtg gtggttacgc        420
gcagcgtgac cgctacactt gccagcgccc tagcgcccgc tcctttcgct ttcttccctt        480
cctttctcgc cacgttcgcc ggctttcccc gtcaagctct aaatcggggg ctccctttag        540
ggttccgatt tagtgcttta cggcacctcg accccaaaaa acttgattag ggtgatggtt        600
cacgtagtgg gccatcgccc tgatagacgg tttttcgccc tttgacgttg gagtccacgt        660
tctttaatag tggactcttg ttccaaactg gaacaacact caaccctatc tcggtctatt        720
cttttgattt ataagggatt ttgccgattt cggcctattg gttaaaaaat gagctgattt        780
aacaaaaatt taacgcgaac tttaacaaaa tattaacgtt tacaatttaa atatttgctt        840
atacaatctt cctgttttg gggcttttct gattatcaac cggggtacat atgattgaca        900
```

```
tgctagtttt acgattaccg ttcatcgccc tgcgcgctcg ctcgctcact gaggccgccc      960
gggcaaagcc cgggcgtcgg gcgacctttg gtcgcccggc ctcagtgagc gagcgagcgc     1020
gcagagaggg agtggaattc acgcgtggat ctgaattctg tacaggcgtg gtacggccgc     1080 ggagggggc ccctgggct gacagggact ggaagctctg agctggccag agggatgttg      1140
caatcctgcc agggtcttgt ctatgctgtc cttttcacaa ccatcccct actgccaggc      1200 tgacacgtgg ttgcggggc acaaggccag ccaacctaga gtctgaggct aggcggagga      1260
caccctcccc accagctgcc agggtcactg gcggtcaaag gcagctggtg gggaaggcat     1320
tggactccag ccttgggga cggatgtagg gtacccactg ggaggatgtt gagtaagatg      1380
gaaaactact gatgaccctt gcagagacag agtattagga catgtttgaa caggggccgg     1440
gcgatcagca ggtagctcta gaggatcccc gtctgtctgc acatttcgta gagcgagtgt     1500
tccgatactc taatctccct aggcaaggtt catatttgtg taggttactt attctccttt     1560
tgttgactaa gtcaataatc agaatcagca ggtttggagt cagcttggca gggatcagca     1620
gcctgggttg gaaggagggg gtataaaagc cccttcacca ggagaagccg tcacacagat     1680
ccacaagctc ctggctagaa agaggtaagg gtttaaggga tggttggttg gtggggtatt     1740
aatgtttaat tacctggagc acctgcctga aatcactttt tttcaggttg ggctagccca     1800
ccatgcagcg cgtgaacatg atcatggccg agagccccgg cctgatcacc atctgcctgc     1860
tgggctacct gctgagcgcc gagtgcaccg tgttcctgga ccacgagaac gccaacaaga     1920
tcctgaaccg ccccaagcgc tacaacagcg gcaagctgga ggagttcgtg cagggcaacc     1980
tggagcgcga gtgcatggag gagaagtgca gcttcgagga ggcccgcgag gtgttcgaga     2040
acaccgagcg caccaccgag ttctggaagc agtacgtgga cggcgaccag tgcgagagca     2100 accccctgcct gaacgcggc agctgcaagg acgacatcaa cagctacgag tgctggtgcc     2160
ccttcggctt cgagggcaag aactgcgagc tggacgtgac ctgcaacatc aagaacggcc     2220
gctgcgagca gttctgcaag aacagcgccg acaacaaggt ggtgtgcagc tgcaccgagg     2280
gctaccgcct ggccgagaac cagaagagct gcgagcccgc cgtgcccttc ccctgcggcc     2340
gcgtgagcgt gagccagacc agcaagctga cccgcgccga ggccgtgttc cccgacgtgg     2400
actacgtgaa cagcaccgag gccgagacca tcctggacaa catcacccag agcacccaga     2460
gcttcaacga cttcacccgc gtggtgggcg gcgaggacgc caagcccggc cagttcccct     2520
ggcaggtggt gctgaacggc aaggtggacg ccttctgcgg cggcagcatc gtgaacgaga     2580
agtggatcgt gaccgccgcc cactgcgtgg agaccggcgt gaagatcacc gtggtggccg     2640
gcgagcacaa catcgaggag accgagcaca ccgagcagaa gcgcaacgtg atccgcatca     2700
tcccccacca caactacaac gccgccatca acaagtacaa ccacgacatc gccctgctgg     2760
agctggacga gcccctggtg ctgaacagct acgtgacccc catctgcatc gccgacaagg     2820
agtacaccaa catcttcctg aagttcggca gcggctacgt gagcggctgg ggccgcgtgt     2880
tccacaaggg ccgcagcgcc ctggtgctgc agtacctgcg cgtgcccctg gtggaccgcg     2940
ccacctgcct gctgagcacc aagttcacca tctacaacaa catgttctgc gccggcttcc     3000
acgagggcgg ccgcgacagc tgccagggcg acagcggcgg ccccacgtg accgaggtgg      3060 agggcaccag cttcctgacc ggcatcatca gctggggcga ggagtgcgcc atgaagggca     3120
agtacggcat ctacaccaag gtgagccgct acgtgaactg gatcaaggag aagaccaagc     3180
tgacctaatg aaagatggat ttccaaggtt aattcattgg aattgaaaat taacagcccc     3240 ccccccccc ccctgcaga tctgagccga attcctgcag cccggggat cagcctcgac        3300
```

-continued

```
tgtgccttct agttgccagc catctgttgt ttgcccctcc cccgtgcctt ccttgaccct     3360
ggaaggtgcc actcccactg tcctttccta ataaaatgag gaaattgcat cgcattgtct     3420
gagtaggtgt cattctattc tggggggtgg ggtggggcag gacagcaagg gggaggattg     3480
ggaagacaat agcaggcatg ctggggatgc ggtgggctct atggcttctg aggcggaaag     3540
aaccagctgg ggaccggtgg atctcgatag caggcatgct ggggagagat cgatctgagg     3600
aacccctagt gatggagttg gccactccct ctctgcgcgc tcgctcgctc actgaggccg     3660
cccgggcaaa gcccgggcgt cgggcgacct ttggtcgccc ggcctcagtg agcgagcgag     3720
cgcgcagaga gggagtggcc aacccccccc cccccccccc ccggcgattc tcttgtttgc     3780
tccagactct caggcaatga cctgatagcc tttgtagaga cctctcaaaa atagctaccc     3840
tctccggcat gaatttatca gctagaacgg ttgaatatca tattgatggt gatttgactg     3900
tctccggcct ttctcacccg tttgaatctt tacctacaca ttactcaggc attgcattta     3960
aaatatatga gggttctaaa aatttttatc cttgcgttga aataaaggct tctcccgcaa     4020
aagtattaca gggtcataat gtttttggta caaccgattt agctttatgc tctgaggctt     4080
tattgcttaa ttttgctaat tctttgcctt gcctgtatga tttattggat gttggaatcg     4140
cctgatgcgg tattttctcc ttacgcatct gtgcggtatt tcacaccgca tatggtgcac     4200
tctcagtaca atctgctctg atgccgcata gttatatggt gcactctcag tacaatctgc     4260
tctgatgccg catagttaag ccagccccga cacccgccaa cacagccagc cccgacaccc     4320
gccaacaccc gctgacgcgc cctgacgggc ttgtctgctc ccggcatccg cttacagaca     4380
agctgtgacc gtctccggga gctgcatgtg tcagaggttt tcaccgtcat caccgaaacg     4440
cgcgagacga aagggcctcg tgatacgcct attttttatag gttaatgtca tgataataat     4500
ggtttcttag acgtcaggtg gcacttttcg gggaaatgtg cgcggaaccc ctatttgttt     4560 attttttctaa atacattcaa atatgtatcc gctcatgaga caataaccct gataaatgct     4620
caataatatt gaaaaaggaa gagtatgagt attcaacatt tccgtgtcgc ccttattccc     4680
ttttttgcgg cattttgcct tcctgttttt gctcacccag aaacgctggt gaaagtaaaa     4740
gatgctgaag atcagttggg tgcacgagtg ggttacatcg aactggatct caacagcggt     4800
aagatccttg agagttttcg ccccgaagaa cgttttccaa tgatgagcac ttttaaagtt     4860
ctgctatgtg gcgcggtatt atcccgtatt gacgccgggc aagagcaact cggtcgccgc     4920
atacactatt ctcagaatga cttggttgag tactcaccag tcacagaaaa gcatcttacg     4980
gatggcatga cagtaagaga attatgcagt gctgccataa ccatgagtga taacactgcg     5040
gccaacttac ttctgacaac gatcggagga ccgaaggagc taaccgcttt tttgcacaac     5100
atgggggatc atgtaactcg ccttgatcgt tgggaaccgg agctgaatga agccatacca     5160
aacgacgagc gtgacaccac gatgcctgta gcaatggcaa caacgttgcg caaactatta     5220
actggcgaac tacttactct agcttcccgg caacaattaa tagactggat ggaggcggat     5280
aaagttgcag gaccacttct gcgctcggcc cttccggctg gctggtttat tgctgataaa     5340
tctggagccg gtgagcgtgg gtctcgcggt atcattgcag cactggggcc agatggtaag     5400
ccctcccgta tcgtagttat ctacacgacg gggagtcagg caactatgga tgaacgaaat     5460
agacagatcg ctgagatagg tgcctcactg attaagcatt ggtaactgtc agaccaagtt     5520
tactcatata tactttagat tgatttaaaa cttcattttt aatttaaaag gatctaggtg     5580
aagatccttt ttgataatct catgaccaaa atcccttaac gtgagttttc gttccactga     5640
```

-continued

```
gcgtcagacc ccgtagaaaa gatcaaagga tcttcttgag atcctttttt tctgcgcgta   5700
atctgctgct tgcaaacaaa aaaaccaccg ctaccagcgg tggtttgttt gccggatcaa   5760
gagctaccaa ctctttttcc gaaggtaact ggcttcagca gagcgcagat accaaatact   5820
gtccttctag tgtagccgta gttaggccac cacttcaaga actctgtagc accgcctaca   5880
tacctcgctc tgctaatcct gttaccagtg gctgctgcca gtggcgataa gtcgtgtctt   5940
accgggttgg actcaagacg atagttaccg gataaggcgc agcggtcggg ctgaacgggg   6000
ggttcgtgca cacagcccag cttggagcga acgacctaca ccgaactgag atacctacag   6060
cgtgagctat gagaaagcgc cacgcttccc gaagggagaa aggcggacag gtatccggta   6120
agcggcaggg tcggaacagg agagcgcacg agggagcttc caggggggaaa cgcctggtat   6180 ctttatagtc ctgtcgggtt cgccacctc tgacttgagc gtcgattttt gtgatgctcg   6240
tcaggggggc ggagcctatg gaaaaacgcc agcaacgcgg ccttttttacg gttcctggcc   6300 ttttgctggc cttttgctca catgttcttt cctgcgttat cccctgattc tgtggataac   6360
cgtattaccg cctttgagtg agctgatacc gctcgccgca gccgaacgac cgagcgcagc   6420
gagtcagtga gcgaggaagc ggaagagcgc ccaatacgca aaccgcctct ccccgcgcgt   6480
tggccgattc attaatg                                                  6497
```

```
<210> SEQ ID NO 39
<211> LENGTH: 6543
<212> TYPE: DNA
<213> ORGANISM: Artificial Sequence
<220> FEATURE:
<223> OTHER INFORMATION: AAVsc-HS-CRE7-TTRenh-TTRm-MVM-hFIXcoPadua-
      bghpolyA

<400> SEQUENCE: 39
```

```
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt acaatttaa atatttgctt    840 atacaatctt cctgttttg gggcttttct gattatcaac cggggtacat atgattgaca    900
tgctagtttt acgattaccg ttcatcgccc tgcgcgctcg ctcgctcact gaggccgccc    960
gggcaaagcc cggcgtcgg cgacctttg gtcgcccggc ctcagtgagc gagcgagcgc   1020
gcagagaggg agtggaattc acgcgtggat ctgaattctg tacaggcgtg gtacggccgc   1080
ggtacaggcc tggggtcccg gcttagagga cctctgagag ctccggggcc ccttctgggt   1140
```

```
cgtggttgcc  tcatcgtggt  cgggtgggtc  tccaggttct  cccaggctca  gtcccgcagg      1200
cgccaaatct  gcgcaggaga  gcactagcaa  ccgatgacgt  attgaggccc  acacctctgg      1260
gattggctgt  cctgcttcga  cagccttgaa  agtgggtaag  ctgggtgggg  ggctctggga      1320
gaggtcagtg  ctgagtaagg  caattcccag  cagcttgagc  cccaccaggt  cactccagta      1380
ttcctcccca  ttcttggtac  ccactgggag  gatgttgagt  aagatggaaa  actactgatg      1440
acccttgcag  agacagagta  ttaggacatg  tttgaacagg  ggccgggcga  tcagcaggta      1500
gctctagagg  atccccgtct  gtctgcacat  ttcgtagagc  gagtgttccg  atactctaat      1560
ctccctaggc  aaggttcata  tttgtgtagg  ttacttattc  tccttttgtt  gactaagtca      1620
ataatcagaa  tcagcaggtt  tggagtcagc  cttggcaggga  tcagcagcct  gggttggaag      1680
gagggggtat  aaaagcccct  tcaccaggag  aagccgtcac  acagatccac  aagctcctgg      1740
ctagaaagag  gtaagggttt  aagggatggt  tggttggtgg  ggtattaatg  tttaattacc      1800
tggagcacct  gcctgaaatc  acttttttc   aggttgggct  agcccaccat  gcagcgcgtg      1860
aacatgatca  tggccgagag  ccccggcctg  atcaccatct  gcctgctggg  ctacctgctg      1920
agcgccgagt  gcaccgtgtt  cctggaccac  gagaacgcca  acaagatcct  gaaccgcccc      1980
aagcgctaca  cagcggcaa   gctggaggag  ttcgtgcagg  gcaacctgga  gcgcgagtgc      2040
atggaggaga  agtgcagctt  cgaggaggcc  cgcgaggtgt  tcgagaacac  cgagcgcacc      2100
accgagttct  ggaagcagta  cgtggacggc  gaccagtgcg  agagcaaccc  ctgcctgaac      2160
ggcggcagct  gcaaggacga  catcaacagc  tacgagtgct  ggtgccccctt  cggcttcgag      2220 ggcaagaact  gcgagctgga  cgtgacctgc  aacatcaaga  acggccgctg  cgagcagttc      2280
tgcaagaaca  gcgccgacaa  caaggtggtg  tgcagctgca  ccgagggcta  ccgcctggcc      2340
gagaaccaga  gagctgcga   gcccgccgtg  cccttcccct  gcggccgcgt  gagcgtgagc      2400
cagaccagca  agctgacccg  cgccgaggcc  gtgttccccg  acgtggacta  cgtgaacagc      2460
accgaggccg  agaccatcct  ggacaacatc  acccagagca  cccagagctt  caacgacttc      2520
acccgcgtgg  tgggcggcga  ggacgccaag  cccggccagt  tccctggca   ggtggtgctg      2580 aacggcaagg  tggacgcctt  ctgcggcggc  agcatcgtga  cgagaagtg   gatcgtgacc      2640 gccgcccact  gcgtggagac  cggcgtgaag  atcaccgtgg  tggccggcga  gcacaacatc      2700
gaggagaccg  agcacaccga  gcagaagcgc  aacgtgatcc  gcatcatccc  ccaccacaac      2760
tacaacgccg  ccatcaacaa  gtacaaccac  gacatcgccc  tgctggagct  ggacgagccc      2820
ctggtgctga  acagctacgt  gaccccccatc  tgcatcgccg  acaaggagta  caccaacatc      2880
ttcctgaagt  tcggcagcgg  ctacgtgagc  ggctggggcc  gcgtgttcca  caagggccgc      2940
agcgccctgg  tgctgcagta  cctgcgcgtg  cccctggtgg  accgcgccac  ctgcctgctg      3000
agcaccaagt  tcaccatcta  caacaacatg  ttctgcgccg  gcttccacga  gggcggccgc      3060
gacagctgcc  agggcgacag  cggcggcccc  cacgtgaccg  aggtggaggg  caccagcttc      3120
ctgaccggca  tcatcagctg  gggcgaggag  tgcgccatga  agggcaagta  cggcatctac      3180
accaaggtga  gccgctacgt  gaactggatc  aaggagaaga  ccaagctgac  ctaatgaaag      3240
atggatttcc  aaggttaatt  cattggaatt  gaaaattaac  agccccccc   ccccccccc       3300 tgcagatctg  agccgaattc  ctgcagcccg  ggggatcagc  ctcgactgtg  ccttctagtt      3360
gccagccatc  tgttgtttgc  ccctcccccg  tgccttcctt  gaccctggaa  ggtgccactc      3420
ccactgtcct  ttcctaataa  aatgaggaaa  ttgcatcgca  ttgtctgagt  aggtgtcatt      3480
ctattctggg  gggtggggtg  gggcaggaca  gcaaggggga  ggattgggaa  gacaatagca      3540
```

-continued

```
ggcatgctgg ggatgcggtg ggctctatgg cttctgaggc ggaaagaacc agctggggac      3600
cggtggatct cgatagcagg catgctgggg agagatcgat ctgaggaacc cctagtgatg      3660
gagttggcca ctccctctct gcgcgctcgc tcgctcactg aggccgcccg ggcaaagccc      3720
gggcgtcggg cgacctttgg tcgcccggcc tcagtgagcg agcgagcgcg cagagaggga      3780
gtggccaacc cccccccccc ccccccccgg cgattctctt gtttgctcca gactctcagg      3840
caatgacctg atagcctttg tagagacctc tcaaaaatag ctaccctctc cggcatgaat      3900
ttatcagcta gaacggttga atatcatatt gatggtgatt tgactgtctc cggcctttct      3960
cacccgtttg aatctttacc tacacattac tcaggcattg catttaaaat atatgagggt      4020
tctaaaaatt tttatccttg cgttgaaata aaggcttctc ccgcaaaagt attacagggt      4080
cataatgttt ttggtacaac cgatttagct ttatgctctg aggctttatt gcttaatttt      4140
gctaattctt tgccttgcct gtatgattta ttggatgttg gaatcgcctg atgcggtatt      4200
ttctccttac gcatctgtgc ggtatttcac accgcatatg gtgcactctc agtacaatct      4260
gctctgatgc cgcatagtta tatggtgcac tctcagtaca atctgctctg atgccgcata      4320
gttaagccag ccccgacacc cgccaacaca gccagccccg acacccgcca cacccgctg       4380 acgcgccctg acgggcttgt ctgctcccgg catccgctta cagacaagct gtgaccgtct      4440 ccggagctg catgtgtcag aggttttcac cgtcatcacc gaaacgcgcg agacgaaagg       4500
gcctcgtgat acgcctattt ttataggtta atgtcatgat aataatggtt tcttagacgt      4560
caggtggcac ttttcgggga atgtgcgcg gaacccctat ttgtttattt ttctaaatac       4620
attcaaatat gtatccgctc atgagacaat aaccctgata aatgctcaat aatattgaaa      4680
aaggaagagt atgagtattc aacatttccg tgtcgccctt attcccttt ttgcggcatt       4740 ttgccttcct gtttttgctc acccagaaac gctggtgaaa gtaaaagatg ctgaagatca      4800
gttgggtgca cgagtgggtt acatcgaact ggatctcaac agcggtaaga tccttgagag      4860
ttttcgcccc gaagaacgtt ttccaatgat gagcactttt aaagttctgc tatgtggcgc      4920
ggtattatcc cgtattgacg ccgggcaaga gcaactcggt cgccgcatac actattctca      4980
gaatgacttg gttgagtact caccagtcac agaaaagcat cttacggatg gcatgacagt      5040
aagagaatta tgcagtgctg ccataaccat gagtgataac actgcggcca acttacttct      5100
gacaacgatc ggaggaccga aggagctaac cgcttttttg cacaacatgg gggatcatgt      5160
aactcgcctt gatcgttggg aaccggagct gaatgaagcc ataccaaacg acgagcgtga      5220
caccacgatg cctgtagcaa tggcaacaac gttgcgcaaa ctattaactg gcgaactact      5280
tactctagct tcccggcaac aattaataga ctggatggag gcggataaag ttgcaggacc      5340
acttctgcgc tcggcccttc cggctggctg gtttattgct gataaatctg gagccggtga      5400
gcgtgggtct cgcggtatca ttgcagcact ggggccagat ggtaagccct cccgtatcgt      5460
agttatctac acgacgggga gtcaggcaac tatggatgaa cgaaatagac agatcgctga      5520
gataggtgcc tcactgatta agcattggta actgtcagac caagtttact catatatact      5580
ttagattgat ttaaaacttc attttttaatt taaaaggatc taggtgaaga tcctttttga      5640
taatctcatg accaaaatcc cttaacgtga gttttcgttc cactgagcgt cagacccgt       5700 agaaaagatc aaaggatctt cttgagatcc tttttttctg cgcgtaatct gctgcttgca      5760
aacaaaaaaa ccaccgctac cagcggtggt ttgtttgccg gatcaagagc taccaactct      5820
ttttccgaag gtaactggct tcagcagagc gcagatacca aatactgtcc ttctagtgta      5880
```

```
gccgtagtta ggccaccact tcaagaactc tgtagcaccg cctacatacc tcgctctgct      5940
aatcctgtta ccagtggctg ctgccagtgg cgataagtcg tgtcttaccg ggttggactc      6000
aagacgatag ttaccggata aggcgcagcg gtcgggctga acgggggggtt cgtgcacaca     6060 gcccagcttg gagcgaacga cctacaccga actgagatac ctacagcgtg agctatgaga      6120
aagcgccacg cttcccgaag ggagaaaggc ggacaggtat ccggtaagcg gcagggtcgg      6180
aacaggagag cgcacgaggg agcttccagg gggaaacgcc tggtatcttt atagtcctgt      6240
cgggtttcgc cacctctgac ttgagcgtcg atttttgtga tgctcgtcag ggggggcggag      6300 cctatggaaa aacgccagca acgcggcctt tttacggttc ctggccttt tgctggcctt       6360 tgctcacatg ttctttcctg cgttatcccc tgattctgtg ataaccgta ttaccgcctt       6420 tgagtgagct gataccgctc gccgcagccg aacgaccgag cgcagcgagt cagtgagcga      6480
ggaagcggaa gagcgcccaa tacgcaaacc gcctctcccc gcgcgttggc cgattcatta      6540
atg                                                                     6543

<210> SEQ ID NO 40
<211> LENGTH: 6743
<212> TYPE: DNA
<213> ORGANISM: Artificial Sequence
<220> FEATURE:
<223> OTHER INFORMATION: AAVsc-HS-CRE8-TTRenh-TTRm-MVM-hFIXcoPadua-
      bghpolyA

<400> SEQUENCE: 40
agctggcgta atagcgaaga ggcccgcacc gatcgccctt cccaacagtt gcgcagcctg       60
aatggcgaat ggcgattccg ttgcaatggc tggcggtaat attgttctgg atattaccag      120
caaggccgat agtttgagtt cttctactca ggcaagtgat gttattacta atcaaagaag      180
tattgcgaca acggttaatt tgcgtgatgg acagactctt ttactcggtg gcctcactga      240
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg ttttttcgccc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt acaatttaa atatttgctt       840 atacaatctt cctgtttttg gggcttttct gattatcaac cggggtacat atgattgaca      900
tgctagtttt acgattaccg ttcatcgccc tgcgcgctcg ctcgctcact gaggccgccc      960
gggcaaagcc cggcgtcgg gcgacctttg gtcgcccggc ctcagtgagc gagcgagcgc      1020
gcagagaggg agtggaattc acgcgtggat ctgaattctg tacaggcgtg gtacggccgc      1080
ggcccgaacg aataaacccc ttccttaact cagcgtctga ggattttgt ctgcggctcc       1140 tcctgctaca ttctgagtgg ggaaagggac taaggtggtc tgaggacccc acagagtcag      1200
gaagattgag aggtgagagt gctgaacggg gaggggcttt ggggctaagg gaagtgcccg      1260
ggaccccacc tgaccccaac gctcacggga caggggcaga ggagaaaaac gtgggtggac      1320
```

-continued

```
agagggaggc aggcggtcag gggaaggctc aggaggaggg agatcaacat caacctgccc    1380
cgccccctcc ccagcctgat aaaggtcctg cgggcaggac aggacctccc aaccaagccc    1440
tccagcaagg attcaggttg gtgctgagtg cctgggaggg acacccgcct acactctgca    1500
agaaactcaa aaagggagat gaggggatcg tgggagggga gtagggaggg aggagggtgc    1560
cactgatccc ctgaacccct gcctctgcct ccagaggtac ccactgggag gatgttgagt    1620
aagatggaaa actactgatg acccttgcag agacagagta ttaggacatg tttgaacagg    1680
ggccgggcga tcagcaggta gctctagagg atccccgtct gtctgcacat ttcgtagagc    1740
gagtgttccg atactctaat ctccctaggc aaggttcata tttgtgtagg ttacttattc    1800
tccttttgtt gactaagtca ataatcagaa tcagcaggtt tggagtcagc cttggcaggga   1860 tcagcagcct gggttggaag gagggggtat aaaagcccct tcaccaggag aagccgtcac    1920
acagatccac aagctcctgg ctagaaagag gtaagggttt aagggatggt tggttggtgg    1980
ggtattaatg tttaattacc tggagcacct gcctgaaatc actttttttc aggttgggct    2040
agcccaccat gcagcgcgtg aacatgatca tggccgagag ccccggcctg atcaccatct    2100
gcctgctggg ctacctgctg agcgccgagt gcaccgtgtt cctggaccac gagaacgcca    2160
acaagatcct gaaccgcccc aagcgctaca acagcggcaa gctggaggag ttcgtgcagg    2220
gcaacctgga gcgcgagtgc atggaggaga agtgcagctt cgaggaggcc cgcgaggtgt    2280
tcgagaacac cgagcgcacc accgagttct ggaagcagta cgtggacggc gaccagtgcg    2340
agagcaaccc ctgcctgaac ggcggcagct gcaaggacga catcaacagc tacgagtgct    2400
ggtgcccctt cggcttcgag ggcaagaact gcgagctgga cgtgacctgc aacatcaaga    2460
acggccgctg cgagcagttc tgcaagaaca cgcgccgacaa caaggtggtg tgcagctgca    2520
ccgagggcta ccgcctggcc gagaaccaga gagctgcga gcccgccgtg cccttcccct    2580
gcggccgcgt gagcgtgagc cagaccagca gctgacccg cgccgaggcc gtgttccccg    2640
acgtggacta cgtgaacagc accgaggccg agaccatcct ggacaacatc acccagagca    2700
cccagagctt caacgacttc acccgcgtgg tgggcggcga ggacgccaag cccggccagt    2760
tcccctggca ggtggtgctg aacggcaagg tggacgcctt ctgcggcggc agcatcgtga    2820
acgagaagtg gatcgtgacc gccgcccact gcgtggagac cggcgtgaag atcaccgtgg    2880
tggccggcga gcacaacatc gaggagaccg agcacaccga gcagaagcgc aacgtgatcc    2940
gcatcatccc ccaccacaac tacaacgccg ccatcaacaa gtacaaccac gacatcgccc    3000
tgctggagct ggacgagccc ctggtgctga acagctacgt gacccccatc tgcatcgccg    3060
acaaggagta caccaacatc ttcctgaagt tcggcagcgg ctacgtgagc ggctggggcc    3120
gcgtgttcca caaggccgc agcgccctgg tgctgcagta cctgcgcgtg cccctggtgg    3180
accgcgccac ctgcctgctg agcaccaagt tcaccatcta caacaacatg ttctgcgccg    3240
gcttccacga gggcggccgc gacagctgcc agggcgacag cggcggcccc cacgtgaccg    3300
aggtggaggg caccagcttc ctgaccggca tcatcagctg gggcgaggag tgcgccatga    3360
agggcaagta cggcatctac accaaggtga gccgctacgt gaactggatc aaggagaaga    3420
ccaagctgac ctaatgaaag atggatttcc aaggttaatt cattggaatt gaaaattaac    3480
agcccccccc ccccccccc tgcagatctg agccgaattc ctgcagcccg ggggatcagc    3540
ctcgactgtg ccttctagtt gccagccatc tgttgtttgc ccctcccccg tgccttcctt    3600
gaccctggaa ggtgccactc ccactgtcct ttcctaataa aatgaggaaa ttgcatcgca    3660
ttgtctgagt aggtgtcatt ctattctggg gggtggggtg gggcaggaca gcaagggga    3720
```

```
ggattgggaa  gacaatagca  ggcatgctgg  ggatgcggtg  ggctctatgg  cttctgaggc   3780
ggaaagaacc  agctggggac  cggtggatct  cgatagcagg  catgctgggg  agagatcgat   3840
ctgaggaacc  cctagtgatg  gagttggcca  ctccctctct  gcgcgctcgc  tcgctcactg   3900
aggccgcccg  ggcaaagccc  gggcgtcggg  cgacctttgg  tcgcccggcc  tcagtgagcg   3960
agcgagcgcg  cagagaggga  gtggccaacc  cccccccccc  cccccccggg  cgattctctt   4020
gtttgctcca  gactctcagg  caatgacctg  atagcctttg  tagagacctc  tcaaaaatag   4080
ctaccctctc  cggcatgaat  ttatcagcta  gaacggttga  atatcatatt  gatggtgatt   4140
tgactgtctc  cggcctttct  cacccgtttg  aatctttacc  tacacattac  tcaggcattg   4200
catttaaaat  atatgagggt  tctaaaaatt  tttatccttg  cgttgaaata  aaggcttctc   4260
ccgcaaaagt  attacagggt  cataatgttt  ttggtacaac  cgatttagct  ttatgctctg   4320
aggctttatt  gcttaatttt  gctaattctt  tgccttgcct  gtatgattta  ttggatgttg   4380
gaatcgcctg  atgcggtatt  ttctccttac  gcatctgtgc  ggtatttcac  accgcatatg   4440
gtgcactctc  agtacaatct  gctctgatgc  cgcatagtta  tatggtgcac  tctcagtaca   4500
atctgctctg  atgccgcata  gttaagccag  ccccgacacc  cgccaacaca  gccagccccg   4560
acacccgcca  acacccgctg  acgcgccctg  acgggcttgt  ctgctcccgg  catccgctta   4620
cagacaagct  gtgaccgtct  ccgggagctg  catgtgtcag  aggttttcac  cgtcatcacc   4680
gaaacgcgcg  agacgaaagg  gcctcgtgat  acgcctattt  ttataggtta  atgtcatgat   4740
aataatggtt  tcttagacgt  caggtggcac  ttttcgggga  aatgtgcgcg  gaacccctat   4800
ttgtttattt  ttctaaatac  attcaaatat  gtatccgctc  atgagacaat  aaccctgata   4860
aatgctcaat  aatattgaaa  aaggaagagt  atgagtattc  aacatttccg  tgtcgccctt   4920
attccctttt  ttgcggcatt  ttgccttcct  gttttttgctc  acccagaaac  gctggtgaaa   4980
gtaaaagatg  ctgaagatca  gttgggtgca  cgagtgggtt  acatcgaact  ggatctcaac   5040
agcggtaaga  tccttgagag  ttttcgcccc  gaagaacgtt  ttccaatgat  gagcactttt   5100
aaagttctgc  tatgtggcgc  ggtattatcc  cgtattgacg  ccgggcaaga  gcaactcggt   5160
cgccgcatac  actattctca  gaatgacttg  gttgagtact  caccagtcac  agaaaagcat   5220
cttacggatg  gcatgacagt  aagagaatta  tgcagtgctg  ccataaccat  gagtgataac   5280
actgcggcca  acttacttct  gacaacgatc  ggaggaccga  aggagctaac  cgcttttttg   5340
cacaacatgg  gggatcatgt  aactcgcctt  gatcgttggg  aaccggagct  gaatgaagcc   5400
ataccaaacg  acgagcgtga  caccacgatg  cctgtagcaa  tggcaacaac  gttgcgcaaa   5460
ctattaactg  gcgaactact  tactctagct  tcccggcaac  aattaataga  ctggatggag   5520
gcggataaag  ttgcaggacc  acttctgcgc  tcggcccttc  cggctggctg  gtttattgct   5580
gataaatctg  gagccggtga  gcgtgggtct  cgcggtatca  ttgcagcact  ggggccagat   5640
ggtaagccct  cccgtatcgt  agttatctac  acgacgggga  gtcaggcaac  tatggatgaa   5700
cgaaatagac  agatcgctga  gataggtgcc  tcactgatta  agcattggta  actgtcagac   5760
caagtttact  catatatact  ttagattgat  ttaaaacttc  attttttaatt  taaaaggatc   5820 taggtgaaga  tcctttttga  taatctcatg  accaaaatcc  cttaacgtga  gttttcgttc   5880
cactgagcgt  cagaccccgt  agaaaagatc  aaaggatctt  cttgagatcc  ttttttttctg   5940 cgcgtaatct  gctgcttgca  acaaaaaaaa  ccaccgctac  cagcggtggt  ttgtttgccg   6000
gatcaagagc  taccaactct  ttttccgaag  gtaactggct  tcagcagagc  gcagatacca   6060
```

```
aatactgtcc ttctagtgta gccgtagtta ggccaccact tcaagaactc tgtagcaccg    6120
cctacatacc tcgctctgct aatcctgtta ccagtggctg ctgccagtgg cgataagtcg    6180
tgtcttaccg ggttggactc aagacgatag ttaccggata aggcgcagcg gtcgggctga    6240
acggggggtt cgtgcacaca gcccagcttg gagcgaacga cctacaccga actgagatac    6300
ctacagcgtg agctatgaga aagcgccacg cttcccgaag ggagaaaggc ggacaggtat    6360
ccggtaagcg gcagggtcgg aacaggagag cgcacgaggg agcttccagg gggaaacgcc    6420
tggtatcttt atagtcctgt cgggtttcgc cacctctgac ttgagcgtcg attttttgtga   6480 tgctcgtcag ggggcggag cctatggaaa aacgccagca acgcggcctt tttacggttc    6540
ctggcctttt gctggccttt tgctcacatg ttctttcctg cgttatcccc tgattctgtg    6600
gataaccgta ttaccgcctt tgagtgagct gataccgctc gccgcagccg aacgaccgag    6660
cgcagcgagt cagtgagcga ggaagcggaa gagcgcccaa tacgcaaacc gcctctcccc    6720
gcgcgttggc cgattcatta atg                                           6743
```

<210> SEQ ID NO 41
<211> LENGTH: 6536
<212> TYPE: DNA
<213> ORGANISM: Artificial Sequence
<220> FEATURE:
<223> OTHER INFORMATION: AAVsc-HS-CRE9-TTRenh-TTRm-MVM-hFIXcoPadua-
    bghpolyA

<400> SEQUENCE: 41

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg ttttttcgccc tttgacgttg gagtccacgt     660
tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt acaatttaa atatttgctt     840 atacaatctt cctgtttttg gggcttttct gattatcaac cggggtacat atgattgaca     900
tgctagtttt acgattaccg ttcatcgccc tgcgcgctcg ctcgctcact gaggccgccc     960
gggcaaagcc cggcgtcgg gcgacctttg gtcgcccggc ctcagtgagc gagcgagcgc    1020
gcagagaggg agtggaattc acgcgtggat ctgaattctg tacaggcgtg gtacggccgc    1080
gggatgagtg cagggaaccc cgaccccacc cgggagacct gcaagcctgc agacactccc    1140
ctcccgcccc cactgaaccc ttgacccctg cctgcagcc cccgcagctt gctgtttgcc    1200
cactctattt gcccagcccc aggacagag ctgatccttg aactcttaag ttccacattg    1260
ccaggaccag tgagcagcaa cagggccggg gctgggctta tcagcctccc agcccagacc    1320
```

-continued

```
ctggctgcag acataaatag gccctgcaag agctggctgc ttagagactg cgagaaggag    1380
gtgcgtccgg tacccactgg gaggatgttg agtaagatgg aaaactactg atgacccttg    1440
cagagacaga gtattaggac atgtttgaac aggggccggg cgatcagcag gtagctctag    1500
aggatccccg tctgtctgca catttcgtag agcgagtgtt ccgatactct aatctcccta    1560
ggcaaggttc atatttgtgt aggttactta ttctcctttt gttgactaag tcaataatca    1620
gaatcagcag gtttggagtc agcttggcag ggatcagcag cctgggttgg aaggaggggg    1680
tataaaagcc ccttcaccag gagaagccgt cacacagatc cacaagctcc tggctagaaa    1740
gaggtaaggg tttaagggat ggttggttgg tggggtatta atgtttaatt acctggagca    1800
cctgcctgaa atcacttttt ttcaggttgg gctagcccac catgcagcgc gtgaacatga    1860
tcatggccga gagccccggc ctgatcacca tctgcctgct gggctacctg ctgagcgccg    1920
agtgcaccgt gttcctggac cacgagaacg ccaacaagat cctgaaccgc cccaagcgct    1980
acaacagcgg caagctggag gagttcgtgc agggcaacct ggagcgcgag tgcatggagg    2040
agaagtgcag cttcgaggag gcccgcgagg tgttcgagaa caccgagcgc accaccgagt    2100
tctggaagca gtacgtggac ggcgaccagt gcgagagcaa ccccctgcctg aacggcggca    2160 gctgcaagga cgacatcaac agctacgagt gctggtgccc cttcggcttc gagggcaaga    2220
actgcgagct ggacgtgacc tgcaacatca gaacggccg ctgcgagcag ttctgcaaga    2280
acagcgccga caacaaggtg gtgtgcagct gcaccgaggg ctaccgcctg gccgagaacc    2340
agaagagctg cgagcccgcc gtgcccttcc cctgcggccg cgtgagcgtg agccagacca    2400
gcaagctgac ccgcgccgag gccgtgttcc ccgacgtgga ctacgtgaac agcaccgagg    2460
ccgagaccat cctggacaac atcacccaga gcacccagag cttcaacgac ttcacccgcg    2520
tggtgggcgg cgaggacgcc aagcccggcc agttcccctg gcaggtggtg ctgaacggca    2580
aggtggacgc cttctgcggc ggcagcatcg tgaacgagaa gtggatcgtg accgccgccc    2640
actgcgtgga gaccggcgtg aagatcaccg tggtggccgg cgagcacaac atcgaggaga    2700
ccgagcacac cgagcagaag cgcaacgtga tccgcatcat cccccaccac aactacaacg    2760
ccgccatcaa caagtacaac cacgacatcg ccctgctgga gctggacgag cccctggtgc    2820
tgaacagcta cgtgacccccc atctgcatcg ccgacaagga gtacaccaac atcttcctga    2880
agttcggcag cggctacgtg agcggctggg gccgcgtgtt ccacaagggc cgcagcgccc    2940
tggtgctgca gtacctgcgc gtgcccctgg tggaccgcgc cacctgcctg ctgagcacca    3000
agttcaccat ctacaacaac atgttctgcg ccggcttcca cgagggcggc cgcgacagct    3060
gccagggcga cagcggcggc ccccacgtga ccgaggtgga gggcaccagc ttcctgaccg    3120
gcatcatcag ctggggcgag gagtgcgcca tgaagggcaa gtacggcatc tacaccaagg    3180
tgagccgcta cgtgaactgg atcaaggaga agaccaagct gacctaatga aagatggatt    3240
tccaaggtta attcattgga attgaaaatt aacagccccc cccccccccc ccctgcagat    3300
ctgagccgaa ttcctgcagc ccgggggatc agcctcgact gtgccttcta gttgccagcc    3360
atctgttgtt tgcccctccc ccgtgccttc cttgaccctg gaaggtgcca ctcccactgt    3420
cctttcctaa taaaatgagg aaattgcatc gcattgtctg agtaggtgtc attctattct    3480
ggggggtggg gtggggcagg acagcaaggg ggaggattgg gaagacaata gcaggcatgc    3540
tggggatgcg gtgggctcta tggcttctga ggcggaaaga accagctggg gaccggtgga    3600
tctcgatagc aggcatgctg gggagagatc gatctgagga accccctagtg atggagttgg    3660 ccactccctc tctgcgcgct cgctcgctca ctgaggccgc ccgggcaaag cccgggcgtc    3720
```

-continued

```
gggcgacctt tggtcgcccg gcctcagtga gcgagcgagc gcgcagagag ggagtggcca    3780 acccccccc ccccccccc cggcgattct cttgtttgct ccagactctc aggcaatgac    3840
ctgatagcct ttgtagagac ctctcaaaaa tagctaccct ctccggcatg aatttatcag    3900
ctagaacggt tgaatatcat attgatggtg atttgactgt ctccggcctt tctcacccgt    3960
ttgaatcttt acctacacat tactcaggca ttgcatttaa aatatatgag ggttctaaaa    4020 attttatcc ttgcgttgaa ataaaggctt ctcccgcaaa agtattacag ggtcataatg    4080
tttttggtac aaccgattta gctttatgct ctgaggcttt attgcttaat tttgctaatt    4140
ctttgccttg cctgtatgat ttattggatg ttggaatcgc ctgatgcggt attttctcct    4200
tacgcatctg tgcggtattt cacaccgcat atggtgcact ctcagtacaa tctgctctga    4260
tgccgcatag ttatatggtg cactctcagt acaatctgct ctgatgccgc atagttaagc    4320
cagccccgac acccgccaac acagccagcc ccgacacccg ccaacacccg ctgacgcgcc    4380
ctgacgggct tgtctgctcc cggcatccgc ttacagacaa gctgtgaccg tctccgggag    4440
ctgcatgtgt cagaggtttt caccgtcatc accgaaacgc gcgagacgaa agggcctcgt    4500
gatacgccta ttttttatagg ttaatgtcat gataataatg gtttcttaga cgtcaggtgg    4560
cacttttcgg ggaaatgtgc gcggaacccc tatttgttta ttttttctaaa tacattcaaa    4620 tatgtatccg ctcatgagac aataaccctg ataaatgctc aataatattg aaaaaggaag    4680
agtatgagta ttcaacattt ccgtgtcgcc cttattccct tttttgcggc attttgcctt    4740
cctgtttttg ctcacccaga aacgctggtg aaagtaaaag atgctgaaga tcagttgggt    4800
gcacgagtgg gttacatcga actggatctc aacagcggta agatccttga gagttttcgc    4860
cccgaagaac gttttccaat gatgagcact tttaaagttc tgctatgtgg cgcggtatta    4920
tcccgtattg acgccgggca agagcaactc ggtcgccgca tacactattc tcagaatgac    4980
ttggttgagt actcaccagt cacagaaaag catcttacgg atggcatgac agtaagagaa    5040
ttatgcagtg ctgccataac catgagtgat aacactgcgg ccaacttact tctgacaacg    5100
atcggaggac cgaaggagct aaccgctttt ttgcacaaca tgggggatca tgtaactcgc    5160
cttgatcgtt gggaaccgga gctgaatgaa gccataccaa acgacgagcg tgacaccacg    5220
atgcctgtag caatggcaac aacgttgcgc aaactattaa ctggcgaact acttactcta    5280
gcttcccggc aacaattaat agactggatg gaggcggata aagttgcagg accacttctg    5340
cgctcggccc ttccggctgg ctggtttatt gctgataaat ctggagccgg tgagcgtggg    5400
tctcgcggta tcattgcagc actggggcca gatggtaagc cctcccgtat cgtagttatc    5460
tacacgacgg ggagtcaggc aactatggat gaacgaaata gacagatcgc tgagataggt    5520
gcctcactga ttaagcattg gtaactgtca gaccaagttt actcatatat actttagatt    5580
gatttaaaac ttcatttta atttaaaagg atctaggtga agatcctttt tgataatctc    5640
atgaccaaaa tcccttaacg tgagttttcg ttccactgag cgtcagaccc cgtagaaaag    5700
atcaaaggat cttcttgaga tcctttttt ctgcgcgtaa tctgctgctt gcaaacaaaa    5760
aaaccaccgc taccagcggt ggtttgtttg ccggatcaag agctaccaac tcttttttccg    5820 aaggtaactg gcttcagcag agcgcagata ccaaatactg tccttctagt gtagccgtag    5880
ttaggccacc acttcaagaa ctctgtagca ccgcctacat acctcgctct gctaatcctg    5940
ttaccagtgg ctgctgccag tggcgataag tcgtgtctta ccgggttgga ctcaagacga    6000
tagttaccgg ataaggcgca gcggtcgggc tgaacggggg gttcgtgcac acagcccagc    6060
```

```
ttggagcgaa cgacctacac cgaactgaga tacctacagc gtgagctatg agaaagcgcc       6120
acgcttcccg aagggagaaa ggcggacagg tatccggtaa gcggcagggt cggaacagga       6180
gagcgcacga gggagcttcc aggggggaaac gcctggtatc tttatagtcc tgtcgggttt       6240
cgccacctct gacttgagcg tcgattttttg tgatgctcgt caggggggcg gagcctatgg       6300
aaaaacgcca gcaacgcggc cttttttacgg ttcctggcct tttgctggcc ttttgctcac       6360
atgttctttc ctgcgttatc ccctgattct gtggataacc gtattaccgc ctttgagtga       6420
gctgataccg ctcgccgcag ccgaacgacc gagcgcagcg agtcagtgag cgaggaagcg       6480
gaagagcgcc caatacgcaa accgcctctc cccgcgcgtt ggccgattca ttaatg          6536
```

<210> SEQ ID NO 42
<211> LENGTH: 6636
<212> TYPE: DNA
<213> ORGANISM: Artificial Sequence
<220> FEATURE:
<223> OTHER INFORMATION: AAVsc-HS-CRE10-TTRenh-TTRm-MVM-hFIXcoPadua-
      bghpolyA

<400> SEQUENCE: 42

```
agctggcgta atagcgaaga ggcccgcacc gatcgccctt cccaacagtt gcgcagcctg          60
aatggcgaat ggcgattccg ttgcaatggc tggcggtaat attgttctgg atattaccag         120
caaggccgat agtttgagtt cttctactca ggcaagtgat gttattacta atcaaagaag         180
tattgcgaca acggttaatt tgcgtgatgg acagactctt ttactcggtg gcctcactga         240
ttataaaaac acttctcagg attctggcgt accgttcctg tctaaaatcc ctttaatcgg         300
cctcctgttt agctcccgct ctgattctaa cgaggaaagc acgttatacg tgctcgtcaa         360
agcaaccata gtacgcgccc tgtagcggcg cattaagcgc ggcgggtgtg gtggttacgc         420
gcagcgtgac cgctacactt gccagcgccc tagcgcccgc tcctttcgct ttcttccctt         480
cctttctcgc cacgttcgcc ggctttcccc gtcaagctct aaatcggggg ctccctttag         540
ggttccgatt tagtgcttta cggcacctcg accccaaaaa acttgattag ggtgatggtt         600
cacgtagtgg gccatcgccc tgatagacgg tttttcgccc tttgacgttg gagtccacgt         660
tctttaatag tggactcttg ttccaaactg gaacaacact caaccctatc tcggtctatt         720
cttttgattt ataagggatt ttgccgattt cggcctattg gttaaaaaat gagctgattt         780
aacaaaaatt taacgcgaac tttaacaaaa tattaacgtt acaatttaa atatttgctt          840 atacaatctt cctgttttttg gggcttttct gattatcaac cggggtacat atgattgaca         900
tgctagtttt acgattaccg ttcatcgccc tgcgcgctcg ctcgctcact gaggccgccc         960
gggcaaagcc cgggcgtcgg cgacctttg tcgcccggc ctcagtgagc gagcgagcgc         1020
gcagagaggg agtggaattc acgcgtggat ctgaattctg tacaggcgtg gtacggccgc        1080
ggttctatca ttatcttcaa tcagaaactg atgtgtgggg aggtgatgta tcataactca        1140
tccagggtca ggcagctgga tttgaacctg cctgacccttt agatttgagg ttttctggct        1200
ccagaatctt ctctgaagtg aaaggcatga ggccgaccac tccctgatct ggtaaacaga        1260
gatgtcagcc tggtttctag tgttagggag tttcctggag tgatggtaca gggtacattt        1320
ctgccctgca tcccaagtcc agagactggg ttctaggtcc agcctttctt ctaactccct        1380
gagagatgac agcctctggg caaagtccct ctgtgctctt cagtctcttc atctgtgaga        1440
tggtggcatg gggagaggct ggagtgatgt cacagttcct ctcagcctgg tacccactgg        1500
gaggatgttg agtaagatgg aaaactactg atgacccttg cagagacaga gtattaggac        1560
```

-continued

```
atgtttgaac aggggccggg cgatcagcag gtagctctag aggatccccg tctgtctgca     1620
catttcgtag agcgagtgtt ccgatactct aatctccta ggcaaggttc atatttgtgt      1680
aggttactta ttctcctttt gttgactaag tcaataatca gaatcagcag gtttggagtc     1740
agcttggcag ggatcagcag cctgggttgg aaggaggggg tataaaagcc ccttcaccag     1800
gagaagccgt cacacagatc cacaagctcc tggctagaaa gaggtaaggg tttaagggat     1860
ggttggttgg tggggtatta atgtttaatt acctggagca cctgcctgaa atcactttt      1920 ttcaggttgg gctagcccac catgcagcgc gtgaacatga tcatggccga gagccccggc     1980
ctgatcacca tctgcctgct gggctacctg ctgagcgccg agtgcaccgt gttcctggac     2040
cacgagaacg ccaacaagat cctgaaccgc cccaagcgct acaacagcgg caagctggag     2100
gagttcgtgc agggcaacct ggagcgcgag tgcatggagg agaagtgcag cttcgaggag     2160
gcccgcgagg tgttcgagaa caccgagcgc accaccgagt tctggaagca gtacgtggac     2220
ggcgaccagt gcgagagcaa cccctgcctg aacggcggca gctgcaagga cgacatcaac     2280
agctacgagt gctggtgccc cttcggcttc gagggcaaga actgcgagct ggacgtgacc     2340
tgcaacatca gaacggccg ctgcgagcag ttctgcaaga cagcgccga caacaaggtg      2400 gtgtgcagct gcaccgaggg ctaccgcctg gccgagaacc agaagagctg cgagcccgcc     2460
gtgcccttcc cctgcggccg cgtgagcgtg agccagacca gcaagctgac ccgcgccgag     2520
gccgtgttcc ccgacgtgga ctacgtgaac agcaccgagg ccgagaccat cctggacaac     2580
atcacccaga gcacccagag cttcaacgac ttcacccgcg tggtgggcgg cgaggacgcc     2640
aagcccggcc agttcccctg gcaggtggtg ctgaacggca aggtggacgc cttctgcggc     2700
ggcagcatcg tgaacgagaa gtggatcgtg accgccgccc actgcgtgga gaccggcgtg     2760
aagatcaccg tggtggccgg cgagcacaac atcgaggaga ccgagcacac cgagcagaag     2820
cgcaacgtga tccgcatcat ccccccaccac aactacaacg ccgccatcaa caagtacaac     2880
cacgacatcg ccctgctgga gctggacgag ccccctggtgc tgaacagcta cgtgacccc      2940 atctgcatcg ccgacaagga gtacaccaac atcttcctga gttcggcag cggctacgtg      3000 agcggctggg gccgcgtgtt ccacaagggc cgcagcgccc tggtgctgca gtacctgcgc     3060
gtgcccctgg tggaccgcgc cacctgcctg ctgagcacca agttcaccat ctacaacaac     3120
atgttctgcg ccggcttcca cgagggcggc cgcgacagct gccagggcga cagcggcggc     3180
ccccacgtga ccgaggtgga gggcaccagc ttcctgaccg gcatcatcag ctggggcgag     3240
gagtgcgcca tgaagggcaa gtacggcatc tacaccaagg tgagccgcta cgtgaactgg     3300
atcaaggaga agaccaagct gacctaatga aagatggatt tccaaggtta attcattgga     3360
attgaaaatt aacagccccc ccccccccc ccctgcagat ctgagccgaa ttcctgcagc       3420 ccggggatc agcctcgact gtgccttcta gttgccagcc atctgttgtt tgcccctccc       3480
ccgtgccttc cttgacccctg gaaggtgcca ctcccactgt cctttcctaa taaaatgagg     3540
aaattgcatc gcattgtctg agtaggtgtc attctattct ggggggtggg gtggggcagg      3600
acagcaaggg ggaggattgg gaagacaata gcaggcatgc tggggatgcg gtgggctcta      3660
tggcttctga ggcggaaaga accagctggg gaccggtgga tctcgatagc aggcatgctg      3720
gggagagatc gatctgagga acccctagtg atggagttgg ccactccctc tctgcgcgct      3780
cgctcgctca ctgaggccgc ccgggcaaag cccgggcgtc gggcgacctt ggtcgcccg       3840 gcctcagtga gcgagcgagc gcgcagagag ggagtggcca accccccccc ccccccccc       3900 cggcgattct cttgtttgct ccagactctc aggcaatgac ctgatagcct ttgtagagac      3960
```

-continued

```
ctctcaaaaa tagctaccct ctccggcatg aatttatcag ctagaacggt tgaatatcat    4020
attgatggtg atttgactgt ctccggcctt tctcacccgt ttgaatcttt acctacacat    4080
tactcaggca ttgcatttaa aatatatgag ggttctaaaa attttttatcc ttgcgttgaa   4140 ataaaggctt ctcccgcaaa agtattacag ggtcataatg tttttggtac aaccgattta    4200
gctttatgct ctgaggcttt attgcttaat tttgctaatt cttttgccttg cctgtatgat   4260 ttattggatg ttggaatcgc ctgatgcggt attttctcct tacgcatctg tgcggtattt    4320
cacaccgcat atggtgcact ctcagtacaa tctgctctga tgccgcatag ttatatggtg    4380
cactctcagt acaatctgct ctgatgccgc atagttaagc cagccccgac acccgccaac    4440
acagccagcc ccgacacccg ccaacacccg ctgacgcgcc ctgacgggct tgtctgctcc    4500
cggcatccgc ttacagacaa gctgtgaccg tctccgggag ctgcatgtgt cagaggtttt    4560
caccgtcatc accgaaacgc gcgagacgaa agggcctcgt gatacgccta ttttttatagg   4620 ttaatgtcat gataataatg gtttcttaga cgtcaggtgg cacttttcgg ggaaatgtgc    4680
gcggaacccc tatttgttta tttttctaaa tacattcaaa tatgtatccg ctcatgagac    4740
aataaccctg ataaatgctc aataatattg aaaaaggaag agtatgagta ttcaacattt    4800
ccgtgtcgcc cttattccct tttttgcggc attttgcctt cctgttttttg ctcacccaga   4860 aacgctggtg aaagtaaaag atgctgaaga tcagttgggt gcacgagtgg gttacatcga    4920
actggatctc aacagcggta agatccttga gagttttcgc cccgaagaac gttttccaat    4980
gatgagcact tttaaagttc tgctatgtgg cgcggtatta tcccgtattg acgccgggca    5040
agagcaactc ggtcgccgca tacactattc tcagaatgac ttggttgagt actcaccagt    5100
cacagaaaag catcttacgg atggcatgac agtaagagaa ttatgcagtg ctgccataac    5160
catgagtgat aacactgcgg ccaacttact tctgacaacg atcggaggac cgaaggagct    5220
aaccgctttt ttgcacaaca tgggggatca tgtaactcgc cttgatcgtt gggaaccgga    5280
gctgaatgaa gccataccaa acgacgagcg tgacaccacg atgcctgtag caatggcaac    5340
aacgttgcgc aaactattaa ctggcgaact acttactcta gcttcccggc aacaattaat    5400
agactggatg gaggcggata aagttgcagg accacttctg cgctcggccc ttccggctgg    5460
ctggtttatt gctgataaat ctggagccgg tgagcgtggg tctcgcggta tcattgcagc    5520
actggggcca gatggtaagc cctcccgtat cgtagttatc tacacgacgg ggagtcaggc    5580
aactatggat gaacgaaata gacagatcgc tgagataggt gcctcactga ttaagcattg    5640
gtaactgtca gaccaagttt actcatatat actttagatt gatttaaaac ttcatttttta   5700 atttaaaagg atctaggtga agatcctttt tgataatctc atgaccaaaa tcccttaacg    5760
tgagttttcg ttccactgag cgtcagaccc cgtagaaaag atcaaaggat cttcttgaga    5820
tccttttttt ctgcgcgtaa tctgctgctt gcaaacaaaa aaaccaccgc taccagcggt    5880
ggtttgtttg ccggatcaag agctaccaac tcttttttccg aaggtaactg gcttcagcag   5940
agcgcagata ccaaatactg tccttctagt gtagccgtag ttaggccacc acttcaagaa    6000
ctctgtagca ccgcctacat acctcgctct gctaatcctg ttaccagtgg ctgctgccag    6060
tggcgataag tcgtgtctta ccgggttgga ctcaagacga tagttaccgg ataaggcgca    6120
gcggtcgggc tgaacggggg gttcgtgcac acagcccagc ttggagcgaa cgacctacac    6180
cgaactgaga tacctacagc gtgagctatg agaaagcgcc acgcttcccg aagggagaaa    6240
ggcggacagg tatccggtaa gcggcagggt cggaacagga gagcgcacga gggagcttcc    6300
```

-continued

```
aggggggaaac gcctggtatc tttatagtcc tgtcgggttt cgccacctct gacttgagcg    6360
tcgatttttg tgatgctcgt caggggggcg gagcctatgg aaaaacgcca gcaacgcggc    6420 cttttttacgg ttcctggcct tttgctggcc ttttgctcac atgttctttc ctgcgttatc    6480
ccctgattct gtggataacc gtattaccgc ctttgagtga gctgataccg ctcgccgcag    6540
ccgaacgacc gagcgcagcg agtcagtgag cgaggaagcg gaagagcgcc caatacgcaa    6600
accgcctctc cccgcgcgtt ggccgattca ttaatg                              6636
```

```
<210> SEQ ID NO 43
<211> LENGTH: 6734
<212> TYPE: DNA
<213> ORGANISM: Artificial Sequence
<220> FEATURE:
<223> OTHER INFORMATION: AAVsc-HS-CRE11-TTRenh-TTRm-MVM-hFIXcoPadua-
      bghpolyA

<400> SEQUENCE: 43
```

```
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg ttttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt acaatttaa atatttgctt    840 atacaatctt cctgttttg gggcttttct gattatcaac cggggtacat atgattgaca    900
tgctagtttt acgattaccg ttcatcgccc tgcgcgctcg ctcgctcact gaggccgccc    960
gggcaaagcc cggcgtcgg gcgacctttg gtcgcccggc ctcagtgagc gagcgagcgc   1020
gcagagaggg agtggaattc acgcgtggat ctgaattctg tacaggcgtg gtacggccgc   1080
ggacaaaagc tgcagcaaaa ttgccaaaag taggaactac tgggggtggg ggtcctgtct   1140
cccctgctca gtcaccacct cccctcccta actctcattc tggctcatac cacgtgctcc   1200
cagaagaaac gttctgagca ggggctggta tgagactgcc tcccctccca ggacccactc   1260
ctccctatga ccaggctggt gaccctccct ctagggtgcc agtgccattc actgagcaga   1320
tgtttggcag gtgtctgtta tgtgccagac ctagcagggg acagagtcct cccgatacag   1380
atggaccagt atgtttggac ataaattgtg aaaggagttg ctaatctttc tgtgcaaaat   1440
ccactcttgc ggtcaccgcc aacactccta cacatgtcag gcatccagg ccaggactt   1500 ggtaaccctg ttcaggagca gtcgctctgg agactcccaa gacgagggaa agaaatgggt   1560
ggaaacaggg gcctacactg tgggccggta cccactggga ggatgttgag taagatggaa   1620
aactactgat gacccttgca gagacagagt attaggacat gtttgaacag gggccgggcg   1680
```

-continued

```
atcagcaggt agctctagag gatccccgtc tgtctgcaca tttcgtagag cgagtgttcc     1740
gatactctaa tctccctagg caaggttcat atttgtgtag gttacttatt ctccttttgt     1800
tgactaagtc aataatcaga atcagcaggt ttggagtcag cttggcaggg atcagcagcc     1860
tgggttggaa ggaggggta taaaagcccc ttcaccagga gaagccgtca cacagatcca      1920
caagctcctg gctagaaaga ggtaagggtt taagggatgg ttggttggtg gggtattaat     1980
gtttaattac ctggagcacc tgcctgaaat cacttttttt caggttgggc tagcccacca     2040
tgcagcgcgt gaacatgatc atggccgaga gccccggcct gatcaccatc tgcctgctgg     2100
gctacctgct gagcgccgag tgcaccgtgt cctggacca cgagaacgcc aacaagatcc      2160
tgaaccgccc caagcgctac aacagcggca agctggagga gttcgtgcag ggcaacctgg     2220
agcgcgagtg catggaggag aagtgcagct cgaggaggc ccgcgaggtg ttcgagaaca      2280
ccgagcgcac caccgagttc tggaagcagt acgtggacgg cgaccagtgc gagagcaacc     2340
cctgcctgaa cggcggcagc tgcaaggacg acatcaacag ctacgagtgc tggtgcccct     2400
tcggcttcga gggcaagaac tgcgagctgg acgtgacctg caacatcaag aacggccgct     2460
gcgagcagtt ctgcaagaac agcgccgaca caaggtggt gtgcagctgc accgagggct      2520
accgcctggc cgagaaccag aagagctgcg agcccgccgt gcccttcccc tgcggccgcg     2580
tgagcgtgag ccagaccagc aagctgaccc gcgccgaggc cgtgttcccc gacgtggact     2640
acgtgaacag caccgaggcc gagaccatcc tggacaacat cacccagagc acccagagct     2700
tcaacgactt caccccgcgtg gtgggcggcg aggacgccaa gcccggccag ttcccctggc     2760
aggtggtgct gaacggcaag gtggacgcct tctgcggcgg cagcatcgtg aacgagaagt     2820
ggatcgtgac cgccgcccac tgcgtggaga ccggcgtgaa gatcaccgtg gtggccggcg     2880
agcacaacat cgaggagacc gagcacaccg agcagaagcg caacgtgatc cgcatcatcc     2940
cccaccacaa ctacaacgcc gccatcaaca gtacaacca cgacatcgcc ctgctggagc     3000
tggacgagcc cctggtgctg aacagctacg tgacccccat ctgcatcgcc gacaaggagt     3060
acaccaacat cttcctgaag ttcggcagcg gctacgtgag cggctggggc cgcgtgttcc     3120
acaagggccg cagcgcccctg gtgctgcagt acctgcgcgt gccccctggtg gaccgcgcca     3180 cctgcctgct gagcaccaag ttcaccatct acaacaacat gttctgcgcc ggcttccacg     3240
agggcggccg cgacagctgc cagggcgaca gcggcggccc ccacgtgacc gaggtggagg     3300
gcaccagctt cctgaccggc atcatcagct ggggcgagga gtgcgccatg aagggcaagt     3360
acggcatcta caccaaggtg agccgctacg tgaactggat caaggagaag accaagctga     3420
cctaatgaaa gatggatttc caaggttaat tcattggaat tgaaaattaa cagcccccccc     3480 ccccccccccc ctgcagatct gagccgaatt cctgcagccc gggggatcag cctcgactgt     3540
gccttctagt tgccagccat ctgttgtttg cccctccccc gtgccttcct tgaccctgga     3600
aggtgccact cccactgtcc tttcctaata aaatgaggaa attgcatcgc attgtctgag     3660
taggtgtcat tctattctgg ggggtggggt ggggcaggac agcaaggggg aggattggga     3720
agacaatagc aggcatgctg gggatgcggt gggctctatg gcttctgagg cggaaagaac     3780
cagctgggga ccggtggatc tcgatagcag gcatgctggg gagagatcga tctgaggaac     3840
ccctagtgat ggagttggcc actccctctc tgcgcgctcg ctcgctcact gaggccgccc     3900
gggcaaagcc cgggcgtcgg gcgacctttg gtcgcccggc ctcagtgagc gagcgagcgc     3960
gcagagaggg agtggccaac ccccccccccc cccccccccg gcgattctct tgtttgctcc     4020
agactctcag gcaatgacct gatagccttt gtagagacct ctcaaaaata gctaccctct     4080
```

```
ccggcatgaa tttatcagct agaacggttg aatatcatat tgatggtgat ttgactgtct    4140
ccggcctttc tcaccgtttt gaatctttac ctacacatta ctcaggcatt gcatttaaaa    4200
tatatgaggg ttctaaaaat tttatcctt gcgttgaaat aaaggcttct cccgcaaaag     4260
tattacaggt tcataatgtt tttggtacaa ccgatttagc tttatgctct gaggctttat    4320
tgcttaattt tgctaattct ttgccttgcc tgtatgattt attggatgtt ggaatcgcct    4380
gatgcggtat tttctcctta cgcatctgtg cggtatttca caccgcatat ggtgcactct    4440
cagtacaatc tgctctgatg ccgcatagtt atatggtgca ctctcagtac aatctgctct    4500
gatgccgcat agttaagcca gccccgacac ccgccaacac agccagcccc gacacccgcc    4560
aacacccgct gacgcgccct gacgggcttg tctgctcccg gcatccgctt acagacaagc    4620
tgtgaccgtc tccgggagct gcatgtgtca gaggttttca ccgtcatcac cgaaacgcgc    4680
gagacgaaag ggcctcgtga tacgcctatt tttataggtt aatgtcatga taataatggt    4740
ttcttagacg tcaggtggca cttttcgggg aaatgtgcgc ggaacccta tttgtttatt     4800 tttctaaaata cattcaaata tgtatccgct catgagacaa taaccctgat aaatgctcaa    4860
taatattgaa aaaggaagag tatgagtatt caacatttcc gtgtcgccct tattcccttt    4920
tttgcggcat tttgccttcc tgttttgct cacccagaaa cgctggtgaa agtaaaagat     4980
gctgaagatc agttgggtgc acgagtgggt tacatcgaac tggatctcaa cagcggtaag    5040
atccttgaga gttttcgccc cgaagaacgt tttccaatga tgagcacttt taaagttctg    5100
ctatgtggcg cggtattatc ccgtattgac gccgggcaag agcaactcgg tcgccgcata    5160
cactattctc agaatgactt ggttgagtac tcaccagtca cagaaaagca tcttacggat    5220
ggcatgacag taagagaatt atgcagtgct gccataacca tgagtgataa cactgcggcc    5280
aacttacttc tgacaacgat cggaggaccg aaggagctaa ccgcttttt gcacaacatg     5340 ggggatcatg taactcgcct tgatcgttgg gaaccggagc tgaatgaagc cataccaaac    5400
gacgagcgtg acaccacgat gcctgtagca atggcaacaa cgttgcgcaa actattaact    5460
ggcgaactac ttactctagc ttcccggcaa caattaatag actggatgga ggcggataaa    5520
gttgcaggac cacttctgcg ctcggccctt ccggctggct ggtttattgc tgataaatct    5580
ggagccggtg agcgtgggtc tcgcggtatc attgcagcac tggggccaga tggtaagccc    5640
tcccgtatcg tagttatcta cacgacgggg agtcaggcaa ctatggatga acgaaataga    5700
cagatcgctg agataggtgc ctcactgatt aagcattggt aactgtcaga ccaagtttac    5760
tcatatatac tttagattga tttaaaactt catttttaat ttaaaaggat ctaggtgaag    5820
atcctttttg ataatctcat gaccaaaatc ccttaacgtg agttttcgtt ccactgagcg    5880
tcagaccccg tagaaaagat caaaggatct cttgagatc cttttttct gcgcgtaatc      5940 tgctgcttgc aaacaaaaaa accaccgcta ccagcggtgg tttgtttgcc ggatcaagag    6000
ctaccaactc tttttccgaa ggtaactggc ttcagcagag cgcagatacc aaatactgtc    6060
cttctagtgt agccgtagtt aggccaccac ttcaagaact ctgtagcacc gcctacatac    6120
ctcgctctgc taatcctgtt accagtggct gctgccagtg cgataagtc gtgtcttacc     6180 gggttggact caagacgata gttaccggat aaggcgcagc ggtcgggctg aacggggggt    6240
tcgtgcacac agcccagctt ggagcgaacg acctacaccg aactgagata cctacagcgt    6300
gagctatgag aaagcgccac gcttcccgaa gggagaaagg cggacaggta tccggtaagc    6360
ggcagggtcg aacaggaga gcgcacgagg gagcttccag ggggaaacgc ctggtatctt     6420
```

```
tatagtcctg tcgggtttcg ccacctctga cttgagcgtc gattttttgtg atgctcgtca    6480 gggggggcgga gcctatggaa aaacgccagc aacgcggcct tttttacggtt cctggccttt    6540 tgctggcctt ttgctcacat gttctttcct gcgttatccc ctgattctgt ggataaccgt    6600
attaccgcct ttgagtgagc tgataccgct cgccgcagcc gaacgaccga gcgcagcgag    6660
tcagtgagcg aggaagcgga agagcgccca atacgcaaac cgcctctccc cgcgcgttgg    6720
ccgattcatt aatg                                                      6734

<210> SEQ ID NO 44
<211> LENGTH: 6661
<212> TYPE: DNA
<213> ORGANISM: Artificial Sequence
<220> FEATURE:
<223> OTHER INFORMATION: AAVsc-HS-CRE12-TTRenh-TTRm-MVM-hFIXcoPadua-
      bghpolyA

<400> SEQUENCE: 44
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg ttttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt tacaatttaa atatttgctt    840
atacaatctt cctgtttttg gggcttttct gattatcaac cggggtacat atgattgaca    900
tgctagtttt acgattaccg ttcatcgccc tgcgcgctcg ctcgctcact gaggccgccc    960
gggcaaagcc cggcgtcgg gcgacctttg gtcgcccggc ctcagtgagc gagcgagcgc    1020
gcagagaggg agtggaattc acgcgtggat ctgaattctg tacaggcgtg gtacggccgc    1080
gggtgaggcc acgtcttcc cgccaggttg actcgagcct cctgccagag ccactggccc    1140
cggaggccac cctagaccgc agctggcggc cgctggcacg agtgcagggt aactgagcca    1200
gggccgctgg cgcatttggc ctggccgagg ccaccccgcg cggccgctcc actgtgcccg    1260
aggctgtcct ggaggtgagg ccggcccaca gggaccctgc ccgtgcccgg gctccggtga    1320
gtcagggcgc gttatgcaag tgccccggc gcctcccctt cggtctttca ccccgcgcgg    1380
ttacgaaagc gcgacccccct ccccccggcg ctataaagca gcggggcggc cgcggcgcgc    1440
tcgcctccct cgctccacgc gcgccccgac tcggcggcca ggcttgcgcg cggttcccct    1500
cccggtggtg agtggtaccc actgggagga tgttgagtaa gatggaaaac tactgatgac    1560
ccttgcagag acagagtatt aggacatgtt tgaacagggg ccgggcgatc agcaggtagc    1620
tctagaggat ccccgtctgt ctgcacattt cgtagagcga gtgttccgat actctaatct    1680
```

-continued

```
ccctaggcaa ggttcatatt tgtgtaggtt acttattctc cttttgttga ctaagtcaat    1740
aatcagaatc agcaggtttg gagtcagctt ggcaggatc agcagcctgg gttggaagga    1800
gggggtataa aagcccttc accaggagaa gccgtcacac agatccacaa gctcctggct    1860
agaaagaggt aagggtttaa gggatggttg gttggtgggg tattaatgtt taattacctg    1920
gagcacctgc ctgaaatcac tttttttcag gttgggctag cccaccatgc agcgcgtgaa    1980
catgatcatg gccgagagcc ccggcctgat caccatctgc ctgctgggct acctgctgag    2040
cgccgagtgc accgtgttcc tggaccacga gaacgccaac aagatcctga accgccccaa    2100
gcgctacaac agcggcaagc tggaggagtt cgtgcagggc aacctggagc gcgagtgcat    2160
ggaggagaag tgcagcttcg aggaggcccg cgaggtgttc gagaacaccg agcgcaccac    2220
cgagttctgg aagcagtacg tggacggcga ccagtgcgag agcaaccct gcctgaacgg    2280 cggcagctgc aaggacgaca tcaacagcta cgagtgctgg tgccccttcg gcttcgaggg    2340
caagaactgc gagctggacg tgacctgcaa catcaagaac ggccgctgcg agcagttctg    2400
caagaacagc gccgacaaca aggtggtgtg cagctgcacc gagggctacc gcctggccga    2460
gaaccagaag agctgcgagc ccgccgtgcc cttcccctgc ggccgcgtga gcgtgagcca    2520
gaccagcaag ctgacccgcg ccgaggccgt gttccccgac gtggactacg tgaacagcac    2580
cgaggccgag accatcctgg acaacatcac ccagagcacc cagagcttca cgacttcac    2640 ccgcgtggtg ggcggcgagg acgccaagcc cggccagttc ccctggcagg tggtgctgaa    2700
cggcaaggtg gacgccttct gcggcggcag catcgtgaac gagaagtgga tcgtgaccgc    2760
cgcccactgc gtggagaccg gcgtgaagat caccgtggtg gccggcgagc acaacatcga    2820
ggagaccgag cacaccgagc agaagcgcaa cgtgatccgc atcatcccc accacaacta    2880 caacgccgcc atcaacaagt acaaccacga catcgccctg ctggagctgg acgagcccct    2940
ggtgctgaac agctacgtga cccccatctg catcgccgac aaggagtaca ccaacatctt    3000
cctgaagttc ggcagcggct acgtgagcgg ctggggccgc gtgttccaca agggccgcag    3060
cgccctggtg ctgcagtacc tgcgcgtgcc cctggtggac cgcgccacct gcctgctgag    3120
caccaagttc accatctaca acaacatgtt ctgcgccggc ttccacgagg cgcggccgcga    3180 cagctgccag ggcgacagcg gcggccccca cgtgaccgag gtggagggca ccagcttcct    3240
gaccggcatc atcagctggg gcgaggagtg cgccatgaag ggcaagtacg gcatctacac    3300
caaggtgagc cgctacgtga actggatcaa ggagaagacc aagctgacct aatgaaagat    3360
ggatttccaa ggttaattca ttggaattga aaattaacag ccccccccc cccccctg     3420 cagatctgag ccgaattcct gcagcccggg ggatcagcct cgactgtgcc ttctagttgc    3480
cagccatctg ttgtttgccc ctcccccgtg ccttccttga ccctggaagg tgccactccc    3540
actgtccttt cctaataaaa tgaggaaatt gcatcgcatt gtctgagtag gtgtcattct    3600
attctggggg gtggggtggg gcaggacagc aaggggagg attgggaaga caatagcagg    3660
catgctgggg atgcggtggg ctctatggct tctgaggcgg aaagaaccag ctggggaccg    3720
gtggatctcg atagcaggca tgctggggag agatcgatct gaggaacccc tagtgatgga    3780
gttggccact ccctctctgc gcgctcgctc gctcactgag gccgcccggg caaagcccgg    3840
gcgtcgggcg acctttggtc gcccggcctc agtgagcgag cgagcgcgca gagagggagt    3900
ggccaacccc cccccccccc ccccccggcg attctcttgt ttgctccaga ctctcaggca    3960
atgacctgat agcctttgta gagacctctc aaaaatagct accctctccg gcatgaattt    4020
atcagctaga acggttgaat atcatattga tggtgatttg actgtctccg gcctttctca    4080
```

-continued

```
cccgtttgaa tctttaccta cacattactc aggcattgca tttaaaatat atgagggttc    4140
taaaaatttt tatccttgcg ttgaaataaa ggcttctccc gcaaaagtat tacagggtca    4200
taatgttttt ggtacaaccg atttagcttt atgctctgag gctttattgc ttaattttgc    4260
taattctttg ccttgcctgt atgatttatt ggatgttgga atcgcctgat gcggtatttt    4320
ctccttacgc atctgtgcgg tatttcacac cgcatatggt gcactctcag tacaatctgc    4380
tctgatgccg catagttata tggtgcactc tcagtacaat ctgctctgat gccgcatagt    4440
taagccagcc ccgacacccg ccaacacagc cagccccgac acccgccaac acccgctgac    4500
gcgccctgac gggcttgtct gctcccggca tccgcttaca gacaagctgt gaccgtctcc    4560
gggagctgca tgtgtcagag gttttcaccg tcatcaccga aacgcgcgag acgaaagggc    4620
ctcgtgatac gcctattttt ataggttaat gtcatgataa taatggtttc ttagacgtca    4680
ggtggcactt ttcggggaaa tgtgcgcgga acccctattt gtttattttt ctaaatacat    4740
tcaaatatgt atccgctcat gagacaataa ccctgataaa tgctcaataa tattgaaaaa    4800
ggaagagtat gagtattcaa catttccgtg tcgcccttat tccctttttt gcggcatttt    4860
gccttcctgt ttttgctcac ccagaaacgc tggtgaaagt aaaagatgct gaagatcagt    4920
tgggtgcacg agtgggttac atcgaactgg atctcaacag cggtaagatc cttgagagtt    4980
ttcgccccga agaacgtttt ccaatgatga gcacttttaa agttctgcta tgtggcgcgg    5040
tattatcccg tattgacgcc gggcaagagc aactcggtcg ccgcatacac tattctcaga    5100
atgacttggt tgagtactca ccagtcacag aaaagcatct tacggatggc atgacagtaa    5160
gagaattatg cagtgctgcc ataaccatga gtgataacac tgcggccaac ttacttctga    5220
caacgatcgg aggaccgaag gagctaaccg cttttttgca caacatgggg gatcatgtaa    5280
ctcgccttga tcgttgggaa ccggagctga atgaagccat accaaacgac gagcgtgaca    5340
ccacgatgcc tgtagcaatg gcaacaacgt tgcgcaaact attaactggc gaactactta    5400
ctctagcttc ccggcaacaa ttaatagact ggatggaggc ggataaagtt gcaggaccac    5460
ttctgcgctc ggcccttccg gctggctggt ttattgctga taaatctgga gccggtgagc    5520
gtgggtctcg cggtatcatt gcagcactgg ggccagatgg taagccctcc cgtatcgtag    5580
ttatctacac gacggggagt caggcaacta tggatgaacg aaatagacag atcgctgaga    5640
taggtgcctc actgattaag cattggtaac tgtcagacca agtttactca tatatacttt    5700
agattgattt aaaacttcat ttttaattta aaaggatcta ggtgaagatc ctttttgata    5760
atctcatgac caaaatccct taacgtgagt tttcgttcca ctgagcgtca gaccccgtag    5820
aaaagatcaa aggatcttct tgagatcctt tttttctgcg cgtaatctgc tgcttgcaaa    5880
caaaaaaacc accgctacca gcggtggttt gtttgccgga tcaagagcta ccaactcttt    5940
ttccgaaggt aactggcttc agcagagcgc agataccaaa tactgtcctt ctagtgtagc    6000
cgtagttagg ccaccacttc aagaactctg tagcaccgcc tacatacctc gctctgctaa    6060
tcctgttacc agtggctgct gccagtggcg ataagtcgtg tcttaccggg ttggactcaa    6120
gacgatagtt accggataag gcgcagcggt cgggctgaac ggggggttcg tgcacacagc    6180
ccagcttgga gcgaacgacc tacaccgaac tgagatacct acagcgtgag ctatgagaaa    6240
gcgccacgct tcccgaaggg agaaaggcgg acaggtatcc ggtaagcggc agggtcggaa    6300
caggagagcg cacgagggag cttccagggg gaaacgcctg gtatctttat agtcctgtcg    6360
ggtttcgcca cctctgactt gagcgtcgat ttttgtgatg ctcgtcaggg gggcggagcc    6420
```

-continued

```
tatggaaaaa cgccagcaac gcggcctttt tacggttcct ggccttttgc tggccttttg        6480
ctcacatgtt ctttcctgcg ttatcccctg attctgtgga taaccgtatt accgcctttg        6540
agtgagctga taccgctcgc cgcagccgaa cgaccgagcg cagcgagtca gtgagcgagg        6600
aagcggaaga gcgcccaata cgcaaaccgc ctctccccgc gcgttggccg attcattaat        6660
g                                                                        6661

<210> SEQ ID NO 45
<211> LENGTH: 6678
<212> TYPE: DNA
<213> ORGANISM: Artificial Sequence
<220> FEATURE:
<223> OTHER INFORMATION: AAVsc-HS-CRE13-TTRenh-TTRm-MVM-hFIXcoPadua-
      bghpolyA

<400> SEQUENCE: 45
agctggcgta atagcgaaga ggcccgcacc gatcgccctt cccaacagtt gcgcagcctg          60
aatggcgaat ggcgattccg ttgcaatggc tggcggtaat attgttctgg atattaccag         120
caaggccgat agtttgagtt cttctactca ggcaagtgat gttattacta atcaaagaag         180
tattgcgaca acggttaatt tgcgtgatgg acagactctt ttactcggtg gcctcactga         240
ttataaaaac acttctcagg attctggcgt accgttcctg tctaaaatcc ctttaatcgg         300
cctcctgttt agctcccgct ctgattctaa cgaggaaagc acgttatacg tgctcgtcaa         360
agcaaccata gtacgcgccc tgtagcggcg cattaagcgc ggcgggtgtg gtggttacgc         420
gcagcgtgac cgctacactt gccagcgccc tagcgcccgc tcctttcgct ttcttccctt         480
cctttctcgc cacgttcgcc ggctttcccc gtcaagctct aaatcggggg ctccctttag         540
ggttccgatt tagtgcttta cggcacctcg accccaaaaa acttgattag ggtgatggtt         600
cacgtagtgg gccatcgccc tgatagacgg tttttcgccc tttgacgttg gagtccacgt         660
tctttaatag tggactcttg ttccaaactg gaacaacact caaccctatc tcggtctatt         720
cttttgattt ataagggatt ttgccgattt cggcctattg gttaaaaaat gagctgattt         780
aacaaaaatt taacgcgaac tttaacaaaa tattaacgtt tacaatttaa atatttgctt         840
atacaatctt cctgtttttg gggcttttct gattatcaac cggggtacat atgattgaca         900
tgctagtttt acgattaccg ttcatcgccc tgcgcgctcg ctcgctcact gaggccgccc         960
gggcaaagcc cggcgtcgg gcgacctttg tcgcccggc ctcagtgagc gagcgagcgc         1020
gcagagaggg agtggaattc acgcgtggat ctgaattctg tacaggcgtg gtacggccgc        1080
ggaaatacct aaactagtca cactgttttg attcaattgg ctactgaagt tatagaatgt        1140
tgtttactct tctctccttt gtctactccc cagccaacaa aacaaccgac cttagctgtt        1200
ttgaaaataa atgaaaattc aacatgggt ttgaaataaa attgcatcat aaacaatcgg        1260
taggtgtttt tcaaagtggt ttcagggaag tgccacggag taagcaggcg accaccgagg        1320
ctgctaaaat atttcctgtc ctgaccaggg ttgcgtttct ggagaatatt taacaggag        1380 ggttttaacg cttttaaaga tgttgaaact aaagaacaaa tattgaccag agggcaccac        1440
aacgctcctg aaagagagta aaatacatcc tttataaaat gaaaaactac ttggatgaat        1500
tattccaaaa ttcctgcaca gtggacctc ggtacccact gggaggatgt tgagtaagat        1560
ggaaaactac tgatgaccct tgcagagaca gagtattagg acatgtttga acaggggccg        1620
ggcgatcagc aggtagctct agaggatccc cgtctgtctg cacatttcgt agagcgagtg        1680
ttccgatact ctaatctccc taggcaaggt tcatatttgt gtaggttact tattctcctt        1740
```

-continued

```
ttgttgacta agtcaataat cagaatcagc aggtttggag tcagcttggc agggatcagc    1800
agcctgggtt ggaaggaggg ggtataaaag cccccttcacc aggagaagcc gtcacacaga    1860
tccacaagct cctggctaga aagaggtaag ggtttaaggg atggttggtt ggtggggtat    1920
taatgtttaa ttacctggag cacctgcctg aaatcacttt ttttcaggtt gggctagccc    1980
accatgcagc gcgtgaacat gatcatggcc gagagccccg gcctgatcac catctgcctg    2040
ctgggctacc tgctgagcgc cgagtgcacc gtgttcctgg accacgagaa cgccaacaag    2100
atcctgaacc gccccaagcg ctacaacagc ggcaagctgg aggagttcgt gcagggcaac    2160
ctggagcgcg agtgcatgga ggagaagtgc agcttcgagg aggcccgcga ggtgttcgag    2220
aacaccgagc gcaccaccga gttctggaag cagtacgtgg acggcgacca gtgcgagagc    2280
aacccctgcc tgaacggcgg cagctgcaag gacgacatca acagctacga gtgctggtgc    2340
cccttcggct tcgagggcaa gaactgcgag ctggacgtga cctgcaacat caagaacggc    2400
cgctgcgagc agttctgcaa gaacagcgcc gacaacaagg tggtgtgcag ctgcaccgag    2460
ggctaccgcc tggccgagaa ccagaagagc tgcgagcccg ccgtgccctt ccctgcggc    2520 cgcgtgagcg tgagccagac cagcaagctg acccgcgccg aggccgtgtt ccccgacgtg    2580
gactacgtga acagcaccga ggccgagacc atcctggaca acatcacccca gagcacccag    2640 agcttcaacg acttcaccccg cgtggtgggc ggcgaggacg ccaagcccgg ccagttcccc    2700
tggcaggtgg tgctgaacgg caaggtggac gccttctgcg gcggcagcat cgtgaacgag    2760
aagtggatcg tgaccgccgc ccactgcgtg gagaccggcg tgaagatcac cgtggtggcc    2820
ggcgagcaca acatcgagga gaccgagcac accgagcaga gcgcaacgt gatccgcatc    2880 atcccccacc acaactacaa cgccgccatc aacaagtaca accacgacat cgccctgctg    2940
gagctggacg agcccctggt gctgaacagc tacgtgaccc ccatctgcat cgccgacaag    3000
gagtacacca acatcttcct gaagttcggc agcggctacg tgagcggctg gggccgcgtg    3060
ttccacaagg gccgcagcgc cctggtgctg cagtacctgc gcgtgcccct ggtggaccgc    3120
gccacctgcc tgctgagcac caagttcacc atctacaaca acatgttctg cgccggcttc    3180
cacgagggcg gccgcgacag ctgccagggc gacagcggcg gcccccacgt gaccgaggtg    3240
gagggcacca gcttcctgac cggcatcatc agctggggcg aggagtgcgc catgaagggc    3300
aagtacggca tctacaccaa ggtgagccgc tacgtgaact ggatcaagga gaagaccaag    3360
ctgacctaat gaaagatgga tttccaaggt taattcattg gaattgaaaa ttaacagccc    3420
cccccccccc cccctgcag atctgagccg aattcctgca gcccggggga tcagcctcga    3480
ctgtgccttc tagttgccag ccatctgttg tttgcccctc ccccgtgcct tccttgaccc    3540
tggaaggtgc cactcccact gtcctttcct aataaaatga ggaaattgca tcgcattgtc    3600
tgagtaggtg tcattctatt ctggggggtg gggtggggca ggacagcaag ggggaggatt    3660
gggaagacaa tagcaggcat gctggggatg cggtgggctc tatggcttct gaggcggaaa    3720
gaaccagctg gggaccggtg gatctcgata gcaggcatgc tggggagaga tcgatctgag    3780
gaacccctag tgatggagtt ggccactccc tctctgcgcg ctcgctcgct cactgaggcc    3840
gcccgggcaa agcccgggcg tcgggcgacc tttggtcgcc cggcctcagt gagcgagcga    3900
gcgcgcagag agggagtggc caacccccccc ccccccccc cccggcgatt ctcttgtttg    3960
ctccagactc tcaggcaatg acctgatagc ctttgtagag acctctcaaa aatagctacc    4020
ctctccggca tgaatttatc agctagaacg gttgaatatc atattgatgg tgatttgact    4080
gtctccggcc tttctcaccc gtttgaatct ttacctacac attactcagg cattgcattt    4140
```

-continued

```
aaaatatatg agggttctaa aaattttat ccttgcgttg aaataaaggc ttctcccgca      4200
aaagtattac agggtcataa tgttttggt acaaccgatt tagctttatg ctctgaggct       4260
ttattgctta attttgctaa ttctttgcct tgcctgtatg atttattgga tgttggaatc     4320
gcctgatgcg gtattttctc cttacgcatc tgtgcggtat ttcacaccgc atatggtgca     4380
ctctcagtac aatctgctct gatgccgcat agttatatgg tgcactctca gtacaatctg     4440
ctctgatgcc gcatagttaa gccagccccg acacccgcca acacagccag ccccgacacc     4500
cgccaacacc cgctgacgcg ccctgacggg cttgtctgct cccggcatcc gcttacagac     4560
aagctgtgac cgtctccggg agctgcatgt gtcagaggtt ttcaccgtca tcaccgaaac     4620
gcgcgagacg aaagggcctc gtgatacgcc tattttata ggttaatgtc atgataataa      4680
tggtttctta gacgtcaggt ggcactttc ggggaaatgt gcgcggaacc cctatttgtt      4740 tattttcta aatacattca aatatgtatc cgctcatgag acaataaccc tgataaatgc      4800
tcaataatat tgaaaaagga agagtatgag tattcaacat ttccgtgtcg cccttattcc     4860
cttttttgcg gcattttgcc ttcctgtttt tgctcaccca gaaacgctgg tgaaagtaaa     4920
agatgctgaa gatcagttgg gtgcacgagt gggttacatc gaactggatc tcaacagcgg     4980
taagatcctt gagagttttc gccccgaaga acgttttcca atgatgagca cttttaaagt     5040
tctgctatgt ggcgcggtat tatcccgtat tgacgccggg caagagcaac tcggtcgccg     5100
catacactat tctcagaatg acttggttga gtactcacca gtcacagaaa agcatcttac     5160
ggatggcatg acagtaagag aattatgcag tgctgccata accatgagtg ataacactgc     5220
ggccaactta cttctgacaa cgatcggagg accgaaggag ctaaccgctt ttttgcacaa     5280
catgggggat catgtaactc gccttgatcg ttgggaaccg gagctgaatg aagccatacc     5340
aaacgacgag cgtgacacca cgatgcctgt agcaatggca caacgttgc gcaaactatt      5400 aactggcgaa ctacttactc tagcttcccg gcaacaatta atagactgga tggaggcgga     5460
taaagttgca ggaccacttc tgcgctcggc ccttccggct ggctggttta ttgctgataa     5520
atctggagcc ggtgagcgtg ggtctcgcgg tatcattgca gcactggggc cagatggtaa     5580
gccctcccgt atcgtagtta tctacacgac ggggagtcag gcaactatgg atgaacgaaa     5640
tagacagatc gctgagatag gtgcctcact gattaagcat tggtaactgt cagaccaagt     5700
ttactcatat atactttaga ttgatttaaa acttcattt taatttaaaa ggatctaggt      5760
gaagatcctt tttgataatc tcatgaccaa atcccttaa cgtgagtttt cgttccactg       5820
agcgtcagac cccgtagaaa agatcaaagg atcttcttga tccttttt ttctgcgcgt        5880 aatctgctgc ttgcaaacaa aaaaaccacc gctaccagcg gtggtttgtt tgccggatca     5940
agagctacca actcttttc cgaaggtaac tggcttcagc agagcgcaga taccaaatac      6000
tgtccttcta gtgtagccgt agttaggcca ccacttcaag aactctgtag caccgcctac     6060
atacctcgct ctgctaatcc tgttaccagt ggctgctgcc agtggcgata agtcgtgtct     6120
taccgggttg gactcaagac gatagttacc ggataaggcg cagcggtcgg gctgaacggg     6180
gggttcgtgc acacagccca gcttggagcg aacgacctac accgaactga gatacctaca     6240
gcgtgagcta tgagaaagcg ccacgcttcc cgaagggaga aaggcggaca ggtatccggt     6300
aagcggcagg gtcggaacag gagagcgcac gagggagctt ccaggggaa acgcctggta       6360 tctttatagt cctgtcgggt ttcgccacct ctgacttgag cgtcgatttt tgtgatgctc     6420
gtcagggggg cggagcctat ggaaaaacgc cagcaacgcg gcctttttac ggttcctggc     6480
```

-continued

```
cttttgctgg ccttttgctc acatgttctt tcctgcgtta tcccctgatt ctgtggataa   6540
ccgtattacc gcctttgagt gagctgatac cgctcgccgc agccgaacga ccgagcgcag   6600
cgagtcagtg agcgaggaag cggaagagcg cccaatacgc aaaccgcctc tccccgcgcg   6660
ttggccgatt cattaatg                                                 6678

<210> SEQ ID NO 46
<211> LENGTH: 6565
<212> TYPE: DNA
<213> ORGANISM: Artificial Sequence
<220> FEATURE:
<223> OTHER INFORMATION: AAVsc-HS-CRE14-TTRenh-TTRm-MVM-hFIXcoPadua-
      bghpolyA

<400> SEQUENCE: 46
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt acaatttaa atatttgctt    840 atacaatctt cctgtttttg gggcttttct gattatcaac cggggtacat atgattgaca    900
tgctagtttt acgattaccg ttcatcgccc tgcgcgctcg ctcgctcact gaggccgccc    960
gggcaaagcc cgggcgtcgg gcgacctttg gtcgcccggc ctcagtgagc gagcgagcgc   1020
gcagagaggg agtggaattc acgcgtggat ctgaattctg tacaggcgtg gtacggccgc   1080
ggctgagctc atctgggctg cagggctggc gggacagcag cgtggactca gtctcctagg   1140
gatttcccaa ctctcccgcc cgcttgctgc atctggacac cctgcctcag gccctcatct   1200
ccactggtca gcaggtgacc tttgcccagc gccctgggtc ctcagtgcct gctgccctgg   1260
agatgatata aaacaggtca gaaccctcct gcctgtctgc tcagttcatc cctagaggca   1320
gctgctccag gtaatgccct ctggggaggg gaaagaggag gggaggagga tgaagagggg   1380
caagaggagc tccctgccca gcccagccag caagcctggt acccactggg aggatgttga   1440
gtaagatgga aaactactga tgacccttgc agagacagag tattaggaca tgtttgaaca   1500
ggggccgggc gatcagcagg tagctctaga ggatccccgt ctgtctgcac atttcgtaga   1560
gcgagtgttc cgatactcta atctccctag gcaaggttca tatttgtgta ggttacttat   1620
tctccttttg ttgactaagt caataatcag aatcagcagg tttggagtca gcttggcagg   1680
gatcagcagc ctgggttgga aggaggggggt ataaaagccc cttcaccagg agaagccgtc   1740
acacagatcc acaagctcct ggctagaaag aggtaagggt ttaagggatg gttggttggt   1800
```

-continued

```
ggggtattaa tgtttaatta cctggagcac ctgcctgaaa tcactttttt tcaggttggg      1860
ctagcccacc atgcagcgcg tgaacatgat catggccgag agccccggcc tgatcaccat      1920
ctgcctgctg ggctacctgc tgagcgccga gtgcaccgtg ttcctggacc acgagaacgc      1980
caacaagatc ctgaaccgcc ccaagcgcta caacagcggc aagctggagg agttcgtgca      2040
gggcaacctg gagcgcgagt gcatggagga gaagtgcagc ttcgaggagg cccgcgaggt      2100
gttcgagaac accgagcgca ccaccgagtt ctggaagcag tacgtggacg cgaccagtg      2160 cgagagcaac ccctgcctga acggcggcag ctgcaaggac gacatcaaca gctacgagtg      2220
ctggtgcccc ttcggcttcg agggcaagaa ctgcgagctg gacgtgacct gcaacatcaa      2280
gaacggccgc tgcgagcagt tctgcaagaa cagcgccgac aacaaggtgg tgtgcagctg      2340
caccgagggc taccgcctgg ccgagaacca gaagagctgc gagcccgccg tgcccttccc      2400
ctgcggccgc gtgagcgtga gccagaccag caagctgacc cgcgccgagg ccgtgttccc      2460
cgacgtggac tacgtgaaca gcaccgaggc cgagaccatc ctggacaaca tcacccagag      2520
cacccagagc ttcaacgact tcacccgcgt ggtgggcggc gaggacgcca gcccggcca      2580 gttcccctgg caggtggtgc tgaacggcaa ggtggacgcc ttctgcggcg gcagcatcgt      2640
gaacgagaag tggatcgtga ccgccgccca ctgcgtggag accggcgtga agatcaccgt      2700
ggtggccggc gagcacaaca tcgaggagac cgagcacacc gagcagaagc gcaacgtgat      2760
ccgcatcatc ccccaccaca actacaacgc cgccatcaac aagtacaacc acgacatcgc      2820
cctgctggag ctggacgagc ccctggtgct gaacagctac gtgacccca tctgcatcgc      2880 cgacaaggag tacaccaaca tcttcctgaa gttcggcagc ggctacgtga gcggctgggg      2940
ccgcgtgttc cacaagggcc gcagcgccct ggtgctgcag tacctgcgcg tgcccctggt      3000
ggaccgcgcc acctgcctgc tgagcaccaa gttcaccatc tacaacaaca tgttctgcgc      3060
cggcttccac gagggcggcc gcgacagctg ccagggcgac agcggcggcc cccacgtgac      3120
cgaggtggag ggcaccagct tcctgaccgg catcatcagc tggggcgagg agtgcgccat      3180
gaagggcaag tacggcatct acaccaaggt gagccgctac gtgaactgga tcaaggagaa      3240
gaccaagctg acctaatgaa agatggattt ccaaggttaa ttcattggaa ttgaaaatta      3300
acagcccccc cccccccccc cctgcagatc tgagccgaat tcctgcagcc cggggatca      3360 gcctcgactg tgccttctag ttgccagcca tctgttgttt gcccctcccc cgtgccttcc      3420
ttgaccctgg aaggtgccac tcccactgtc ctttcctaat aaaatgagga aattgcatcg      3480
cattgtctga gtaggtgtca ttctattctg gggggtgggg tggggcagga cagcaagggg      3540
gaggattggg aagacaatag caggcatgct ggggatgcgg tgggctctat ggcttctgag      3600
gcggaaagaa ccagctgggg accggtggat ctcgatagca ggcatgctgg ggagagatcg      3660
atctgaggaa ccctagtga tggagttggc cactccctct ctgcgcgctc gctcgctcac      3720
tgaggccgcc cgggcaaagc ccgggcgtcg ggcgaccttt ggtcgcccgg cctcagtgag      3780
cgagcgagcg cgcagagagg gagtggccaa cccccccccc cccccccccc ggcgattctc      3840
ttgtttgctc cagactctca ggcaatgacc tgatagcctt tgtagagacc tctcaaaaat      3900
agctaccctc tccggcatga atttatcagc tagaacggtt gaatatcata ttgatggtga      3960
tttgactgtc tccggccttt ctcacccgtt tgaatcttta cctacacatt actcaggcat      4020
tgcatttaaa atatatgagg gttctaaaaa tttttatcct tgcgttgaaa taaaggcttc      4080
tcccgcaaaa gtattacagg gtcataatgt tttttggtaca accgatttag ctttatgctc      4140
tgaggcttta ttgcttaatt ttgctaattc tttgccttgc ctgtatgatt tattggatgt      4200
```

-continued

```
tggaatcgcc tgatgcggta ttttctcctt acgcatctgt gcggtatttc acaccgcata      4260
tggtgcactc tcagtacaat ctgctctgat gccgcatagt tatatggtgc actctcagta      4320
caatctgctc tgatgccgca tagttaagcc agccccgaca cccgccaaca cagccagccc      4380
cgacacccgc caacacccgc tgacgcgccc tgacgggctt gtctgctccc ggcatccgct      4440
tacagacaag ctgtgaccgt ctccgggagc tgcatgtgtc agaggttttc accgtcatca      4500
ccgaaacgcg cgagacgaaa gggcctcgtg atacgcctat ttttataggt taatgtcatg      4560
ataataatgg tttcttagac gtcaggtggc acttttcggg gaaatgtgcg cggaacccct      4620
atttgtttat ttttctaaat acattcaaat atgtatccgc tcatgagaca ataaccctga      4680
taaatgctca ataatattga aaaaggaaga gtatgagtat tcaacatttc cgtgtcgccc      4740
ttattccctt ttttgcggca ttttgccttc ctgtttttgc tcacccagaa acgctggtga      4800
aagtaaaaga tgctgaagat cagttgggtg cacgagtggg ttacatcgaa ctggatctca      4860
acagcggtaa gatccttgag agttttcgcc ccgaagaacg ttttccaatg atgagcactt      4920
ttaaagttct gctatgtggc gcggtattat cccgtattga cgccgggcaa gagcaactcg      4980
gtcgccgcat acactattct cagaatgact tggttgagta ctcaccagtc acagaaaagc      5040
atcttacgga tggcatgaca gtaagagaat tatgcagtgc tgccataacc atgagtgata      5100
acactgcggc caacttactt ctgacaacga tcggaggacc gaaggagcta accgcttttt      5160
tgcacaacat gggggatcat gtaactcgcc ttgatcgttg ggaaccggag ctgaatgaag      5220
ccataccaaa cgacgagcgt gacaccacga tgcctgtagc aatggcaaca cgttgcgca      5280 aactattaac tggcgaacta cttactctag cttcccggca acaattaata gactggatgg      5340
aggcggataa agttgcagga ccacttctgc gctcggccct tccggctggc tggtttattg      5400
ctgataaatc tggagccggt gagcgtgggt ctcgcggtat cattgcagca ctggggccag      5460
atggtaagcc ctcccgtatc gtagttatct acacgacggg gagtcaggca actatggatg      5520
aacgaaatag acagatcgct gagataggtg cctcactgat taagcattgg taactgtcag      5580
accaagttta ctcatatata ctttagattg atttaaaact tcattttaa tttaaaagga      5640 tctaggtgaa gatccttttt gataatctca tgaccaaaat cccttaacgt gagttttcgt      5700
tccactgagc gtcagacccc gtagaaaaga tcaaaggatc ttcttgagat ccttttttc      5760 tgcgcgtaat ctgctgcttg caaacaaaaa aaccaccgct accagcggtg gtttgtttgc      5820
cggatcaaga gctaccaact cttttccga aggtaactgg cttcagcaga gcgcagatac      5880
caaatactgt ccttctagtg tagccgtagt taggccacca cttcaagaac tctgtagcac      5940
cgcctacata cctcgctctg ctaatcctgt taccagtggc tgctgccagt ggcgataagt      6000
cgtgtcttac cgggttggac tcaagacgat agttaccgga taaggcgcag cggtcgggct      6060
gaacgggggg ttcgtgcaca gcccagct tggagcgaac gacctacacc gaactgagat      6120
acctacagcg tgagctatga gaaagcgcca cgcttcccga aggagaaag gcggacaggt      6180 atccggtaag cggcagggtc ggaacaggag agcgcacgag ggagcttcca gggggaaacg      6240
cctggtatct ttatagtcct gtcgggtttc gccacctctg acttgagcgt cgatttttgt      6300
gatgctcgtc aggggggcgg agcctatgga aaaacgccag caacgcggcc tttttacggt      6360
tcctggcctt ttgctggcct tttgctcaca tgttctttcc tgcgttatcc cctgattctg      6420
tggataaccg tattaccgcc tttgagtgag ctgataccgc tcgccgcagc cgaacgaccg      6480
agcgcagcga gtcagtgagc gaggaagcgg aagagcgccc aatacgcaaa ccgcctctcc      6540
```

-continued

```
ccgcgcgttg gccgattcat taatg                                       6565

<210> SEQ ID NO 47
<211> LENGTH: 6661
<212> TYPE: DNA
<213> ORGANISM: Artificial Sequence
<220> FEATURE:
<223> OTHER INFORMATION: AAVsc-HS-CRE15-TTRenh-TTRm-MVM-hFIXcoPadua-
      bghpolyA

<400> SEQUENCE: 47
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt tacaatttaa atatttgctt    840
atacaatctt cctgtttttg gggcttttct gattatcaac cggggtacat atgattgaca    900
tgctagtttt acgattaccg ttcatcgccc tgcgcgctcg ctcgctcact gaggccgccc    960
gggcaaagcc cggcgtcgg gcgacctttg gtcgcccggc ctcagtgagc gagcgagcgc   1020
gcagagaggg agtggaattc acgcgtggat ctgaattctg tacaggcgtg gtacggccgc   1080
ggagaagggt cagcggcccc tcctggacca ccgactcccc gcagaactcc tctgtgccct   1140
ctcctcacca gaccttgttc ctcccagttg ctcccacagc caggggggcag tgagggctgc   1200 tcttccccca gccccactga ggaacccagg aaggtgaacg agagaatcag tcctggtggg   1260
ggctggggag ggcccagac atgagaccag ctcctccccc aggggatgtt atcagtgggt   1320
ccagagggca aaatagggag cctggtggag ggaggggcaa aggcctcggg ctctgagcgg   1380
ccttggccct tctccaccaa cccctgccct acactaaggg ggaggcagcg ggggcacac   1440 agggtggggg cggtgggggg ctgctgggt gagcagcact cgcctgcctg gattgaaacc   1500
cagagatgga ggtggtaccc actgggagga tgttgagtaa gatggaaaac tactgatgac   1560
ccttgcagag acagagtatt aggacatgtt tgaacagggg ccgggcgatc agcaggtagc   1620
tctagaggat ccccgtctgt ctgcacattt cgtagagcga gtgttccgat actctaatct   1680
ccctaggcaa ggttcatatt tgtgtaggtt acttattctc cttttgttga ctaagtcaat   1740
aatcagaatc agcaggtttg gagtcagctt ggcaggatc agcagcctgg gttggaagga   1800 ggggtataa aagccccttc accaggagaa gccgtcacac agatccacaa gctcctggct   1860
agaaagaggt aagggtttaa gggatggttg gttggtgggg tattaatgtt taattacctg   1920
gagcacctgc ctgaaatcac ttttttttcag gttgggctag cccaccatgc agcgcgtgaa   1980
```

-continued

```
catgatcatg gccgagagcc ccggcctgat caccatctgc ctgctgggct acctgctgag      2040
cgccgagtgc accgtgttcc tggaccacga gaacgccaac aagatcctga accgcccaa       2100 gcgctacaac agcggcaagc tggaggagtt cgtgcagggc aacctggagc gcgagtgcat      2160
ggaggagaag tgcagcttcg aggaggcccg cgaggtgttc gagaacaccg agcgcaccac      2220
cgagttctgg aagcagtacg tggacggcga ccagtgcgag agcaacccct gcctgaacgg      2280
cggcagctgc aaggacgaca tcaacagcta cgagtgctgg tgcccccttcg gcttcgaggg     2340 caagaactgc gagctggacg tgacctgcaa catcaagaac ggccgctgcg agcagttctg      2400
caagaacagc gccgacaaca aggtggtgtg cagctgcacc gagggctacc gcctggccga      2460
gaaccagaag agctgcgagc ccgccgtgcc cttcccctgc ggccgcgtga gcgtgagcca      2520
gaccagcaag ctgacccgcg ccgaggccgt gttccccgac gtggactacg tgaacagcac      2580
cgaggccgag accatcctgg acaacatcac ccagagcacc cagagcttca cgacttcac      2640 ccgcgtggtg ggcggcgagg acgccaagcc cggccagttc ccctggcagg tggtgctgaa     2700
cggcaaggtg gacgccttct gcggcggcag catcgtgaac gagaagtgga tcgtgaccgc      2760
cgcccactgc gtggagaccg gcgtgaagat caccgtggtg gccggcgagc acaacatcga     2820
ggagaccgag cacaccgagc agaagcgcaa cgtgatccgc atcatccccc accacaacta      2880
caacgccgcc atcaacaagt acaaccacga catcgccctg ctggagctgg acgagcccct      2940
ggtgctgaac agctacgtga cccccatctg catcgccgac aaggagtaca ccaacatctt      3000
cctgaagttc ggcagcggct acgtgagcgg ctggggccgc gtgttccaca agggccgcag     3060
cgccctggtg ctgcagtacc tgcgcgtgcc cctggtggac cgcgccacct gcctgctgag     3120
caccaagttc accatctaca acaacatgtt ctgcgccggc ttccacgagg gcggccgcga      3180
cagctgccag ggcgacagcg gcggccccca cgtgaccgag gtggagggca ccagcttcct     3240
gaccggcatc atcagctggg gcgaggagtg cgccatgaag ggcaagtacg gcatctacac     3300
caaggtgagc cgctacgtga actggatcaa ggagaagacc aagctgacct aatgaaagat     3360
ggatttccaa ggttaattca ttggaattga aaattaacag cccccccccc cccccccctg     3420
cagatctgag ccgaattcct gcagcccggg ggatcagcct cgactgtgcc ttctagttgc      3480
cagccatctg ttgtttgccc ctccccgtg ccttccttga ccctggaagg tgccactccc      3540 actgtcctttt cctaataaaa tgaggaaatt gcatcgcatt gtctgagtag gtgtcattct     3600
attctggggg gtggggtggg gcaggacagc aaggggggagg attgggaaga caatagcagg      3660
catgctgggg atgcggtggg ctctatggct tctgaggcgg aaagaaccag ctggggaccg      3720
gtggatctcg atagcaggca tgctggggag agatcgatct gaggaacccc tagtgatgga     3780
gttggccact ccctctctgc gcgctcgctc gctcactgag gccgcccggg caaagcccgg      3840
gcgtcgggcg acctttggtc gcccggcctc agtgagcgag cgagcgcgca gagagggagt      3900
ggccaacccc cccccccccc cccccggcg attctcttgt ttgctccaga ctctcaggca      3960
atgacctgat agcctttgta gagacctctc aaaaatagct accctctccg gcatgaattt      4020
atcagctaga acggttgaat atcatattga tggtgatttg actgtctccg gcctttctca     4080
cccgtttgaa tctttaccta cacattactc aggcattgca tttaaaatat atgagggttc     4140
taaaaatttt tatccttgcg ttgaaataaa ggcttctccc gcaaaagtat tacagggtca     4200
taatgttttt ggtacaaccg atttagcttt atgctctgag gctttattgc ttaattttgc     4260
taattctttg ccttgcctgt atgatttatt ggatgttgga atcgcctgat gcggtatttt     4320
ctccttacgc atctgtgcgg tatttcacac cgcatatggt gcactctcag tacaatctgc     4380
```

-continued

```
tctgatgccg catagttata tggtgcactc tcagtacaat ctgctctgat gccgcatagt    4440
taagccagcc ccgacacccg ccaacacagc cagccccgac acccgccaac acccgctgac    4500
gcgccctgac gggcttgtct gctcccggca tccgcttaca gacaagctgt gaccgtctcc    4560
gggagctgca tgtgtcagag gttttcaccg tcatcaccga aacgcgcgag acgaaagggc    4620
ctcgtgatac gcctattttt ataggttaat gtcatgataa taatggtttc ttagacgtca    4680
ggtggcactt ttcggggaaa tgtgcgcgga acccctattt gtttattttt ctaaatacat    4740
tcaaatatgt atccgctcat gagacaataa ccctgataaa tgctcaataa tattgaaaaa    4800
ggaagagtat gagtattcaa catttccgtg tcgcccttat tccctttttt gcggcatttt    4860
gccttcctgt ttttgctcac ccagaaacgc tggtgaaagt aaaagatgct gaagatcagt    4920
tgggtgcacg agtgggttac atcgaactgg atctcaacag cggtaagatc cttgagagtt    4980
ttcgccccga agaacgtttt ccaatgatga gcacttttaa agttctgcta tgtggcgcgg    5040
tattatcccg tattgacgcc gggcaagagc aactcggtcg ccgcatacac tattctcaga    5100
atgacttggt tgagtactca ccagtcacag aaaagcatct tacggatggc atgacagtaa    5160
gagaattatg cagtgctgcc ataaccatga gtgataacac tgcggccaac ttacttctga    5220
caacgatcgg aggaccgaag gagctaaccg ctttttttgca caacatgggg gatcatgtaa    5280
ctcgccttga tcgttgggaa ccggagctga atgaagccat accaaacgac gagcgtgaca    5340
ccacgatgcc tgtagcaatg gcaacaacgt tgcgcaaact attaactggc gaactactta    5400
ctctagcttc ccggcaacaa ttaatagact ggatggaggc ggataaagtt gcaggaccac    5460
ttctgcgctc ggcccttccg gctggctggt ttattgctga taaatctgga gccggtgagc    5520
gtgggtctcg cggtatcatt gcagcactgg ggccagatgg taagccctcc cgtatcgtag    5580
ttatctacac gacggggagt caggcaacta tggatgaacg aaatagacag atcgctgaga    5640
taggtgcctc actgattaag cattggtaac tgtcagacca agtttactca tatatacttt    5700
agattgattt aaaacttcat ttttaattta aaaggatcta ggtgaagatc cttttttgata    5760 atctcatgac caaaatccct taacgtgagt tttcgttcca ctgagcgtca gaccccgtag    5820
aaaagatcaa aggatcttct tgagatcctt tttttctgcg cgtaatctgc tgcttgcaaa    5880
caaaaaaacc accgctacca gcggtggttt gtttgccgga tcaagagcta ccaactcttt    5940
ttccgaaggt aactggcttc agcagagcgc agataccaaa tactgtcctt ctagtgtagc    6000
cgtagttagg ccaccacttc aagaactctg tagcaccgcc tacatacctc gctctgctaa    6060
tcctgttacc agtggctgct gccagtggcg ataagtcgtg tcttaccggg ttggactcaa    6120
gacgatagtt accggataag gcgcagcggt cgggctgaac ggggggttcg tgcacacagc    6180
ccagcttgga gcgaacgacc tacaccgaac tgagatacct acagcgtgag ctatgagaaa    6240
gcgccacgct tcccgaaggg agaaaggcgg acaggtatcc ggtaagcggc agggtcggaa    6300
caggagagcg cacgagggag cttccagggg gaaacgcctg gtatctttat agtcctgtcg    6360
ggtttcgcca cctctgactt gagcgtcgat ttttgtgatg ctcgtcaggg gggcggagcc    6420
tatggaaaaa cgccagcaac gcggcctttt tacggttcct ggccttttgc tggccttttg    6480
ctcacatgtt ctttcctgcg ttatcccctg attctgtgga taaccgtatt accgcctttg    6540
agtgagctga taccgctcgc cgcagccgaa cgaccgagcg cagcgagtca gtgagcgagg    6600
aagcggaaga gcgcccaata cgcaaaccgc ctctccccgc gcgttggccg attcattaat    6660
g                                                                    6661
```

<210> SEQ ID NO 48
<211> LENGTH: 6789
<212> TYPE: DNA
<213> ORGANISM: Artificial Sequence
<220> FEATURE:
<223> OTHER INFORMATION: AAVsc-HS-CRE16-TTRenh-TTRm-MVM-hFIXcoPadua-
      bghpolyA

<400> SEQUENCE: 48
agctggcgta atagcgaaga ggcccgcacc gatcgccctt cccaacagtt gcgcagcctg       60
aatggcgaat ggcgattccg ttgcaatggc tggcggtaat attgttctgg atattaccag      120
caaggccgat agtttgagtt cttctactca ggcaagtgat gttattacta atcaaagaag      180
tattgcgaca acggttaatt tgcgtgatgg acagactctt ttactcggtg gcctcactga      240
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg ttttttcgcc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt acaatttaa atatttgctt      840 atacaatctt cctgtttttg gggcttttct gattatcaac cggggtacat atgattgaca      900
tgctagtttt acgattaccg ttcatcgccc tgcgcgctcg ctcgctcact gaggccgccc      960
gggcaaagcc cgggcgtcgg gcgacctttg gtcgcccggc ctcagtgagc gagcgagcgc     1020
gcagagaggg agtggaattc acgcgtggat ctgaattctg tacaggcgtg gtacggccgc     1080
gggtagctga tgggaagagc agactgcctt ccagccaggc ctggtcctgt gagtcaggga     1140
cgtccatctt agtgggcatg aaaggcctgt gtgatctcga gggagacatc gcctctccaa     1200
gcctctcctt atctgtgcaa caggcagact taatgattgg tgaggcaatg aggctgatag     1260
ctcagcatta gctacagcca cccctcctgg ccaaccacac agggatcaaa ccaggggtca     1320
gtccagaggt cagagtcagg agcagacaac tcagatccag ccagggacag gcaggtcaca     1380
cggacatgtg cctcacgtat gcttcaaggg gccctccccc gggcagaact gaaggacagc     1440
tcctgttgcc ataggaggga gctgggtgag atactaggag gaacttccgg catgatgatg     1500
tgtgatgaac aagggcctct ggccaacagg tctgaatcag ggctgcccag cccagcctgg     1560
tgggaagggc atggagcatg ggggctcatg tactaaacct cacctggaca caaggtgaaa     1620
cagcccaacc ccagaggacc aggtacccac tgggaggatg ttgagtaaga tggaaaacta     1680
ctgatgaccc ttgcagagac agagtattag gacatgtttg aacaggggcc gggcgatcag     1740
caggtagctc tagaggatcc ccgtctgtct gcacatttcg tagagcgagt gttccgatac     1800
tctaatctcc ctaggcaagg ttcatatttg tgtaggttac ttattctcct tttgttgact     1860
aagtcaataa tcagaatcag caggtttgga gtcagcttgg cagggatcag cagcctgggt     1920
tggaaggagg gggtataaaa gccccttcac caggagaagc cgtcacacag atccacaagc     1980
tcctggctag aaagaggtaa gggtttaagg gatggttggt tggtggggta ttaatgttta     2040

-continued

```
attacctgga gcacctgcct gaaatcactt tttttcaggt tgggctagcc caccatgcag     2100
cgcgtgaaca tgatcatggc cgagagcccc ggcctgatca ccatctgcct gctgggctac     2160
ctgctgagcg ccgagtgcac cgtgttcctg gaccacgaga acgccaacaa gatcctgaac     2220
cgccccaagc gctacaacag cggcaagctg gaggagttcg tgcagggcaa cctggagcgc     2280
gagtgcatgg aggagaagtg cagcttcgag gaggcccgcg aggtgttcga gaacaccgag     2340
cgcaccaccg agttctggaa gcagtacgtg gacggcgacc agtgcgagag caaccccctgc    2400 ctgaacggcg gcagctgcaa ggacgacatc aacagctacg agtgctggtg ccccttcggc     2460
ttcgagggca gaaactgcga gctggacgtg acctgcaaca tcaagaacgg ccgctgcgag     2520
cagttctgca agaacagcgc cgacaacaag gtggtgtgca gctgcaccga gggctaccgc     2580
ctggccgaga accagaagag ctgcgagccc gccgtgccct tcccctgcgg ccgcgtgagc     2640
gtgagccaga ccagcaagct gacccgcgcc gaggccgtgt tccccgacgt ggactacgtg     2700
aacagcaccg aggccgagac catcctggac aacatcaccc agagcaccca gagcttcaac     2760
gacttcaccc gcgtggtggg cggcgaggac gccaagcccg gccagttccc ctggcaggtg     2820
gtgctgaacg gcaaggtgga cgccttctgc ggcggcagca tcgtgaacga gaagtggatc     2880
gtgaccgccg cccactgcgt ggagaccggc gtgaagatca ccgtggtggc cggcgagcac     2940
aacatcgagg agaccgagca caccgagcag aagcgcaacg tgatccgcat catcccccac     3000
cacaactaca acgccgccat caacaagtac aaccacgaca tcgccctgct ggagctggac     3060
gagcccctgg tgctgaacag ctacgtgacc cccatctgca tcgccgacaa ggagtacacc     3120
aacatcttcc tgaagttcgg cagcggctac gtgagcggct ggggccgcgt gttccacaag     3180
ggccgcagcg ccctggtgct gcagtacctg cgcgtgcccc tggtggaccg cgccacctgc     3240
ctgctgagca ccaagttcac catctacaac aacatgttct gcgccggctt ccacgagggc     3300
ggccgcgaca gctgccaggg cgacagcggc ggcccccacg tgaccgaggt ggagggcacc     3360
agcttcctga ccggcatcat cagctggggc gaggagtgcg ccatgaaggg caagtacggc     3420
atctacacca aggtgagccg ctacgtgaac tggatcaagg agaagaccaa gctgacctaa     3480
tgaaagatgg atttccaagg ttaattcatt ggaattgaaa attaacagcc ccccccccc     3540 cccccctgca gatctgagcc gaattcctgc agcccggggg atcagcctcg actgtgcctt     3600
ctagttgcca gccatctgtt gtttgcccct ccccgtgcc ttccttgacc ctggaaggtg      3660
ccactcccac tgtcctttcc taataaaatg aggaaattgc atcgcattgt ctgagtaggt     3720
gtcattctat tctggggggt ggggtggggc aggacagcaa gggggaggat tgggaagaca     3780
atagcaggca tgctggggat gcggtgggct ctatggcttc tgaggcggaa agaaccagct     3840
ggggaccggt ggatctcgat agcaggcatg ctggggagag atcgatctga ggaacccta     3900 gtgatggagt tggccactcc ctctctgcgc gctcgctcgc tcactgaggc cgcccgggca     3960
aagcccgggc gtcgggcgac ctttggtcgc ccggcctcag tgagcgagcg agcgcgcaga     4020
gagggagtgg ccaaccccc cccccccc ccccggcgat tctcttgttt gctccagact     4080
ctcaggcaat gacctgatag cctttgtaga gacctctcaa aaatagctac cctctccggc     4140
atgaatttat cagctagaac ggttgaatat catattgatg tgatttgac tgtctccggc      4200 ctttctcacc cgtttgaatc tttacctaca cattactcag gcattgcatt taaaatatat     4260
gagggttcta aaaattttta tccttgcgtt gaaataaagg cttctcccgc aaaagtatta     4320
cagggtcata atgtttttgg tacaaccgat ttagctttat gctctgaggc tttattgctt     4380
aattttgcta attctttgcc ttgcctgtat gatttattgg atgttggaat cgcctgatgc     4440
```

-continued

```
ggtattttct ccttacgcat ctgtgcggta tttcacaccg catatggtgc actctcagta   4500
caatctgctc tgatgccgca tagttatatg gtgcactctc agtacaatct gctctgatgc   4560
cgcatagtta agccagcccc gacacccgcc aacacagcca gccccgacac ccgccaacac   4620
ccgctgacgc gccctgacgg gcttgtctgc tcccggcatc cgcttacaga caagctgtga   4680
ccgtctccgg gagctgcatg tgtcagaggt tttcaccgtc atcaccgaaa cgcgcgagac   4740
gaaagggcct cgtgatacgc ctattttat aggttaatgt catgataata atggtttctt   4800
agacgtcagg tggcactttt cggggaaatg tgcgcggaac ccctatttgt ttattttct   4860 aaatacattc aaatatgtat ccgctcatga dacaataacc ctgataaatg ctcaataata   4920
ttgaaaaagg aagagtatga gtattcaaca tttccgtgtc gcccttattc cctttttgc   4980 ggcattttgc cttcctgttt ttgctcaccc agaaacgctg gtgaaagtaa aagatgctga   5040
agatcagttg ggtgcacgag tgggttacat cgaactggat ctcaacagcg gtaagatcct   5100
tgagagtttt cgccccgaag aacgttttcc aatgatgagc acttttaaag ttctgctatg   5160
tggcgcggta ttatcccgta ttgacgccgg gcaagagcaa ctcggtcgcc gcatacacta   5220
ttctcagaat gacttggttg agtactcacc agtcacagaa aagcatctta cggatggcat   5280
gacagtaaga gaattatgca gtgctgccat aaccatgagt gataacactg cggccaactt   5340
acttctgaca cgatcggag gaccgaagga gctaaccgct tttttgcaca acatggggga   5400
tcatgtaact cgccttgatc gttgggaacc ggagctgaat gaagccatac caaacgacga   5460
gcgtgacacc acgatgcctg tagcaatggc aacaacgttg cgcaaactat taactggcga   5520
actacttact ctagcttccc ggcaacaatt aatagactgg atggaggcgg ataaagttgc   5580
aggaccactt ctgcgctcgg cccttccggc tggctggttt attgctgata atctggagc   5640 cggtgagcgt gggtctcgcg gtatcattgc agcactgggg ccagatggta agccctcccg   5700
tatcgtagtt atctcacga cggggagtca ggcaactatg gatgaacgaa atagacagat   5760
cgctgagata ggtgcctcac tgattaagca ttggtaactg tcagaccaag tttactcata   5820
tatactttag attgatttaa aacttcattt ttaatttaaa aggatctagg tgaagatcct   5880
ttttgataat ctcatgacca aaatccctta acgtgagttt tcgttccact gagcgtcaga   5940
ccccgtagaa aagatcaaag gatcttcttg agatcctttt tttctgcgcg taatctgctg   6000
cttgcaaaca aaaaaaccac cgctaccagc ggtggtttgt ttgccggatc aagagctacc   6060
aactcttttt ccgaaggtaa ctggcttcag cagagcgcag ataccaaata ctgtccttct   6120
agtgtagccg tagttaggcc accacttcaa gaactctgta gcaccgccta cataacctcgc   6180 tctgctaatc ctgttaccag tggctgctgc cagtggcgat aagtcgtgtc ttaccgggtt   6240
ggactcaaga cgatagttac cggataaggc gcagcggtcg gctgaacggg ggggttcgtg   6300
cacacagccc agcttggagc gaacgaccta caccgaactg agatacctac agcgtgagct   6360
atgagaaagc gccacgcttc ccgaagggag aaaggcggac aggtatccgg taagcggcag   6420
ggtcggaaca ggagagcgca cgagggagct tccagggga aacgcctggt atctttatag   6480
tcctgtcggg tttcgccacc tctgacttga gcgtcgattt ttgtgatgct cgtcaggggg   6540
gcggagccta tggaaaaacg ccagcaacgc ggcctttta cggttcctgg cctttgctg   6600 gccttttgct cacatgttct ttcctgcgtt atccctgat tctgtggata accgtattac   6660
cgcctttgag tgagctgata ccgctcgccg cagccgaacg accgagcgca gcgagtcagt   6720
gagcgaggaa gcggaagagc gcccaatacg caaaccgcct ctccccgcgc gttggccgat   6780
``` tcattaatg                                                                    6789

<210> SEQ ID NO 49
<211> LENGTH: 6600
<212> TYPE: DNA
<213> ORGANISM: Artificial Sequence
<220> FEATURE:
<223> OTHER INFORMATION: AAVsc-HS-CRE17-TTRenh-TTRm-MVM-hFIXcoPadua-
      bghpolyA

<400> SEQUENCE: 49
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg tttttcgccc tttgacgttg gagtccacgt     660
tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt tacaatttaa atatttgctt     840
atacaatctt cctgttttg gggcttttct gattatcaac cggggtacat atgattgaca     900
tgctagtttt acgattaccg ttcatcgccc tgcgcgctcg ctcgctcact gaggccgccc     960
gggcaaagcc cggcgtcgg gcgacctttg gtcgcccggc ctcagtgagc gagcgagcgc    1020
gcagagaggg agtggaattc acgcgtggat ctgaattctg tacaggcgtg gtacggccgc    1080
gggcttgcaa caatgtctgg cacataggaa aagtgatcac taaatgttag ccacgtctta    1140
ctcctgcaag gctcacctcc ctggaaccca tcggtcccaa ccctgctcct gaatcaggca    1200
cagtccagct tgcagcggga gcaaaggtca gtactcagtg cccctgtccc ttccccaggc    1260 cagagggggag gaggagactg agtcacgaat gacacctcag ccgcagtttg acctccagga    1320
cttacagtcc tagcagccgg tgccactagc atgtgagagg tccagaggcg cttctgtctc    1380
acccgcccgc ctgggtgcac ccatgctggg agcgcctgca ccatttgagc atgtccgaga    1440
gcatccacca gaggtaccca ctgggaggat gttgagtaag atggaaaact actgatgacc    1500
cttgcagaga cagagtatta ggacatgttt gaacaggggc cgggcgatca gcaggtagct    1560
ctagaggatc cccgtctgtc tgcacatttc gtagagcgag tgttccgata ctctaatctc    1620
cctaggcaag gttcatattt gtgtaggtta cttattctcc ttttgttgac taagtcaata    1680
atcagaatca gcaggtttgg agtcagcttg gcagggatca gcagcctggg ttggaaggag    1740
ggggtataaa agccccttca ccaggagaag ccgtcacaca gatccacaag ctcctggcta    1800
gaaagaggta agggtttaag ggatggttgg ttggtggggt attaatgttt aattacctgg    1860
agcacctgcc tgaaatcact tttttttcagg ttggctagc ccaccatgca gcgcgtgaac    1920
atgatcatgg ccgagagccc cggcctgatc accatctgcc tgctgggcta cctgctgagc    1980

-continued

```
gccgagtgca ccgtgttcct ggaccacgag aacgccaaca agatcctgaa ccgccccaag  2040
cgctacaaca gcggcaagct ggaggagttc gtgcagggca acctggagcg cgagtgcatg  2100
gaggagaagt gcagcttcga ggaggcccgc gaggtgttcg agaacaccga gcgcaccacc  2160
gagttctgga agcagtacgt ggacggcgac cagtgcgaga gcaacccctg cctgaacggc  2220
ggcagctgca aggacgacat caacagctac gagtgctggt gccccttcgg cttcgagggc  2280
aagaactgcg agctggacgt gacctgcaac atcaagaacg gccgctgcga gcagttctgc  2340
aagaacagcg ccgacaacaa ggtggtgtgc agctgcaccg agggctaccg cctggccgag  2400
aaccagaaga gctgcgagcc cgccgtgccc ttcccctgcg gccgcgtgag cgtgagccag  2460
accagcaagc tgacccgcgc cgaggccgtg ttccccgacg tggactacgt gaacagcacc  2520
gaggccgaga ccatcctgga caacatcacc cagagcaccc agagcttcaa cgacttcacc  2580
cgcgtggtgg gcggcgagga cgccaagccc ggccagttcc cctggcaggt ggtgctgaac  2640
ggcaaggtgg acgccttctg cggcggcagc atcgtgaacg agaagtggat cgtgaccgcc  2700
gcccactgcg tggagaccgg cgtgaagatc accgtggtgg ccggcgagca caacatcgag  2760
gagaccgagc acaccgagca gaagcgcaac gtgatccgca tcatccccca ccacaactac  2820
aacgccgcca tcaacaagta caaccacgac atcgccctgc tggagctgga cgagcccctg  2880
gtgctgaaca gctacgtgac ccccatctgc atcgccgaca aggagtacac caacatcttc  2940
ctgaagttcg gcagcggcta cgtgagcggc tggggccgcg tgttccacaa gggccgcagc  3000
gccctggtgc tgcagtacct gcgcgtgccc ctggtggacc gcgccacctg cctgctgagc  3060
accaagttca ccatctacaa caacatgttc tgcgccggct tccacgaggg cggccgcgac  3120
agctgccagg gcgacagcgg cggcccccac gtgaccgagg tggagggcac cagcttcctg  3180
accggcatca tcagctgggg cgaggagtgc gccatgaagg gcaagtacgg catctacacc  3240
aaggtgagcc gctacgtgaa ctggatcaag gagaagacca agctgaccta atgaaagatg  3300
gatttccaag gttaattcat tggaattgaa aattaacagc cccccccccc cccccctgc  3360 agatctgagc cgaattcctg cagcccgggg gatcagcctc gactgtgcct tctagttgcc  3420
agccatctgt tgtttgcccc tcccccgtgc cttccttgac cctggaaggt gccactccca  3480
ctgtcctttc ctaataaaat gaggaaattg catcgcattg tctgagtagg tgtcattcta  3540
ttctgggggg tggggtgggg caggacagca aggggggagga ttgggaagac aatagcaggc  3600
atgctgggga tgcggtgggc tctatggctt ctgaggcgga aagaaccagc tggggaccgg  3660
tggatctcga tagcaggcat gctgggggaga gatcgatctg aggaacccct agtgatggag  3720
ttggccactc cctctctgcg cgctcgctcg ctcactgagg ccgcccgggc aaagcccggg  3780
cgtcgggcga cctttggtcg cccggcctca gtgagcgagc gagcgcgcag agagggagtg  3840 gccaacccccc cccccccccc cccccggcga ttctcttgtt tgctccagac tctcaggcaa  3900
tgacctgata gcctttgtag agacctctca aaaatagcta ccctctccgg catgaattta  3960
tcagctagaa cggttgaata tcatattgat ggtgatttga ctgtctccgg cctttctcac  4020
ccgtttgaat ctttacctac acattactca ggcattgcat ttaaaatata tgagggttct  4080
aaaaattttt atccttgcgt tgaaataaag gcttctcccg caaaagtatt acagggtcat  4140 aatgttttg gtacaaccga tttagcttta tgctctgagg ctttattgct taattttgct  4200
aattctttgc cttgcctgta tgatttattg gatgttggaa tcgcctgatg cggtattttc  4260
tccttacgca tctgtgcggt atttcacacc gcatatggtg cactctcagt acaatctgct  4320
ctgatgccgc atagttatat ggtgcactct cagtacaatc tgctctgatg ccgcatagtt  4380
```

```
aagccagccc cgacacccgc caacacagcc agccccgaca cccgccaaca cccgctgacg      4440
cgccctgacg ggcttgtctg ctcccggcat ccgcttacag acaagctgtg accgtctccg      4500
ggagctgcat gtgtcagagg ttttcaccgt catcaccgaa acgcgcgaga cgaaagggcc      4560
tcgtgatacg cctattttta taggttaatg tcatgataat aatggtttct tagacgtcag      4620
gtggcacttt tcgggggaaat gtgcgcggaa cccctatttg tttatttttc taaatacatt      4680
caaatatgta tccgctcatg agacaataac cctgataaat gctcaataat attgaaaaag      4740
gaagagtatg agtattcaac atttccgtgt cgcccttatt cccttttttg cggcattttg      4800
ccttcctgtt tttgctcacc cagaaacgct ggtgaaagta aaagatgctg aagatcagtt      4860
gggtgcacga gtgggttaca tcgaactgga tctcaacagc ggtaagatcc ttgagagttt      4920
tcgccccgaa gaacgttttc caatgatgag cacttttaaa gttctgctat gtggcgcggt      4980
attatcccgt attgacgccg ggcaagagca actcggtcgc cgcatacact attctcagaa      5040
tgacttggtt gagtactcac cagtcacaga aaagcatctt acggatggca tgacagtaag      5100
agaattatgc agtgctgcca taaccatgag tgataacact gcggccaact tacttctgac      5160
aacgatcgga ggaccgaagg agctaaccgc ttttttgcac aacatggggg atcatgtaac      5220
tcgccttgat cgttgggaac cggagctgaa tgaagccata ccaaacgacg agcgtgacac      5280
cacgatgcct gtagcaatgg caacaacgtt gcgcaaacta ttaactggcg aactacttac      5340
tctagcttcc cggcaacaat taatagactg gatggaggcg gataaagttg caggaccact      5400
tctgcgctcg gcccttccgg ctggctggtt tattgctgat aaatctggag ccggtgagcg      5460
tgggtctcgc ggtatcattg cagcactggg gccagatggt aagccctccc gtatcgtagt      5520
tatctacacg acggggagtc aggcaactat ggatgaacga aatagacaga tcgctgagat      5580
aggtgcctca ctgattaagc attggtaact gtcagaccaa gtttactcat atatacttta      5640
gattgattta aaacttcatt tttaatttaa aaggatctag gtgaagatcc tttttgataa      5700
tctcatgacc aaaatccctt aacgtgagtt ttcgttccac tgagcgtcag accccgtaga      5760
aaagatcaaa ggatcttctt gagatccttt ttttctgcgc gtaatctgct gcttgcaaac      5820
aaaaaaacca ccgctaccag cggtggtttg tttgccggat caagagctac caactctttt      5880
tccgaaggta actggcttca gcagagcgca gataccaaat actgtccttc tagtgtagcc      5940
gtagttaggc caccacttca agaactctgt agcaccgcct acatacctcg ctctgctaat      6000
cctgttacca gtggctgctg ccagtggcga taagtcgtgt cttaccgggt tggactcaag      6060
acgatagtta ccggataagg cgcagcggtc gggctgaacg ggggggttcgt gcacacagcc      6120 cagcttggag cgaacgacct acaccgaact gagataccta cagcgtgagc tatgagaaag      6180
cgccacgctt cccgaaggga gaaaggcgga caggtatccg gtaagcggca gggtcggaac      6240
aggagagcgc acgagggagc ttccaggggg aaacgcctgg tatctttata gtcctgtcgg      6300
gtttcgccac ctctgacttg agcgtcgatt tttgtgatgc tcgtcagggg ggcggagcct      6360
atggaaaaac gccagcaacg cggccttttt acggttcctg gccttttgct ggccttttgc      6420
tcacatgttc tttcctgcgt tatcccctga ttctgtggat aaccgtatta ccgcctttga      6480
gtgagctgat accgctcgcc gcagccgaac gaccgagcgc agcgagtcag tgagcgagga      6540
agcggaagag cgcccaatac gcaaaccgcc tctccccgcg cgttggccga ttcattaatg      6600
```

<210> SEQ ID NO 50
<211> LENGTH: 6661
<212> TYPE: DNA

-continued

```
<213> ORGANISM: Artificial Sequence
<220> FEATURE:
<223> OTHER INFORMATION: AAVsc-HS-CRE18-TTRenh-TTRm-MVM-hFIXcoPadua-
      bghpolyA

<400> SEQUENCE: 50
agctggcgta atagcgaaga ggcccgcacc gatcgccctt cccaacagtt gcgcagcctg       60
aatggcgaat ggcgattccg ttgcaatggc tggcggtaat attgttctgg atattaccag      120
caaggccgat agtttgagtt cttctactca ggcaagtgat gttattacta atcaaagaag      180
tattgcgaca acggttaatt tgcgtgatgg acagactctt ttactcggtg gcctcactga      240
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg ttttttcgcc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt acaatttaa atatttgctt      840 atacaatctt cctgttttg gggctttct gattatcaac cggggtacat atgattgaca      900
tgctagtttt acgattaccg ttcatcgccc tgcgcgctcg ctcgctcact gaggccgccc      960
gggcaaagcc cgggcgtcgg gcgacctttg gtcgcccggc ctcagtgagc gagcgagcgc     1020
gcagagaggg agtggaattc acgcgtggat ctgaattctg tacaggcgtg gtacggccgc     1080
ggctgggcag gagcagctgg cttgagcaga atcttgggac ctgaggctct caggggacct     1140
cccattgggg gatggagggc aatggtggtg gtgcccagga ggtcttctac ttagatgtct     1200
attggatctc taaatgaggc tgcatgcata atcacacaca aacatccact gagaaggtga     1260
cacaccacgt cagcatgggt ccctctgccg gaccacacca ctcctagtga ctatgaggtg     1320
acatccaggc acgttgcact attggctcct gtcggtgagt gcagtgcctg acaacagtga     1380
gctacattta tttgtaaaaa tgaacgccat cagagtagac cacaattgta ctaactctaa     1440
tttgctttgt gttcattttt tcagtttcca gaagtggctt aatgtttcct agggtcaaag     1500
gcagtcaaat gacggtaccc actgggagga tgttgagtaa gatggaaaac tactgatgac     1560
ccttgcagag acagagtatt aggacatgtt tgaacagggg ccgggcgatc agcaggtagc     1620
tctagaggat ccccgtctgt ctgcacattt cgtagagcga gtgttccgat actctaatct     1680
ccctaggcaa ggttcatatt tgtgtaggtt acttattctc cttttgttga ctaagtcaat     1740
aatcagaatc agcaggtttg gagtcagctt ggcaggatc agcagcctgg gttggaagga     1800
gggggtataa aagccccttc accaggagaa gccgtcacac agatccacaa gctcctggct     1860
agaaagaggt aagggtttaa gggatggttg gttggtgggg tattaatgtt taattacctg     1920
gagcacctgc ctgaaatcac tttttttcag gttgggctag cccaccatgc agcgcgtgaa     1980
catgatcatg gccgagagcc ccggcctgat caccatctgc ctgctgggct acctgctgag     2040
cgccgagtgc accgtgttcc tggaccacga gaacgccaac aagatcctga accgccccaa     2100
gcgctacaac agcggcaagc tggaggagtt cgtgcagggc aacctggagc gcgagtgcat     2160
```

```
ggaggagaag tgcagcttcg aggaggcccg cgaggtgttc gagaacaccg agcgcaccac   2220
cgagttctgg aagcagtacg tggacggcga ccagtgcgag agcaacccct gcctgaacgg   2280
cggcagctgc aaggacgaca tcaacagcta cgagtgctgg tgccccttcg gcttcgaggg   2340
caagaactgc gagctggacg tgacctgcaa catcaagaac ggccgctgcg agcagttctg   2400
caagaacagc gccgacaaca aggtggtgtg cagctgcacc gagggctacc gcctggccga   2460
gaaccagaag agctgcgagc ccgccgtgcc cttcccctgc ggccgcgtga gcgtgagcca   2520
gaccagcaag ctgacccgcg ccgaggccgt gttccccgac gtggactacg tgaacagcac   2580
cgaggccgag accatcctgg acaacatcac ccagagcacc cagagcttca acgacttcac   2640
ccgcgtggtg ggcggcgagg acgccaagcc cggccagttc ccctggcagg tggtgctgaa   2700
cggcaaggtg gacgccttct gcggcggcag catcgtgaac gagaagtgga tcgtgaccgc   2760
cgcccactgc gtggagaccg gcgtgaagat caccgtggtg gccggcgagc acaacatcga   2820
ggagaccgag cacaccgagc agaagcgcaa cgtgatccgc atcatccccc accacaacta   2880
caacgccgcc atcaacaagt acaaccacga catcgccctg ctggagctgg acgagcccct   2940
ggtgctgaac agctacgtga cccccatctg catcgccgac aaggagtaca ccaacatctt   3000
cctgaagttc ggcagcggct acgtgagcgg ctggggccgc gtgttccaca agggccgcag   3060
cgccctggtg ctgcagtacc tgcgcgtgcc cctggtggac cgcgccacct gcctgctgag   3120
caccaagttc accatctaca acaacatgtt ctgcgccggc ttccacgagg cgggccgcga   3180
cagctgccag ggcgacagcg gcggcccccca cgtgaccgag gtggagggca ccagcttcct   3240
gaccggcatc atcagctggg gcgaggagtg cgccatgaag ggcaagtacg gcatctacac   3300
caaggtgagc cgctacgtga actggatcaa ggagaagacc aagctgacct aatgaaagat   3360
ggatttccaa ggttaattca ttggaattga aaattaacag ccccccccc ccccccctg    3420 cagatctgag ccgaattcct gcagcccggg ggatcagcct cgactgtgcc ttctagttgc   3480
cagccatctg ttgtttgccc ctcccccgtg ccttccttga ccctggaagg tgccactccc   3540
actgtccttt cctaataaaa tgaggaaatt gcatcgcatt gtctgagtag gtgtcattct   3600
attctggggg gtggggtggg gcaggacagc aagggggagg attgggaaga caatagcagg   3660
catgctgggg atgcggtggg ctctatggct tctgaggcgg aaagaaccag ctggggaccg   3720
gtggatctcg atagcaggca tgctggggag agatcgatct gaggaacccc tagtgatgga   3780
gttggccact ccctctctgc gcgctcgctc gctcactgag gccgcccggg caaagcccgg   3840
gcgtcgggcg acctttggtc gcccggcctc agtgagcgag cgagcgcgca gagagggagt   3900
ggccaacccc cccccccccc ccccccggcg attctcttgt ttgctccaga ctctcaggca   3960
atgacctgat agcctttgta gagacctctc aaaaatagct accctctccg gcatgaattt   4020
atcagctaga acggttgaat atcatattga tggtgatttg actgtctccg gcctttctca   4080
cccgtttgaa tctttaccta cacattactc aggcattgca tttaaaatat atgagggttc   4140
taaaaatttt tatccttgcg ttgaaataaa ggcttctccc gcaaaagtat tacagggtca   4200
taatgttttt ggtacaaccg atttagcttt atgctctgag gctttattgc ttaattttgc   4260
taattctttg ccttgcctgt atgatttatt ggatgttgga atcgcctgat gcggtatttt   4320
ctccttacgc atctgtgcgg tatttcacac cgcatatggt gcactctcag tacaatctgc   4380
tctgatgccg catagttata tggtgcactc tcagtacaat ctgctctgat gccgcatagt   4440
taagccagcc ccgacacccg ccaacacagc cagccccgac acccgccaac acccgctgac   4500
gcgccctgac gggcttgtct gctcccggca tccgcttaca gacaagctgt gaccgtctcc   4560
```

-continued

```
gggagctgca tgtgtcagag gttttcaccg tcatcaccga aacgcgcgag acgaaagggc      4620
ctcgtgatac gcctattttt ataggttaat gtcatgataa taatggtttc ttagacgtca      4680
ggtggcactt ttcggggaaa tgtgcgcgga acccctattt gtttattttt ctaaatacat      4740
tcaaatatgt atccgctcat gagacaataa ccctgataaa tgctcaataa tattgaaaaa      4800
ggaagagtat gagtattcaa catttccgtg tcgcccttat tccctttttt gcggcatttt      4860
gccttcctgt ttttgctcac ccagaaacgc tggtgaaagt aaaagatgct gaagatcagt      4920
tgggtgcacg agtgggttac atcgaactgg atctcaacag cggtaagatc cttgagagtt      4980
ttcgccccga agaacgtttt ccaatgatga gcacttttaa agttctgcta tgtggcgcgg      5040
tattatcccg tattgacgcc gggcaagagc aactcggtcg ccgcatacac tattctcaga      5100
atgacttggt tgagtactca ccagtcacag aaaagcatct tacggatggc atgacagtaa      5160
gagaattatg cagtgctgcc ataaccatga gtgataacac tgcggccaac ttacttctga      5220
caacgatcgg aggaccgaag gagctaaccg cttttttgca caacatgggg gatcatgtaa      5280
ctcgccttga tcgttgggaa ccggagctga atgaagccat accaaacgac gagcgtgaca      5340
ccacgatgcc tgtagcaatg gcaacaacgt tgcgcaaact attaactggc gaactactta      5400
ctctagcttc ccggcaacaa ttaatagact ggatggaggc ggataaagtt gcaggaccac      5460
ttctgcgctc ggcccttccg gctggctggt ttattgctga taaatctgga gccggtgagc      5520
gtgggtctcg cggtatcatt gcagcactgg ggccagatgg taagccctcc cgtatcgtag      5580
ttatctacac gacggggagt caggcaacta tggatgaacg aaatagacag atcgctgaga      5640
taggtgcctc actgattaag cattggtaac tgtcagacca agtttactca tatatacttt      5700
agattgattt aaaacttcat ttttaattta aaaggatcta ggtgaagatc ctttttgata      5760
atctcatgac caaaatccct taacgtgagt tttcgttcca ctgagcgtca gaccccgtag      5820
aaaagatcaa aggatcttct tgagatcctt tttttctgcg cgtaatctgc tgcttgcaaa      5880
caaaaaaacc accgctacca gcggtggttt gtttgccgga tcaagagcta ccaactcttt      5940
ttccgaaggt aactggcttc agcagagcgc agataccaaa tactgtcctt ctagtgtagc      6000
cgtagttagg ccaccacttc aagaactctg tagcaccgcc tacatacctc gctctgctaa      6060
tcctgttacc agtggctgct gccagtggcg ataagtcgtg tcttaccggg ttggactcaa      6120
gacgatagtt accggataag gcgcagcggt cgggctgaac ggggggttcg tgcacacagc      6180
ccagcttgga gcgaacgacc tacaccgaac tgagatacct acagcgtgag ctatgagaaa      6240
gcgccacgct tcccgaaggg agaaaggcgg acaggtatcc ggtaagcggc agggtcggaa      6300
caggagagcg cacgagggag cttccagggg gaaacgcctg gtatctttat agtcctgtcg      6360
ggtttcgcca cctctgactt gagcgtcgat ttttgtgatg ctcgtcaggg gggcggagcc      6420
tatggaaaaa cgccagcaac gcggcctttt tacggttcct ggccttttgc tggccttttg      6480
ctcacatgtt ctttcctgcg ttatcccctg attctgtgga taaccgtatt accgcctttg      6540
agtgagctga taccgctcgc cgcagccgaa cgaccgagcg cagcgagtca gtgagcgagg      6600
aagcggaaga gcgcccaata cgcaaaccgc ctctccccgc gcgttggccg attcattaat      6660
g                                                                        6661
```

<210> SEQ ID NO 51
<211> LENGTH: 6711
<212> TYPE: DNA
<213> ORGANISM: Artificial Sequence
<220> FEATURE:

<223> OTHER INFORMATION: AAVsc-HS-CRE19-TTRenh-TTRm-MVM-hFIXcoPadua-bghpolyA

<400> SEQUENCE: 51

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg ttttttcgccc tttgacgttg gagtccacgt     660
tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt tacaatttaa atatttgctt     840
atacaatctt cctgtttttg gggcttttct gattatcaac cggggtacat atgattgaca     900
tgctagtttt acgattaccg ttcatcgccc tgcgcgctcg ctcgctcact gaggccgccc     960
gggcaaagcc cggcgtcgg gcgacctttg gtcgcccggc ctcagtgagc gagcgagcgc    1020
gcagagaggg agtggaattc acgcgtggat ctgaattctg tacaggcgtg gtacggccgc    1080
gggaaggggg aagagaccca ctgaaatcct atctcccagc ctcacctctg ctgtctcctc    1140
cacgcttcct gtctccagag ccccgagttc agcataagca gaaagcggcc tgttccctct    1200
ctagggagag gagggttgcg gtctggaggt ctggctcgtc tttatctgcg cattctccca    1260
gcctcctggc ttcagacctc agcgaggcgg cggctgccgg ccggctctcc tcttcctgcc    1320
tgcagacctg gcctgctgct tctttctcct tcctccctcc ctgcctgccc tgcggtttca    1380
aagtagatta gaaataacag tgtcccacat ggaagcctct acttcttcct gggtcaactt    1440
tgatgacgag gctccagaaa acctttgcaa tgctgtgtgg aattttttaaa tcggtgagct    1500 cgtgctcttg ccctatttat ttgtccagcg tacatttctg aacattgtga acgtcgaatg    1560
ggcggtaccc actgggagga tgttgagtaa gatggaaaac tactgatgac ccttgcagag    1620
acagagtatt aggacatgtt tgaacagggg ccgggcgatc agcaggtagc tctagaggat    1680
ccccgtctgt ctgcacattt cgtagagcga gtgttccgat actctaatct ccctaggcaa    1740
ggttcatatt tgtgtaggtt acttattctc cttttgttga ctaagtcaat aatcagaatc    1800
agcaggtttg gagtcagctt ggcagggatc agcagcctgg gttggaagga ggggtataa    1860 aagcccccttc accaggagaa gccgtcacac agatccacaa gctcctggct agaaagaggt    1920
aagggtttaa gggatggttg gttggtgggg tattaatgtt taattacctg gagcacctgc    1980
ctgaaatcac ttttttttcag gttgggctag cccaccatga gcgcgtgaa catgatcatg    2040 gccgagagcc ccggcctgat caccatctgc ctgctgggct acctgctgag cgccgagtgc    2100
accgtgttcc tggaccacga gaacgccaac aagatcctga accgcccaaa gcgctacaac    2160
agcggcaagc tggaggagtt cgtgcagggc aacctggagc gcgagtgcat ggaggagaag    2220
```

-continued

```
tgcagcttcg aggaggcccg cgaggtgttc gagaacaccg agcgcaccac cgagttctgg    2280
aagcagtacg tggacggcga ccagtgcgag agcaacccct gcctgaacgg cggcagctgc    2340
aaggacgaca tcaacagcta cgagtgctgg tgccccttcg gcttcgaggg caagaactgc    2400
gagctggacg tgacctgcaa catcaagaac ggccgctgcg agcagttctg caagaacagc    2460
gccgacaaca aggtggtgtg cagctgcacc gagggctacc gcctggccga gaaccagaag    2520
agctgcgagc ccgccgtgcc cttcccctgc ggccgcgtga gcgtgagcca gaccagcaag    2580
ctgacccgcg ccgaggccgt gttccccgac gtggactacg tgaacagcac cgaggccgag    2640
accatcctgg acaacatcac ccagagcacc cagagcttca cgacttcac ccgcgtggtg     2700 ggcggcgagg acgccaagcc cggccagttc ccctggcagg tggtgctgaa cggcaaggtg    2760
gacgccttct gcggcggcag catcgtgaac gagaagtgga tcgtgaccgc cgcccactgc    2820
gtggagaccg gcgtgaagat caccgtggtg gccggcgagc acaacatcga ggagaccgag    2880
cacaccgagc agaagcgcaa cgtgatccgc atcatcccc accacaacta caacgccgcc     2940
atcaacaagt acaaccacga catcgccctg ctggagctgg acgagcccct ggtgctgaac    3000
agctacgtga cccccatctg catcgccgac aaggagtaca ccaacatctt cctgaagttc    3060
ggcagcggct acgtgagcgg ctggggccgc gtgttccaca agggccgcag cgccctggtg    3120
ctgcagtacc tgcgcgtgcc cctggtggac cgcgccacct gcctgctgag caccaagttc    3180
accatctaca caacatgtt ctgcgccggc ttccacgagg cgggccgcga cagctgccag     3240
ggcgacagcg gcggccccca cgtgaccgag gtggagggca ccagcttcct gaccggcatc    3300
atcagctggg gcgaggagtg cgccatgaag ggcaagtacg gcatctacac caaggtgagc    3360
cgctacgtga actggatcaa ggagaagacc aagctgacct aatgaaagat ggatttccaa    3420
ggttaattca ttggaattga aaattaacag cccccccccc cccccccctg cagatctgag    3480
ccgaattcct gcagcccggg ggatcagcct cgactgtgcc ttctagttgc cagccatctg    3540
ttgtttgccc ctccccgtg ccttccttga ccctggaagg tgccactccc actgtccttt     3600
cctaataaaa tgaggaaatt gcatcgcatt gtctgagtag gtgtcattct attctggggg    3660
gtggggtggg gcaggacagc aagggggagg attgggaaga caatagcagg catgctgggg    3720
atgcggtggg ctctatggct tctgaggcgg aaagaaccag ctggggaccg gtggatctcg    3780
atagcaggca tgctggggag agatcgatct gaggaacccc tagtgatgga gttggccact    3840
ccctctctgc gcgctcgctc gctcactgag gccgcccggg caaagcccgg gcgtcgggcg    3900
acctttggtc gcccggcctc agtgagcgag cgagcgcgca gagagggagt ggccaaccc    3960 cccccccccc cccccggcg attctcttgt ttgctccaga ctctcaggca atgacctgat     4020
agcctttgta gagacctctc aaaaatagct accctctccg gcatgaattt atcagctaga    4080
acggttgaat atcatattga tggtgatttg actgtctccg gcctttctca cccgtttgaa    4140
tctttaccta cacattactc aggcattgca tttaaaatat atgagggttc taaaaatttt    4200
tatccttgcg ttgaaataaa ggcttctccc gcaaaagtat tacagggtca taatgttttt    4260
ggtacaaccg atttagcttt atgctctgag gctttattgc ttaattttgc taattctttg    4320
ccttgcctgt atgatttatt ggatgttgga atcgcctgat gcggtatttt ctccttacgc    4380
atctgtgcgg tatttcacac cgcatatggt gcactctcag tacaatctgc tctgatgccg    4440
catagttata tggtgcactc tcagtacaat ctgctctgat gccgcatagt taagccagcc    4500
ccgacacccg ccaacacagc cagccccgac acccgccaac acccgctgac gcgccctgac    4560
gggcttgtct gctcccggca tccgcttaca gacaagctgt gaccgtctcc gggagctgca    4620
```

```
tgtgtcagag gttttcaccg tcatcaccga aacgcgcgag acgaaagggc ctcgtgatac    4680
gcctattttt ataggttaat gtcatgataa taatggtttc ttagacgtca ggtggcactt    4740
ttcggggaaa tgtgcgcgga acccctattt gtttattttt ctaaatacat tcaaatatgt    4800
atccgctcat gagacaataa ccctgataaa tgctcaataa tattgaaaaa ggaagagtat    4860
gagtattcaa catttccgtg tcgcccttat tccctttttt gcggcatttt gccttcctgt    4920
ttttgctcac ccagaaacgc tggtgaaagt aaaagatgct gaagatcagt tgggtgcacg    4980
agtgggttac atcgaactgg atctcaacag cggtaagatc cttgagagtt ttcgccccga    5040
agaacgtttt ccaatgatga gcacttttaa agttctgcta tgtggcgcgg tattatcccg    5100
tattgacgcc gggcaagagc aactcggtcg ccgcatacac tattctcaga atgacttggt    5160
tgagtactca ccagtcacag aaaagcatct tacggatggc atgacagtaa gagaattatg    5220
cagtgctgcc ataaccatga gtgataacac tgcggccaac ttacttctga caacgatcgg    5280
aggaccgaag gagctaaccg cttttttgca caacatgggg gatcatgtaa ctcgccttga    5340
tcgttgggaa ccggagctga atgaagccat accaaacgac gagcgtgaca ccacgatgcc    5400
tgtagcaatg gcaacaacgt tgcgcaaact attaactggc gaactactta ctctagcttc    5460
ccggcaacaa ttaatagact ggatggaggc ggataaagtt gcaggaccac ttctgcgctc    5520
ggcccttccg gctggctggt ttattgctga taaatctgga gccggtgagc gtgggtctcg    5580
cggtatcatt gcagcactgg ggccagatgg taagccctcc cgtatcgtag ttatctacac    5640
gacggggagt caggcaacta tggatgaacg aaatagacag atcgctgaga taggtgcctc    5700
actgattaag cattggtaac tgtcagacca agtttactca tatatacttt agattgattt    5760
aaaacttcat ttttaattta aaaggatcta ggtgaagatc cttttttgata atctcatgac    5820 caaaatccct taacgtgagt tttcgttcca ctgagcgtca gaccccgtag aaaagatcaa    5880
aggatcttct tgagatcctt tttttctgcg cgtaatctgc tgcttgcaaa caaaaaaacc    5940
accgctacca gcggtggttt gtttgccgga tcaagagcta ccaactcttt ttccgaaggt    6000
aactggcttc agcagagcgc agataccaaa tactgtcctt ctagtgtagc cgtagttagg    6060
ccaccacttc aagaactctg tagcaccgcc tacatacctc gctctgctaa tcctgttacc    6120
agtggctgct gccagtggcg ataagtcgtg tcttaccggg ttggactcaa gacgatagtt    6180
accggataag cgcagcggt cgggctgaac ggggggttcg tgcacacagc ccagcttgga    6240
gcgaacgacc tacaccgaac tgagatacct acagcgtgag ctatgagaaa gcgccacgct    6300
tcccgaaggg agaaaggcgg acaggtatcc ggtaagcggc agggtcggaa caggagagcg    6360
cacgagggag cttccagggg gaaacgcctg gtatctttat agtcctgtcg ggtttcgcca    6420
cctctgactt gagcgtcgat ttttgtgatg ctcgtcaggg gggcggagcc tatggaaaaa    6480
cgccagcaac gcggcctttt tacggttcct ggccttttgc tggccttttg ctcacatgtt    6540
ctttcctgcg ttatccctg attctgtgga taaccgtatt accgcctttg agtgagctga    6600
taccgctcgc cgcagccgaa cgaccgagcg cagcgagtca gtgagcgagg aagcggaaga    6660
gcgcccaata cgcaaaccgc ctctccccgc gcgttggccg attcattaat g            6711
```

<210> SEQ ID NO 52
<211> LENGTH: 6575
<212> TYPE: DNA
<213> ORGANISM: Artificial Sequence
<220> FEATURE:
<223> OTHER INFORMATION: AAVsc-HS-CRE20-TTRenh-TTRm-MVM-hFIXcoPadua-
    bghpolyA -continued

```
<400> SEQUENCE: 52
agctggcgta atagcgaaga ggcccgcacc gatcgccctt cccaacagtt gcgcagcctg     60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctcccttag    540 ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt acaatttaa atatttgctt    840 atacaatctt cctgttttg gggctttct gattatcaac cggggtacat atgattgaca    900
tgctagtttt acgattaccg ttcatcgccc tgcgcgctcg ctcgctcact gaggccgccc    960
gggcaaagcc cggcgtcgg gcgacctttg gtcgcccggc ctcagtgagc gagcgagcgc   1020
gcagagaggg agtggaattc acgcgtggat ctgaattctg tacaggcgtg gtacggccgc   1080
ggggaaaaca gggagacagt ttcctgtttg agatgttggg agatgcttcg agtagtatat   1140
ttactggaaa tagacattca acttggatgt ccctttttgg aaatgtgcct gcgtccaggg   1200
ctgggttggg gccccaatga actttggctc tgacacagct gttgccacac tcagtggaac   1260
tgaatctatg tttgtcttcc ccggcatcct tcaccccaac tctccccgcc acaacataca   1320
tcccatgcca gcctggggac cctcaaaggt ggcttcatca ttaggtttgt ggctgggtcc   1380
cactgaagta agtcttggca ctcagaggga taggaattga atgaagaggt acccactggg   1440
aggatgttga gtaagatgga aaactactga tgacccttgc agagacagag tattaggaca   1500
tgtttgaaca ggggccgggc gatcagcagg tagctctaga ggatccccgt ctgtctgcac   1560
atttcgtaga gcgagtgttc cgatactcta atctccctag gcaaggttca tatttgtgta   1620
ggttacttat tctccttttg ttgactaagt caataatcag aatcagcagg tttggagtca   1680
gcttggcagg gatcagcagc ctgggttgga aggaggggt ataaaagccc cttcaccagg   1740
agaagccgtc acacagatcc acaagctcct ggctagaaag aggtaagggt ttaagggatg   1800
gttggttggt ggggtattaa tgtttaatta cctggagcac ctgcctgaaa tcactttttt   1860
tcaggttggg ctagcccacc atgcagcgcg tgaacatgat catggccgag agccccggcc   1920
tgatcaccat ctgcctgctg ggctacctgc tgagcgccga gtgcaccgtg ttcctggacc   1980
acgagaacgc caacaagatc ctgaaccgcc ccaagcgcta caacagcggc aagctggagg   2040
agttcgtgca gggcaacctg gagcgcgagt gcatggagga gaagtgcagc ttcgaggagg   2100
cccgcgaggt gttcgagaac accgagcgca ccaccgagtt ctggaagcag tacgtggacg   2160
gcgaccagtg cgagagcaac ccctgcctga acggcggcag ctgcaaggac gacatcaaca   2220
gctacgagtg ctggtgcccc ttcggcttcg agggcaagaa ctgcgagctg gacgtgacct   2280
```

```
gcaacatcaa gaacggccgc tgcgagcagt tctgcaagaa cagcgccgac aacaaggtgg    2340
tgtgcagctg caccgagggc taccgcctgg ccgagaacca gaagagctgc gagcccgccg    2400
tgcccttccc ctgcggccgc gtgagcgtga gccagaccag caagctgacc cgcgccgagg    2460
ccgtgttccc cgacgtggac tacgtgaaca gcaccgaggc cgagaccatc ctggacaaca    2520
tcacccagag cacccagagc ttcaacgact tcacccgcgt ggtgggcggc gaggacgcca    2580
agcccggcca gttccctggg caggtggtgc tgaacggcaa ggtggacgcc ttctgcggcg    2640
gcagcatcgt gaacgagaag tggatcgtga ccgccgccca ctgcgtggag accggcgtga    2700
agatcaccgt ggtggccggc gagcacaaca tcgaggagac cgagcacacc gagcagaagc    2760
gcaacgtgat ccgcatcatc ccccaccaca actacaacgc cgccatcaac aagtacaacc    2820
acgacatcgc cctgctggag ctggacgagc ccctggtgct gaacagctac gtgacccccca    2880 tctgcatcgc cgacaaggag tacaccaaca tcttcctgaa gttcggcagc ggctacgtga    2940
gcggctgggg ccgcgtgttc cacaagggcc gcagcgccct ggtgctgcag tacctgcgcg    3000
tgcccctggt ggaccgcgcc acctgcctgc tgagcaccaa gttcaccatc tacaacaaca    3060
tgttctgcgc cggcttccac gagggcggcc gcgacagctg ccagggcgac agcggcggcc    3120
cccacgtgac cgaggtggag ggcaccagct tcctgaccgg catcatcagc tggggcgagg    3180
agtgcgccat gaagggcaag tacggcatct acaccaaggt gagccgctac gtgaactgga    3240
tcaaggagaa gaccaagctg acctaatgaa agatggattt ccaaggttaa ttcattggaa    3300
ttgaaaatta acagcccccc cccccccccc cctgcagatc tgagccgaat tcctgcagcc    3360
cgggggatca gcctcgactg tgccttctag ttgccagcca tctgttgttt gcccctcccc    3420
cgtgccttcc ttgaccctgg aaggtgccac tcccactgtc cttttcctaat aaaatgagga    3480 aattgcatcg cattgtctga gtaggtgtca ttctattctg gggggtgggg tggggcagga    3540
cagcaagggg gaggattggg aagacaatag caggcatgct ggggatgcgg tgggctctat    3600
ggcttctgag gcggaaagaa ccagctgggg accggtggat ctcgatagca ggcatgctgg    3660
ggagagatcg atctgaggaa cccctagtga tggagttggc cactccctct ctgcgcgctc    3720
gctcgctcac tgaggccgcc cgggcaaagc ccgggcgtcg ggcgaccttt ggtcgcccgg    3780
cctcagtgag cgagcgagcg cgcagagagg gagtggccaa cccccccccc cccccccccc    3840
ggcgattctt ttgtttgctc cagactctca ggcaatgacc tgatagcctt tgtagagacc    3900
tctcaaaaat agctacccct tccggcatga atttatcagc tagaacggtt gaatatcata    3960
ttgatggtga tttgactgtc tccggccttt ctcacccgtt tgaatctttta cctacacatt    4020 actcaggcat tgcatttaaa atatatgagg gttctaaaaa tttttatcct tgcgttgaaa    4080
taaaggcttc tcccgcaaaa gtattacagg gtcataatgt ttttggtaca accgatttag    4140
ctttatgctc tgaggcttta ttgcttaatt ttgctaattc tttgccttgc ctgtatgatt    4200
tattggatgt tggaatcgcc tgatgcggta ttttctcctt acgcatctgt gcggtatttc    4260
acaccgcata tggtgcactc tcagtacaat ctgctctgat gccgcatagt tatatggtgc    4320
actctcagta caatctgctc tgatgccgca tagttaagcc agccccgaca cccgccaaca    4380
cagccagccc cgacacccgc caacaccccgc tgacgcgccc tgacgggctt gtctgctccc    4440
ggcatccgct tacagacaag ctgtgaccgt ctccgggagc tgcatgtgtc agaggttttc    4500
accgtcatca ccgaaacgcg cgagacgaaa gggcctcgtg atacgcctat ttttataggt    4560
taatgtcatg ataataatgg tttcttagac gtcaggtggc actttcgggg gaaatgtgcg    4620
cggaacccct atttgtttat ttttctaaat acattcaaat atgtatccgc tcatgagaca    4680
```

```
ataaccctga taaatgctca ataatattga aaaaggaaga gtatgagtat tcaacatttc    4740
cgtgtcgccc ttattccctt ttttgcggca ttttgccttc ctgttttttgc tcacccagaa    4800 acgctggtga aagtaaaaga tgctgaagat cagttgggtg cacgagtggg ttacatcgaa    4860
ctggatctca acagcggtaa gatccttgag agttttcgcc ccgaagaacg ttttccaatg    4920
atgagcactt ttaaagttct gctatgtggc gcggtattat cccgtattga cgccgggcaa    4980
gagcaactcg gtcgccgcat acactattct cagaatgact tggttgagta ctcaccagtc    5040
acagaaaagc atcttacgga tggcatgaca gtaagagaat tatgcagtgc tgccataacc    5100
atgagtgata acactgcggc caacttactt ctgacaacga tcggaggacc gaaggagcta    5160
accgcttttt tgcacaacat gggggatcat gtaactcgcc ttgatcgttg ggaaccggag    5220
ctgaatgaag ccataccaaa cgacgagcgt gacaccacga tgcctgtagc aatggcaaca    5280
acgttgcgca aactattaac tggcgaacta cttactctag cttcccggca acaattaata    5340
gactggatgg aggcggataa agttgcagga ccacttctgc gctcggccct tccggctggc    5400
tggtttattg ctgataaatc tggagccggt gagcgtgggt ctcgcggtat cattgcagca    5460
ctggggccag atggtaagcc ctcccgtatc gtagttatct acacgacggg gagtcaggca    5520
actatggatg aacgaaatag acagatcgct gagataggtg cctcactgat taagcattgg    5580
taactgtcag accaagttta ctcatatata ctttagattg atttaaaact tcattttttaa    5640 tttaaaagga tctaggtgaa gatcctttt gataatctca tgaccaaaat cccttaacgt    5700
gagttttcgt tccactgagc gtcagacccc gtagaaaaga tcaaaggatc ttcttgagat    5760 ccttttttttc tgcgcgtaat ctgctgcttg caaacaaaaa aaccaccgct accagcggtg    5820
gtttgtttgc cggatcaaga gctaccaact cttttttccga aggtaactgg cttcagcaga    5880
gcgcagatac caaatactgt ccttctagtg tagccgtagt taggccacca cttcaagaac    5940
tctgtagcac cgcctacata cctcgctctg ctaatcctgt taccagtggc tgctgccagt    6000
ggcgataagt cgtgtcttac cgggttggac tcaagacgat agttaccgga taaggcgcag    6060
cggtcgggct gaacggggggg ttcgtgcaca gcccagct tggagcgaac gacctacacc    6120
gaactgagat acctacagcg tgagctatga aaagcgcca cgcttcccga agggagaaag    6180
gcggacaggt atccggtaag cggcagggtc ggaacaggag agcgcacgag ggagcttcca    6240
gggggaaacg cctggtatct ttatagtcct gtcgggtttc gccacctctg acttgagcgt    6300
cgatttttgt gatgctcgtc aggggggcgg agcctatgga aaaacgccag caacgcggcc    6360 ttttttacggt tcctggcctt ttgctggcct tttgctcaca tgttctttcc tgcgttatcc    6420
cctgattctg tggataaccg tattaccgcc tttgagtgag ctgataccgc tcgccgcagc    6480
cgaacgaccg agcgcagcga gtcagtgagc gaggaagcgg aagagcgccc aatacgcaaa    6540
ccgcctctcc ccgcgcgttg gccgattcat taatg                               6575
```

<210> SEQ ID NO 53
<211> LENGTH: 6616
<212> TYPE: DNA
<213> ORGANISM: Artificial Sequence
<220> FEATURE:
<223> OTHER INFORMATION: AAVsc-HS-CRE21-TTRenh-TTRm-MVM-hFIXcoPadua-
      bghpolyA

<400> SEQUENCE: 53

```
agctggcgta atagcgaaga ggcccgcacc gatcgccctt cccaacagtt gcgcagcctg    60
aatggcgaat ggcgattccg ttgcaatggc tggcggtaat attgttctgg atattaccag    120
```

-continued

```
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg tttttcgccc tttgacgttg gagtccacgt    660
tctttaatag tggactcttg ttccaaactg gaacaacact caaccctatc tcggtctatt    720
cttttgattt ataagggatt ttgccgattt cggcctattg gttaaaaaat gagctgattt    780
aacaaaaatt taacgcgaac tttaacaaaa tattaacgtt tacaatttaa atatttgctt    840
atacaatctt cctgtttttg gggcttttct gattatcaac cggggtacat atgattgaca    900
tgctagtttt acgattaccg ttcatcgccc tgcgcgctcg ctcgctcact gaggccgccc    960
gggcaaagcc cgggcgtcgg cgacctttg tcgcccggc ctcagtgagc gagcgagcgc    1020
gcagagaggg agtggaattc acgcgtggat ctgaattctg tacaggcgtg gtacggccgc    1080
ggggaggttg cagtaagcca agattgtgcc actgcactcc aacctgggtg acagagccag    1140
actctgtctc aagaaaataa agagaaaaag aactagattc aggctgtatg tgggcaccat    1200
ctacagacat cagacacaca catttaggag taataatgat gcaatattgc caaatgtttc    1260
tcagcaacca tgtgcaactg ttgcatgtac tgtttatttc taactcagga ggatctctct    1320
aaccacacat tgcaagaaaa tagactttca gtgtttctgg caaaacaaag agttttttg    1380 ttggcattta tgctgaaagg gaagagttaa aatgttaatt tgtctttttt cttacctcca    1440
agttcactca aatcctctct tgaagcaggg tacccactgg gaggatgttg agtaagatgg    1500
aaaactactg atgacccttg cagagacaga gtattaggac atgtttgaac aggggccggg    1560
cgatcagcag gtagctctag aggatccccg tctgtctgca catttcgtag agcgagtgtt    1620
ccgatactct aatctcccta ggcaaggttc atatttgtgt aggttactta ttctcctttt    1680
gttgactaag tcaataatca gaatcagcag gtttggagtc agcttggcag ggatcagcag    1740
cctgggttgg aaggagggg tataaaagcc ccttcaccag gagaagccgt cacacagatc    1800
cacaagctcc tggctagaaa gaggtaaggg tttaagggat ggttggttgg tggggtatta    1860
atgtttaatt acctggagca cctgcctgaa atcactttttt ttcaggttgg gctagcccac    1920
catgcagcgc gtgaacatga tcatggccga gagccccggc ctgatcacca tctgcctgct    1980
gggctacctg ctgagcgccg agtgcaccgt gttcctggac cacgagaacg ccaacaagat    2040
cctgaaccgc cccaagcgct acaacagcgg caagctggag gagttcgtgc agggcaacct    2100
ggagcgcgag tgcatggagg agaagtgcag cttcgaggag gcccgcgagg tgttcgagaa    2160
caccgagcgc accaccgagt ctgtgaagca gtacgtggac ggcgaccagt gcgagagcaa    2220
cccctgcctg aacggcggca gctgcaagga cgacatcaac agctacgagt gctggtgccc    2280
cttcggcttc gagggcaaga actgcgagct ggacgtgacc tgcaacatca gaacggccg    2340 ctgcgagcag ttctgcaaga acagcgccga caacaaggtg gtgtgcagct gcaccgaggg    2400
ctaccgcctg gccgagaacc agaagagctg cgagcccgcc gtgcccttcc cctgcggccg    2460
```

-continued

```
cgtgagcgtg agccagacca gcaagctgac ccgcgccgag gccgtgttcc ccgacgtgga    2520
ctacgtgaac agcaccgagg ccgagaccat cctggacaac atcacccaga gcacccagag    2580
cttcaacgac ttcacccgcg tggtgggcgg cgaggacgcc aagcccggcc agttcccctg    2640
gcaggtggtg ctgaacggca aggtggacgc cttctgcggc ggcagcatcg tgaacgagaa    2700
gtggatcgtg accgccgccc actgcgtgga gaccggcgtg aagatcaccg tggtggccgg    2760
cgagcacaac atcgaggaga ccgagcacac cgagcagaag cgcaacgtga tccgcatcat    2820
cccccaccac aactacaacg ccgccatcaa caagtacaac cacgacatcg ccctgctgga    2880
gctggacgag cccctggtgc tgaacagcta cgtgacccc atctgcatcg ccgacaagga    2940
gtacaccaac atcttcctga agttcggcag cggctacgtg agcggctggg gccgcgtgtt    3000
ccacaagggc cgcagcgccc tggtgctgca gtacctgcgc gtgcccctgg tggaccgcgc    3060
cacctgcctg ctgagcacca agttcaccat ctacaacaac atgttctgcg ccggcttcca    3120
cgagggcggc cgcgacagct gccagggcga cagcggcggc ccccacgtga ccgaggtgga    3180
gggcaccagc ttcctgaccg gcatcatcag ctggggcgag gagtgcgcca tgaagggcaa    3240
gtacggcatc tacaccaagg tgagccgcta cgtgaactgg atcaaggaga agaccaagct    3300
gacctaatga aagatggatt tccaaggtta attcattgga attgaaaatt aacagccccc    3360 ccccccccc ccctgcagat ctgagccgaa ttcctgcagc ccgggggatc agcctcgact    3420
gtgccttcta gttgccagcc atctgttgtt tgcccctccc ccgtgccttc cttgaccctg    3480
gaaggtgcca ctcccactgt cctttcctaa taaaatgagg aaattgcatc gcattgtctg    3540
agtaggtgtc attctattct ggggggtggg gtggggcagg acagcaaggg ggaggattgg    3600
gaagacaata gcaggcatgc tggggatgcg gtgggctcta tggcttctga ggcggaaaga    3660
accagctggg gaccggtgga tctcgatagc aggcatgctg gggagagatc gatctgagga    3720 accccctagtg atggagttgg ccactccctc tctgcgcgct cgctcgctca ctgaggccgc    3780
ccgggcaaag cccgggcgtc gggcgacctt tggtcgcccg gcctcagtga gcgagcgagc    3840
gcgcagagag ggagtggcca accccccccc cccccccccc cggcgattct cttgtttgct    3900
ccagactctc aggcaatgac ctgatagcct ttgtagagac ctctcaaaaa tagctaccct    3960
ctccggcatg aatttatcag ctagaacggt tgaatatcat attgatggtg atttgactgt    4020
ctccggcctt tctcacccgt ttgaatcttt acctacacat tactcaggca ttgcatttaa    4080
aatatatgag ggttctaaaa attttttatcc ttgcgttgaa ataaaggctt ctcccgcaaa    4140
agtattacag ggtcataatg tttttggtac aaccgattta gctttatgct ctgaggcttt    4200
attgcttaat tttgctaatt ctttgccttg cctgtatgat ttattggatg ttggaatcgc    4260
ctgatgcggt attttctcct tacgcatctg tgcggtattt cacaccgcat atggtgcact    4320
ctcagtacaa tctgctctga tgccgcatag ttatatggtg cactctcagt acaatctgct    4380
ctgatgccgc atagttaagc cagccccgac acccgccaac acagccagcc ccgacacccg    4440
ccaacacccg ctgacgcgcc ctgacgggct tgtctgctcc cggcatccgc ttacagacaa    4500
gctgtgaccg tctccgggag ctgcatgtgt cagaggtttt caccgtcatc accgaaacgc    4560
gcgagacgaa agggcctcgt gatacgccta ttttttatagg ttaatgtcat gataataatg    4620
gtttcttaga cgtcaggtgg cacttttcgg ggaaatgtgc gcggaacccc tatttgttta    4680 ttttttctaaa tacattcaaa tatgtatccg ctcatgagac aataaccctg ataaatgctc    4740
aataatattg aaaaaggaag agtatgagta ttcaacattt ccgtgtcgcc cttattccct    4800
tttttgcggc attttgcctt cctgtttttg ctcacccaga aacgctggtg aaagtaaaag    4860
```

-continued

```
atgctgaaga tcagttgggt gcacgagtgg gttacatcga actggatctc aacagcggta       4920
agatccttga gagtttttcgc cccgaagaac gtttttccaat gatgagcact ttttaaagttc     4980 tgctatgtgg cgcggtatta tcccgtattg acgccgggca agagcaactc ggtcgccgca       5040
tacactattc tcagaatgac ttggttgagt actcaccagt cacagaaaag catcttacgg       5100
atggcatgac agtaagagaa ttatgcagtg ctgccataac catgagtgat aacactgcgg       5160
ccaacttact tctgacaacg atcggaggac cgaaggagct aaccgctttt ttgcacaaca       5220
tgggggatca tgtaactcgc cttgatcgtt gggaaccgga gctgaatgaa gccataccaa       5280
acgacgagcg tgacaccacg atgcctgtag caatggcaac aacgttgcgc aaactattaa       5340
ctggcgaact acttactcta gcttcccggc aacaattaat agactggatg gaggcggata       5400
aagttgcagg accacttctg cgctcggccc ttccggctgg ctggtttatt gctgataaat       5460
ctggagccgg tgagcgtggg tctcgcggta tcattgcagc actggggcca gatggtaagc       5520
cctcccgtat cgtagttatc tacacgacgg ggagtcaggc aactatggat gaacgaaata       5580
gacagatcgc tgagataggt gcctcactga ttaagcattg gtaactgtca gaccaagttt       5640
actcatatat actttagatt gatttaaaac ttcatttttta atttaaaagg atctaggtga       5700 agatccttttt tgataatctc atgaccaaaa tcccttaacg tgagttttcg ttccactgag       5760
cgtcagaccc cgtagaaaag atcaaaggat cttcttgaga tcctttttttt ctgcgcgtaa       5820 tctgctgctt gcaaacaaaa aaaccaccgc taccagcggt ggtttgtttg ccggatcaag       5880
agctaccaac tcttttttccg aaggtaactg gcttcagcag agcgcagata ccaaatactg       5940
tccttctagt gtagccgtag ttaggccacc acttcaagaa ctctgtagca ccgcctacat       6000
acctcgctct gctaatcctg ttaccagtgg ctgctgccag tggcgataag tcgtgtctta       6060
ccgggttgga ctcaagacga tagttaccgg ataaggcgca gcggtcgggc tgaacggggg       6120
gttcgtgcac acagcccagc ttggagcgaa cgacctacac cgaactgaga tacctacagc       6180
gtgagctatg agaaagcgcc acgcttcccg aagggagaaa ggcggacagg tatccggtaa       6240
gcggcagggt cggaacagga gagcgcacga gggagcttcc aggggggaaac gcctggtatc       6300 tttatagtcc tgtcgggttt cgccacctct gacttgagcg tcgattttttg tgatgctcgt       6360 caggggggcg gagcctatgg aaaaacgcca gcaacgcggc ctttttttacgg ttcctggcct      6420 tttgctggcc ttttgctcac atgttctttc ctgcgttatc ccctgattct gtggataacc       6480
gtattaccgc ctttgagtga gctgataccg ctcgccgcag ccgaacgacc gagcgcagcg       6540
agtcagtgag cgaggaagcg gaagagcgcc caatacgcaa accgcctctc cccgcgcgtt       6600
ggccgattca ttaatg                                                       6616
```

<210> SEQ ID NO 54
<211> LENGTH: 14
<212> TYPE: PRT
<213> ORGANISM: Artificial Sequence
<220> FEATURE:
<223> OTHER INFORMATION: linker

<400> SEQUENCE: 54

Ser Phe Ser Gln Asn Pro Pro Val Leu Thr Arg His Gln Arg
1               5                   10

<210> SEQ ID NO 55
<211> LENGTH: 20
<212> TYPE: DNA
<213> ORGANISM: Artificial Sequence

```
<220> FEATURE:
<223> OTHER INFORMATION: primer

<400> SEQUENCE: 55
cacgagaacg ccaacaagat                                             20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
cacttctcct ccatgcactc                                             20

<210> SEQ ID NO 57
<211> LENGTH: 771
<212> TYPE: DNA
<213> ORGANISM: Homo sapiens

<400> SEQUENCE: 57
caggctcaga ggcacacagg agtttctggg ctcaccctgc cccttccaa ccccctcagtt     60 cccatcctcc agcagctgtt tgtgtgctgc ctctgaagtc cacactgaac aaacttcagc    120
ctactcatgt ccctaaaatg ggcaaacatt gcaagcagca aacagcaaac acacagccct    180
ccctgcctgc tgaccttgga gctggggcag aggtcagaga cctctctggg cccatgccac    240
ctccaacatc cactcgaccc cttggaattt cggtggagag gagcagaggt tgtcctggcg    300
tggtttaggt agtgtgagag ggtccgggtt caaaaccact tgctgggtgg ggagtcgtca    360
gtaagtggct atgccccgac cccgaagcct gtttccccat ctgtacaatg gaaatgataa    420
agacgcccat ctgatagggt ttttgtggca aataaacatt tggttttttt gttttgtttt    480
gttttgtttt ttgagatgga ggtttgctct gtcgcccagg ctggagtgca gtgacacaat    540
ctcatctcac cacaaccttc ccctgcctca gcctcccaag tagctgggat tacaagcatg    600
tgccaccaca cctggctaat tttctatttt tagtagagac gggtttctcc atgttggtca    660
gcctcagcct cccaagtaac tgggattaca ggcctgtgcc accacacccg gctaattttt    720 tctattttg acaggacgg ggtttcacca tgttggtcag gctcctctag a              771

<210> SEQ ID NO 58
<211> LENGTH: 328
<212> TYPE: DNA
<213> ORGANISM: Homo sapiens

<400> SEQUENCE: 58
caggctcaga ggcacacagg agtttctggg ctcaccctgc cccttccaa ccccctcagtt     60 cccatcctcc agcagctgtt tgtgtgctgc ctctgaagtc cacactgaac aaacttcagc    120
ctactcatgt ccctaaaatg ggcaaacatt gcaagcagca aacagcaaac acacagccct    180
ccctgcctgc tgaccttgga gctggggcag aggtcagaga cctctctggg cccatgccac    240
ctccaacatc cactcgaccc cttggaattt cggtggagag gagcagaggt tgtcctggcg    300
tggtttaggt agtgtgagag ggtccggg                                      328
```

LIVER-SPECIFIC NUCLEIC ACID REGULATORY ELEMENTS AND METHODS AND USE THEREOF

CROSS-REFERENCE TO RELATED APPLICATIONS

This application is the US national phase under 35 U.S.C. § 371 of International Application No. PCT/EP2019/079358, filed Oct. 28, 2019, which claims priority to European Patent Application No. 18202986.8, filed Oct. 26, 2018, the contents of each of which are hereby incorporated by reference in their entirety.

FIELD

The present invention relates to nucleic acid regulatory elements that are able to enhance liver-specific expression of genes, methods employing these regulatory elements and uses thereof. The invention further encompasses expression cassettes, vectors and pharmaceutical compositions comprising these regulatory elements. The present invention is particularly useful for applications using gene therapy, more particularly liver-directed gene therapy, and for vaccination purposes.

BACKGROUND

Convincing evidence continues to emerge from clinical trials that gene therapy is yielding therapeutic effects in patients suffering from a wide range of diseases. In particular, liver-directed gene therapy is a promising modality to obtain sustained hepatocyte-specific expression of secreted factors into the circulation. Indeed, many acquired, complex and genetic diseases (hepatic diseases sensu stricto as well as some hereditary disorders that do not directly lead to liver disease but manifest themselves primarily elsewhere in the body, e.g. hemophilia A or B, familial hypercholesterolemia, ornithine transcarbamylase deficiency, or α-antitrypsin deficiency) are associated with altered gene expression in the liver. In addition, the liver often falls prey to infections with pathogens (such as hepatitis viruses). Finally, the liver can undergo malignant transformation and give rise to liver cancer (hepatocellular carcinoma) or functionally degenerate as a consequence of pharmaceutical treatments, chemotherapy, drug or alcohol abuse. Consequently, there has been substantial and increasing interest in the use of gene therapy to express a functional gene in the liver to replace a needed protein or to block the expression of an altered or undesired gene product, for instance by RNA interference or dominant-negative inhibitory proteins, or to restore hepatocyte function in a degenerating liver. Liver-directed gene therapy can also be used to express anti-viral compounds, such as VP22 protein fused to the C terminal of hepatitis B virus core protein (i.e. VP22 fusion protein-based dominant negative mutant), which can inhibit hepatitis B virus replication, ISG56 and IFITM1, which can inhibit hepatitis C virus replication, and interferon-inducible MyD88 protein, which can inhibit hepatitis B virus replication. Transduction of liver cells with immunomodulatory cytokines may be useful to induce immune responses against e.g. viral hepatitis or liver neoplasms, or to suppress immune responses towards the gene delivery vectors or the transgene. Another application of transgene delivery to the liver is for DNA vaccination. The optimisation of antigen expression is an important consideration in DNA vaccine vector design. It is clear that transgene expression may be increased through the use of optimised promoters and polyadenylation (polyA) sequences. However, in some circumstances, for example to express antigens that induce cell death upon overexpression, it may be necessary to optimise DNA vaccines to produce reduced transgene expression. Tissue-specificity is also considered important. Also other aspects of vector design may influence the efficacy of the vaccine. A rational approach to improve the efficacy of DNA vaccination would optimise the: (i) vector backbone DNA sequence; (ii) transgene sequence; (iii) co-expression of stimulatory sequences; (iv) delivery system used for the vector; and (v) targeting of the vector for appropriate immune stimulation (as reviewed in Garmory et al. 2003). The backbone of a DNA vaccine vector could be further modified to enhance immunogenicity via the manipulation of the DNA to include certain sequences, so that the DNA itself will have an adjuvantising effect. DNA vaccine vectors contain many CpG motifs (consisting of unmethylated CpG dinucleotides flanked by two 5' purines and two 3' pyrimidines) that, overall, induce a Th1-like pattern of cytokine production, and are thought to account for strong CTL responses frequently seen following DNA vaccination. It is possible to augment responses to DNA vaccine vectors by incorporating CpG motifs into the DNA backbone of the plasmid. Alternatively, immune responses may be modulated or enhanced by the co-expression of stimulatory molecules or cytokines or through the use of localisation or secretory signals, or ligand to direct antigens to sites appropriate for immune modulation. Finally, a variety of routes of administration of DNA vaccines have been studied, including intramuscular, intradermal, subcutaneous, intravenous, intraperitoneal, oral, vaginal, intranasal and, more recently, non-invasive delivery to the skin.

Efforts to deliver transgenes to liver have focused on vectors derived from adenoviruses, retroviruses, lentiviruses, and adeno-associated viruses (AAV), and plasmids. Adeno-associated viral (AAV) vector is by far the most promising gene delivery vehicle for liver-directed gene therapy. AAV vectors have a favorable safety profile and are capable of achieving persistent transgene expression. Further, several immunologically distinct AAV serotypes have been isolated from human and non-human primates, and they induce minimal immune responses, which make AAV vectors well suited for liver-directed gene therapy. The major limitation of AAV vectors is the limited packaging capacity of the vector particles (i.e. approximately 4.7 kb), constraining the size of the transgene expression cassette to obtain functional vectors.

There remain however concerns regarding the efficacy and safety of some gene delivery approaches. The major limiting factors are: insufficient and/or transient transgene expression levels, and inappropriate expression of the transgene in unwanted cell types. Higher vector doses are typically used in gene therapy clinical trials to improve therapeutic efficacy. However, this often triggers T-cell-mediated immune responses against the vector capsid antigens displayed by transduced cells, particularly hepatocytes, in the context of MHC class I. This contributes to the elimination of the gene-modified cells and liver toxicity, resulting in short-term gene expression. Moreover, inadvertent transgene expression in antigen-presenting cells (APCs), increases the risk of untoward immune responses against the gene-modified hepatocytes and/or the therapeutic transgene product. Consequently, there is a need to generate improved gene therapy vectors allowing the use of lower and safer vector doses that enable sustained hepatocyte-specific expression of the therapeutic gene. The availability of more potent vectors would also ease manufacturing needs.

Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules, which is particularly relevant for clinical translation.

A computational approach depending upon a modified distance difference matrix (DDM)–multidimensional scaling (MDS) strategy (De Bleser et al. 2007. Genome Biol 8, R83) has proven to be useful for the in silico identification of clusters of evolutionary conserved transcription factor binding site (TFBS) motifs associated with robust tissue-specific expression in liver (WO 2009/130208) and heart (WO2011/051450). The combination of one of these liver-specific regulatory elements, in particular the Serpin enhancer, with a synthetic codon-optimized hyperfunctional FIX transgene (i.e., Padua R338L) has been shown to significantly increase FIX expression and activity (WO 2014/064277).

It is an object of the present invention to further increase the efficiency and safety of liver-directed gene therapy.

SUMMARY

The present inventors have relied on a computational approach to identify evolutionarily conserved transcription factor binding site (TFBS) motifs associated with highly expressed liver-specific genes defined herein as nucleic acid regulatory elements. This required several consecutive computational steps: (1) liver-specific genes were identified that are highly expressed based on RNAseq (RNA sequencing) expression data obtained with normal human tissues; (2) publicly available databases were used to extract the corresponding promoter sequences; (3) a computational approach was employed to identify clusters of transcription factor binding site motifs (TFBS); (4) the genomic context of the highly expressed genes was screened for evolutionary conserved clusters of TFBS (i.e. CREs). These regulatory elements were subsequently validated in vivo yielding efficient gene expression. The nucleic acid regulatory elements identified herein, allow for the use of lower and thus safer vector doses in gene therapy, while maximizing therapeutic efficacy.

The invention therefore provides the following aspects:

Aspect 1. A nucleic acid regulatory element for enhancing liver-specific gene expression, comprising a sequence selected from the group consisting of: SEQ ID NO: 6, SEQ ID NO: 4, SEQ ID NO: 12, SEQ ID NO: 1, SEQ ID NO: 5, SEQ ID NO: 9, SEQ ID NO: 11, SEQ ID NO: 13, SEQ ID NO: 14, SEQ ID NO: 16, SEQ ID NO: 20, a sequence having at least 95% identity to any of said sequences, or a functional fragment thereof; wherein said nucleic acid regulatory element comprises at least a transcription factor binding site (TFBS) for SP1 and for EP300.

Aspect 2. The nucleic acid regulatory element according to aspect 1, comprising a sequence selected from the group consisting of: SEQ ID NO: 6, SEQ ID NO: 4 and SEQ ID NO: 12, a sequence having at least 95% identity to any of said sequences, or a functional fragment thereof; wherein said nucleic acid regulatory element further comprises a TFBS for HNF 4G, a TFBS for CEBPB, a TFBS for P300, a TFBS for HDAC2, a TFBS for JUND, a TFBS for FOSL2, a TFBS for ZBTB7A, a TFBS for CEBPD and a TFBS for RXRA.

Aspect 3. The nucleic acid regulatory element according to aspect 1, comprising a sequence selected from the group consisting of: SEQ ID NO: 1, SEQ ID NO: 5 and SEQ ID NO: 13, a sequence having at least 95% identity to any of said sequences, or a functional fragment thereof; wherein said nucleic acid regulatory element further comprises a TFBS for POLR2A, a TFBS for MYBL2, a TFBS for FOXA1, a TFBS for FOXA2, a TFBS for ARID3A, a TFBS for POLR2A and a TFBS for HEY1.

Aspect 4. The nucleic acid regulatory element according to aspect 1, comprising a sequence selected from the group consisting of: SEQ ID NO: 9, SEQ ID NO: 11, SEQ ID NO: 14, SEQ ID NO: 16 and SEQ ID NO: 20, a sequence having at least 95% identity to any of said sequences, or a functional fragment thereof; wherein said nucleic acid regulatory element further comprises a TFBS for HNF 4G, a TFBS for CEBPB, a TFBS for P300 and a TFBS for HNF 4A.

Aspect 5. The nucleic acid regulatory element according to any one of aspects 1 to 4, wherein said functional fragment comprises at least 20, preferably at least 25, contiguous nucleotides from the sequence from which it is derived, and wherein said functional fragment comprises at least 1, preferably at least 5, of the TFBS that are present in the sequence from which it is derived.

Aspect 6. A nucleic acid regulatory element for enhancing liver-specific gene expression hybridizing under stringent conditions to the nucleic acid regulatory element according to any one of aspect 1 to 5, or to its complement.

Aspect 7. The nucleic acid regulatory element according to any one of aspects 1 to 6, having a maximal length of 600 nucleotides, preferably of 500 nucleotides, more preferably of 400 nucleotides, even more preferably of 300 nucleotides.

Aspect 8. A nucleic acid expression cassette comprising at least one nucleic acid regulatory element according to any one of aspects 1 to 7, operably linked to a promoter and a transgene.

Aspect 9. The nucleic acid expression cassette according to aspect 8, further comprising at least one, preferably three, liver-specific regulatory element(s) different from the nucleic acid regulatory element according to any one of aspects 1 to 4, preferably wherein said at least one, preferably three, liver-specific regulatory element(s) comprise SEQ ID NO: 22 or a sequence having at least 95% identity to said sequence.

Aspect 10. The nucleic acid expression cassette according to aspect 9, comprising a nucleic acid regulatory element comprising SEQ ID NO: 6, SEQ ID NO: 4; SEQ ID NO: 12, or a sequence having at least 95% identity to any one of said sequences, and at least one, preferably three, nucleic acid regulatory element(s) comprising SEQ ID NO: 22 or a sequence having at least 95% identity to said sequence.

Aspect 11. The nucleic acid expression cassette according to any one of aspects 8 to 10, wherein the transgene encodes for a therapeutic protein or an immunogenic protein.

5

6

Aspect 12. The nucleic acid expression cassette according to aspect 11, wherein the transgene encodes for coagulation factor IX (FIX), preferably wherein said transgene is codon-optimized coagulation factor FIX, or wherein said coagulation factor FIX contains a hyper-activating mutation, preferably wherein said hyper-activating mutation corresponds to an R338L amino acid substitution, more preferably wherein said transgene encoding for coagulation factor FIX has a nucleic acid sequence as defined by SEQ ID NO: 25.

Aspect 13. The nucleic acid expression cassette according to aspect 11, wherein the transgene encodes for coagulation factor VIII (FVIII), preferably wherein said transgene is codon-optimized coagulation factor FVIII, or wherein said coagulation factor VIII has a deletion of the B domain, preferably wherein said B domain of said FVIII is replaced by a linker defined by SEQ ID NO: 54, more preferably wherein said transgene encodes for coagulation factor VIII has a nucleic acid sequence defined by SEQ ID NO: 26.

Aspect 14. The nucleic acid expression cassette according to any one of aspects 8 to 13, wherein the promoter is a liver-specific promoter, preferably a promoter derived from the transthyretin (TTR) promoter, more preferably the minimal promotor of the transthyretin gene (TTRmin) defined by SEQ ID NO: 27.

Aspect 15. The nucleic acid expression cassette according to aspect 14, further comprising a liver-specific regulatory element comprising SEQ ID NO: 24, thereby comprising the combination of the TTRe and TTRm nucleic acids as defined by SEQ ID NO: 28.

Aspect 16. The nucleic acid expression cassette according to any one of aspects 8 to 15, further comprising a minute virus of mouse (MVM) intron, preferably the MVM intron defined by SEQ ID NO: 29.

Aspect 17. The nucleic acid expression cassette according to any one of aspects 8 to 16, further comprising a transcriptional termination signal derived from the bovine growth hormone polyadenylation signal (BGHpA), preferably the BGHpA defined by SEQ ID NO: 30.

Aspect 18. A vector comprising the nucleic acid regulatory element according to any one of aspects 1 to 7, or the nucleic acid expression cassette according to any one of aspects 8 to 17, preferably a viral vector, more preferably a vector derived from an adeno-associated virus (AAV), even more preferably a self-complementary AAV vector.

Aspect 19. The vector according to aspect 18, having SEQ ID NO: 38, SEQ ID NO: 36 or SEQ ID NO: 44, preferably SEQ ID NO: 38.

Aspect 20. A pharmaceutical composition comprising the nucleic acid expression cassette according to any one of aspects 8 to 17, or the vector according to aspect 18 or 19, and a pharmaceutically acceptable carrier.

Aspect 21. The nucleic acid regulatory element according to any one of aspects 1 to 7, the nucleic acid expression cassette according to any one of aspects 8 to 17, the vector according to aspect 18 or 19, or the pharmaceutical composition according to aspect 20 for use in gene therapy, preferably liver-directed gene therapy, or in vaccination therapy, preferably prophylactic vaccination.

Aspect 22. The nucleic acid regulatory element, the nucleic acid expression cassette, the vector, or the pharmaceutical composition for use according to aspect 21, wherein the gene therapy is for the treatment of hemophilia A or hemophilia B.

Aspect 23. An in vitro or ex vivo method for expressing a transgene product in liver cells comprising:
introducing the nucleic acid expression cassette according to any one of aspects 8 to 17, or the vector according to aspect 18 or 19 into the liver cells;
expressing the transgene product in the liver cells.

Aspect 24. The nucleic acid regulatory elements according to any one of aspects 1 to 7, the nucleic acid expression cassettes according to any one of aspects 8 to 17 or the vectors according to any one of aspects 18 to 19 for use in enhancing liver-specific gene expression of a transgene, preferably wherein said use is an in vitro use.

Aspect 25. A method for enhancing liver-specific gene expression of a transgene comprising the use of the nucleic acid regulatory elements according to any one of aspects 1 to 7, the nucleic acid expression cassettes according to any one of aspects 8 to 17 or the vectors according to any one of aspects 18 or 19.

DESCRIPTION

Figure 1:
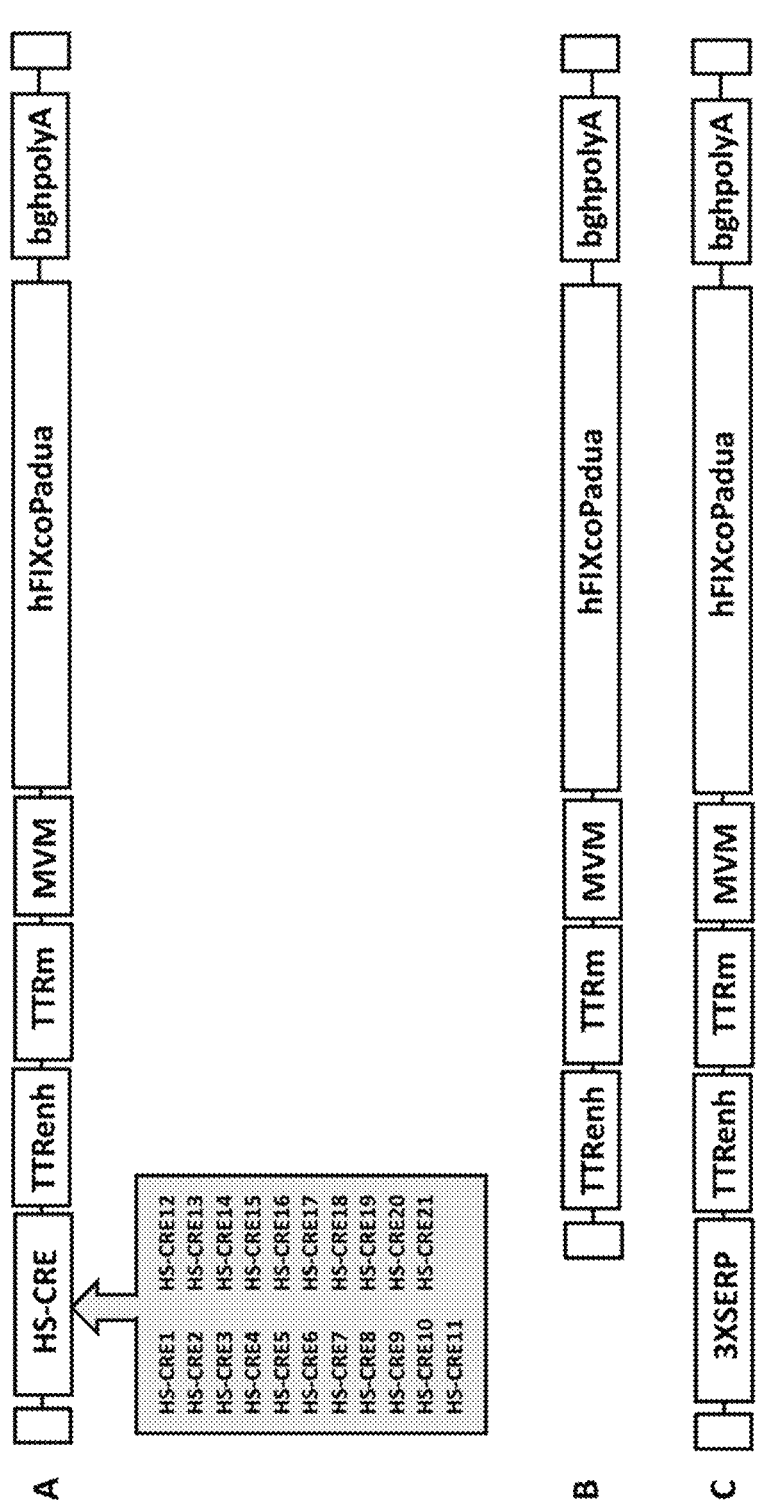
FIG. 1: Schematic representation of the AAVsc constructs. Design of the AAVsc-HS-CRE-TTRenh-TTRm-MVM-hFIXcoPadua-bghpolyA (SEQ ID NO: 33-53) (A), AAVsc-TTRenh-TTRm-MVM-hFIXcoPadua-bghpolyA (SEQ ID NO: 31) (B) and AAVsc-3xSERP-TTRenh-TTRm-MVM-hFIXcoPadua-bghpolyA (SEQ ID NO: 32) (C). SERP: Serpin; TTRm: minimal transthyretin; TTRenh: TTR enhancer; MVM: minute virus of mouse intron; hFIXcoPadua: codon-optimized human FIX Padua R338L; bghpolyA: polyadenylation signal derived from bovine growth hormone. All constructs used are flanked with AAV inverted terminal repeat.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 or etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The terms or definitions provided herein are provided to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art.

In an aspect, the invention relates to a nucleic acid regulatory element for enhancing liver-specific gene expression comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 or a sequence having at least 80%, preferably at least 85%, more preferably at least 90%, even more preferably at least 95%, such as 95%, 96%, 97%, 98%, or 99%, identity to any of these sequences, or a functional fragment thereof (i.e. a functional fragment of a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 or of a sequence having high percentage sequence identity to any of said sequences, and still performing the function of said regulatory element, i.e. increasing expression).

A "nucleic acid regulatory element" or "regulatory element", also called "CRE" (cis-regulatory element), "CRM" (cis-regulatory module), or "HS-CRE" (hepatocyte-specific cis-regulatory element) as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a liver-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory element hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for E-box binding proteins E47 and E12, CCAAT/enhancer-binding protein, also known as CEB/P, C/EPB or CEPB; hepatocyte nuclear factor 1 homeobox A, also known as HNF-1A, HNF1, IDDM20, LFB1, MODY3, TCF-1 or TCF; interferon regulatory factor 1, also known as IRF1, IRF-1 or MAR; lymphoid enhancer-binding factor 1, also known as LEF1, LEF-1, TCF10, TCF1ALPHA or TCF7L3; forkhead box protein 04, also known as FOXO4, AFX, AFX1 or MLLT7; forkhead box protein O1, also known as forkhead in rhabdomyosarcoma, FOXO1, FKH1, FKHR or FOXO1A. Transcription factor binding sites may be found in databases such as Transfac®.

Sequences disclosed herein may be part of sequences of regulatory elements capable of controlling transcription of liver-specific genes in vivo, in particular controlling the following genes: albumin also known as ALB, apolipoprotein A2 also known as ApoA2, apolipoprotein C2 also known as ApoC2, apolipoprotein C1 also known as ApoC1, apolipoprotein A1 also known as ApoA1, apolipoprotein C3 also known as APOC3, APOCIII, transthyretin, also known as TTR, retinal binding protein 4, also known as RBP4, Cytochrome P450 2E1 also known as CYP2E1, alpha-1-acid glycoprotein 1 also known as orosomucoid 1 or ORM1.

Accordingly, in embodiments, the nucleic acid regulatory elements disclosed herein comprise a sequence from ALB regulatory elements, i.e. regulatory elements that control expression of the ALB gene in vivo, e.g. regulatory elements comprising SEQ ID NO: 1 and SEQ ID NO 2 or functional fragments thereof as described herein elsewhere. In embodiments, the nucleic acid regulatory elements disclosed herein comprise a sequence from APOA2 regulatory elements, i.e. regulatory elements that control expression of the APOA2 gene in vivo, e.g. regulatory elements comprising SEQ ID NO: 3 AND SEQ ID NO: 4 or functional fragments thereof as described herein elsewhere. In embodiments, the nucleic acid regulatory elements disclosed herein comprise a sequence from TTR regulatory elements, i.e. regulatory elements that control expression of the TTR gene in vivo, e.g. regulatory elements comprising SEQ ID NO: 5 or functional fragments thereof as described herein elsewhere. In embodiments, the nucleic acid regulatory elements disclosed herein comprise a sequence from APOC1 regulatory elements, i.e. regulatory elements that control expression of the APOC1 gene in vivo, e.g. regulatory elements comprising SEQ ID NO: 6, SEQ ID NO: 7, SEQ ID NO: 8, SEQ ID NO: 9, SEQ ID NO: 10, SEQ ID NO: 11, or functional fragments thereof as described herein elsewhere. In embodiments, the nucleic acid regulatory elements disclosed herein comprise a sequence from RBP4 regulatory elements, i.e. regulatory elements that control expression of the RBP4 gene in vivo, e.g. regulatory elements comprising SEQ ID NO: 12, SEQ ID NO: 13 or functional fragments thereof as described herein elsewhere. In embodiments, the nucleic acid regulatory elements disclosed herein comprise a sequence from APOC3 regulatory elements, i.e. regulatory elements that control expression of the APOC3 gene in vivo, e.g. regulatory elements comprising SEQ ID NO: 14, SEQ ID NO: 15, SEQ ID NO: 16, SEQ ID NO: 17, SEQ ID NO: 18, or functional fragments thereof as described herein elsewhere. In embodiments, the nucleic acid regulatory elements disclosed herein comprise a sequence from CYP2E1 regulatory elements, i.e. regulatory elements that control expression of the CYP2E1 gene in vivo, e.g. regulatory elements comprising SEQ ID NO: 19 or functional fragments thereof as described herein elsewhere. In embodiments, the nucleic acid regulatory elements disclosed herein comprise a sequence from ORM1 regulatory elements, i.e. regulatory elements that control expression of the ORM1 gene in vivo, e.g. regulatory elements comprising SEQ ID NO: 20, SEQ ID NO: 21, or functional fragments thereof as described herein elsewhere.

The nucleic acid regulatory elements comprising SEQ ID NO: 6, SEQ ID NO: 4, SEQ ID NO: 12, SEQ ID NO: 1, SEQ ID NO: 5, SEQ ID NO: 9, SEQ ID NO: 11, SEQ ID NO: 13, SEQ ID NO: 14, SEQ ID NO: 16 or SEQ ID NO: 20, comprise the TFBS for SP1 and the TFBS for EP300.

The nucleic acid regulatory element comprising SEQ ID NO: 6, SEQ ID NO: 4, SEQ ID NO: 12 comprise the TFBS for SP1, the TFBS for EP300, the TFBS for HNF 4G, the TFBS for CEBPB, the TFBS for P300, the TFBS for HDAC2, the TFBS for JUND, the TFBS for FOSL2, the TFBS for ZBTB7A, the TFBS for CEBPD and the TFBS for RXRA.

The nucleic acid regulatory element comprising SEQ ID NO: 1, SEQ ID NO: 5 and SEQ ID NO: 13 comprise the TFBS for SP1, the TFBS for EP300, the TFBS for POLR2A, the TFBS for MYBL2, the TFBS for FOXA1, the TFBS for FOXA2, the TFBS for ARID3A, the TFBS for POLR2A and the TFBS for HEY1.

The nucleic acid regulatory element comprising SEQ ID NO: 9, SEQ ID NO: 11, SEQ ID NO: 14, SEQ ID NO: 16 and SEQ ID NO: 20 comprise the TFBS for SP1, the TFBS for EP300, the TFBS for HNF 4G, the TFBS for CEBPB, the TFBS for P300 and the TFBS for HNF 4A.

As used herein, the terms "sequence identity" and "identical sequence" and the like refer to the degree in sequence identity or similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term "functional fragment" as used in the application refers to fragments of the regulatory element sequences disclosed herein that retain the capability of regulating liver-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5 or all of the transcription factor binding sites (TFBS) that are present in the sequence from which they are derived.

The term "liver-specific expression" as used in the application, refers to the preferential or predominant expression of a (trans)gene (as RNA and/or polypeptide) in the liver, in liver tissue or in liver cells, as compared to other (i.e. non-liver) tissues or cells. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within liver tissue or liver cells. According to a particular embodiment, liver-specific expression entails that there is no 'leakage' of expressed gene product to other organs or tissue than liver, such as lung, muscle, brain, kidney and/or spleen.

The same applies mutatis mutandis for hepatocyte-specific expression and hepatoblast-specific expression, which may be considered as particular forms of liver-specific expression. Throughout the application, where liver-specific is mentioned in the context of expression, hepatocyte-specific expression and hepatoblast-specific expression are also explicitly envisaged.

As used herein, the term "liver cells" encompasses the cells predominantly populating the liver and encompasses mainly hepatocytes, oval cells, liver sinusoidal endothelial cells (LSEC) and cholangiocytes (epithelial cells forming the bile ducts).

The term "hepatocyte," as used herein, refers to a cell that has been differentiated from a progenitor hepatoblast such that it is capable of expressing liver-specific phenotype under appropriate conditions. The term "hepatocyte" also refers to hepatocytes that are de-differentiated. The term includes cells in vivo and cells cultured ex vivo regardless of whether such cells are primary or passaged.

The term "hepatoblast" as used herein, refers to an embryonic cell in the mesoderm that differentiates to give rise to a hepatocyte, an oval cell, or a cholangiocyte. The term includes cells in vivo and cells cultured ex vivo regardless of whether such cells are primary or passaged.

In embodiments, the invention relates to a nucleic acid regulatory element for enhancing liver-specific gene expression comprising, consisting essentially of, or consisting of a functional fragment of a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 80%, preferably at least 85%, more preferably at least 90%, even more preferably at least 95%, such as 95%, 96%, 97%, 98%, or 99%, identity to any of these sequences. Said "functional fragments" of the regulatory elements identified herein are defined as comprising at least 20, preferably at least 25, more preferably at least 50, at least 100, at least 200 or at least 250, contiguous nucleotides from the sequence from which it is derived, and/or as comprising at least 1, preferably at least 5, more preferably all of the transcription factor binding sites (TFBS) that are present in the sequence from which it is derived.

In further embodiments, the invention provides a nucleic acid regulatory element for enhancing liver-specific gene expression comprising, consisting essentially of, or consisting of a sequence selected from the group consisting of: SEQ ID NO: 6, SEQ ID NO: 4, SEQ ID NO: 12, SEQ ID NO: 1, SEQ ID NO: 5, SEQ ID NO: 9, SEQ ID NO: 11, SEQ ID NO: 13, SEQ ID NO: 14, SEQ ID NO: 16, SEQ ID NO: 20, a sequence having at least 80%, preferably at least 85%, more preferably at least 90%, even more preferably at least 95%, such as 95%, 96%, 97%, 98%, or 99%, identity to any of these sequences, or a functional fragment thereof. Said "functional fragments" of the regulatory elements identified herein are defined as comprising the TFBS for SP1 and the TFBS for EP300, and/or comprising at least 20, preferably at least 25, more preferably at least 50, at least 100, at least 200 or at least 250, contiguous nucleotides from the sequence from which it is derived, and/or as comprising at least 1, preferably at least 5, more preferably all of the TFBS that are present in the sequence from which it is derived.

In further embodiments, the invention provides a nucleic acid regulatory element for enhancing liver-specific gene expression comprising, consisting essentially of, or consisting of a sequence selected from the group consisting of: SEQ ID NO: 6, SEQ ID NO: 4, SEQ ID NO: 12, SEQ ID NO: 1, SEQ ID NO: 5, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof. Said "functional fragments" of the regulatory elements identified herein are defined as comprising at least the TFBS for SP1 and the TFBS for EP300, and/or as comprising at least 20, preferably at least 25, more preferably at least 50, at least 100, at least 200 or at least 250, contiguous nucleotides from the sequence from which it is derived, or and/or as comprising at least 1, preferably all of the TFBS that are present in the sequence from which it is derived.

In further embodiments, the invention provides a nucleic acid regulatory element for enhancing liver-specific gene expression comprising, consisting essentially of, or consisting of, a sequence selected from the group consisting of: SEQ ID NO: 6, SEQ ID NO: 4, SEQ ID NO: 12 or a sequence having at least 80%, preferably at least 85%, more preferably at least 90%, even more preferably at least 95%, such as 95%, 96%, 97%, 98%, or 99%, identity to any of these sequences, or a functional fragment thereof, wherein said nucleic acid regulatory element comprises the TFBS for SP1, the TFBS for EP300, the TFBS for HNF 4G, the TFBS for CEBPB, the TFBS for P300, the TFBS for HDAC2, the TFBS for JUND, the TFBS for FOSL2, the TFBS for ZBTB7A, the TFBS for CEBPD and the TFBS for RXRA; and wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the TFBS that are present in the sequence from which it is derived.

In further embodiments, the invention provides a nucleic acid regulatory element for enhancing liver-specific gene expression comprising, consisting essentially of, or consisting of, a sequence selected from the group consisting of: SEQ ID NO: 1, SEQ ID NO: 5 and SEQ ID NO: 13, or a sequence having at least 80%, preferably at least 85%, more preferably at least 90%, even more preferably at least 95%, such as 95%, 96%, 97%, 98%, or 99%, identity to any of these sequences, or a functional fragment thereof, wherein said nucleic acid regulatory element comprises the TFBS for SP1, the TFBS for EP300, the TFBS for POLR2A, the TFBS for MYBL2, the TFBS for FOXA1, the TFBS for FOXA2, the TFBS for ARID3A, the TFBS for POLR2A and the TFBS for HEY1; and wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the TFBS that are present in the sequence from which it is derived.

In further embodiments, the invention provides a nucleic acid regulatory element for enhancing liver-specific gene expression comprising, consisting essentially of, or consisting of, a sequence selected from the group consisting of: SEQ ID NO: 9, SEQ ID NO: 11, SEQ ID NO: 14, SEQ ID NO: 16 and SEQ ID NO: 20, or a sequence having at least 80%, preferably at least 85%, more preferably at least 90%, even more preferably at least 95%, such as 95%, 96%, 97%, 98%, or 99%, identity to any of these sequences, or a functional fragment thereof, wherein said nucleic acid regulatory element comprises the TFBS for SP1, the TFBS for EP300, the TFBS for HNF 4G, the TFBS for CEBPB, the TFBS for P300 and the TFBS for HNF 4A; and wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the TFBS that are present in the sequence from which it is derived.

In further embodiments, the invention provides a nucleic acid regulatory element for enhancing liver-specific gene expression comprising, consisting essentially of, or consisting of a sequence selected from the group consisting of: SEQ ID NO: 6, or a sequence having at least 80%, preferably at least 85%, more preferably at least 90%, even more preferably at least 95%, such as 95%, 96%, 97%, 98%, or 99%, identity to SEQ ID NO: 6, or a functional fragment thereof as described herein.

In further embodiments, the invention provides a nucleic acid regulatory element for enhancing liver-specific gene expression comprising, consisting essentially of, or consisting of a sequence selected from the group consisting of: SEQ ID NO: 4, or a sequence having at least 80%, preferably at least 85%, more preferably at least 90%, even more preferably at least 95%, such as 95%, 96%, 97%, 98%, or 99%, identity to SEQ ID NO: 4, or a functional fragment thereof as described herein.

In further embodiments, the invention provides a nucleic acid regulatory element for enhancing liver-specific gene expression comprising, consisting essentially of, or consisting of a sequence selected from the group consisting of: SEQ ID NO: 12, or a sequence having at least 80%, preferably at least 85%, more preferably at least 90%, even more preferably at least 95%, such as 95%, 96%, 97%, 98%, or 99%, identity to SEQ ID NO: 12, or a functional fragment thereof as described herein.

It is also possible to make nucleic acid regulatory elements that comprise an artificial sequence by combining two or more (e.g. two, three, four, five or more) identical or different sequences disclosed herein or functional fragments thereof as described herein.

Accordingly, in certain embodiments a nucleic acid regulatory element for enhancing liver-specific gene expression is provided comprising at least two sequences selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or a sequence having at least 90%, preferably at least 95%, such as 95%, 96%, 97%, 98%, or 99%, identity to any of these sequences, or a functional fragment thereof, preferably selected from the group consisting of: SEQ ID NO: 6, SEQ ID NO: 4, SEQ ID NO: 12, SEQ ID NO: 1, SEQ ID NO: 5 and SEQ ID NO: 13, or a sequence having at least 90%, preferably at least 95%, such as 95%, 96%, 97%, 98%, or 99%, identity to any of these sequences, or a functional fragment thereof as described herein, more preferably selected from the group consisting of: SEQ ID NO: 6, SEQ ID NO: 4, SEQ ID NO: 12, or a sequence having at least 90%, preferably at least 95%, such as 95%, 96%, 97%, 98%, or 99%, identity to any of these sequences, or a functional fragment thereof as described herein elsewhere.

For example, disclosed herein is a nucleic acid regulatory element comprising, consisting essentially of, or consisting of SEQ ID NO:6, SEQ ID NO: 4 and SEQ ID NO: 12; a nucleic acid regulatory element comprising, consisting essentially of, or consisting of 2, 3, 4, or 5 repeats, e.g. tandem repeats, of SEQ ID NO:6; a nucleic acid regulatory element comprising, consisting essentially of, or consisting of 2, 3, 4, or 5 repeats, e.g. tandem repeats, of SEQ ID NO: 4; or a nucleic acid regulatory element comprising, consisting essentially of, or consisting of 2, 3, 4, or 5 repeats, e.g. tandem repeats, of SEQ ID NO: 12. It is also possible to make nucleic acid regulatory elements that comprise an artificial sequence by combining one or more (e.g. one, two, three, four, five or more) sequences disclosed herein or functional fragments thereof as described herein with one or more liver-specific regulatory elements which are known in the art. Non-limiting examples of known liver-specific regulatory elements are disclosed in WO 2009/130208, WO 2016/146757 or WO 01/98482 which are incorporated by reference in their entirety herein.

A particularly preferred example of a liver-specific regulatory element for combining with a nucleic acid regulatory element disclosed herein is a nucleic acid regulatory element derived from the SERPINA1 gene promoter, more particularly a regulatory element comprising the sequence as defined in SEQ ID NO: 22, a sequence having at least 85%, preferably at least 90%, more preferably at least 95%, such as 96%, 97%, 98% or 99%, identity to said sequence, or a functional fragment thereof as described herein. The liver-specific regulatory element consisting of the sequence as defined in SEQ ID NO: 22 is herein referred to as "Serpin enhancer", "SerpEnh", or "Serp".

Accordingly, in certain embodiments a nucleic acid regulatory element for enhancing liver-specific gene expression is provided comprising the sequence SEQ ID NO: 22, a sequence having at least 85%, preferably at least 90%, more preferably at least 95%, such as 96%, 97%, 98% or 99%, identity to said sequence, or a functional fragment thereof as described herein, and at least one or two or more (e.g. two, three, four, five or more) identical or different sequences selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 or a sequence having at least 90%, preferably at least 95%, such as 95%, 96%, 97%, 98%, or 99%, identity to any of these sequences, or a functional fragment thereof as described herein; preferably selected from the group consisting of SEQ ID NO: 6, SEQ ID NO: 4, SEQ ID NO: 12, SEQ ID NO: 1, SEQ ID NO: 5, SEQ ID NO: 9, SEQ ID NO: 11, SEQ ID NO: 13, SEQ ID NO: 14, SEQ ID NO: 16, SEQ ID NO: 20, or a sequence having at least 90%, preferably at least 95%, such as 95%, 96%, 97%, 98%, or 99%, identity to any of these sequences, or a functional fragment thereof as described herein; more preferably selected from the group SEQ ID NO: 6, SEQ ID NO: 4, SEQ ID NO: 12, SEQ ID NO: 1, SEQ ID NO: 5, SEQ ID NO: 13, or a sequence having at least 90%, preferably at least 95%, such as 95%, 96%, 97%, 98%, or 99%, identity to any of these sequences, or a functional fragment thereof as described herein; more preferably SEQ ID NO: 6 or a sequence having at least 90%, preferably at least 95%, such as 95%, 96%, 97%, 98%, or 99%, identity to any of these sequences, or a functional fragment thereof as described herein; even more preferably selected from the group SEQ ID NO: 6, SEQ ID NO: 4 and SEQ ID NO: 12, or a sequence having at least 90%, preferably at least 95%, such as 95%, 96%, 97%, 98%, or 99%, identity to any of these sequences, or a functional fragment thereof as described herein; more preferably SEQ ID NO: 6 or a sequence having at least 90%, preferably at least 95%, such as 95%, 96%, 97%, 98%, or 99%, identity to any of these sequences, or a functional fragment thereof as described herein.

In a particular embodiment, a nucleic acid regulatory element for enhancing liver-specific gene expression is provided comprising, consisting essentially of, or consisting of SEQ ID NO: 22, more particularly 3 repeats, e.g. tandem repeats, of SEQ ID NO:22 (Serp), and SEQ ID NO: 6. In a more particular embodiment, a nucleic acid regulatory element for enhancing liver-specific gene expression is provided comprising, consisting essentially of, or consisting of SEQ ID NO: 23 (3xSerp) and SEQ ID NO: 6.

In a particular embodiment, a nucleic acid regulatory element for enhancing liver-specific gene expression is provided comprising, consisting essentially of, or consisting of SEQ ID NO: 22, more particularly 3 repeats, e.g. tandem repeats, of SEQ ID NO: 22 (Serp), and SEQ ID NO: 4. In a more particular embodiment, a nucleic acid regulatory element for enhancing liver-specific gene expression is provided comprising, consisting essentially of, or consisting of SEQ ID NO: 23 (3xSerp) and SEQ ID NO: 4.

In a particular embodiment, a nucleic acid regulatory element for enhancing liver-specific gene expression is provided comprising, consisting essentially of, or consisting of SEQ ID NO: 22, more particularly 3 repeats, e.g. tandem repeats, of SEQ ID NO: 22 (Serp), and SEQ ID NO: 12. In a more particular embodiment, a nucleic acid regulatory element for enhancing liver-specific gene expression is provided comprising, consisting essentially of, or consisting of SEQ ID NO: 23 (3xSerp) and SEQ ID NO: 12.

A further particularly preferred example of a liver-specific regulatory element for combining with a nucleic acid regulatory element disclosed herein is the "TTR enhancer", "TTRe" or "TTREnh", more particularly a regulatory element comprising the sequence as defined in SEQ ID NO: 24, a sequence having at least 85%, preferably at least 90%, more preferably at least 95%, such as 96%, 97%, 98% or 99%, identity to said sequence, or a functional fragment thereof as described herein. Accordingly, in certain embodiments a nucleic acid regulatory element for enhancing liver-specific gene expression is provided comprising the sequence SEQ ID NO: 24, a sequence having at least 85%, preferably at least 90%, more preferably at least 95%, such as 96%, 97%, 98% or 99%, identity to said sequence, or a functional fragment thereof as described herein, and at least one or two or more (e.g. two, three, four, five or more) identical or different sequences selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 or a sequence having at least 90%, preferably at least 95%, such as 95%, 96%, 97%, 98%, or 99%, identity to any of these sequences, or a functional fragment thereof as described herein; preferably selected from the group consisting of SEQ ID NO: 6, SEQ ID NO: 4, SEQ ID NO: 12, SEQ ID NO: 1, SEQ ID NO: 5, SEQ ID NO: 9, SEQ ID NO: 11, SEQ ID NO: 13, SEQ ID NO: 14, SEQ ID NO: 16, SEQ ID NO: 20, or a sequence having at least 90%, preferably at least 95%, such as 95%, 96%, 97%, 98%, or 99%, identity to any of these sequences, or a functional fragment thereof as described herein; more preferably selected from the group SEQ ID NO: 6, SEQ ID NO: 4, SEQ ID NO: 12, SEQ ID NO: 1, SEQ ID NO: 5, SEQ ID NO: 13, or a sequence having at least 90%, preferably at least 95%, such as 95%, 96%, 97%, 98%, or 99%, identity to any of these sequences, or a functional fragment thereof as described herein; more preferably SEQ ID NO: 6 or a sequence having at least 90%, preferably at least 95%, such as 95%, 96%, 97%, 98%, or 99%, identity to any of these sequences, or a functional fragment thereof as described herein; even more preferably selected from the group SEQ ID NO: 6, SEQ ID NO: 4 and SEQ ID NO: 12, or a sequence having at least 90%, preferably at least 95%, such as 95%, 96%, 97%, 98%, or 99%, identity to any of these sequences, or a functional fragment thereof as described herein; more preferably SEQ ID NO: 6 or a sequence having at least 90%, preferably at least 95%, such as 95%, 96%, 97%, 98%, or 99%, identity to any of these sequences, or a functional fragment thereof as described herein.

A further particularly preferred example of a liver-specific regulatory element for combining with a nucleic acid regulatory element disclosed herein is a regulatory element comprising the "hepatic locus control element" as described in WO 01/98482 (which is hereby incorporated by reference herein), more particularly a regulatory element comprising the sequence as defined in SEQ ID NO: 57 or SEQ ID NO: 58, a sequence having at least 85%, preferably at least 90%, more preferably at least 95%, such as 96%, 97%, 98% or 99%, identity to said sequence, or a functional fragment thereof as described herein.

A further particularly preferred example of a liver-specific regulatory element for combining with a nucleic acid regulatory element disclosed herein is a regulatory element comprising at least one, preferably three tandem repeats of the Serpin enhancer (e.g. SEQ ID NO: 22), such as a regulatory element comprising SEQ ID NO: 23 (3xSerp) and the transthyretin enhancer (TTRe) as defined by SEQ ID NO: 24. Examples of liver-specific regulatory elements comprising at least one, preferably three tandem repeats of the Serpin enhancer and the TTRe are described in WO 2016/146757 which is incorporated by reference in its entirety herein.

The one or more liver-specific regulatory elements which are known in the art may be located upstream or downstream of the one or more (e.g. one, two, three, four, five or more) nucleic acid regulatory elements disclosed herein Preferably, the one or more (e.g. one, two, three, four, five or more) nucleic acid regulatory elements disclosed herein or functional fragments thereof as described herein are located upstream of the one or more liver-specific regulatory elements which are known in the art.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing liver-specific gene expression comprising binding sites for ATF3, AR1D3A, 2BTB7A, BHLHE40, CEBPB, CEBPD, CHD2, CTCF, EP300, ELF1, EZH2, ESRRA, FOXA1, FOXA2, FOSL2, HEY1, GATA2, GABPA, HEY1, HDAC2, HNF 4A, HNF 4G, HSF1, JUN, JUND, MAFF, MAFK, MAX, MYBL2, MBD4, MAZ, MXI1, MYC, NF1C, NR2C2, NR2F2, POLR2A, P012, p300, PPARGC1A, RAD21, RXR5, RXRA, RCOR1, REST, SMC3, SUZ12, SHC3, SP1, SRF, SREBP1, SIN3AK20, TAF1, TCF7L2, TBP, TEAD4, TBP, TCF12, TCF4, USF1, USF2, YY1, ZBTB7A and/or ZBTB33. In further examples, these nucleic acid regulatory elements comprise at least two, such as 2, 3, 4, or more copies of one or more of the recited TFBSs.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing liver-specific gene expression comprising, consisting essentially of, or consisting of the complement of a sequence described herein, in particular a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO:

14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 80%, preferably at least 85%, more preferably at least 90%, even more preferably at least 95%, such as 95%, 96%, 97%, 98%, or 99%, identity to any of these sequences, or a functional fragment thereof as described herein.

Also disclosed herein is a nucleic acid regulatory element for enhancing liver-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 90%, preferably at least 95%, such as 95%, 96%, 97%, 98%, or 99%, identity to any of these sequences, a functional fragment thereof as described herein, or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression "hybridize under stringent conditions", refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 600 nucleotides or less, 500 nucleotides or less, 400 nucleotides or less, 300 nucleotides or less, 250 nucleotides or less, 200 nucleotides or less, 190 nucleotides or less, or 180 nucleotides or less, preferably 500 nucleotides or less, more preferably 300 nucleotides or less.

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 160 nucleotides, 170 nucleotides, or all nucleotides of the respective sequences of the regulatory elements define by SEQ ID NO: 1 to 21.

In certain embodiments, the invention provides for a nucleic acid regulatory element of 600 nucleotides or less, 500 nucleotides or less, 400 nucleotides or less, 300 nucleotides or less, 250 nucleotides or less, 200 nucleotides or less, 190 nucleotides or less, or 180 nucleotides or less, preferably 500 nucleotides or less, more preferably 300 nucleotides or less, for enhancing liver-specific gene expression comprising a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21a sequence having at least 80%, preferably at least 85%, more preferably at least 90%, even more preferably at least 95%, such as 95%, 96%, 97%, 98%, or 99%, identity to any of these sequences, or a functional fragment thereof as described herein. The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term "nucleic acid expression cassette" refers to nucleic acid molecules that include one or more transcriptional control elements (such as, but not limited to promoters, enhancers and/or regulatory elements, polyadenylation sequences, and introns) that direct (trans) gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term "operably linked" as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein or a functional fragment thereof as described herein. In alternative embodiments, the nucleic acid expression cassette comprises two or more, such as, e.g., 2, 3, 4, 5, 6, 7, 8, 9, or 10, nucleic acid regulatory elements as described herein, or functional fragments thereof as described herein, i.e. they are combined modularly to enhance their regulatory (and/or enhancing) effect. In yet alternative embodiments, the nucleic acid expression cassette comprises at least one nucleic acid regulatory element as described herein, or functional fragments thereof as described herein; and at least one liver-specific nucleic acid regulatory element known in the art, or functional fragments thereof as described herein. In further embodiments, at least two of the two or more nucleic acid regulatory elements, or functional fragments thereof as described herein, are identical or substantially identical. In yet further embodiments, all of the two or more regulatory elements, or functional fragments thereof as described herein, are identical or substantially identical. The copies of the identical or substantially identical nucleic acid regulatory elements, or functional fragments thereof as described herein, may be provided as tandem repeats in the nucleic acid expression cassette. In alternative further embodiments, at least two of the two or more nucleic acid regulatory elements, or functional fragments thereof as described herein, are different from each other. The nucleic acid expression cassette may also comprise a combination of identical and substantially identical nucleic acid regulatory elements, or functional fragments thereof as described herein, and non-identical nucleic acid regulatory elements, or functional fragments thereof as described herein.

For example, the nucleic acid expression cassette may comprise a nucleic acid regulatory element comprising SEQ ID NO: 6, and a nucleic acid regulatory element comprising SEQ ID NO: 22 (SERP); the nucleic acid expression cassette may comprise a nucleic acid regulatory element comprising SEQ ID NO: 6 and 2, 3, or 4 nucleic acid regulatory elements comprising SEQ ID NO: 22 (SERP); the nucleic acid expression cassette may comprise 2, 3, or 4 nucleic acid regulatory element comprising SEQ ID NO: 6 and a nucleic acid regulatory elements comprising SEQ ID NO: 22 (SERP); the nucleic acid expression cassette may comprise 2, 3, or 4 nucleic acid regulatory element comprising SEQ ID NO: 6 and 2, 3, or 4 nucleic acid regulatory elements comprising SEQ ID NO: 22 (SERP). Similarly, the nucleic acid expression cassette may comprise 2, 3, or 4 nucleic acid regulatory element comprising SEQ ID NO: 6 and a nucleic acid regulatory elements comprising SEQ ID NO: 23 (3xSERP).

As used in the application, the term "promoter" refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of liver-specific expression in vivo (and/or in hepatoblasts, hepatocytes, oval cells, cholangiocytes, liver stem cells or liver-derived cell lines in vitro) of the transgene and/or (2) can increase the level of expression of the transgene in the liver and/or in hepatoblasts, hepatocytes, oval cells, liver stem cells and cholangiocytes (in vivo) or in cell lines derived therefrom (in vitro).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

The enrichment in liver-specific TFBS in the nucleic acid regulatory elements disclosed herein in principle allows the regulatory elements to direct liver-specific expression even from a promoter that itself is not liver-specific. Hence, the regulatory elements disclosed herein can be used in nucleic acid expression cassettes in conjunction with their natural promoter, as well as with another promoter. Preferably, the nucleic acid expression cassettes disclosed herein comprise a liver-specific promoter. This is to increase liver specificity and/or avoid leakage of expression in other tissues. Non-limiting examples of liver-specific promoters are provided on the Liver Specific Gene Promoter Database (LSPD, http://rulai.cshl.edu/LSPD/), and include, for example, the albumin (ALB) promoter, the apolipoprotein A2 (APOA2) promoter, the transthyretin (TTR) promoter, the apolipoprotein C1 (APOC1) promoter, the retinol binding protein 4 (RBP4) promoter, the apolipoprotein C3 (APOC3) promoter, the cytochrome P450 2E1 (CYP2E1) promoter, the alpha-1-acid glycoprotein 1 (ORM1) promoter, the serpin A1 (SERPINA1) promoter, the apolipoprotein A1 (APOA1) promoter, the complement factor B (CFB) promoter, the ketohexokinase (KHK) promoter, the hemopexin (HPX) promoter, the nicotinamide N-methyltransferase (NNMT) promoter, the (liver) carboxylesterase 1 (CES1) promoter, the protein C (PROC) promoter, the apolipoprotein C3 (APOC3) promoter, the mannan-binding lectin serine protease 2 (MASP2) promoter, the hepcidin antimicrobial peptide (HAMP) promoter, the serpin peptidase inhibitor, clade C (antithrombin), member 1 (SERPINC1) promoter, the alpha 1-antitrypsin (AAT) promoter.

In particularly preferred embodiments, the promoter is a mammalian liver-specific promoter, in particular a murine or human liver-specific promoter.

In preferred embodiments, the promoter is from the transthyretin gene, in particular the murine or human transthyretin gene, such as the minimal transthyretin promoter (TTRm) as defined in SEQ ID NO: 27.

In particular embodiments, if the nucleic acid regulatory element for enhancing liver-specific gene expression as taught herein is combined with the TTRe enhancer (e.g. as defined in SEQ ID NO: 24) the promotor is preferably TTRm (e.g. as defined in SEQ ID NO: 27), and the combination of the TTRe and TTRm nucleic acid modules is preferably as set forth in SEQ ID NO: 28. Accordingly, in particular embodiments, the promoter is the transthyretin (TTR) promoter, thereby comprising the combination of the TTRe and TTRm nucleic acids as defined by SEQ ID NO: 28.

In particular embodiments, if the nucleic acid regulatory element for enhancing liver-specific gene expression as taught herein is combined with the "hepatic locus control element" as described in WO 01/98482 hereby incorporated by reference, more particularly a regulatory element comprising the sequence as defined in SEQ ID NO: 57 or SEQ ID NO: 58, the promotor is preferably the AAT promoter.

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A "minimal promoter" (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less.

The term "transgene" as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to gRNA, shRNA, circRNA, siRNA, antisense-RNA, and the like. etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular mammal, in which it is introduced, e.g. in cases where the nucleic acid expression cassette is used for gene therapy).

The transgene may be codon-optimized.

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/ or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein or an immunogenic protein.

In embodiments, the transgene encodes a therapeutic protein. Non-limiting examples of therapeutic proteins include factor VIII, factor IX, factor VII, factor VIIa, factor X, von Willebrand factor, phenylalaninehydroxylase (PAH), α-glucosidase (GAA), C1 esterase inhibitor (C1-INH), lysosomal enzymes, lysosomal enzyme iduronate-2-sulfatase (I2S), erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α1-antitrypsin, α-galactosidase A, α-L-iduronidase, ATP7b, ornithine transcarbamoylase, phenylalanine hydroxylase, lipoprotein lipase, apoliproteins, low-density lipoprotein receptor (LDL-R), albumin, glucose-6-phosphatase, VP22 fusion protein-based dominant negative mutant, ISG56, IFITM1, interferon-inducible MyD88 protein transgenes encoding antibodies, nanobodies, anti-viral dominant-negative proteins, and fragments, subunits or mutants thereof, etc.

In embodiments, the transgene encodes an immunogenic protein. Non-limiting examples of immunogenic proteins include epitopes and antigens derived from a pathogen such as hepatitis A, B, or C surface antigen proteins.

As used herein, the term "immunogenic" refers to a substance or composition capable of eliciting an immune response.

In certain embodiments, the transgene encodes FIX. The term "coagulation factor IX" has the meaning as known in the art. Synonyms of coagulation factor IX are "FIX" or "Christmas factor" or "F9" and can be used interchangeably. In particular, the term "coagulation factor IX" encompasses the human protein encoded by the mRNA sequence as defined in Genbank accession number NM_000133. Preferably, said FIX is a mutated FIX, which is hyperactive or hyper-functional as compared to the wild type FIX. Modifying functional activity of human coagulation factor can be done by bioengineering e.g. by introduction of point mutations. By this approach a hyperactive R338A variant was reported, which showed a 3-fold increased clotting activity compared to the wild-type human FIX in an in vitro activated partial thromboplastin time assay (APPT) (Chang et al., 1998) and a 2 to 6-fold higher specific activity in hemophilia B mice transduced with the mutant FIX gene (Schuettrumpf et al., 2005). Further exemplary FIX point-mutants or domain exchange mutants with even higher clotting activities have been described: FIX, with the EGF-1 domain replaced with the EGF-1 domain from FVII, alone or in combination with a R338A point mutation (Brunetti-Pierri et al., 2009); the V86A/E277A/R338A triple mutant (Lin et al., 2010); the Y259F, K265T, and/or Y345T single, double or triple mutants (Milanov, et al., 2012); and the G190V point mutant (Kao et al., 2010); all incorporated herein by reference. Further exemplary FIX variants include Factor IX dalcinonacog alfa ("CB 2679d/ISU304") (Catalyst Biosciences Inc.).

In a particularly preferred embodiment, the FIX mutant is the one described by Simioni et al., in 2009 and denominated as the "factor IX Padua" mutant, causing X-linked thrombophilia. Said mutant factor IX is hyperactive and carries an R338L amino acid substitution. In an embodiment of the present invention, the FIX transgene encodes the human FIX protein, preferably the FIX transgene encodes for the Padua mutant of the human FIX protein. In an embodiment, the FIX transgene encodes for the Padua mutant of the human FIX protein with a sequence as set forth in SEQ ID NO: 25 (co-FIX-R338L).

In certain embodiments, the transgene encodes FVIII. The term "coagulation factor VIII" has the meaning as known in the art. Synonyms of coagulation factor VIII are "FVIII" or "anti-hemophilic factor" or "AHF" and can be used interchangeably herein. The term "coagulation factor VIII" encompasses, for example, the human protein having the amino acid sequence as defined in Uniprot accession number P00451. Preferably, said FVIII is a FVIII wherein the B domain is deleted (i.e. B domain deleted FVIII, also referred to as BDD FVIII or FVIIIAB herein). The term "B domain deleted FVIII" encompasses for example, but without limitation, FVIII mutants wherein whole or a part of the B domain is deleted and FVIII mutants wherein the B domain is replaced by a linker. Non-limiting examples of B domain deleted FVIII are described in Ward et al. (2011), WO 2011/005968 and McIntosh et al. (2013), which are specifically incorporated by reference herein. In certain embodiments, said FVIII is B domain deleted FVIII wherein the B domain is replaced by a linker having the following sequence: SFSQNPPVLTRHQR (SEQ ID NO: 54) (i.e. SQ FVIII as defined in Ward et al. (2011)). In certain embodiments, said FVIII has SEQ ID NO: 26 (i.e. codon-optimized B domain deleted human FVIII or hFVIIIcopt), as disclosed also in WO 2011/0059, which is specifically incorporated by reference herein.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Preferably, the intron is a minute virus of mouse (MVM) intron, more preferably the MVM intron as defined by SEQ ID NO: 29.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA s(SPA) site as described in Levitt et al. (1989, Genes Dev 3:1019-1025). Preferably, the polyadenylation signal is the bovine growth hormone (BGH) polyadenylation signal (SEQ ID NO: 30).

In a particular embodiment, a nucleic acid expression cassette is disclosed and comprises:

a liver-specific nucleic acid regulatory element comprising a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 95% identity to any of said sequences, or a functional fragment thereof as described herein;

the transthyretin enhancer (TTRe) as defined by SEQ ID NO: 24;

the liver-specific TTRm promoter (e.g. defined by SEQ ID NO: 27), and a transgene, preferably wherein the combination of the TTRe and TTRm nucleic acids is defined by SEQ ID NO: 28.

In a particular embodiment, a nucleic acid expression cassette is disclosed and comprises:

a liver-specific nucleic acid regulatory element comprising a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 95% identity to any of said sequences, or a functional fragment thereof as described herein;

the transthyretin enhancer (TTRe) as defined by SEQ ID NO: 24;

the liver-specific TTRm promoter (e.g. defined by SEQ ID NO: 27), and an intron, preferably the MVM intron (e.g. as defined by SEQ ID NO: 29), and a transgene, preferably wherein said transgene encodes for coagulation factor IX (FIX), preferably wherein said transgene is codon-optimized coagulation factor FIX, or wherein said coagulation factor FIX contains a hyper-activating mutation, preferably wherein said hyper-activating mutation corresponds to an R338L amino acid substitution, more preferably wherein said transgene encoding for coagulation factor FIX has a nucleic acid sequence as defined by SEQ ID NO: 25; or wherein said transgene encodes for coagulation factor VIII (FVIII), preferably wherein said transgene is codon-optimized coagulation factor FVIII, or wherein said coagulation factor VIII has a deletion of the B domain, preferably wherein said B domain of said FVIII is replaced by a linker defined by SEQ ID NO: 54, more preferably wherein said transgene encodes for coagulation factor VIII has a nucleic acid sequence defined by SEQ ID NO: 26;

preferably wherein the combination of the TTRe and TTRm nucleic acids is defined by SEQ ID NO: 28.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term "vector" as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector.

AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), although the use of single-stranded AAV vectors (ssAAV) are also encompassed herein.

Different serotypes of AAVs have been isolated and characterized, such as, for example AAV serotype 2, AAV serotype 5, AAV serotype 8, and AAV serotype 9, and all AAV serotypes are contemplated herein. AAV serotype 9 (AAV9) is ideally suited to achieve efficient transduction in liver. Accordingly, in certain embodiments, the vector is an AAV9 vector, more particularly a self-complementary AAV9 vector (scAAV9). Alternatively, engineered AAV capsids can be employed that impact on the efficacy of liver transduction, including this obtained by molecular evolution and selection, as described by Grimm et al. (2008) or Lisowski et al (2014).

In other embodiments, the vector is a non-viral vector, preferably a plasmid, a minicircle, or a transposon-based vector. Preferably, said transposon-based vectors are derived from Sleeping Beauty (SB) or PiggyBac (PB). A preferred SB transposon has been described in Ivies et al. (1997) and its hyperactive versions, including SB100X, as described in Mates et al. (2009). PiggyBac-based transposons are safe vectors in that they do no enhance the tumorigenic risk. Furthermore, liver-directed gene therapy with these vectors was shown to induce immune tolerance towards the transgene, in particular the hFIX or hFVIII transgene, comprised in the vector.

The transposon-based vectors are preferably administered in combination with a vector encoding a transposase for gene therapy. For example, the PiggyBac-derived transposon-based vector can be administered with wild-type PiggyBac transposase (Pbase) or mouse codon-optimized PiggyBac transposase (mPBase) Preferably, said transposases are hyperactive transposases, such as, for example, hyperactive PB (hyPB) transposase containing seven amino acid substitutions (I30V, S103P, G165S, M282V, S509G, N538K, N570S) as described in Yusa et al. (2011), which is specifically incorporated by reference herein.

Transposon/transposase constructs can be delivered by hydrodynamic injection or using non-viral nanoparticles to transfect hepatocytes.

In yet other embodiments, the vector comprises viral and non-viral elements.

In specific embodiments, the following vectors are provided: AAVsc-HS-CRE1-TTRenh-TTRm-MVM-hFIXcoPadua-bghpolyA (SEQ ID NO: 33), AAVsc-HS-CRE2-TTRenh-TTRm-MVM-hFIXcoPadua-bghpolyA (SEQ ID NO: 34), AAVsc-HS-CRE3-TTRenh-TTRm-MVM-hFIXcoPadua-bghpolyA (SEQ ID NO: 35), AAVsc-HS-CRE4-TTRenh-TTRm-MVM-hFIXcoPadua-bghpolyA (SEQ ID NO: 36), AAVsc-HS-CRE5-TTRenh-TTRm-MVM-hFIXcoPadua-bghpolyA (SEQ ID NO: 37), AAVsc-HS-CRE6-TTRenh-TTRm-MVM-hFIXcoPadua-bghpolyA (SEQ ID NO: 38), AAVsc-HS-CRE7-TTRenh-TTRm- MVM-hFIXcoPadua-bghpolyA (SEQ ID NO: 39), AAVsc-HS-CRE8-TTRenh-TTRm-MVM-hFIXcoPadua-bghpolyA (SEQ ID NO: 40), AAVsc-HS-CRE9-TTRenh-TTRm-MVM-hFIXcoPadua-bghpolyA (SEQ ID NO: 41), AAVsc-HS-CRE10-TTRenh-TTRm-MVM-hFIXcoPadua-bgh-polyA (SEQ ID NO: 42), AAVsc-HS-CRE11-TTRenh-TTRm-MVM-hFIXcoPadua-bghpolyA (SEQ ID NO: 43), AAVsc-HS-CRE12-TTRenh-TTRm-MVM-hFIXcoPadua-bghpolyA (SEQ ID NO: 44), AAVsc-HS-CRE13-TTRenh-TTRm-MVM-hFIXcoPadua-bghpolyA (SEQ ID NO: 45), AAVsc-HS-CRE14-TTRenh-TTRm-MVM-hFIXcoPadua-bghpolyA (SEQ ID NO: 46), AAVsc-HS-CRE15-TTRenh-TTRm-MVM-hFIXcoPadua-bghpolyA (SEQ ID NO: 47), AAVsc-HS-CRE16-TTRenh-TTRm-MVM-hFIXcoPadua-bghpolyA (SEQ ID NO: 48), AAVsc-HS-CRE17-TTRenh-TTRm-MVM-hFIXcoPadua-bghpolyA (SEQ ID NO: 49), AAVsc-HS-CRE18-TTRenh-TTRm-MVM-hFIXcoPadua-bghpolyA (SEQ ID NO: 50), AAVsc-HS-CRE19-TTRenh-TTRm-MVM-hFIXcoPadua-bghpolyA (SEQ ID NO: 51), AAVsc-HS-CRE20-TTRenh-TTRm-MVM-hFIXcoPadua-bghpolyA (SEQ ID NO: 52), AAVsc-HS-CRE21-TTRenh-TTRm-MVM-hFIXcoPadua-bghpolyA (SEQ ID NO: 53).

Accordingly, in particular embodiments, the vector has a sequence as set forth in SEQ ID NO: 38, 36, 44, 33, 37, 41, 43, 45, 46, 48 or 52, preferably a sequence as set forth in SEQ ID NO: 38, 36, 44, 33, 37 or 45, more preferably a sequence as set forth in SEQ ID NO: 38, 36 or 44, even more preferably a sequence as set forth in SEQ ID NO: 38.

In a further aspect, the invention relates to the nucleic acid regulatory elements, the nucleic acid expression cassettes, the vectors, or the pharmaceutical compositions described herein for use in medicine.

More particularly, the nucleic acid expression cassettes and vectors disclosed herein may be used, for example, to express proteins that are normally expressed and utilized in liver (i.e. structural proteins), or to express proteins that are expressed in liver and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes.

Accordingly, in particular embodiments, the nucleic acid regulatory elements, the nucleic acid expression cassettes, the vectors, or the pharmaceutical compositions described herein may be for use in gene therapy, in particular liver-directed gene therapy.

Also disclosed herein is the use of the nucleic acid regulatory elements, the nucleic acid expression cassettes, the vectors, or the pharmaceutical compositions described herein for the manufacture of a medicament for gene therapy, in particular liver-directed gene therapy.

Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, installation in airways, application to endothelium, intra-hepatic parenchyma, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993a &b).

According to particular embodiments, the use of the nucleic acid expression cassettes and vectors as described herein is envisaged for gene therapy of liver cells (i.e. liver-directed gene therapy). According to a further particular embodiment, the use of the regulatory elements, expression cassettes or vectors is for gene therapy, in particular liver-directed gene therapy, in vivo. According to yet a further particular embodiment, the use is for a method of gene therapy, in particular liver-directed gene therapy, to treat hemophilia, in particular to treat hemophilia B or hemophilia A.

Gene transfer into mammalian hepatocytes has been performed using both ex vivo and in vivo procedures. The ex vivo approach requires harvesting of the liver cells, in vitro transduction with long-term expression vectors, and reintroduction of the transduced hepatocytes into the portal circulation (Kay et al., 1992; Chowdhury et al., 1991). In vivo targeting has been done by injecting DNA or viral vectors into the liver parenchyma, hepatic artery, or portal vein, as well as via transcriptional targeting (Kuriyama et al., 1991; Kistner et al., 1996). Recent methods also include intraportal delivery of naked DNA (Budker et al., 1996) and hydrodynamic tail vein transfection (Liu et al., 1999; Zhang et al., 1999).

Also disclosed herein is the use of the nucleic acid regulatory elements, the nucleic acid expression cassettes, or the vectors disclosed herein for in vivo or in vitro expressing a protein in liver cells, more particularly by in vitro or in vivo transfecting or transducing liver cells with the nucleic acid expression cassette or the vector as described herein. According to a further aspect, methods for expressing a protein in liver cells are provided, comprising the steps of introducing in liver cells the nucleic acid regulatory element, the nucleic acid expression cassette or the vector as described herein, for example by transfection or transduction, and expressing the transgene protein product in the liver cells. These methods may be performed in vitro, ex vitro and in vivo.

A further aspect provides the nucleic acid regulatory elements, the nucleic acid expression cassettes or the vectors as taught herein for use in enhancing liver-specific gene expression of a transgene, preferably wherein said use is an in vitro use. A further aspect provides the nucleic acid regulatory elements, the nucleic acid expression cassettes or the vectors as taught herein for use in enhancing liver-specific expression of a protein or polypeptide encoded by a transgene, preferably wherein said use is an in vitro use A further aspect provides a method for enhancing liver-specific gene expression of a transgene using the nucleic acid regulatory elements, the nucleic acid expression cassettes or the vectors as taught herein.

A further aspect provides a method for enhancing liver-specific expression of a protein or polypeptide encoded by a transgene using the nucleic acid regulatory elements, the nucleic acid expression cassettes or the vectors as taught herein.

In vivo methods of gene therapy for a subject in need thereof are also provided, comprising the steps of introducing in the liver of the subject a nucleic acid expression cassette containing a transgene encoding a therapeutic protein, and expressing a therapeutic amount of the therapeutic protein in the liver.

According to a further embodiment, the method comprises the steps of introducing in the liver of the subject a vector comprising the nucleic acid expression cassette containing a transgene encoding a therapeutic protein, and expressing a therapeutic amount of the therapeutic protein in the liver.

Non-viral transfection or viral vector-mediated transduction of liver cells may also be performed by in vitro or ex vivo procedures. The in vitro approach requires the in vitro transfection or transduction of liver cells, e.g. liver cells previously harvested from a subject, liver cell lines or liver cells differentiated from e.g. induced pluripotent stem cells or embryonic cells. The ex vivo approach requires harvesting of the liver cells from a subject, in vitro transfection or transduction, and optionally re-introduction of the transfected liver cells into the subject.

Also disclosed herein are in vitro or ex vivo methods for the production of therapeutic proteins, said method comprising:

transfecting or transducing liver cells, preferably hepatic cell lines, with a nucleic acid expression cassette or a vector disclosed herein, wherein the nucleic acid expression cassette or the vector comprises a nucleic acid regulatory element disclosed herein operably linked to a promoter and a transgene, wherein the transgene encodes a therapeutic protein;

culturing the liver cells under conditions suitable for expressing the transgene in the liver cells; and harvesting the therapeutic protein from the liver cell or the culture medium.

The herein disclosed in vitro uses and methods for expressing a transgene product in liver cells, more particularly in hepatic cell lines, may be particularly suitable for the recombinant production of therapeutic proteins such as therapeutics used in protein replacement therapy (e.g. factor VIII, factor IX, factor VIIa). The use of the nucleic acid regulatory elements disclosed herein allows to enhance liver-specific expression of transgenes, which advantageously results in increased production of the transgene product, more particularly the therapeutic protein.

It is understood by the skilled person that the use of the nucleic acid regulatory elements, the nucleic acid expression cassettes and vectors disclosed herein has implications beyond gene therapy, e.g. coaxed differentiation of stem cells into hepatogenic cells, transgenic models for overexpression of proteins in liver, etc.

The transgene product may be a polypeptide, in particular a therapeutic protein such as, e.g. factor VIII, factor IX, factor VII or factor VIIa, factor X, α-glucosidase (secretable GAA), von Willebrand factor, phenylalaninehydroxylase (PAH), C1 esterase inhibitor (C1-INH), lysosomal enzymes, lysosomal enzyme iduronate-2-sulfatase (I2S), erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α1-antitrypsin, α-galactosidase A, α-L-iduronidase, ATP7b, ornithine transcarbamoylase, phenylalanine hydroxylase, lipoprotein lipase, apoliproteins, low-density lipoprotein receptor (LDL-R), albumin, glucose-6-phosphatase, transgenes encoding antibodies, nanobodies, anti-viral dominant-negative proteins, and fragments, subunits or mutants thereof. Alternatively, the transgene product may be RNA, such as siRNA.

Exemplary diseases and disorders that may benefit from gene therapy using the nucleic acid regulatory elements, the nucleic acid expression cassettes, the vectors, or the pharmaceutical compositions described herein are liver diseases and disorders such as hepatitis infection, hemophilia, including hemophilia A and B, glycogen storage disorders (GSD) such as Pompe (e.g. GSD II, GSD III, and GSD IVall), (non-alcoholic) fatty liver disease (NAFLD), lysosomal storage diseases, Hunter syndrome, phenylketonuria (PKU), hereditary angioedema (HAE), liver cirrhosis, fascioliasis, alcoholic liver disease, liver cancer, including primary liver cancer (e.g., hepatocellular carcinoma and/or cholangiocarcinoma, angiosarcoma or hemangiosarcoma) and liver metastases, biliary cirrhosis, sclerosing cholangitis, centrilobular necrosis of liver, Budd-Chiari syndrome, hemochromatosis, Wilson's disease, transthyretin-related hereditary amyloidosis, Gilbert's syndrome, and pediatric liver diseases and disorders such as biliary atresia, alpha-1 antitrypsin deficiency, Alagille syndrome, and progressive familial intrahepatic cholestasis "Fascioliasis" refers to a parasitic infection of the liver caused by a liver fluke of the *Fasciola* genus, mostly the *Fasciola hepatica*. "Hepatitis" refers to inflammation of the liver, and may be caused by various viruses (viral hepatitis) but also by some liver toxins (e.g. alcoholic hepatitis), autoimmunity (autoimmune hepatitis) or hereditary conditions. With "alcoholic liver disease" is meant herein any hepatic manifestation of alcohol overconsumption, including fatty liver disease, alcoholic hepatitis, and cirrhosis. Analogous terms such as "drug-induced" or "toxic" liver disease are also used herein to refer to the range of disorders caused by various drugs and environmental chemicals. "Fatty liver disease" (or hepatic steatosis) refers herein to a reversible condition where large vacuoles of triglyceride fat accumulate in liver cells. "Non-alcoholic fatty liver disease" denotes a spectrum of disease associated with obesity and metabolic syndrome, among other causes. Fatty liver may lead to inflammatory disease (i.e. steatohepatitis) and, eventually, cirrhosis. "Cirrhosis" denotes the formation of fibrous tissue (fibrosis) in the place of liver cells that have died due to a variety of causes, including e.g., viral hepatitis, alcohol overconsumption, and other forms of liver toxicity. Cirrhosis may cause chronic liver failure. "Primary liver cancer" most commonly manifests as "hepatocellular carcinoma" and/or "cholangiocarcinoma", rarer forms include angiosarcoma and "hemangiosarcoma" of the liver. Many liver malignancies are secondary lesions that have metastasized from primary cancers in the gastrointestinal tract or other organs, such as the kidneys, lungs, breast, or prostate. "Primary biliary cirrhosis" refers to a serious autoimmune disease of the bile capillaries. "Primary sclerosing cholangitis" refers to a serious chronic inflammatory disease of the bile duct, which is believed to be autoimmune in origin. "Centrilobular necrosis of liver" can be caused by leakage of enteric toxins into circulation. For example, *Salmonella* toxins in ileum have been shown to cause severe damage to liver hepatic cells. "Budd-Chiari syndrome" denotes the clinical picture caused by occlusion of the hepatic vein, which in some cases may lead to cirrhosis. Hereditary diseases that cause damage to the liver include "hemochromatosis", involving accumulation of iron in the body, and "Wilson's disease", which causes the body to retain copper. Liver damage is also a clinical feature of "alpha 1-antitrypsin deficiency" and "glycogen storage disease type II". In "transthyretin-related hereditary amyloidosis", the liver produces a mutated transthyretin protein which has severe neurodegenerative and/or cardiopathic effects. "Gilbert's syndrome" refers to a genetic disorder of bilirubin metabolism, which can cause mild jaundice.

According to a very specific embodiment, the therapeutic protein encoded by the transgene in the nucleic acid expression cassette or the vector is factor IX, and the method is a method for treating hemophilia B. By expressing factor IX in the liver via gene therapy, hemophilia B can be treated (Snyder et al., 1999). According to another very specific embodiment, the therapeutic protein encoded by the transgene in the nucleic acid expression cassette or the vector is factor VIII, and the method is a method for treating hemophilia A.

Except when noted differently, the terms "subject" or "patient" are used interchangeably and refer to animals, preferably vertebrates, more preferably mammals, and specifically includes human patients and non-human mammals, such as e.g. mice. Preferred patients or subjects are human subjects.

As used herein, the terms "treat" or "treatment" refer to both therapeutic treatment and prophylactic or preventative measures, wherein the object is to prevent or slow down (lessen) an undesired physiological change or disorder, such as the development or spread of proliferative disease, e.g., cancer. Beneficial or desired clinical results include, but are not limited to, alleviation of symptoms, diminishment of extent of disease, stabilised (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a phrase such as "a subject in need of treatment" includes subjects, such as mammalian subjects, that would benefit from treatment of a given condition, such as, hemophilia B or hemophilia A. Such subjects will typically include, without limitation, those that have been diagnosed with the condition, those prone to have or develop the said condition and/or those in whom the condition is to be prevented.

The term "therapeutically effective amount" refers to an amount of a compound or pharmaceutical composition effective to treat a given condition in a subject, i.e., to obtain a desired local or systemic effect and performance. The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the disease or disorder being treated. In particular, these terms refer to the quantity of compound or pharmaceutical composition according to the invention which is necessary to prevent, cure, ameliorate, or at least minimize the clinical impairment, symptoms, or complications associated with a given condition, such as hemophilia if therapeutic protein encoded by the transgene is factor IX or VIII, in either a single or multiple dose.

In a particular embodiment, if the therapeutic protein encoded by the transgene is factor IX, the term implies that levels of factor IX in plasma are equal to or higher than the therapeutic concentration of at least about 1% of physiological activity, i.e. 10 mU/ml (milli-units per milliliter) plasma, at least 5% of physiological activity or 50 mU/ml plasma, at least 10% of physiological activity or 100 mU/ml plasma, at least 15% of physiological activity or 150 mU/ml, at least 20% of physiological activity or 200 mU/ml plasma, at least 25% of physiological activity or 250 mU/ml, at least 30% of physiological activity or 300 mU/ml, at least 35% of physiological activity or 350 mU/ml, at least 40% of physiological activity or 400 mU/ml, at least 45% of physiological activity or 400 mU/ml, at least 45% of physiological activity or 450 mU/ml, at least 50% of physiological activity or 500 mU/ml, at least 65% of physiological activity or 650 mU/ml, at least 70% of physiological activity or 700 mU/ml, at least 75% of physiological activity or 750 mU/ml, at least 80% of physiological activity or 800 mU/ml, at least 85% of physiological activity or 850 mU/ml, at least 95% of physiological activity or 950 mU/ml, or at least 100% of physiological activity or 1000 mU/ml, in a subject can be obtained by transduction or transfection of the vector according to any one the embodiments described herein into a subject. Due to the very high efficiency of the nucleic acid expression cassettes and vectors of the present invention, this high therapeutic levels of factor IX in the subject can be obtained even by administering relatively low doses of vector.

In another particular embodiment, if the therapeutic protein encoded by the transgene is factor VIII, the term implies that through levels of factor VIII in plasma equal to or higher than the therapeutic concentration of 10 mU/ml (milli-units per milliliter) plasma, 50 mU/ml plasma, 100 mU/ml plasma, 150 mU/ml plasma, 200 mU/ml plasma, 250 mU/ml plasma, 300 mU/ml plasma, 350 mU/ml plasma, 400 mU/ml plasma, 450 mU/ml plasma, 500 mU/ml plasma, 550 mU/ml plasma, 600 mU/ml plasma, 650 mU/ml plasma, 750 mU/ml plasma, 800 mU/ml plasma, 850 mU/ml plasma, 900 mU/ml plasma, 950 mU/ml plasma, or higher can be obtained by transduction or transfection of any of the vectors disclosed herein into a subject. Due to the very high efficiency of the vectors and nucleic acid expression cassettes disclosed herein, these high therapeutic levels of factor VIII in the subject can be obtained even by administering relatively low doses of vector.

In particular embodiments, if the transgene encodes factor IX or factor VIII, the transduction of the vector according to any one of the embodiments defined herein into the subject can be done at a dose lower than $6 \times 10^{13}$ vg/kg (viral genomes per kilogram) to obtain a therapeutic factor IX level of 100 mU/ml plasma or higher in a subject. For example, a level of factor IX of 300 mU/ml plasma or higher in a subject may be achieved at a dose lower than $5 \times 10^{11}$ vg/kg. For hemophilia therapy, efficacy of the treatment can, for example, be measured by assessing the hemophilia-caused bleeding in the subject. In vitro tests such as, but not limited to the in vitro activated partial thromboplastin time assay (APPT), test factor IX chromogenic activity assays, blood clotting times, factor IX or human factor VIII-specific ELISAs are also available. Any other tests for assessing the efficacy of the treatment known in the art can of course be used.

The nucleic acid expression cassette, the vector or the pharmaceutical composition of the invention may be used alone or in combination with any of the know hemophilia therapies, such as the administration of recombinant or purified clotting factors. The nucleic acid expression cassette, the vector or the pharmaceutical composition of the invention can thus be administered alone or in combination with one or more active compounds. The latter can be administered before, after or simultaneously with the administration of the said agent(s).

A further object of the invention are pharmaceutical preparations which comprise a therapeutically effective amount of the nucleic acid expression cassette or the expression vector as defined herein, and a pharmaceutically acceptable carrier, i.e., one or more pharmaceutically acceptable carrier substances and/or additives, e.g., buffers, carriers, excipients, stabilisers, etc. The pharmaceutical composition may be provided in the form of a kit. The term "pharmaceutically acceptable" as used herein is consistent with the art and means compatible with the other ingredients of the pharmaceutical composition and not deleterious to the recipient thereof. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine. The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The pharmaceutical composition can be prepared in a manner known per se to one of skill in the art. For this purpose, the nucleic acid expression cassette or the expression vector as defined herein, one or more solid or liquid pharmaceutically acceptable excipients and, if desired, in combination with other pharmaceutical active compounds, are brought into a suitable administration form or dosage form which can then be used as a pharmaceutical in human medicine or veterinary medicine.

According to another aspect, a pharmaceutical composition is provided comprising a nucleic acid expression cassette containing a transgene encoding a therapeutic protein, and a pharmaceutically acceptable carrier. According to another embodiment, the pharmaceutical composition comprises a vector containing the nucleic acid expression cassette containing a transgene encoding a therapeutic protein, and a pharmaceutically acceptable carrier. According to further particular embodiments, the transgene encodes factor IX and the pharmaceutical composition is for treating hemophilia B or the transgene encodes factor VIII and the pharmaceutical composition is for treating hemophilia A.

The use of the nucleic acid expression cassette, its regulatory elements and the vector components as disclosed herein for the manufacture of these pharmaceutical compositions for use in treating hemophilia, preferably hemophilia B or hemophilia A, is also envisaged.

In an alternative example, the expression cassettes and vectors disclosed herein may be used to express an immunological amount of a gene product (such as a polypeptide, in particular an immunogenic protein, or RNA) for vaccination purposes.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), Corynebacterium parvum, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of a vaccine, in particular for the manufacture of a prophylactic vaccine.

Also disclosed herein is a method of vaccination, in particular prophylactic vaccination, of a subject in need of said vaccination comprising:

introducing in the subject, in particular in liver of the subject, a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing an immunologically effective amount of the transgene product in the subject, in particular in liver of the subject.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as taught herein (i.e., with at least one liver-specific nucleic acid regulatory element comprising a sequence selected from the group consisting of: SEQ ID NO: 6, SEQ ID NO: 4, SEQ ID NO: 12, SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, a sequence having at least 95% identity to any of said sequences, or a functional fragment thereof as described herein elsewhere) are higher than when an identical expression cassette or vector is used but without at least one liver-specific nucleic acid regulatory element as taught herein therein (e.g., comprising TTRe and/or Serp). More particularly, the expression is from about 1.1-fold to about 1.5-fold the expression obtained by the same nucleic acid expression cassette or vector without at least one liver-specific nucleic acid regulatory element as taught herein but comprising 3xSerp; or is from about 2-fold to about 6-fold the expression obtained by the same nucleic acid expression cassette or vector without at least one liver-specific nucleic acid regulatory element as taught herein (e.g., comprising TTRe and/or Serp). Moreover, the higher expression remains specific to liver. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

It is to be understood that although particular embodiments, specific constructions and configurations, as well as materials, have been discussed herein for methods and applications according to the present invention, various changes or modifications in form and detail may be made without departing from the scope and spirit of this invention.

The following examples are provided to better illustrate particular embodiments, and they should not be considered limiting the application. The application is limited only by the claims.

EXAMPLES

Example 1: Identification of Liver-Specific Regulatory Elements

Materials and Methods

A computational approach to identify evolutionarily conserved transcription factor binding site (TFBS) motifs associated with highly expressed liver-specific genes defined herein as nucleic acid regulatory elements. This required several consecutive computational steps: (1) liver-specific genes were identified that are highly expressed based on RNAseq (RNA sequencing) expression data obtained with normal human tissues; The mRNA expression levels based on RNAseq of the top liver-expressed genes are as follows (in arbitrary units): ALB (46017,49); APOA2 (21859,94); TTR (9551,38); APOC1 (9505,84); APOA1 (9277,21); RBP4 (8322,91); APOC3 (8105,76); CYP2E1 (5932,55); ORM1 (5860,23); (2) publicly available databases were used to extract the corresponding promoter sequences; (3) a computational approach was employed to identify clusters of transcription factor binding site motifs (TFBS); (4) the genomic context of the highly expressed genes was screened for evolutionary conserved clusters of TFBS (i.e. CREs).

Results

RNA sequence (RNAseq) analysis led to a comprehensive list of highly expressed hepatocyte-specific genes. Based on these expression data, the promoters of these highly expressed genes were subjected to the aforementioned computational approach that led to the identification of 21 liver-specific cis-regulatory sequences (SEQ ID NO: 1 to 21) and Table 1.

TABLE 1

| HS-CRE | Gene | Size (bp) | Position | SEQ ID NO |
|---|---|---|---|---|
| HS-CRE1 | ALB | 336 | Chr4: 74269710-74270045 | 1 |
| HS-CRE2 | ALB | 347 | Chr4: 74267148-74267494 | 2 |
| HS-CRE3 | APOA2 | 386 | Chr1: 161193242-161193627 | 3 |
| HS-CRE4 | APOA2 | 426 | Chr1: 161193972-161194397 | 4 |
| HS-CRE5 | TTR | 260 | Chr18: 29171606-29171865 | 5 |
| HS-CRE6 | APOC1 | 267 | Chr19: 45416160-45416426 | 6 |
| HS-CRE7 | APOC1 | 313 | Chr19: 45418262-45418574 | 7 |
| HS-CRE8 | APOC1 | 513 | Chr19: 45417617-45418129 | 8 |
| HS-CRE9 | APOA1 | 306 | Chr11: 116708313-116708618 | 9 |
| HS-CRE10 | APOA1 | 406 | Chr11: 116709482-116709887 | 10 |
| HS-CRE11 | APOA1 | 504 | Chr11: 116711498-116712001 | 11 |
| HS-CRE12 | RBP4 | 431 | Chr10: 95360922-95361352 | 12 |
| HS-CRE13 | RBP4 | 448 | Chr10: 95361438-95361885 | 13 |
| HS-CRE14 | APOC3 | 335 | Chr11: 116700409-116700743 | 14 |
| HS-CRE15 | APOC3 | 431 | Chr11: 116699651-116700081 | 15 |
| HS-CRE16 | APOC3 | 559 | Chr11: 116697474-116698032 | 16 |
| HS-CRE17 | APOC3 | 370 | Chr11: 116696862-116697231 | 17 |
| HS-CRE18 | APOC3 | 431 | Chr11: 116696149-116696579 | 18 |
| HS-CRE19 | CYP2E1 | 481 | Chr10: 135342646-135343126 | 19 |
| HS-CRE20 | ORM1 | 345 | Chr9: 117084721-117085065 | 20 |
| HS-CRE21 | ORM1 | 386 | Chr9: 117080121-117080506 | 21 |

Example 2: In Vivo Validation of the Identified Hepatocyte-Specific Cis-Regulatory Elements (CREs) by Hydrodynamic Plasmid Transfection

Materials and Methods

Generation of the AAV Plasmid Constructs (pAAV-HS-CRE-TTRenh-TTRm-MVM-hFIXcoPadua-bghpolyA)

The hepatocyte-specific (HS) cis-regulatory elements (CRE) HS-CRE1, HS-CRE2, HS-CRE3, HS-CRE4, HS-CRE5, HS-CRE6, HS-CRE7, HS-CRE8, HS-CRE9, HS-CRE10, HS-CRE11, HS-CRE12, HS-CRE13, HS-CRE14, HS-CRE15, HS-CRE16, HS-CRE17, HS-CRE18, HS-CRE19, HS-CRE20, HS-CRE21, identified in Example 1 were synthesized by conventional oligonucleotide synthesis and cloned into an AAVsc-TTRenh-TTRm-MVM-hFIXcoPadua-bghpolyA construct (SEQ ID NO: 33, 34, 35, 36, 37, 38, 39, 40, 41, 42, 43, 44, 45, 46, 47, 48, 49, 50, 51, 52 and 53, respectively). This construct was based on a self-complementary adeno-associated viral vector (scAAV) design and contained a minimal transthyretin promoter (TTRm) (SEQ ID NO: 27) coupled to a TTR enhancer (TTRe or TTRenh) (SEQ ID NO: 24) driving expression of a codon-optimized hyperactive human factor IX Padua (R338L) (SEQ ID NO: 25) cDNA. The different HS-CREs were cloned upstream of the TTRm/TTRe promoter/enhancer. The construct also contained an intron from minute virus of mouse (MVM) (SEQ ID NO: 29) and a bovine growth hormone polyadenylation site (bghpolyA) (SEQ ID NO: 30).

An additional plasmid construct containing the previously identified Serpin (SERP) cis-regulatory element as triplicate (SEQ ID NO: 22) (equivalent to HS-CRM8 as described in Nair et al., Blood, 2014; Chuah et al.; Mol Ther, 2014), designated as pAAVsc-3xSERP-TTRe-TTRm-MVM-FIXcoPadua-bghpA (SEQ ID NO: 32), was included for comparison (WO 2009/130208 and WO 2016/146757 which are specifically incorporated by reference herein). The different constructs are schematically represented in FIG. 1.

Hydrodynamic Gene Delivery

The AAV plasmid constructs AAVsc-HS-CRE-TTRenh-TTRm-MVM-hFIXcoPadua-bghpolyA (containing the following HS-CRE: HS-CRE1, HS-CRE2, HS-CRE3, HS-CRE4, HS-CRE5, HS-CRE6, HS-CRE7, HS-CRE8, HS-CRE9, HS-CRE10, HS-CRE11, HS-CRE12, HS-CRE13, HS-CRE14, HS-CRE15, HS-CRE16, HS-CRE17, HS-CRE18, HS-CRE19, HS-CRE20 or HS-CRE21, identified in Example 1) were injected hydrodynamically via the tail vein in adult C57BL/6 mice (18 to 19 g) at a dose of 750 ng per mouse in a total volume of 2 ml phosphate buffered saline (PBS). The AAVsc-TTRenh-TTRm-MVM-hFIXcoPadua-bghpolyA plasmid (SEQ ID NO: 31) without any HS-CRE element upstream of TTR-enh-TTRm was used as a reference construct to assess the impact of the different cis-regulatory elements on the FIX expression levels. Two days after hydrodynamic injection, blood was collected into buffered citrate for all mice by phlebotomy of the retro-orbital plexus. The concentration of hFIX antigens in citrated plasma was measured by enzyme-linked immunosorbent assay (ELISA) based on the manufacturer's protocol (Diagnostica Stago, France). Each cohort included 3 mice per vector.

Results

Figure 2:
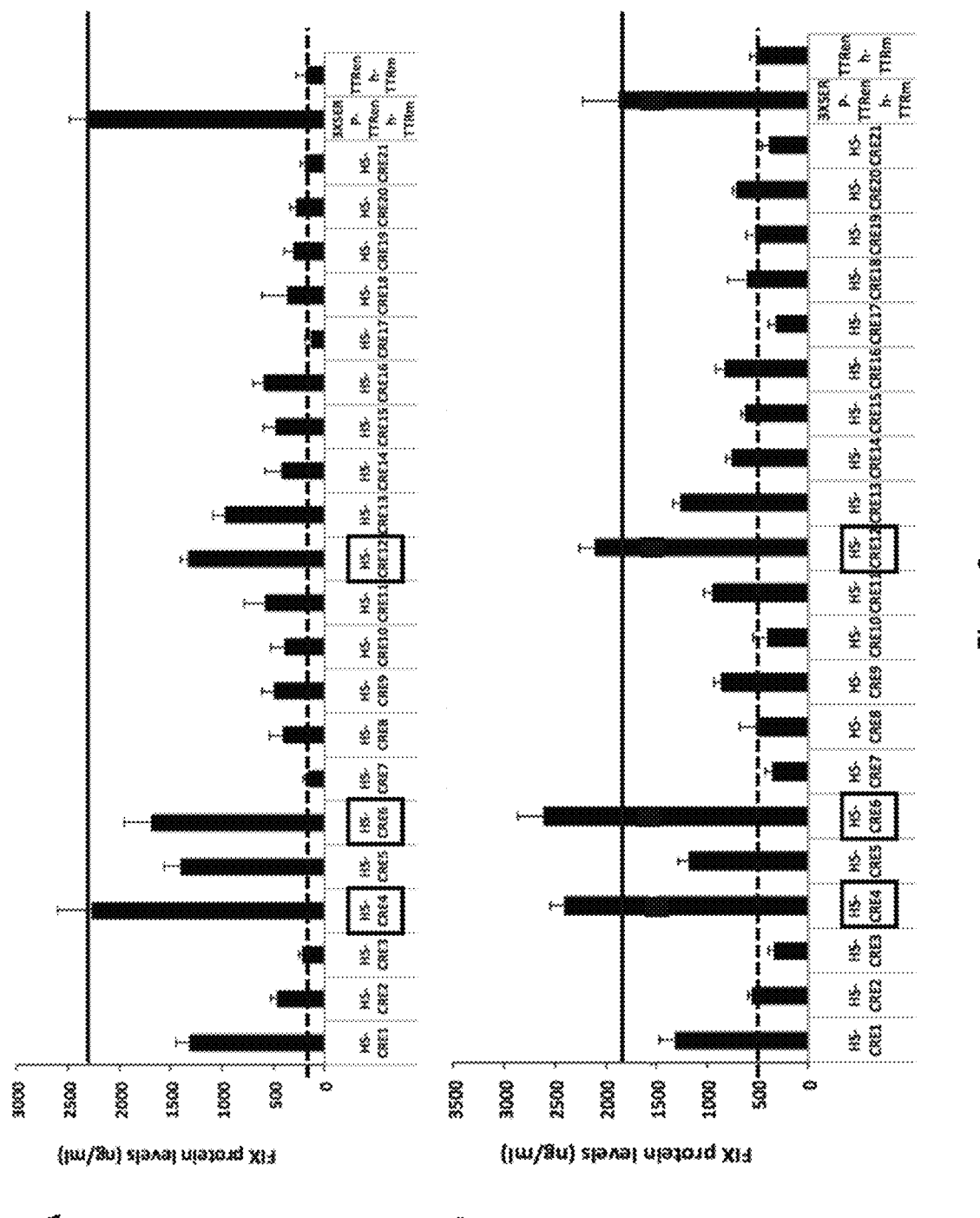
FIG. 2: Comprehensive in vivo comparison of transgene expression levels obtained with HS-CRE-containing constructs versus controls without HS-CRE. Adult C57BL/6 male mice were hydrodynamically transfected with AAVsc-HS-CRE1-TTRenh-TTRm-MVM-hFIXcoPadua-bghpolyA (SEQ ID NO: 33), AAVsc-HS-CRE2-TTRenh-TTRm-MVM-hFIXcoPadua-bghpolyA (SEQ ID NO: 34), AAVsc-HS-CRE3-TTRenh-TTRm-MVM-hFIXcoPadua-bghpolyA (SEQ ID NO: 35), AAVsc-HS-CRE4-TTRenh-TTRm-MVM-hFIXcoPadua-bghpolyA (SEQ ID NO: 36), AAVsc-HS-CRE5-TTRenh-TTRm-MVM-hFIXcoPadua-bghpolyA (SEQ ID NO: 37), AAVsc-HS-CRE6-TTRenh-TTRm-MVM-hFIXcoPadua-bghpolyA (SEQ ID NO: 38), AAVsc-HS-CRE7-TTRenh-TTRm-MVM-hFIXcoPadua-bghpolyA (SEQ ID NO: 39), AAVsc-HS-CRE8-TTRenh-TTRm-MVM-hFIXcoPadua-bghpolyA (SEQ ID NO: 40), AAVsc-HS-CRE9-TTRenh-TTRm-MVM-hFIXcoPadua-bghpolyA (SEQ ID NO: 41), AAVsc-HS-CRE10-TTRenh-TTRm-MVM-hFIXcoPadua-bghpolyA (SEQ ID NO: 42), AAVsc-HS-CRE11-TTRenh-TTRm-MVM-hFIXcoPadua-bghpolyA (SEQ ID NO: 43), AAVsc-HS-CRE12-TTRenh-TTRm-MVM-hFIXcoPadua-bghpolyA (SEQ ID NO: 44), AAVsc-HS-CRE13-TTRenh-TTRm-MVM-hFIXcoPadua-bghpolyA (SEQ ID NO: 45), AAVsc-HS-CRE14-TTRenh-TTRm-MVM-hFIXcoPadua-bghpolyA (SEQ ID NO: 46), AAVsc-HS-CRE15-TTRenh-TTRm-MVM-hFIXcoPadua-bghpolyA (SEQ ID NO: 47), AAVsc-HS-CRE16-TTRenh-TTRm-MVM-hFIXcoPadua-bghpolyA (SEQ ID NO: 48), AAVsc-HS-CRE17-TTRenh-TTRm-MVM-hFIXcoPadua-bghpolyA (SEQ ID NO: 49), AAVsc-HS-CRE18-TTRenh-TTRm-MVM-hFIXcoPadua-bghpolyA (SEQ ID NO: 50), AAVsc-HS-CRE19-TTRenh-TTRm-MVM-hFIXcoPadua-bghpolyA (SEQ ID NO: 51), AAVsc-HS-CRE20-TTRenh-TTRm-MVM-hFIXcoPadua-bghpolyA (SEQ ID NO: 52), AAVsc-HS-CRE21-TTRenh-TTRm-MVM-hFIXcoPadua-bghpolyA (SEQ ID NO: 53), abbreviated as HS-CRE1, HS-CRE2, HS-CRE3, HS-CRE4, HS-CRE5, HS-CRE6, HS-CRE7, HS-CRE8, HS-CRE9, HS-CRE10, HS-CRE11, HS-CRE12, HS-CRE13, HS-CRE14, HS-CRE15, HS-CRE16, HS-CRE17, HS-CRE18, HS-CRE19, HS-CRE20 and HS-CRE21, respectively. As controls, AAVsc-3xSERP-TTRenh-TTRm-MVM-hFIXcoPadua-bghpolyA (SEQ ID NO: 32) and AAVsc-TTRenh-TTRm-MVM-hFIXcoPadua-bghpolyA (SEQ ID NO: 31) were used, indicated as 3xSERP-TTRenh-TTRmin and TTRenh-TTRmin, respectively. The production of the transgene product (i.e. human FIX-Padua) in the plasma was quantified using a human-FIX specific ELISA, 1 day (panel A) and 2 days (panel B) post-transfection.

The effect of the cis-regulatory elements identified in Example 1 on in vivo expression was assessed by measuring the FIX protein levels in mice that were injected with plasmid constructs expressing human clotting factor IX (hFIX) from a chimeric promoter composed of a potent liver-specific minimal transthyretin promoter in conjunction with the transthyrethin enhancer (TTRenh/TTRmin) in which the different CREs were cloned upstream of the TTRenh/TTRmin. FIX expression was assessed 1 or 2 days post-transfection demonstrating a significant increase in FIX by some of the new HS-CREs. In particular, about 52% (11 of 21 HS-CREs) of the identified cis-regulatory elements induced a significant increase in hFIX expression on day 2 post-transfection (FIG. 2) as compared to the control plasmid construct without any cis-regulatory element (i.e. AAVsc-TTRenh-TTRm-MVM-hFIXcoPadua-bghpolyA (SEQ ID NO: 31)). The newly identified regulatory elements were further compared to the previously identified liver-specific regulatory element designated as Serpin enhancer (WO 2009/130208, which is specifically incorporated by reference herein) present as a triplet repeat in the vector (i.e. pAAVsc-3xSERP-TTRe-TTRm-MVM-FIXcoPadua-bghpA (SEQ ID NO: 32)). We had previously demonstrated that repeating the SERP element 3 times boosts the expression of the gene of interest (e.g. FIX). Unexpectedly, we found that 3 of the new CREs, namely HS-CRE4, HS-CRE6 and HS-CRE12 outperformed all the other CREs (including SERP3X). In particular, HS-CRE4, HS-CRE6 and HS-CRE12 expressed FIX levels comparable or even higher than what could be achieved by incorporating a triplet SERP repeat in the AAV vector. Taking into consideration, the known effect of multiplying the SERP element on transgene expression levels, this indicates that, unexpectedly, HS-CRE4 (ApoA2; SEQ ID NO: 4), HS-CRE6 (ApoC1; SEQ ID NO: 6), and HS-CRE12 (RBP4; SEQ ID NO: 12) therefore significantly outperformed a single SERP element in terms of boosting transgene expression levels. Compared to all CREs, including SERP, HS-CRE6 was the most potent HS-CRE.

Example 3: In Vivo Validation of the Identified Hepatocyte-Specific Cis-Regulatory Elements (CREs) by AAV Viral Vector Transduction To confirm the in vivo results obtained by hydrodynamic (i.e. non-viral) plasmid transfection and broaden the scope of the invention towards also including viral vectors, AAV serotype 9 (designated as AAV9) vector particles were produced that contained the most potent CREs identified in Example 2 (namely HS-CRE4 and HS-CRE6), based on the non-viral, semi-high throughput in vivo screening and validation. The corresponding AAV9 vectors were based on the self-complementary (sc) configuration and designated as AAV9sc-HS-CRE4-TTRenh-TTRm-MVM-hFIXcoPadua-bghpolyA and AAV9sc-HS-CRE6-TTRenh-TTRm-MVM-hFIXcoPadua-bghpolyA. As controls, AAV9 vectors were produced that did not contain any CRE (designated as AAV9sc-TTRenh-TTRm-MVM-hFIXcoPadua-bghpolyA) or that contained a triplet repeat of the SERP element as reference (designated as AAV9sc-3xSERP-TTRenh-TTRm-MVM-hFIXcoPadua-bghpolyA).

Vector Production and Purification and Titration:

The aforementioned AAV serotype 9 vectors, namely AAV9sc-HS-CRE4-TTRenh-TTRm-MVM-hFIXcoPadua-bghpolyA and AAV9sc-HS-CRE6-TTRenh-TTRm-MVM-hFIXcoPadua-bghpolyA, AAV9sc-TTRenh-TTRm-MVM-hFIXcoPadua-bghpolyA, AAV9sc-3xSERP-TTRenh-TTRm-MVM-hFIXcoPadua-bghpolyA, were produced by cotransfecting AAV-293 cells using calcium phosphate (Thermo Fisher Scientific, Waltham, Mass., USA) with the AAV plasmid, a chimeric packaging construct and an adeno-viral helper plasmid, as described previously. (Vanden-Driessche T, Thorrez L, Acosta-Sanchez A, et al. Efficacy and safety of adeno-associated viral vectors based on serotype 8 and 9 vs. lentiviral vectors for hemophilia B gene therapy. J Thromb Haemost. 2007; 5(1):16-24). Two days post-transfection cells were harvested and lysed by successive freeze/thaw cycles and sonication, followed by treatment with benzonase (Novagen, Madison, Wis., USA) and deoxycholic acid (Sigma Aldrich (MERCK, check), St Louis, Mo., USA) and 3 rounds of cesium chloride (Thermo Fisher Scientific, Waltham, Mass., USA) density gradient ultracentrifugation. The fractions containing the AAV particles were collected and dialyzed in Dulbecco's phosphate buffered saline (D-PBS) (Gibco, IRL) containing 1 mM MgCl$_2$.

To determine vector titers, quantitative real-time PCR (ABI Prism 7900HT, Applied Biosystems, Foster City/CA, USA) with SYBR® Green (Thermo Fisher Scientific, Waltham, Mass., USA) and primers for the FIX gene were used. The forward primer sequence was 5'-CACGAGAACGCCAACAAGAT-3' (SEQ ID NO: 55), the reverse primer sequence was 5'-CACTTCTCCTC-CATGCACTC-3' (SEQ ID NO: 56). Standard curves were generated using known copy numbers of the corresponding vector plasmids.

AAV9 Vector Injection

Figure 3:
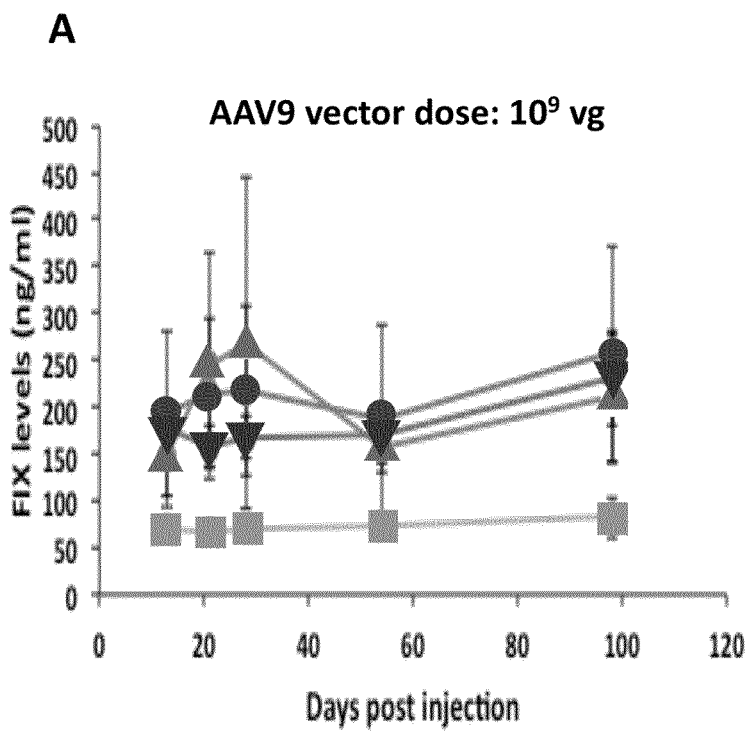
FIG. 3: Comparison of FIX levels (measured as ng/ml mouse plasma) in adult C57BL/6 mice which were injected via the tail vein with $1 \times 10^9$ vector genomes (vg) (A) or $5 \times 10^9$ vg (B) AAV9sc-HS-CRE4-TTRenh-TTRm-MVM-hFIXcoPadua-bghpolyA, AAV9sc-HS-CRE6-TTRenh-TTRm-MVM-hFIXcoPadua-bghpolyA, AAV9sc-TTRenh-TTRm-MVM-hFIXcoPadua-bghpolyA or AAV9sc-SERP3X-TTRenh-TTRm-MVM-hFIXcoPadua-bghpolyA vectors, indicated in abbreviated form as HS-CRE4, HS-CRE6, no HS-CRE and 3xSERP, respectively. Blood was collected on successive days post-injection into buffered citrate and the concentration of hFIX antigen in citrated plasma was measured by ELISA.
Figure 3:
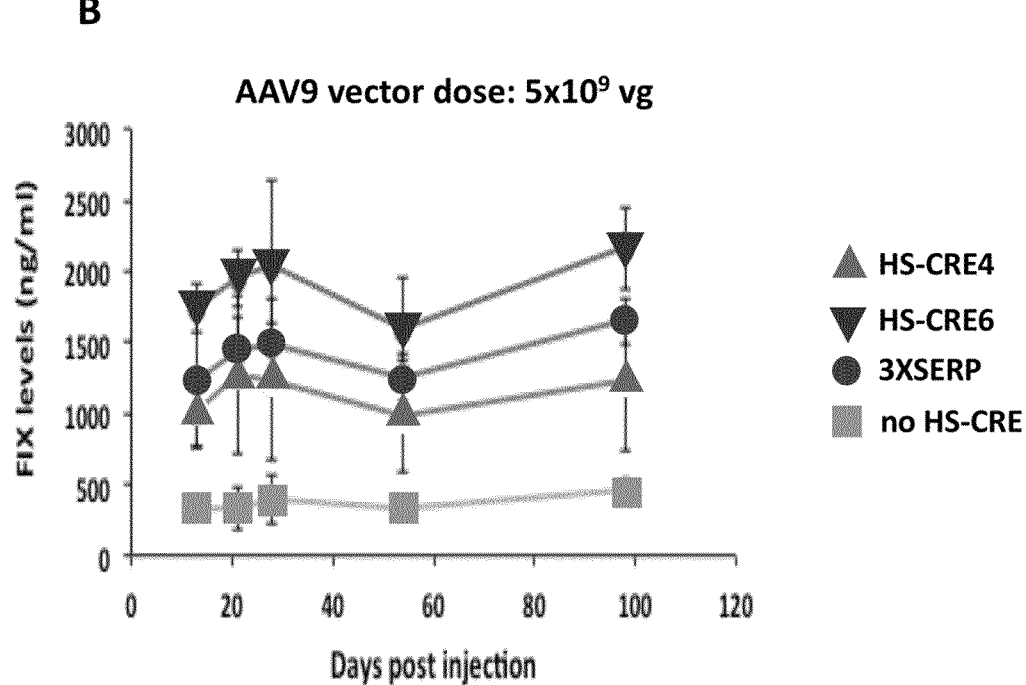

The AAV9sc-HS-CRE4-TTRenh-TTRm-MVM-hFIXcoPadua-bghpolyA, AAV9sc-HS-CRE6-TTRenh-TTRm-MVM-hFIXcoPadua-bghpolyA, AAV9sc-TTRenh-TTRm-MVM-hFIXcoPadua-bghpolyA and AAV9sc-3xSERP-TTRenh-TTRm-MVM-hFIXcoPadua-bghpoly vectors were injected at a dose of $1 \times 10^9$ vg/mouse (FIG. 3A) and a dose of $5 \times 10^9$ vg/mouse (FIG. 3B) into the tail vein of C57BL/6 mice (4-5 weeks old). Each cohort consists of 3 mice. Blood was collected at several time points after injection and plasma was analyzed for FIX protein levels by means of ELISA.

Mice injected with $5 \times 10^9$ vg AAV9sc-HS-CRE4-TTR-enh-TTRm-MVM-hFIXcoPadua-bghpolyA or AAV9sc-HS-CRE6-TTRenh-TTRm-MVM-hFIXcoPadua-bghpolyA yield significantly higher FIX levels than the control mice injected with the AAV9sc-TTRenh-TTRm-MVM-hFIXcoPadua-bghpolyA vector that is devoid of any HS-CRE. This indicates that the HS-CRE4 and HS-CRE6 elements result in a significant 5 to 6-fold increase in FIX levels, that are relatively stable over at least 3 months. Similarly, mice injected with a lower dose (i.e. $10^9$ vg) AAV9sc-HS-CRE4-TTRenh-TTRm-MVM-hFIXcoPadua-bghpolyA or AAV9sc-HS-CRE6-TTRenh-TTRm-MVM-hFIXcoPadua-bghpolyA vectors yield significantly higher FIX levels than the control mice injected with AAV9sc-TTRenh-TTRm-MVM-hFIXcoPadua-bghpolyA that is devoid of any HS-CRE. A dose-response was apparent, consistent with higher stable FIX levels following injection of $5 \times 10^9$ vg compared to $10^9$ vg for all vectors tested.

The newly identified regulatory elements were further compared to the previously identified liver-specific regulatory element designated as Serpin enhancer (WO 2009/130208, which is specifically incorporated by reference herein) present as a triplet repeat in the vector (i.e. AAV9sc-3xSERP-TTRe-TTRm-MVM-FIXcoPadua-bghpA). We had previously demonstrated that repeating the SERP element 3 times boosts the expression of the gene of interest (e.g. FIX). Consistent with the hydrodynamic transfection data shown in Example 2, we found HS-CRE4 and HS-CRE6 expressed FIX levels comparable or even higher than what could be achieved by incorporating a triplet SERP repeat in the AAV vector. Taking into consideration, the known effect of multiplying the SERP element on transgene expression levels, this confirms once again, that, HS-CRE4 (ApoA2; SEQ ID NO: 4) and HS-CRE6 (ApoC1; SEQ ID NO: 6), outperformed a single SERP element in terms of boosting transgene expression levels. Compared to all CREs, including SERP, HS-CRE6 was again the most potent HS-CRE within the context of AAV9-based liver transduction.

Present inventors tested which transcription factors bind on HS-CREs 1-21 through experimental research.

It was found through experimental research that (1) all of HS-CRE6, HS-CRE4 and HS-CRE12 (which are the HS-CREs resulting in the highest liver-specific increase of the protein levels) have transcription factor binding sites for SP1, EP300, HNF 4G, CEBPB, P300, HDAC2, JUND, FOSL2, ZBTB7A, CEBPD and RXRA; (2) all of HS-CRE1, HS-CRE5 and HS-CRE13 (which are the HS-CREs showing a medium high liver-specific increase of the protein levels) have transcription factor binding sites for SP1, EP300, POLR2A, MYBL2, FOXA1, FOXA2, ARID3A, POLR2A and HEY1; and (3) all of HS-CRE9, HS-CRE11, HS-CRE14, HS-CRE16 and HS-CRE20 (which are the HS-CREs showing the lowest liver-specific increase of the protein levels) have transcription factor binding sites for SP1, EP300, HNF 4G, CEBPB, P300 and HNF 4A. Accordingly, all of HS-CRE6, HS-CRE4, HS-CRE12, HS-CRE1, HS-CRE5, HS-CRE13, HS-CRE9, HS-CRE11, HS-CRE14, HS-CRE16 and HS-CRE20 have transcription factor binding sites for SP1 and EP300.

REFERENCES

BUDKER V, ZHANG G, KNECHTLE S, WOLFF J A. Naked DNA delivered intraportally expresses efficiently in hepatocytes. (1996) Gene Ther. July; 3(7):593-8.

BRUNETTI-PIERRI N, GROVE N C, ZUO Y, EDWARDS R, PALMER D, CERULLO V, TERUYA J, N G P. Bioengineered factor IX molecules with increased catalytic activity improve the therapeutic index of gene therapy vectors for hemophilia B. Hum Gene Ther. 2009 May; 20(5):479-85.

CHANG, J., JIN, J., LOLLAR, P., BODE, W., BRAND-STETTER, H., HAMAGUCHI, N., STRAIGHT, D. L. & STAFFORD, D. W. (1998). Changing residue 338 in human factor IX from arginine to alanine causes an increase in catalytic activity. J Biol Chem 273(20): 12089-12094.

CRISTIANO R J, Smith L C, Kay M A, Brinkley B R, Woo S L. (1993a) Hepatic gene therapy; efficient gene delivery and expression in primary hepatocytes utilizing a conjugated adenovirus-DNA complex. Proc Natl Acad Sci USA. 90(24):11548-11552.

CRISTIANO R J, Smith L C, Woo S L. (1993b) Hepatic gene therapy: adenovirus enhancement of receptor-mediated gene delivery and expression in primary hepatocytes. 90(6): 2122-2126.

GRIMM D, LEE J S, WANG L, DESAI T, AKACHE B, STORM T A, KAY M A (2008). J Virol. 82(12):5887-5991.

IVICS Z, HACKETT P B, PLASTERK R H, IZSVÁK Z. (1997) Molecular reconstruction of Sleeping Beauty, a Tc1-like transposon from fish, and its transposition in human cells. Cell. 91(4):501-510.

KAY M A, BALEY P, ROTHENBERG S, LELAND F, FLEMING L, PONDER K P, LIU T, FINEGOLD M, DARLINGTON G, POKORNY W, WOO SLC. (1992) Expression of human alpha 1-antitrypsin in dogs after autologous transplantation of retroviral transduced hepatocytes. Proc Natl Acad Sci USA. January 1; 89(1):89-93.

KAO, C. Y., LIN, C. N., Y U, I. S., TAO, M. H., W U, H. L., SHI, G. Y., YANG, Y. L., KAO, J. T. & LIN, S. W. (2010). FIX-Triple, a gain-of-function factor IX variant, improves haemostasis in mouse models without increased risk of thrombosis. Thromb Haemost 104(2): 355-365.

KISTNER A, GOSSEN M, ZIMMERMANN F, JERECIC J, ULLMER C, LYBBERT H, BUJARD H. (1996) Doxycycline-mediated quantitative and tissue-specific control of gene expression in transgenic mice. Proc Natl Acad Sci USA. October 1; 93(20): 10933-8.

LIN, C. N., KAO, C. Y., MIAO, C. H., HAMAGUCHI, N., W U, H. L., SHI, G. Y., LIU, Y. L., HIGH, K. A. & LIN, S. W. (2010). Generation of a novel factor IX with augmented clotting activities in vitro and in vivo. J Thromb Haemost 8(8): 1773-1783.

LISOWSKI L, DANE A P, CHU K, ZHANG Y, CUNNING-HAM S C, WILSON E M, NYGAARD S, GROMPE M, ALEXANDER I E, KAY M A. (2014) Nature. 506(7488): 382-386.

LIU F, SONG Y, LIU D. (1999) Hydrodynamics-based transfection in animals by systemic administration of plasmid DNA. Gene Ther. July; 6(7):1258-66.

McCARTY D M, MONAHAN P E, and SAMULSKI R J. (2001). Self-complementary recombinant adeno-associated virus (scAAV) vectors promote efficient transduction independently of DNA synthesis. Gene Ther. 8, 1248-54.

McCARTY D M, F U H, MONAHAN P E, TOULSON C E, NAIK P, and SAMULSKI R J. (2003). Adeno-associated virus terminal repeat (T R) mutant generates self-complementary vectors to overcome the rate-limiting step to transduction in vivo. Gene Ther. 10, 2112-8.

MÁTÉS L, CHUAH M K, BELAY E, JERCHOW B, MANOJ N, ACOSTA-SANCHEZ A, GRZELA D P, SCHMITT A, BECKER K, MATRAI J, M A L, SAMARA-KUKO E, GYSEMANS C, PRYPUTNIE-WICZ D, MISKEY C, FLETCHER B, VANDEN-DRIESSCHE T, IVICS Z, and IZSVAK Z. (2009). Molecular evolution of a novel hyperactive Sleeping Beauty transposase enables robust stable gene transfer in vertebrates. Nat Genet. 41, 753-61.

MILANOV, ET AL., 2012 Engineered factor IX variants bypass FVIII and correct hemophilia A phenotype in mice Blood 119:602-611.

NAIR N, RINCON M Y, EVENS H, SARCAR S, DASTI-DAR S, SAMARA-KUKO E, GHANDEHARIAN O, MAN VIECELLI H, THONY B, D E BLESER P, VAN-DENDRIESSCHE T, CHUAH M K. (2014). Computationally designed liver-specific transcriptional modules and hyperactive factor IX improve hepatic gene therapy. Blood 123, 3195-9.

NATHWANI A C, DAVIDOFF A M, HANAWA H, YUNYU H U, HOFFER F A, NIKANOROV A, SLAUGHTER C, N G CYC, ZHOU J, LOZIER J, MANDRELL T D, VANIN E F, and NIENHUIS A W. (2002). Sustained high-level expression of human factor IX (hFIX) after liver-targeted delivery of recombinant adeno-associated virus encoding the hFIX gene in rhesus macaques. Blood 100, 1662-1669.

NATHWANI A C, GRAY J T, N G C Y, ZHOU J, SPENCE Y, WADDINGTON S N, TUDDENHAM E G, KEM-BALL COOK G, McINTOSH J, BOON-SPIJKER M, MERTENS K, DAVIDOFF A M. (2006). Self-complementary adeno-associated virus vectors containing a novel liver-specific human factor IX expression cassette enable highly efficient transduction of murine and non-human primate liver. Blood 107, 2653-61.

NATHWANI A C, TUDDENHAM E G, RANGARAJAN S, ROSALES C, MCINTOSH J, LINCH D C, CHOWDARY P, RIDDELL A, PIE A J, HARRINGTON C, O'BEIRNE J, SMITH K, PASI J, GLADER B, RUS-TAGI P, N G C Y, KAY M A, ZHOU J, SPENCE Y, MORTON C L, ALLAY J, COLEMAN J, SLEEP S, CUNNINGHAM J M, SRIVASTAVA D, BASNER-TSCHAKARJAN E, MINGOZZI F, HIGH K A, GRAY J T, REISS U M, NIENHUIS A W, and DAVIDOFF A M. (2011). Adenovirus-associated virus vector-mediated gene transfer in hemophilia B. N Engl J Med. 365, 2357-2365.

WU Z, SUN J, ZHANG T, YIN C, YIN F, VAN DYKE T, SAMULSKI R J, and MONAHAN P E. (2008). Optimization of self-complementary AAV vectors for liver-directed expression results in sustained correction of hemophilia B at low vector dose. Mol Ther. 16, 280-9.

SCHUETTRUMPF, J., HERZOG, R. W., SCHLACHTER-MAN, A., KAUFHOLD, A., STAFFORD, D. W. & ARRUDA, V. R. (2005). Factor IX variants improve gene therapy efficacy for hemophilia B. Blood 105(6): 2316-2323.

SIMIONI, P., TORMENE, D., TOGNIN, G., GAVASSO, S., BULATO, C., IACOBELLI, N. P., FINN, J. D., SPIEZIA, L., RADU, C. & ARRUDA, V. R. (2009). X-linked thrombophilia with a mutant factor IX (factor IX Padua). N Engl J Med 361(17): 1671-1675.

SNYDER R O, MIAO C, MEUSE L, TUBB J, DONAHUE B A, HUI-FENG LIN, STAFFORD D W, PATEL S, THOMPSON A R, NICHOLS T, READ M S, BELL-INGER D A, BRINKHOUS K M, and KAY M A. (1999). Correction of hemophilia B in canine and murine models using recombinant adeno-associated viral vectors. Nat Med. 5, 64-70.

WARD, N. J. ET AL. Codon optimization of human factor VIII cDNAs leads to high-level expression. Blood 117, 798-807 (2011).

YAMADA T, IWASAKI Y, TADA H, IWABUKI H, CHUAH M K, VANDENDRIESSCHE T, FUKUDA H, KONDO A, UEDA M, SENO M, TANIZAWA K, KURODA S. (2003) Nanoparticles for the delivery of genes and drugs to human hepatocytes. Nat Biotechnol. August; 21 (8):885-90.

YUSA ET AL. A hyperactive piggyBac transposase for mammalian applications. Proc Natl Acad Sci USA. 2011; 108(4):1531-6.

ZHANG G, BUDKER V, WOLFF J A. (1999) High levels of foreign gene expression in hepatocytes after tail vein injections of naked plasmid DNA. Hum Gene Ther. July 1; 10(10):1735-7.

D E BLESER P, HOOGHE B, VLIEGHE D, VAN ROY F. (2007) A distance difference matrix approach to identifying transcription factors that regulate differential gene expression. Genome Biol. 8(5): R83.

CHUAH, M. K., PETRUS, I., D E BLESER, P., L E GUINER, C., GERNOUX, G., ADJALI, O., NAIR, N., WILLEMS, J., EVENS, H., RINCON, M. Y., MATRAI, J., D I MATTEO, M., SAMARA-KUKO, E., YAN, B., ACOSTA-SANCHEZ, A., MELIANI, A., CHEREL, G., BLOUIN, V., CHRISTOPHE, O., MOULLIER, P., MIN-GOZZI, F., VANDENDRIESSCHE, T. (2014) Liver-specific transcriptional modules identified by genome-wide in silico analysis enable efficient gene therapy in mice and non-humans primates. Mol. Ther. 22(9):1605-13

GARMORY HS1, BROWN K A, TITBALL R W. (2003) DNA vaccines: improving expression of antigens. Genet Vaccines Ther. 1(1):2Wu C, Macleod I, Su A I. (2013) BioGPS and MyGene.info: organizing online, gene-centric information. Nucleic Acids Res. 41(Database issue): D561-5.

MCINTOSH J, LENTING P J, ROSALES C, LEE D, RABBANIAN S, RAJ D, PATEL N, TUDDENHAM E G, CHRISTOPHE O D, MCVEY J H, WADDINGTON S, NIENHUIS A W, GRAY J T, FAGONE P, MINGOZZI F, ZHOU S Z, HIGH K A, CANCIO M, N G C Y, ZHOU J, MORTON C L, DAVIDOFF A M, NATHWANI A C. (2003) *Therapeutic levels of FVIII following a single peripheral vein administration of rAAV vector encoding a novel human factor VIII variant.* Blood. 121(17):3335-44XIAO S J, ZHANG C, ZOU Q, JI Z L. (2010) TiSGeD: database for tissue-specific genes. Bioinformatics 26(9): 1273-5.

The invention claimed is:

1. A nucleic acid regulatory element comprising SEQ ID NO: 6 or a sequence having at least 95% identity to SEQ ID NO: 6, or consisting of a functional fragment of SEQ ID NO: 6 comprising at least 200 contiguous nucleotides from SEQ ID NO: 6;

wherein the nucleic acid regulatory element has a maximal length of 600 nucleotides;

wherein the nucleic acid regulatory element forms part of a nucleic acid expression cassette, wherein the nucleic acid regulatory element is operably linked to a promoter and a transgene; and wherein the nucleic acid regulatory element allows enhancing promotor-driven transgene expression relative to transgene expression from the promoter alone.

2. The nucleic acid regulatory element according to claim 1, further comprising at least one liver-specific regulatory element different from the nucleic acid regulatory element comprising SEQ ID NO: 6 or the sequence having at least 95% identity to SEQ ID NO: 6.

3. The nucleic acid regulatory element according to claim 2, comprising a nucleic acid regulatory element comprising SEQ ID NO: 6 or a sequence having at least 95% identity to SEQ ID NO: 6, and at least one nucleic acid regulatory element comprising SEQ ID NO: 22 or a sequence having at least 95% identity to SEQ ID NO: 22.

4. The nucleic acid regulatory element according to claim 1, wherein the transgene encodes a therapeutic protein or an immunogenic protein.

5. The nucleic acid regulatory element according to claim 1, wherein the promoter is a liver-specific promoter.

6. The nucleic acid regulatory element according to claim 5, wherein the liver-specific promoter comprises SEQ ID NO: 27, wherein the nucleic acid regulatory element further comprises a liver-specific regulatory element comprising SEQ ID NO: 24, and wherein the nucleic acid regulatory element comprises the combination of the transthyretin enhancer (TTRe) and minimal transthyretin promoter (TTRm) nucleic acids of SEQ ID NO: 28.

7. The nucleic acid regulatory element according to claim 1, further comprising a minute virus of mouse (MVM) intron.

8. The nucleic acid regulatory element according to claim 1, further comprising a transcriptional termination signal derived from the bovine growth hormone polyadenylation signal (BGHpA).

9. A vector comprising the nucleic acid regulatory element according to claim 1.

10. The vector according to claim 9, comprising SEQ ID NO: 38.

11. A pharmaceutical composition comprising the nucleic acid regulatory element according to claim 1, and a pharmaceutically acceptable carrier.

12. A method of treating a liver disease in a subject in need thereof, comprising administering a therapeutically effective amount of the nucleic acid regulatory element according to claim 1.

13. The method according to claim 12, wherein the liver disease is hemophilia A or hemophilia B.

14. An in vitro or ex vivo method for expressing a transgene product in liver cells comprising:

i) introducing the nucleic acid regulatory element according to claim 1 into the liver cells; and ii) expressing the transgene product in the liver cells.

15. The nucleic acid regulatory element according to claim 1, wherein the functional fragment comprises at least 250 contiguous nucleotides from SEQ ID NO:6.

16. The nucleic acid regulatory element according to claim 1, wherein the promoter is a heterologous promoter.

17. The nucleic acid regulatory element according to claim 1, wherein the promoter is a liver-specific promoter.

* * * * *